(12) United States Patent
Merzenich et al.

(10) Patent No.: US 9,886,866 B2
(45) Date of Patent: **\*Feb. 6, 2018**

(54) NEUROPLASTICITY GAMES FOR SOCIAL COGNITION DISORDERS

(71) Applicant: POSIT SCIENCE CORPORATION, San Francisco, CA (US)

(72) Inventors: Michael M. Merzenich, San Francisco, CA (US); Mor Nahum, San Francisco, CA (US)

(73) Assignee: POSIT SCIENCE CORPORATION, San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/017,904

(22) Filed: Feb. 8, 2016

(65) Prior Publication Data

US 2016/0155354 A1 Jun. 2, 2016

Related U.S. Application Data

(63) Continuation of application No. 14/201,697, filed on Mar. 7, 2014, now Pat. No. 9,308,446.
(Continued)

(51) Int. Cl.
*A63F 9/24* (2006.01)
*G09B 5/02* (2006.01)
(Continued)

(52) U.S. Cl.
CPC ............ *G09B 5/02* (2013.01); *A63F 13/10* (2013.01); *A63F 13/80* (2014.09); *G09B 5/00* (2013.01);
(Continued)

(58) Field of Classification Search
CPC .............. A63F 13/80; A63F 2009/0007; A63F 2009/2402; A63F 2250/26; G09B 19/00; G09B 5/02
See application file for complete search history.

(56) References Cited

U.S. PATENT DOCUMENTS 2,674,923 A 4/1954 Brandt
3,816,664 A 6/1974 Koch
(Continued)

FOREIGN PATENT DOCUMENTS

DE 69529054 8/2003
EP 411713 A1 2/1991
(Continued)

OTHER PUBLICATIONS

Arthur_Story_Scramble.pdf, © 2010 WGBH, (at https://web.archive.org/web/20101128184245l/http://pbskids.org/arthur/games/storyscramble/scramble.html) Last accessed Jul. 1, 2015. p. 1.
(Continued)

*Primary Examiner* — Steve Rowland
(74) *Attorney, Agent, or Firm* — Eric W. Cernyar; James W. Huffman

(57) ABSTRACT

A training program is configured to systematically drive neurological changes to overcome social cognitive deficits. Various games challenge the participant to observe gaze directions in facial images, match faces from different angles, reconstruct face sequence, memorize social details about sequentially presented faces, identify smiling faces, find faces whose expression matches the target, identify emotions implicitly expressed by facial expressions, match pairs of similar facial expressions, match pairs of emotion clips and emotion labels, reconstruct sequences of emotion clips, identify emotional prosodies of progressively shorter sentences, match sentences with tags that identify emotional prosodies with which they are expressed, identify social scenarios that best explain emotions expressed in video clips, answer questions about social interactions in multi-segmented stories, choose expressions and associated prosodies that best describe how a person would sound in given
(Continued)

social scenarios, and/or understand and interpret gradually more complex social scenes.

20 Claims, 143 Drawing Sheets

Related U.S. Application Data

(60) Provisional application No. 61/774,378, filed on Mar. 7, 2013, provisional application No. 61/774,390, filed on Mar. 7, 2013, provisional application No. 61/774,400, filed on Mar. 7, 2013, provisional application No. 61/774,413, filed on Mar. 7, 2013, provisional application No. 61/774,420, filed on Mar. 7, 2013, provisional application No. 61/777,066, filed on Mar. 12, 2013, provisional application No. 61/777,080, filed on Mar. 12, 2013, provisional application No. 61/779,024, filed on Mar. 13, 2013, provisional application No. 61/782,571, filed on Mar. 14, 2013, provisional application No. 61/780,495, filed on Mar. 13, 2013.

(51) Int. Cl.
  *A63F 13/40* (2014.01)
  *G09B 5/00* (2006.01)
  *G09B 19/00* (2006.01)
  *G09B 5/06* (2006.01)
  *A63F 13/80* (2014.01)

(52) U.S. Cl.
  CPC .............. *G09B 5/06* (2013.01); *G09B 5/065* (2013.01); *G09B 19/00* (2013.01)

(56) References Cited

U.S. PATENT DOCUMENTS

| | | |
|---|---|---|
| 4,207,087 A | 6/1980 | Morrison et al. |
| 4,505,682 A | 3/1985 | Thompson |
| 4,586,905 A | 5/1986 | Groff |
| 4,802,228 A | 1/1989 | Silverstein et al. |
| 4,813,076 A | 3/1989 | Miller |
| 4,820,059 A | 4/1989 | Miller et al. |
| 4,839,853 A | 6/1989 | Deerwester et al. |
| 4,879,748 A | 11/1989 | Picone et al. |
| 4,971,434 A | 11/1990 | Ball |
| 5,059,127 A | 10/1991 | Lewis et al. |
| 5,119,826 A | 6/1992 | Baart de la Faille |
| 5,121,434 A | 6/1992 | Mrayati et al. |
| 5,169,342 A | 12/1992 | Steele et al. |
| 5,215,468 A | 6/1993 | Lauffer et al. |
| 5,267,734 A | 12/1993 | Stamper et al. |
| 5,302,132 A | 4/1994 | Corder |
| 5,303,327 A | 4/1994 | Sturner et al. |
| 5,387,104 A | 2/1995 | Corder |
| 5,388,185 A | 2/1995 | Terry et al. |
| 5,393,236 A | 2/1995 | Blackmer et al. |
| 5,429,513 A | 7/1995 | Diaz-Plaza |
| 5,517,595 A | 5/1996 | Kleijn |
| 5,528,726 A | 6/1996 | Cook |
| 5,536,171 A | 7/1996 | Javkin et al. |
| 5,540,589 A | 7/1996 | Waters |
| 5,553,151 A | 9/1996 | Goldberg |
| 5,572,593 A | 11/1996 | Nejime et al. |
| 5,573,403 A | 11/1996 | Beller et al. |
| 5,617,507 A | 4/1997 | Lee et al. |
| 5,683,082 A | 11/1997 | Takemoto et al. |
| 5,690,493 A | 11/1997 | McAlear, Jr. |
| 5,692,906 A | 12/1997 | Corder |
| 5,697,789 A | 12/1997 | Sameth et al. |
| 5,717,818 A | 2/1998 | Nejime et al. |
| 5,727,950 A | 3/1998 | Cook et al. |
| 5,801,810 A | 9/1998 | Roenker |
| 5,806,037 A | 9/1998 | Sogo |
| 5,813,862 A | 9/1998 | Merzenich et al. |
| 5,828,943 A | 10/1998 | Brown |
| 5,868,683 A | 2/1999 | Protopapas et al. |
| 5,885,083 A | 3/1999 | Ferrell |
| 5,911,581 A | 6/1999 | Reynolds et al. |
| 5,927,988 A | 7/1999 | Jenkins et al. |
| 5,929,972 A | 7/1999 | Hutchinson |
| 5,954,581 A | 9/1999 | Ohta et al. |
| 5,957,699 A | 9/1999 | Peterson et al. |
| 6,019,607 A | 2/2000 | Jenkins et al. |
| 6,026,361 A | 2/2000 | Hura |
| 6,036,496 A | 3/2000 | Miller et al. |
| 6,052,512 A | 4/2000 | Peterson et al. |
| 6,067,638 A | 5/2000 | Benitz et al. |
| 6,071,123 A | 6/2000 | Tallal et al. |
| 6,109,107 A | 8/2000 | Wright et al. |
| 6,113,645 A | 9/2000 | Benitz et al. |
| 6,120,298 A | 9/2000 | Jenkins et al. |
| 6,123,548 A | 9/2000 | Tallal et al. |
| 6,146,147 A | 11/2000 | Wasowicz |
| 6,159,014 A | 12/2000 | Jenkins et al. |
| 6,186,794 B1 | 2/2001 | Brown et al. |
| 6,186,795 B1 | 2/2001 | Wilson |
| 6,190,173 B1 | 2/2001 | Jenkins et al. |
| 6,210,166 B1 | 4/2001 | Jenkins et al. |
| 6,224,384 B1 | 5/2001 | Jenkins et al. |
| 6,227,863 B1 | 5/2001 | Spector |
| 6,234,802 B1 | 5/2001 | Pella et al. |
| 6,261,101 B1 | 7/2001 | Benitz et al. |
| 6,289,310 B1 | 9/2001 | Miller et al. |
| 6,290,504 B1 | 9/2001 | Benitz et al. |
| 6,293,801 B1 | 9/2001 | Jenkins et al. |
| 6,299,452 B1 | 10/2001 | Wasowicz et al. |
| 6,302,697 B1 | 10/2001 | Tallal et al. |
| 6,328,569 B1 | 12/2001 | Jenkins et al. |
| 6,331,115 B1 | 12/2001 | Jenkins et al. |
| 6,334,776 B1 | 1/2002 | Jenkins et al. |
| 6,334,777 B1 | 1/2002 | Jenkins et al. |
| 6,356,864 B1 | 3/2002 | Foltz et al. |
| 6,358,056 B1 | 3/2002 | Jenkins et al. |
| 6,364,486 B1 | 4/2002 | Ball et al. |
| 6,364,666 B1 | 4/2002 | Jenkins et al. |
| 6,366,759 B1 | 4/2002 | Burstein et al. |
| 6,386,881 B1 | 5/2002 | Jenkins et al. |
| 6,413,098 B1 | 7/2002 | Tallal et al. |
| 6,435,877 B2 | 8/2002 | Wasowicz |
| 6,464,356 B1 | 10/2002 | Sabel et al. |
| 6,511,324 B1 | 1/2003 | Wasowicz |
| 6,533,584 B1 | 3/2003 | Jenkins et al. |
| 6,585,519 B1 | 7/2003 | Jenkins et al. |
| 6,599,129 B2 | 7/2003 | Jenkins et al. |
| 6,626,676 B2 | 9/2003 | Freer |
| 6,629,844 B1 | 10/2003 | Jenkins et al. |
| 6,632,174 B1 | 10/2003 | Breznitz |
| 6,652,283 B1 | 11/2003 | Van Schaack et al. |
| 6,726,486 B2 | 4/2004 | Budra et al. |
| 6,755,657 B1 | 6/2004 | Wasowicz |
| 6,890,181 B2 | 5/2005 | Warneke et al. |
| 7,294,107 B2 | 11/2007 | Simon et al. |
| 7,367,675 B2 | 5/2008 | Maddalena et al. |
| 7,409,348 B2 | 8/2008 | Wen et al. |
| 7,549,743 B2 | 6/2009 | Huxlin et al. |
| 8,083,523 B2 | 12/2011 | De Ley et al. |
| 2001/0046658 A1 | 11/2001 | Wasowicz |
| 2001/0049085 A1 | 12/2001 | Wasowicz |
| 2002/0034717 A1 | 3/2002 | Jenkins et al. |
| 2003/0092484 A1 | 5/2003 | Schneider et al. |
| 2003/0201982 A1 | 10/2003 | Iesaka |
| 2004/0043364 A1 | 3/2004 | Wasowicz |
| 2004/0175687 A1 | 9/2004 | Burstein et al. |
| 2005/0175972 A1 | 8/2005 | Merzenich et al. |
| 2005/0192513 A1 | 9/2005 | Darby et al. |
| 2005/0213033 A1 | 9/2005 | Sabel |
| 2005/0250082 A1 | 11/2005 | Baldwin et al. |
| 2006/0051727 A1 | 3/2006 | Goldman et al. |
| 2006/0073452 A1 | 4/2006 | Merzenich et al. |
| 2006/0105307 A1 | 5/2006 | Goldman et al. |
| 2006/0161218 A1 | 7/2006 | Danilov |

(56) References Cited

U.S. PATENT DOCUMENTS

| | | |
|---|---|---|
| 2006/0177805 A1 | 8/2006 | Merzenich et al. |
| 2006/0234199 A1 | 10/2006 | Walker et al. |
| 2007/0020595 A1 | 1/2007 | Merzenich et al. |
| 2007/0054249 A1 | 3/2007 | Wade et al. |
| 2007/0065789 A1 | 3/2007 | Merzenich et al. |
| 2007/0111173 A1 | 5/2007 | Hardy et al. |
| 2007/0134635 A1 | 6/2007 | Hardy et al. |
| 2007/0166675 A1 | 7/2007 | Atkins et al. |
| 2007/0166676 A1 | 7/2007 | Bird et al. |
| 2007/0218439 A1 | 9/2007 | Delahunt et al. |
| 2007/0218440 A1 | 9/2007 | Delahunt et al. |
| 2007/0218441 A1 | 9/2007 | Delahunt et al. |
| 2007/0293732 A1 | 12/2007 | Delahunt et al. |
| 2008/0084427 A1 | 4/2008 | Delahunt et al. |
| 2009/0051877 A1 | 2/2009 | Delahunt et al. |
| 2010/0041001 A1 | 2/2010 | Delahunt et al. |
| 2011/0065078 A1 | 3/2011 | Duffy |
| 2012/0214143 A1 | 8/2012 | Severson et al. |

FOREIGN PATENT DOCUMENTS

| | | |
|---|---|---|
| EP | 00502984 | 12/1992 |
| EP | 0534410 A2 | 3/1993 |
| EP | 0534410 A3 | 12/1993 |
| EP | 1069855 | 8/2001 |
| FR | 2695750 A1 | 3/1994 |
| WO | WO9618184 A | 6/1996 |
| WO | WO9952419 | 10/1999 |
| WO | WO03065964 | 8/2003 |
| WO | WO2010100208 A1 | 9/2010 |

OTHER PUBLICATIONS

Two Out of Three—The Association Game Rules of Play. © 2001 Gamebird LLC. pp. 1 and 2.

Yan-Xue Xue et al.,"A Memory Retrieval-Extinction Procedure to Prevent Drug Craving and Relapse," Science, Apr. 13, 2012, pp. 241-245, 336(6078).

Woo-Young Ahn et al.,"Temporal Discounting of Rewards in Patients with Bipolar Disorder and Schizophrenia," Journal of Abnormal Psychology, Nov. 2011, pp. 911-921, vol. 120, No. 4.

Catherine Aldred et al.,"A new social communication intervention for children with autism: pilot randomised control treatment study suggesting effectiveness," Journal of Child Psychology and Psychiatry, 2004, pp. 1420-1430, vol. 45, No. 8, Blackwell Publishing.

Melissa J. Allman et al.,"Pathophysiological distortions in time perception and timed performance," Brain: A Journal of Neurology, 2012, pp. 656-677, vol. 135, Oxford University Press.

Cay Anderson-Hanley,"Autism and exergaming: effects on repetitive behaviors and cognition," Psychology Research and Behavior Management, Sep. 15, 2011, pp. 129-137, vol. 4, Dove Medical Press Ltd.

Gary Aston-Jones et al.,"Adaptive Gain and the Role of the Locus Coerulus-Norepinephrine System in Optimal Performance," The Journal of Comparative Neurology, 2005, pp. 99-110, vol. 493, Wiley-Liss, Inc.

Gary Aston-Jones et al.,"An Integrative Theory of Locus Coeruleus-Norepinephrine Function: Adaptive Gain and Optimal Performance," Annu. Rev. Neurosci., 2005, pp. 403-450, vol. 288, No. 18, University of California—San Francisco.

Angela S. Attwood et al.,"Attentional bias training and cue reactivity in cigarette smokers," Addiction Research Report, 2008, pp. 1875-1882, vol. 103, Society for the Study of Addiction.

Karlene Ball et al.,"Effects of Cognitive Training Interventions With Older Adults," Journal of the American Medical Association, Nov. 13, 2002, pp. 2271-2281, vol. 288, No. 18, American Medical Association.

Karlene Ball et al.,"The Impact of Speed of Processing Training on Cognitive and Everyday Functions," Journals of Gerontology: Series B, 2007, pp. 19-31, vol. 62B, Special Issue 1.

Shaowen Bao et al.,"Temporal plasticity in the primary auditory cortex induced by operant perceptual learning," Nature Neuroscience, Aug. 1, 2004, pp. 974-981, vol. 7, No. 9, Nature Publishing Group.

Russell A. Barkley et al.,"Executive Functioning, Temporal Discounting, and Sense of Time in Adolescents With Attention Deficit Hyperactivity Disorder (ADHD) and Oppositional Defiant Disorder (ODD)," Journal of Abnormal Child Psychology, Dec. 2001, pp. 541-556, vol. 29, No. 6, Plenum Publishing Corporation.

Simon Baron-Cohen et al.,"The Empathy Quotient: An Investigation of Adults with Asperger Syndrome or High Functioning Autism and Normal Sex Differences," Journal of Autism and Developmental Disorders, Apr. 2004, pp. 163-175, vol. 34, No. 2, Plenum Publishing Corporation.

Tammy D. Barry et al.,"Examining the Effectiveness of an Outpatient Clinic-Based Social Skills Group for High-Functioning Children with Autism," Journal of Autism and Developmental Disorders, Dec. 2003, pp. 685-701, vol. 33, No. 6, Plenum Publishing Corporation.

Nirit Bauminger et al.,"The Facilitation of Social-Emotional Understanding and Social Interaction in High-Functioning Children with Autism: Intervention Outcomes," Journal of Autism and Developmental Disorders, Aug. 2002, pp. 283-308, vol. 32, No. 4, Plenum Publishing Corporation.

Renae Beaumont et al.,"A multi-component social skills intervention for children with Asperger syndrome: The Junior Detective Training Program," Journal of Child Psychology and Psychiatry, 2008, pp. 743-753, vol. 47, No. 7, Blackwell Publishing.

Antoine Bechara et al.,"Emotion, Decision Making and the Orbitofrontal Cortex," Cerebral Cortex, Mar. 2000, pp. 295-307, vol. 10, No. 3, Oxford University Press.

Sander Begeer et al.,"Theory of Mind Training in Children with Autism: A Randomized Controlled Trial," J. Autism Dev. Disord., 2011, pp. 997-1006, Springer.

H.A. Berlin et al.,"Impulsivity, time perception, emotion and reinforcement sensitivity in patients with orbitofrontal cortex lesions," Brain, 2004, pp. 1108-1126, vol. 127, No. 5.

Vera Bernard-Opitz et al.,"Enhancing Social Problem Solving in Children with Autism and Normal Children Through Computer-Assisted Instruction," Journal of Autism and Developmental Disorders, 2001, pp. 377-384, vol. 31, No. 4, Plenum Publishing Corporation.

Craig W. Berridge et al.,"The locus coeruleus-noradrenergic system: modulation of behavioral state and state-dependent cognitive processes," Brain Research Reviews, 2003, pp. 33-84, vol. 42, Elsevier Science B. V.

Anne S. Berry et al.,"The Influence of Perceptual Training on Working Memory in Older Adults," Training Transfers in Aging, Jul. 2010, pp. 1-8, vol. 5, Issue 7, e11537, PLoS ONE.

Warren K. Bickel et al.,"Impulsivity and cigarette smoking: delay discounting in current, never, and ex-smokers," Psychophamacology, 1999, pp. 447-454, vol. 146, Springer-Verlag.

Warren K. Bickel et al.,"Remember the future: working memory training decreases delay discounting among stimulant addicts," Biol Psychiatry, Feb. 1, 2011, pp. 260-265, vol. 69, No. 3, Elsevier Inc.

Sven Bölte et al.,"The Development and Evaluation of a Computer-Based Program to Test and to Teach the Recognition of Facial Affect," International Journal of Circumpolar Health, 2002, pp. 61-68, 61 Suppl. 2.

J. Douglas Bremner et al.,"Reduced Volume of Orbitofrontal Cortex in Major Depression," Biol Psychiatry, 2002, pp. 273-279, vol. 51.

Dean V. Buonomano et al.,"Cortical Plasticity: From Synapses to Maps," Annu. Rev. Neurosci., 1998, pp. 149-186, vol. 21.

David D. Burns et al.,"Does Psychotherapy Homework Lead to Improvements in Depression in Cognitive-Behavioral Therapy or Does Improvement Lean to Increased Homework Compliance," Journal of Consulting and Clinical Psychology, 2000, pp. 46-56, vol. 68, No. 1.

M. C. Carrasco et al.,"Time Estimation and Aging: A Comparison Between Young and Elderly Adults," Int'l Aging and Human Development, 2001, pp. 91-101, vol. 52, No. 2, Baywood Publishing Co.

(56) References Cited

OTHER PUBLICATIONS

Gregory M. Chandler et al.,"Validation of the Massachusetts General Hospital Antidepressant Treatment History Questionnaire (ATRQ)," CNS Neuroscience & Therapeutics, 2010, pp. 322-325, Blackwell Publishing Ltd.

Vladimir L. Cherkassky et al.,"Functional connectivity in a baseline resting-state network in autism," Brain Imaging, Nov. 2006, pp. 1687-1690, vol. 17 No. 16.

Dennis R. Combs et al.,"Social Cognition and Interaction Training (SCIT) for inpatients with schizophrenia spectrum disorders;preliminary finding2007s,", , pp. 112-116, vol. 91.

Jennifer T. Coull et al.,"Functional Anatomy of the Attentional Modulation of Time Estimation," Science, 38047, pp. 1506-1508, vol. 303.

Deana B. Davalos et al.,"Deficits in auditory and visual temporal perception in schizophrenia," Psychology Press, 41954, pp. 273-282.

Richard Davidson et al.,"Depression: Perspectives from Affective Neuroscience," Annual Rev. Psychology, 2002, pp. 545-574, vol. 51.

Joseph M. Degutis et al.,"Tonic and phasic alertness training: a novel behavioral therapy to improve spatial and non-spatial attention in patients with hemispatial neglect.," Human Neuroscience, 40414, pp, vol. 4.

Mark R. Dixon et al,"Contextual Control of Delay Discounting by Pathological Gamblers," Journal of Applied Behavior Analysis, winter 20006, pp. 413-422, vol. 4.

David M. Eagleman,"Using Time Perception to Measure Fitness for Duty," Mil Psychology, 40304, pp. 42012.

Rebecca Elliott et al.,"The neural Basis of Mood-Congruent Processing Biases in Depression," Arch Gen Psychiatry, 37438, pp. 597-604, vol. 59, American Medical Association.

Javad Salehi Fadardi et al.,"Reversing the Sequence: Reducing alcohol consumption by overcoming alcohol attentional bias.," Drug and Alcohol Dependance 101, 2009, pp. 137-145.

Susan Faja et al.,"Becoming a Face Expert: A Computerized Face-Training program for High-Functioning Individuals With Autism Spectrum Disorders,,", 2008, pp, Psychology Press.

Matt Field et al.,"Attentioinal bias in addictive behaviors: A review of its development, causes, and consequences," Drug and Alcohol Dependance 97, 2008, pp, vol. 97, Science Direct.

Melissa Fisher et al.,"Using Neuroplasticity-Based Auditory Training to improve verbal Memory in Schizophrenia," American Psychiatry, 2009, pp. 805-811, vol. 166.

Melissa Fisher et al.,"Neuroplasticity-Based Cognitive Training in Schizophrenia:An Interim Report on the Effects 6 months later," Schizophrenia Bulletin, 2009, pp.

N. Gaab et al.,"Neural correlates of rapid auditory processing are disrupted in children with development dyslexia and ameliorated with training:An f MRI study.," Restorative Neurology and Neuroscience, 2007, pp. 295-310, vol. 25, IOS Press.

Michael L. Ganz,"The Lifetime Distribution of the Incremental Societal Costs of Autism Arch Pediatrician Adolescent Medicine,", 39173, pp. 343-349, vol. 161.

Eric L. Garland et al.,"Mindfulness is Inversely Associated with Alcohol Attentional Bias Among Recovering Alcohol-Dependant Adults," Cognit Ther Res, 41183, pp. 441-450, vol. 36.

Golan et al.,"Systemizing empathhy: Teaching adults with Asperger syndrome a high functioning autism to recognize complex emotions using interactive multimedia.," Cambridge University Press, 2006, pp. 591-617, vol. 18, Cambridge University.

Gotlib et al.,"Cognition and Depression: Current Status and Future Directions," Annu Rev Clin Psychol, 40295, pp. 285-312.

Hahn et al.,"Reduced Resting-state functional connectivity between amygdala and orbitofrontal cortex in social anxiety disorder,", 40585, pp. 881-889, vol. 56.

Hamilton,"A Rating Scale for Depression," Jj. Neurol. Neurosurg Psychiat, 1960, pp. 23, 56-58, University of Leeds.

Harrington et al.,"Corticol Networks Underlying Mechanisms of Time, Perception," The Journal of Neuroscience, 35827, pp. 1085-1095, vol. 18.

Hasselbalch et al.,"Cognitive impairment in the remitted state of unipolar depressive disorder: A systematic review," Journal of Affective Disorder, 2011, pp. 20-31, vol. 134.

Heilbronner et al.,"Dissociations between interval timing and intertemporal choice following administration of fluoxetine, cocaine, or methamphetamine,", 41538, pp. 123-134, vol. 101.

Heimann et al.,"Increasing Reading and Communication Skells in Children with Autism Through an Interactive Multimedia Coputer Program," Plenum Publishing Corporation, 1995, pp. 459-480, vol. 25.

Helfinstein, et al.,"Predicting risky choices from brain activity patterns,", 41323, pp. 2470-2475, vol. 111.

Herman et al.,"Neurocircuitry of stress; central control of the hypothalamo-pituitary-adrenocortical axis," Trends Neuroscience, 35736, pp. 78-84, vol. 20, Elsevier Science Ltd.

Hetzroni et al.,"Effects of a Computer-Based Intervention Program on the Communicative Functions of Children with Autism," Journal of Autism and Developmental Disorders, 38078, pp. 95-113, vol. 34, Plenum Publishing Corporation.

Holmes et al.,"Prefrontal functioning during context processing in schizophrenia and major depression: An event-related for MRI study," Schizophrenia Research 76, 2005, pp. 199-206.

Holmes et al.,"Seratonin Transporter Genotype and Action Monitoring Dysfunction: A Possible Substrate Underlying Increased Vulnerability to Depression,", 40154, pp. 1186-1197.

Holmes et al.,"Spatio-temporal Dynamics of Error Processing Dysfunctions in Major Depressive Disorder," Arch Gen Psychiatry, 39479, pp. 179-188, vol. 65.

Holroyd,"Dorsal anterior cingulate cortex shows FMRI response to internal and external error signals," Nature Neuroscience, 38108, pp. 497-498, vol. 7, Nature Publishing Group.

Hopkins,"Avatar Assistant: Improving Social Skills in Students with an ASD Through a Computer Based Intervention," J Autism Dev. Disord, 40576, pp. 1543-1555.

Houben et al.,"Getting a Grip on Drinking Behavior: Training Working Memory to Reduce Alcohol Abuse," Psychological Science, 40711, pp, Association for Psychological Science.

Ivry et al.,"Dedicated and intrinsic models of time perception,", 39605, pp. 273-280.

Klimek et al.,"Reduced levels of Norepinephrine Transporters in the Locus Coeruleus in Major Depression," J Neuroscience, 35735, pp. 8451-8458.

Lacerda et al.,"Anatomic Evaluation of the Orbitofrontal Cortex in Major Depressive Disorder," Biol Psychiatry, 2004, pp. 353-358.

Landro,"Neuropsychological Function in Nonpsychotic Unipolar Major Depression," Neuropsychiatry, 2001, pp. 233-240, vol. 14, No. 4.

Legoff et al.,"Long-term outcome of social skills intervention based on interactive Lego play,", , pp. 317-329, vol. 10 No. 4, Sage Publications.

Liston et al.,"Stress Induced Alterations in Prefrontal Cortical Dendritic Morphology Predict Selective Impairments in Perceptual Attentional Set-Shifting," The Journal of Neuroscience, 38925, pp. 7870-7874, vol. 26 No. 30.

Mahncke et al.,"Memory enhancement in healthy older adults using a brain plasticity training program: A randomized controlled study.," PNAS, 38944, pp. 12523-12528, vol. 103 No. 33, PNAS.

Mangels et al.,"Dissociable contributions of the prefrontal and neocerebellar cortex to time perception.," Cognitive Brain Research, 1998, pp. 15-39, vol. 7.

Mayberg et al.,"Reciprocal Limbic-Cortical Function and Negative Mood: Converging PET Findings in Depression and Normal Sadness," AM J Psychiatry, 36281, pp. 675-682.

Mazurek et al.,"Prevalence and Correlates of Screen-Based Media Use Among Youths with Sutism Spectrum Disorders," J Autism Dev. Disorder, 2012, pp. 1757-1767.

MC Conaghy et al.,"Controlled comparison of aversive therapy and imaginal desensitization in compulsive gambling," BJ Psych, 41949, pp. 142, 366-372, The Royal College of Psychiatrists.

(56) References Cited

OTHER PUBLICATIONS

MC Conaghy et al.,"Comparison of imaginal desensitisation with other behavioral treatments of pathological gambling. A Two to nine year follow up.," The British Journal of Psychiatry, 1991, pp. 390-393.
MC. Hugh et al.,"Brief Report: Teaching Situation-Based Emotions to Children with Autistic Spectrum Disorder," J Autism Dev. Disorder, 2011, pp. 1423-1428.
MC Mains et al.,"Interactions of Top-Down and Bottom-Up Mechanisms in Human Visual Cortex," The Journal of Neuroscience, 36903, pp. 587-597.
Merzenich et al.,"Temporal Processing Deficits of Language-Learning Impared Children Ameliorated by Training," Science, 35069, pp. 77-81.
Milad et al.,"The Role of the Orbitofrontal Cortex in Anxiety Disorders," N.Y. Academy of Sciences, 2007, pp. 546-561.
Miller et al.,"An Integrative Theory of Prefrontal Cortex Function," Annual Rev. Neurosci, 2001, pp. 167-202, Annual Reviews.
Mioni et al.,"Time perception in severe tramautic brain injury patients: A study comparing different methodologies.," Brain and Cognition, 2013, pp. 305-312.
Mitchell et al.,"Impulsive Responding in Alcoholics," Alcoholism: Clinical and Experimental Research, 38687, pp. 2158-2169.
Monterosso et al.,"FrontoparietalCortical Acitvity of Methaphetamine-Dependant and Comparison Subjects performing a Delay Disounting Task," Human Brain Mapping, 38791, pp. 383-393.
Muraven,"Practiing Self-Control Lowers the Risk of Smoking Lapse," Psychology Addict Behav., 40422, pp. 446-452.
Myers,"Information, comopliance, and side effects: A study of patients, antidepressant medication," Br. J. clinic Pharmaceutical, 1984, pp. 17, 21-25.
Myers,"Out-patient Cmpliance With Antidepressant Medication," The British Journal of Psychiatry, 1992, pp. 160, 83-86.
O'Doherty,"Beauty in a smile: the role of medial orbitofrontal cortex in facial attractiveness," Neuropsychologia, 37712, pp. 147-155.
Ozonoff et al.,"Teaching Theory of Mind: A New Approach to Social Skills Training for Individuals with Autism," Journal of Autism and Dev. Disorders, 1995, pp. 415-433, vol. 25 No. 4.
Panyan,"Computer Technology for Autistic Students," Journal of Autism and Dev. Disorders, 1984, pp, vol. 14, No. 4, Plenum Publishing Company.
Papies,"The allure of forbidden food: on the role of attention in self-regulation," Journal of Experimental Social Psychology, 2008, pp.
Pastor et al.,"Time Estimation and Reporoduction is Abnormal in Parkinson's Disease," Brain and Cognition, 1992, pp. 115, 211-225.
Petry et al.,"Shortened time horizons and insensitivity to future consequences in heroin addicts," Addiction, 1998, pp. 729-738.
Pizzagalli,"Toward an Objective Characterization of an Anhedonic Phenotype.," Biology Psychiatry, 38398, pp. 319-327.
Pizzagalli et al.,"Resting Anterior Cingulate Activity and Abnormal Responses to Errors in Subjsects With Elevated Depressive Symptoms: A 128 Channel EEG STudy," Human Brain Mapping, 2006, pp. 185-201, vol. 27.
Pizzagalli,"Frontocingulate Dysfunction in depression: toward Biomakers of Treatment Response," Neuropsychopharmacology Reviews, 2011, pp. 183-206, Nature Publishing Group.
Porter et al.,"Neurocognitive impairment in drug-free patients with major depressive disorder," The British Journal of Psychiatry, 2003, pp. 182, 214-220.
Ramdoss,"Computer based interventions to improve social and emotional skills in individuals with autism spectrum disorders a sys," Developmental Neurorehabilitation, 41000, pp. 119-135, vol. 15, No. 2.
Rao et al.,"The evolution of brain activation during temporal processing," Nature Neuroscience, 36951, pp. 317-323, vol. 4, No. 3.
Recanzone et al.,"Plasticity in the Frequency Representation of Primary Auditory Cortex following Discrimination Training in Adult Owl Monkeys," The Journal of Neuroscience, 33970, pp. 87-103, vol. 13 No. 1.
Ressler and Nemeroff,"Role of Norepinephrine in the Pathophysiology and Treatment of Mood Disorders," Soiety of Biological Psychiatry, 1999, pp. 1219-1233, vol. 46.
Rogers et al.,"Executive and prefrontal dysfunction in unipolar depression: a review of neuropsychological and imaging evidence," Neuroscience Research, 2004, pp, vol. 50.
Rush et al.,"The 16-Item Quick Inventory of Depressive Symptomatology, Clinician Ratins, and Self-Report: A Psychometric evaluation in patients with Chronic Major Depression," Society of Biological Psychiatry, 2003, pp. 573-583, vol. 54.
Santesso et al.,"Enhanced Negative Feedback Responses in Remitted Depression," Neuroreport 2008, pp. 1045-1048, vol. 19, No. 10.
Shoenmakers et al.,"Clinical effectiveneww of attentional bias nodification training in abstinent alcoholic patients," Drug and Alcohol Dependance, 2010, pp. 30-36.
Sharma et al.,"Selective attentional bias to alcohol related stimuli in problem drinkers and non-problem drinkers," Addiction, 2001, pp. 96, 285-295, Carfax Publishing.
Sheline et al.,"NOS," Society of Biological Psychiatry, 2001, pp. 651-658.
Siegle et al.,"Increased Amygdala and Decreased Dorsolateral Prefrontal BOLD Responses in Unipolar Depression Related and Independant Features," Biological Psychiatry, 2007, pp. 198-209.
Silver and Oaks,"Evaluation of a new computer intervention to teach people with autism of Asperger syndrome to recognize and predict emotions in others," Sage publications, , pp. 299-316, vol. 5, No. 3.
Smith et al.,"A Cognitive Training Program Based on Principles of Brain Plasticity: Results from the Improvement in Memory with Plasticity-based Adaptive Cognitive Training (IMPACT) Study," The American Geriatrics Society, 2009, pp.
Solomon et al.,"A Social Adjstment Enhancement for High Functioning Autism, Asperger's Syndrome, and Pervasive Developmental Disorder," Journal of Autism and Developmental Disorders, 38322, pp. 649-668, vol. 34, No. 6.
Sturm and Willmes,"On the Functional Neuroanatomy of Intrinsic and Phasic Alertness NeuroImage," Alertness Neur, 2001, pp. S76-S84.
Swettenham,"Can Children with Autism be taught to Understand False Belief Using Computers?," J Child Psychology Psychiatric, 1996, pp. 157-165, vol. 37, No. 2, Ass. for Child psychology and Psychiatry.
Tanaka et al.,"Using computerized games to teach face recognition skills to hildren with autism spectrum disorder: the Let;s Face It!program," , 2010, pp. 944-952, Blackwell Publishing.
Tallal et al.,"Language Comprehension in Language Learning Impaired Children Improved with Acoustically yModified Speech," Science, 1996, pp. 81-84, vol. 271, American Association for the Advancement of Science.
Tse et al.,"Social Skills Training for Adolescents with Asperger Syndromes and High-Gunctioning Autism," J Autism Development Disord, 2007, pp.
Tsourtos et al.,"Evidence of an early information processing speed deficit in unipolar major depression.," psychological Medicine, 2002, pp. 259-265, Cambridge University press.
Turner et al.,"Brief Report;Feasibility of Social Cognition and Interaction Training for Adults with High Functioning Autism.," J Autism Dev. Disord, 2008, pp. 42018.
Van Wassenhove et al.,"Distortions of Subjective Time Perception Within and Across Senses," PLoS ONE, 2008, pp. 42017.
Vollstadt et al.,"Effects of Cue-Exposure Treatment on Neural Cue Reactivity in Alcohol Dependance;A Randomized trial Biology psychiatry," 2009, 577-585, pp. 1060-1066, Society of Biological Psychiatry.
Wallis,"Orbitofrontal Cortex and Its Contrivution to Decision-making," Annual Review of Neuroscience, 2007, pp. 31-56, Annual Reviews.

(56) References Cited

OTHER PUBLICATIONS

Wardell,"Mood and Implicit Alcohol Expectancy Processes: predicting Alcohol Consumption in the Laboratory," Alcohol Consumption in the Laboratory, 2012, pp. 119-129, Alcohol Clinic Exp Res.

Watson et al.,"Testing a Tripartite Model: 1. Evaluating the Convergent and Discriminant Validity of Anxiety and Depression Symptom Scales," Journal of Abnormal Psychology, 1995, pp. 42077, vol. 104, No. 1, The American Psychological IAss., Inc.

Weller et al.,"Obese women show greater delay discounting than healthy weight women.," Appetite, 2008, pp. 563-569.

Whalen et al.,"Efficacy of TeachBasics computer-assisted intervention for the Intensive Comprehensive Autism Program in Los Angeles Unified School District," Sage Publications, 2010, pp. 179-197, vol. 14, No. 3.

Wiers et al.,"Retraining automatic action-tendencies to approach alcohol in hazardous drinkers.," Addiction 105, , pp. 279-287.

Wiers et al.,"Retraining Automatic Action Tendencies Changes Alcoholic Patients' Approach Bias for Alcohol and Improves Treatment Outcome," Sage Publishers, 2011, pp. 490-497.

Williams et al.,"Do Children with Autism Learn to Read more Readily by Computer Assised Instruction or Traditional Book Methods? A pilot study," Autism 2002, 2002, pp. 71-91, vol. 6, Sage Publisher.

Williams et al.,"Teaching emotion recognition skills to young children with autism; a randomised controlled trial of an emotion training programme. Journal of Child psychology and psychiatry,", 2012, pp. 1268-1276, vol. 53.

Wittmann et al.,"Impaired time perception and motor timing in stimulant dependent subjects.," Drug Alcohol Dependant, 2007, pp. 183-192.

Wolinsky et al.,"The Active Cognitive Training Interventions and the onset of and Recovery from Suspected Clinical Depression," Journal of Gerontology, 2009, pp. 577-585, Oxford University.

Wolinsy et al.,"Does Cognitive Training Improve Internal Locus of Control Among Older Adults?," Journal of Gerontology:Social Sciences, 2009, pp. 42012, Oxford University.

Wolinsky et al.,"Speed of processing training protects self-rated health in older adults: enduring effects observed in the multi-site ACTIVE randomized controlled trial," International Psychogeriatrics, 2010, pp. 470-478.

Wolwer et al.,"Remediation of impairments in facial affect recognition in schizophrenia: Efficacy and specificity of a new training program," Schizophrenia Research 80, 2005, pp. 295-303.

Xerri et al.,"Experience-induced plasticity of sutaneous maps in the primary somatosensory cortex of adult monkeys and rats," J. Physiology, 1996, pp. 277-287.

Xue et al.,"A Memory Retrieval-Extinction Procedure to Prevent Drug Craving and Relapse," Science, 2012, pp. 42015.

Adams, MJ. *Beginning to read: Thinking and learning about print.* Cambridge, MA. MIT Press. 1999. 3 pages of cover sheet.

Anglin, JM. "Vocabulary Development: A Morphological Analysis." *Monographs of the Society for Research in Child Development.* 1993. (58, 10).

*Annabelle's Quotation Guide.* www.annabelle.net. Feb. 7, 2002.

Bryant, P, Nunes, T, & Bindman, M. "The relations between Children's Linguistic Awareness and Spelling: The Case of the Apostrophe" *Reading and Writing: An Interdisciplinary Journal.* 2000. (12: 3/4, 253-276).

Carroll, JB. "The Analysis of Reading Instruction: Perspectives from Psychology and Linguistics." *Scientific Studies of Reading.* (4(1) 3-17).

Daneman & Carpenter. "Individual differences in working memory and reading" *Verbal learning and verbal memory.* 1980. (19, 450-466).

Ehri, L & Wilce, LS. "Movement into reading: Is the first stage of printed word learning visual or phonetic?" *Reading Research Quarterly.* 1985. (20, 163-179).

Ferster, CB & Skinnder, BF. *Schedules of Reinforcement.* New York, NY: Appleton Century Crofts. 1957. 2 pages of cover sheet.

Graves, MF. "Vocabulary Learning and Instruction" In EZ Rothkopf (Ed.) *Review of Research in Education.* (13, 49-89). 1986. Washington, DC: American Educational Research Association.

Hall, SL & Moats, LC. *Straight Talk About Reading.* Chicago, IL: Contemporary Books. 1999. 3 pages of cover sheet.

Kucera, H & Francis, WN. *Computational Analysis of Present-Day American English.* 1967. Providence, RI: Brown University Press. 2 pages of cover sheet.

Laberge & Samuels. "Towards a Theory of Automatic Information Processing in Reading" *Cognitive Psychology.* 1974. (6,293-323).

*Language Arts Curriculum Frameworks and Standards.* 2000. Links to available state language arts curriculum frameworks and standards.

Mahony, D, Singson, M & Mann, VA. "Reading Ability and Sensitivity to Morphophonological Relations." *Reading and Writing An Interdisciplinary Journal.* 2000. (12:3/4, 191-218).

Mann, VA. "Introduction to Special Issue on Morphology and the Acquisition of Alphabetic Writing Systems." *Reading and Writing: An Interdisciplinary Journal.* 2000. (12:3/4, 143-147).

Moats, LC, Furry, AR & Brownell, N. *Learning to Read: Components of Beginning Ready Instruction.* Sacramento, CA: Comprehensive Reading Leadership Center. 1998. p. 33.

National Reading Panel. *Teaching Children to Read: An Evidence-based Assessment of the Scientific Research Literature on Reading and its Implications for Reading Instruction.* Report of the National Reading Panel. p. 1-33.

Oregon Literacy, Inc. *Remarks on Reading.* www.hevanet.com/literacy/features/remarks.htm. Feb. 7, 2002. 6 pages.

Rayner, K & Pollatsek, A. *The Psychology of Reading.* Englewood Cliffs, NJ: Prentice Hall. 1989. 3 pages of cover sheet.

Readence, JE, Bean, TW & Baldwin, RS. *Content Area Literacy: An Integrated Approach.* Dubuque, Iowa: Kendall/Hunt Publishing Co. 1998. 3 pages of cover sheet.

*Reading/Language Arts Framework for California Public Schools.* Sacramento, CA: California Department of Education. 1999. p. 22-95.

Scarborough, HS. "Continuity Between Childhood Dyslexia and Adult Reading." *British Journal of Psychology.* Aug. 1984 (75 (Pt 3), 329-48).

Searfoss, LW & Readence, JE. *Helping Children Learn to Read.* Needham, MA: Allyn and Bacon. 4 pages of Cover sheet.

Shankweiler & Liberman. "Misreading: A Search for Causes." In *Language by Ear and by Eye.* Cambridge, MA: MIT Press. 1972. p. 293-295, 297, 299, 301, 303, 306, 208, 310, 312, 314, 315.

Singson, M, Mahony, D & Mann, VA. "The Relation Between Reading Ability and Morphological Skills: Evidence from Derivational Suffixes." *Reading and Writing: An Interdisciplinary Journal.* 2000. (12: 3/4, 219-252).

Snow, CE, Burns, MS & Griffin, P. *Preventing Reading Difficulties in Young Children.* National Research Council Committee on the Prevention of Reading Difficulties in Young Children. Washington, DC: National Academy Press. 1998. 7 pages.

Taylor, I & Taylor MM. *The Psychology of Reading.* New York, NY: Academic Press, 3 pages of cover sheet.

Venezky, RL. *The American Way of Spelling.* New York, NY: Guilford Press. 1999. p. 4-7, 51-95, 125-159, 164, 165, 168-209, 230-245.

Scientific Learning. *Fast-Forward Reading.* 2001. 5 pages.

*English-Language Arts Content Standards for California Public Schools.* California Department of Education. 1997. p. 1-84.

Kavanagh, J & Mattingly, I. *Language by Ear and Eye: The Relationships Between Speech and Reading.* 1992. 3 pages of cover sheet.

Fiez, J. "PET Studies of Auditory and Phonological Processing: Effects of Stimulus Characteristics and Task Demands." *Journal of Cognitive Neuroscience.* 7:3 1995.

Merzenich, M. *Cortical Plasticity, Learning and Language Dysfunction* 1995.

Barinaga, M. "Giving Language Skills a Boost." *Science.* vol. 271 p. 27-28. Jan. 5, 1996.

Merzenich, M. "Temporal Processing Deficits of Language-Learning Impaired Children Ameliorated by Training." *Science Magazine.* vol. 271 Jan. 5, 1996.

(56) References Cited

OTHER PUBLICATIONS

Merzenich, M. *Cortical Plasticity Underlying Perceptual, Motor and Cognitive Skill Development: Implications for Neurorehabilitation.* 1996.
Alexander et al. "Phonological Awareness Training and Remediation of Analytic Decodig Deficits in a Group of Severe Dyslexics" *Annals of Dyslexia.* 1991. vol. 41: 193-206.
Berkell et al. "Auditory Integration Training for Individuals with Autism." *Education and Training in Mental Retardation and Developmental Disabilities.* Mar. 1996. p. 66-70.
Berard, G. *Hearing Equal Behavior.* Keats Publishing, Inc. p. 77-93.
Rimland, B. *Summaries of Research on Auditory Integration Training. (1993-1995: 11 Studies)* 1995. Autism Research Institute.
Tallal et al. "Developmental Aphasia: Impaired Rate of Non-verbal Processing as a Function of Sensory Modality" *Neuropsychologia.* 1973. vol. 11: 389-398.
Tallal et al. "Developmental Aphasia: Rate of Auditory Processing and Selective Impairment of Consonant Perception" *Neuropsychologia.* 1974. vol. 12: 83-93.
Tallal et al. "Developmental Aphasia: The Perception of Brief Vowels and Extended Stop Consonants" *Neuropsychologia.* 1975. vol. 13: 69-74.
Tallal et al. "Neurobiological Basis of Speech: A Case for the Preeminence of Temporal Processing" *Annals New York Academy of Sciences.* 1993. vol. 682: 27-47.
Elliott et al. "Discrimination of Rising and Falling Simulated Single-Formant Frequency Transitions: Practice and Transition Duration Effects." J. Acoust. Soc. Am. 86(3), 1989.
Flowers, A. "Auditory Perception: Speech, Language and Learning." Chapter 9, *Perceptual Learning Systems.* Dearborn:Michigan. 1983. p. 133-138.
International Dyslexia Organization web site, www.interdys.org (1999).
Levinson et al. *Auditory Processing and Language: Clinical and Research Perspectives.* Chapter 7, Grune & Stratton, New York, New York. 1980. p. 117-133.
Sloan, C. *Treating Auditory Processing Difficulties in Children.* Chapters 4, 5 & 7. Singular Publishing Group, Inc. San Diego, CA 1986; reprinted 1991. p. 35-55, 57-61 and 63-82.
Tallal et al. "The Role of Temporal Processing in Developmental Language-Based Learning Disorders: Research and Clinical Implications." Ch. 7, *Blachman's Foundations of Reading Acquisition and Dyslexia.* 1997.
Formant.pdf—retrieved from http://en.wikipedia.org/wiki/Formant. Downloaded Dec. 13, 2009. pp. 1-5.
BPF.pdf—Wikipedia—Band Pass Filter as it existed on May 13, 2004, retrieved from http://web.archive.org/web/20040513223402/ http://en.wikipedia.org/wiki/Band-pass_filter (1 of 2) Mar. 24, 2011.
Johnson, Chris A. et al. "Properties of Staircase Procedures for Estimating Thresholds in Automated Perimetry." *Investigative Ophthalmology & Visual Science.* vol. 33, No. 10. Sep. 1992. pp. 2966-2974.
Sekuler et al. "Visual localization: age and practice." Optical Society of America. vol. 3, No. 6. Jun. 1986. pp. 864-867.
Ball et al. "Effects of Cognitive Training Interventions With Older Adults: A Randomized Controlled Trial." American Medical Association. Nov. 13, 2002. vol. 288, No. 18. pp. 2271-2281.
Su et al. "De-Emphasis of Distracting Image Regions Using Texture Power Maps." Computer Science and Artificial Intelligence Laboratory Technical Report. Apr. 12, 2005. pp. 1-12. Web Sep. 21, 2009. http://dspace.mit.edu/handle/1721.1/30537.
Phipps et al. "Fast Psychophysical Procedures for Clinical Testing." Clinical and Experimental Optometry 84.5 pp. 264-269. QUP ePrints. May 4, 2007. Web Sep. 21, 2009, http://eprints.qut.edu.au/7481/.
Campanella, S. et al. "Association of the Distinct Visual Representations of Faces and Names: A PET Activation Study." NeuroImage 14, 873-882 (2001) pp. 1-4.
Schweinberger, Stefan R. et al. "Human Brain Potential Correlates of Repetition Priming in Face and Name Recognition." University of Glasgow; Neuropsychologia 40 (2002) 2057-2073.
Pylyshyn, Zenon W. "Visual Indexes, Preconceptual Objects, and Situated Vision." Cognition 80 (2001) 127-158 Rutgers Center for Cognitive Science, Rutgers University, Psychology Building, New Wing, Busch Campus, New Brunswick, NJ 08903.
Baudouin, Jean-Yves et al. "Selective Attention to Facial Emotion and Identity in Schizophrenia." Neuropsychologia 40 (2002) 503-511.
Wallace, Marcie A et al. "Savings in Relearning Face-Name Associations as Evidence for 'Covert Recognition' in Prosopagnosia." ONR Technical Report, Jan. 1992. Department of Psychology, Carnegie Mellon University, Pittsburgh, PA 15213. pp. 1-17.
Herholz, Karl et al. "Learning Face-Name Associations and the Effect of Age and Performance: A PET Activation Study." Neuropsychologia 39 (2001) 643-650.

Nick stopped off at the gas station on his way to work to fill up his car. He was already slightly off track for making an important meeting time. He filled up his car and went inside the station to give the cashier his credit card. The cashier ran it through the machine at the counter. "I'm sorry," she said, "the machine won't accept your card." "Seriously?" John said. "Well, can you try again? I don't have any cash on me." The cashier tried to run the card again but with no luck. John said, "Perfect! Exactly what I needed today."

NEUROPLASTICITY GAMES FOR SOCIAL COGNITION DISORDERS

CROSS REFERENCE TO RELATED APPLICATION(S)

This application is a continuation of U.S. patent application Ser. No. 14/201,697, filed Mar. 7, 2014, which is incorporated herein in its entirety for all purposes. This application also claims the benefit of the following US Provisional Patent Applications, which are incorporated herein in their entireties for all purposes:

| Serial No. | Filing Date: | Title: |
| --- | --- | --- |
| 61/774,378 | Mar. 7, 2013 | Addiction |
| 61/774,390 | Mar. 7, 2013 | Overcoming Attention Deficit and Hyperactivity Disorder |
| 61/774,400 | Mar. 7, 2013 | Increasing Resilience Against Alzheimer's Disease |
| 61/774,413 | Mar. 7, 2013 | Autism |
| 61/774,420 | Mar. 7, 2013 | Major Depressive Disorder |
| 61/777,066 | Mar. 12, 2013 | Software-Based Training to Track and Modify Cognitive Behavior and Emotion through Attention and Stimulus Valuation |
| 61/777,080 | Mar. 12, 2013 | Traumatic Brain Injury |
| 61/779,024 | Mar. 13, 2013 | Program to Ameliorate the Neurological Distortions Arising from a History of Childhood Stress or Abuse |
| 61/782,571 | Mar. 14, 2013 | Novel Strategy to Accelerate Recovery of Speech Understanding in Individuals with Cochlear Implants or Hearing Aids |
| 61/780,495 | Mar. 13, 2013 | New Tool Designed to Establish or Restore Social Cognition and Social Control Abilities in Individuals Which They Have Not Developed Normally, or Have been Degraded or Lost Due to Illness |

FIELD OF THE INVENTION

This invention relates in general to amusement devices, and more particularly, to games that not only entertain but also treat cognitive impairments.

BACKGROUND OF THE INVENTION

Autism. Autistic spectrum disorders (ASDs) are severe, chronic, pervasive disorders arising in early childhood. ASDs are characterized by deficits in all aspects of social interaction and reciprocity, pragmatic communication deficits and language delays, and an assortment of behavioral problems such as restricted interests, sensory sensitivities, and repetitive and stereotypic behaviors. The early onset of autism and its familial patterns of origin support a biological basis of origin. At the same time, evidence of a rapid increase in ASD incidence over the past several decades, the complex and highly varied genetic profiles of individuals with ASDs and the repeated demonstration that genetically-identical individuals may or may not develop ASD show that environmental factors also contribute importantly to the early neurological distortions that contribute to its onset.

The predominant scientific views of ASD origin focus on the severe deficits in "theory of mind" contributing to related impairments in "social cognition," impairments in the development of normal language and related cognitive abilities, delayed and distorted development of executive and social control abilities, or on some form of more general "weak central coherence" impacting most or all brain systems at many or all brain processing levels.

Any theory on the cause of autism must account for the severe deficits in social cognition (SC) that are an invariable part of the disorder. The term "social cognition" refers to mental operations underlying social interactions including the: a) perception, processing and interpretation of information related to them, b) ability to perceive the intentions and dispositions of others; and c) generation and control of responses to those intentions. The scientific literature identifies at least five distinct SC domains: (1) emotion perception: the correct perception of facial and vocal expressions of the emotions in others; (2) social perception: the ability to judge social cues and infer social interactions from contextual information and nonverbal communicative gestures; (3) self-referential style: the explanations that people generate regarding the causes of positive and negative events in their lives (e.g., personalizing bias, "jumping to conclusions", etc.); (4) theory of mind (ToM): the ability to attribute mental states to others, to make inferences about others' intentions, and to understand that others have mental states that differ from one's own, including false beliefs, hints, intentions, irony, sarcasm, etc.; and (5) empathy: the capability to share and understand other's emotions and feelings.

Recent studies in humans and primates have mapped brain areas related to these different dimensions of social cognition. For example, a distributed network of areas has been shown to be involved in the perception and interpretation of social information, with specific areas argued to sub-serve specific SC functions. The lateral fusiform gyrus, superior temporal sulcus and amygdala are activated by facial and emotion perception tasks. The medial frontal, medial prefrontal and orbitofrontal areas are engaged in ToM-related actions. The ventromedial prefrontal cortex is activated in tasks in which social knowledge guides behavior. The orbito-frontal cortex regulates the values that bias and shape self-referential style in social responding. And the anterior and middle cingulate cortex, the supplementary motor area and the anterior insula are engaged by empathic tasks.

Social cognition deficits characterize individuals with ASD. Impairments in SC associated with impairments in communication are signature deficits of ASD. A level of social functioning necessarily underlies personally and societally satisfactory social and general functionality. Signs of social dysfunction in ASD children are evident within the first 6-12 months of life, emerging earlier than do the hypersensitivities and the restricted and repetitive behaviors that are so strongly associated with ASD. These core deficits in social cognition are strong, persistent, cross-modal, and degrade all SC operations. They underlie the social difficulties that are so diagnostic of autistic spectrum disorders.

It should be noted that for children and adults with high-functioning autism (HFA) and Asperger Syndrome (AS), invariably-present social cognition impairments can be substantially or completely distinct from general cognitive abilities. For many of these individuals, "high functioning" in cognitive terms simply does not equate with "high functioning" in social terms. Because of this distinction in the penetration of different expressions of ASD, SC deficits have been argued to be more primal than ASD origins. This discrepancy between cognitive and social skills clearly affects the ability of adults with HFA and AS to secure employment and live independently, and contributes greatly to their predictably poorer quality of life—even while they may have an acceptable or even high level of cognitive ability and control.

Over the past decades, numerous studies have documented severe deficits of individuals with ASD in virtually every aspect of SC tested. ASD individuals have a poor ability to recognize or distinguish between facial emotions. They are impaired in understanding and interpreting prosodic elements of speech that convey emotion or social meaning. Children with ASDs do not appropriately pair gestures with vocalizations and facial expressions that mark different emotional states. Both adults and children are impaired in both their appreciation and their production of emotional expressions.

Children with ASD have severe problems with processing facial stimuli. They are less likely to attend to faces, are impaired in face discrimination, and have difficulty recognizing familiar faces. Opposite to normal individuals, ASD patients spend twice as much time looking at the mouth region than at the eyes, which convey more information about complex emotions.

Severe problems in social cue perception, empathy, affect regulation, self-monitoring and gaze perception have been documented in ASD individuals. Impairments in "theory of mind" (ToM) have been richly catalogued. Subjects with ASDs have particular difficulty judging emotions and mental states expressed by the faces, voices or gestures of others.

Abnormal brain areas subserving SC contribute to the origins and expressions of ASDs. According to one theory, an early developmental failure involving the amygdala has a cascading influence on the development of cortical areas that mediate social perception in the visual domain, specifically impacting the "face area" in the fusiform cortex in the ventral temporal lobe. Indeed, recent imaging studies have documented abnormal activation patterns in a distributed SC system in the brains of individuals with ASD that supports this general perspective. SC deficits are invariably paralleled by amygdala hypo-activation or dysfunction.

Correlational studies also link these patterns to the striking deficits in social perception and in early-stage processing abnormalities of facial expressions. Similarly, ASD deficits are expressed by abnormal functionality in the superior temporal sulcus and medial prefrontal cortex. Hypo-activation of the fusiform face area (FFA) has been recorded in several fMRI and PET investigations, along with abnormal structural changes in the right FFA in brains of males with ASD.

A general conclusion from this emerging body of literature is that the severe SC problems characterizing ASD individuals represent at least one of the most elemental expressions—and possibly the primary neurobehavioral problem—at the heart of these disorders.

Current interventions applied to remediate social cognition deficits in ASD have not proven to be satisfactorily effective. Several reports have documented limited positive outcomes achieved with group-based interventions. Clinicians have outlined suggestions and provided workbooks and guidelines for training HFAs and more severe ASD and PDD-NOS groups in SC. Despite relatively sparse and modest documentation of benefits, these methods have been widely applied in clinical and special education school environments. Some individualized therapies designed to improve social functioning have also been studied, again demonstrating positive but modest improvements in SC achieved through very extensive one-on-one therapy.

In general, approaches to SC training are idiosyncratic, fragmented, and grossly incomplete. Few interventions are based on any theoretical understanding of the neurological processes or systems that underlie SC deficits in ASD. For example, almost all treatment approaches rely exclusively on a top-down, direct instructional approach, with no targeting of core neuronal deficits underlying social impairments. Most interventions target one or a few aspects of SC. No strategy developed up to this time applies multi-faceted training to establish more effective social abilities at every SC system level. Moreover, while many interventions drive improvements on trained abilities, they have failed to result in any significant generalization to everyday situations. Group-based or individualized interventions also require trained, experienced personnel, impose geographical barriers for program delivery, and by their nature limit the number of individuals that can participate in or benefit from any given intervention.

ASDs and related Pervasive Developmental Disorders (PPDs) degrade the lives and prospects of about every 60th child brought into our world. Most affected individuals require a high level of ongoing support. Because of their hypersensitivities, their deficits in language and non-verbal expression and their often-severe limitations in social control, rehabilitation, education and home and school life can be very challenging for parents, therapists and teachers. Given their special demands, the support of these individuals is exceptionally costly. Special education services have to be achieved in small groups or one-on-one, and because many individuals have to be continually monitored into—and not infrequently through—adulthood. There is a pressing need for more effective treatment modalities.

Social Cognition. Apart from sufferers of ASD, a subpopulation of normal humans is socially undeveloped in ways that negatively impact their entire lives. For example, social cognition deficits are a near-universal aspect of normal aging, and are especially impactful in pathological aging. Special and more profound social cognition deficits also limit the lives and personal success of 1) other children and adults with a history of pervasive developmental disability; 2) patients with schizophrenia, where there is a severe degradation of social cognition and control; 3) patients with other psychiatric disorders including bipolar disorder, depression, obsessive-compulsive disorder, hoarding disorders, and anxiety disorders—among many others; and 4) individuals with a great variety of social conduct disorders including psychopathic disorders, and oppositional-defiant disorders—among many others.

The standard of care for social skills interventions includes group-based or individual therapies that are widely applied in clinical and special education school environments. Using an instructional approach, children are didactically taught—using educational, top-down instructional strategies dependent on executive function abilities—to practice social skills. But these abilities are commonly very impaired in socially impaired individuals.

While some of these practical and scientific approaches to SC training have shown good compliance and usually improve directly trained skills in the research environment, current available programs and interventions fall short. Indeed, most well-controlled studies of available SC training approaches have documented modest or no generalization to everyday social behaviors or control.

Positive improvements in social cognition are a crucial facet of establishing or restoring the health and life-quality of millions of children and adults with these (and other related social-impairment) conditions.

Schizophrenia.

Schizophrenia is a severe, chronic mental illness that affects more than two million individuals in the U.S. The healthcare burden attributable to schizophrenia is estimated at $62 billion annually, and is expected to grow as many treatment programs fail to successfully re-integrate these individuals into the larger society. These costs are largely incurred by the functional impairments in living, work, and everyday function, which are an essential diagnostic feature of the illness, found in many patients with schizophrenia. These poor functional outcomes are manifested by the high rates of unemployment, poor social and community functioning, reduced capabilities for independent living, and a generally reduced quality of life.

These fundamental deficits in functional ability in schizophrenia are largely attributable to pervasive and enduring impairments in social cognition (SC): the perception, interpretation and processing of social information. Individuals with schizophrenia exhibit deficits in all core domains of SC: emotion perception (the recognition of facial and vocal affect), social cue perception (the ability to detect and comprehend cues in a social context), theory of mind (the mental capacity to infer one's own and others' mental states), attributional style (attribution of causes of events to the self, to others, or to factors in the environment), and empathy (the ability to share, understand and appropriately react to the emotional states of others). Notably, impairments in each of these domains have been shown to have a significant impact on functional outcome in schizophrenia.

These fundamental, multi-domain SC impairments are not only directly linked with poor social functioning (i.e., inadequate social relationships, weak attachments, limited social support), but also underlie most critical factors of daily living in schizophrenia, such as occupational status, community functioning, independent living skills, relapse rate, and quality of life. Moreover, the degree of SC impairment is a stronger predictor of the level of everyday functional ability than are cognitive abilities or the severity of positive symptoms. This makes SC an important treatment target in schizophrenia. As the ultimate goal of therapeutic interventions is to improve life outcomes for patients, recovery of these individuals to the broader society is dependent upon the recovery of their SC abilities. The fact that SC deficits persist throughout the course of the illness, are seen in prodromal patients, and are even present in unaffected relatives of patients, further stresses their central role in schizophrenia and fuels the need for an effective, scalable treatment for SC deficits.

These severe and broad-ranging SC deficits in schizophrenia are rooted in anatomical and functional abnormalities within a complex brain network collectively termed "the social brain." Specifically, significant anatomical and/or functional abnormalities have been localized to the superior temporal sulcus (STS), anterior insula, amygdala, medial prefrontal cortex (mPFC), and to the cingulate cortex, all are known to be critically involved in perception and processing of social information. Further, abnormally-weak connectivity between functionally-related, cortical and subcortical areas, as well as between sensory cortices and higher-level areas has led to a growing characterization of schizophrenia as an "information processing disorder". Collectively, these abnormalities further imply that effective treatments for schizophrenia should target SC dysfunction from their neurological core, by aiming to improve the speed of processing and accuracy of stimulus representation of social information in the core brain areas which underlie SC.

Despite the importance of SC as a primary source of impairment, frustrating successful treatment and real-world recovery of patients with schizophrenia, there are currently no well-accepted or even broadly administered methods for improving SC function in this large patient group. Further, SC deficits are resistant to pharmacological treatments including second-generation antipsychotic medications that are effective for controlling positive symptom levels. Perhaps more surprisingly, new and demonstrably effective interventions for treating cognitive deficits in schizophrenia have been shown to have only limited impacts on social functioning—perhaps because SC deficits are associated with impaired function of neural networks that are largely distinct from, and parallel those subserving more general cognition. The delivery of an effective, practical, affordable, and scalable solution for this specific need is therefore of the highest clinical significance.

Several experimental, therapist-delivered approaches targeting social skills or SC have been developed over the last decade. These interventions are offered in relatively few clinics nationwide and are usually administered by trained professionals individually or in small groups over the course of several months. The therapist-administered options usually focus on emotion management and social skills building, and require multiple in-person visits to the clinic in the course of a few months. Recently, some computer-aided interventions have been created, but they are limited in scope (mainly target a single SC domain in isolation, facial affect recognition), have undergone only initial testing in schizophrenia, and are not used, to the best of our knowledge, in any clinical treatment programs.

While recent studies have shown the promise of social skills and SC interventions, to date, no single treatment has been widely adopted or is currently seeking FDA clearance for patient reimbursement, and there is no standard of care for SC treatment in schizophrenia. Although the various interventions differ from one another in dosage, mode of administration, and targeted deficit(s), the majority have the following traits in common. First, they use a 'top-down' training strategy, utilizing explicit instructions and coaching strategies in which participants are taught how to work around their deficits. These strategies rely heavily on executive control, declarative memory, and strategic thinking abilities, all of which are substantially impaired in schizophrenia, effectively limiting the potential benefits of this approach. Second, they employ limited stimulus variation, in which only a small number of social stimuli can be modeled in individual or group-administered sessions. Individuals are exposed to a limited set of socially relevant stimuli and scenarios, which may be reducing the potential for generalization beyond the context of therapy. Third, they use a a 'one size fits all' approach, whereby group interventions are administered in an identical format to all participants, without regard to individual differences in level of social functioning across the five major SC domains. Finally, they are not scalable or cost-effective, because they require highly-trained personnel and necessitate frequent visits to the clinic. The relatively large costs associated with their delivery therefore limit the scalability of these forms of treatment to the larger schizophrenia population.

Notably, the goal of SC interventions is to improve functional outcomes by improving social abilities. Rigorous studies that would elucidate the degree of recovery in SC function that must be achieved to support true real-world abilities are therefore highly required. Nonetheless, outcome studies involving the interventions described above have had important limitations, making it difficult to determine which therapeutic approach is actually most effective. First, sample sizes are often small, fail to rigorously account for heterogeneity in the schizophrenia population, and provide little basis for determining predispositions for training gains in the population. Second, the lack of adequate controls that are matched for intensity and experimenter contact have made it difficult to conclusively attribute performance gains to outcomes. Third, the use of only one or two, often non-standardized, SC or functional outcome measures limits our understanding to the true nature of intervention, and its potential for generalization outside the training setting.

In recent years, special emphasis has been given to the need for early intervention in schizophrenia. It is now acknowledged that the early phase of psychotic illness is crucial in terms of the emergence of a range of cognitive deficits that have prognostic implications, and that early intervention can potentially prevent further worsening of symptoms and improve functioning. An important target for early intervention is the domain of social cognition, the mental operations that underlie understanding, interpretation and perception of social information. Severe social cognition deficits, often comparable to those seen in chronic patients, have been repeatedly documented in early-phase schizophrenia. These deficits span the domains of affect perception, social cue perception, including gaze perception, theory of mind, and attributional style.

Importantly, social cognition deficits have been strongly associated with poor functional outcome in schizophrenia. Specifically, affect recognition and social perception have been each linked with community functioning, social problem solving and social skills. ToM, as well as affect perception and social perception, have been found to mediate the relationship between neurocognition and functional outcome. Surprisingly, however, only a few studies to date have examined the direct effects of social cognition training in young adult or early psychosis patients, and none have evaluated a computerized intervention. Studies testing the effects of Cognitive Enhancement Therapy, a computer-based cognitive training with group-based social skills training and of SCIT, a social cognitive group intervention in first episode patients report promising effects on neurocognitive, social cognitive and functional outcome measures. However, these encouraging outcomes are limited by the practicality of applying these treatments in many clinical settings, given long treatment durations, the need for a trained clinician team, and the necessity of organizing patient groups for program delivery.

SUMMARY

A training program is configured to systematically drive neurological changes to overcome social cognitive deficits. The training program comprises a plurality of computerized social cue perception games, emotion perception games, and theory of mind games. Each computerized game is configured to present a plurality of target and/or distractor stimuli; prompt a game participant to respond to the target and/or distractor stimuli; receive the game participant's input through the game piece; and repeat the presenting through providing a signal steps over multiple repetitions while adapting one or more difficulty parameters to target maintenance of a success rate within a predetermined range. In most embodiments, the games are also configured to provide an indication to the game participant of whether the game participant's input was accurate or apt and/or provide a signal indicative of the game participant's performance or game difficulty.

In one embodiment, at least one of the computerized games is configured to prompt the game participant ignore the distractor stimuli and identify a stimulus with a most similar affective value as the target stimulus. In various embodiments, one or more social cue perception games challenge the participant to observe gaze directions in facial images, match faces from different angles, reconstruct a sequence of faces, memorize social details about sequentially presented faces, repeatedly and rapidly identify which person in a plurality of target faces is smiling, find a face that expresses the same facial emotion as the target, identify an emotion implicitly expressed by a facial expression shown in an image or video clip, match pairs of similar facial expressions, match pairs of emotion clips and emotion labels, reconstruct a sequence of emotion clips, identify emotional prosodies of progressively shorter sentences, and/or match pairs of sentences with tags that identify emotional prosodies with which the sentences are aurally expressed.

In various embodiments, one or more theory of mind games challenges the participant to identify a social scenario that best explains an emotion expressed in a video clip, answer questions about social interactions in a multi-segmented story, choose an expression and associated prosody that best describes how a person would sound in a given social scenario, and/or understand and interpret gradually more complex social scenes.

One embodiment of the training program comprises a self-referential game that challenges the participant to match pictures that have a common affect.

Other features and advantages of the present invention will become apparent upon study of the remaining portions of the specification and drawings.

BRIEF DESCRIPTION OF THE DRAWINGS

FIG. 45 illustrates a screenshot of one embodiment of a game called "Grin Hunting," which challenges a game participant to ignore stimuli that trigger unhealthy psychological responses and/or selectively respond to healthy stimuli.

FIG. 46 illustrates another screenshot of the game illustrated in the previous figure.

FIG. 47 illustrates a screenshot of one embodiment of a game called "Category Click," which challenges a game participant to selectively respond to stimuli that fall within a target category except for one or more pre-identified "freeze" stimuli that fall within that category.

FIG. 48 illustrates another screenshot of the game illustrated in the previous figure.

FIG. 49 illustrates another screenshot of the game illustrated in the previous figure.

FIG. 50 illustrates a screenshot of one embodiment of a game called "Mood Matchmaker," which challenges a game participant to match a challenge stimulus to a target stimulus in a context that includes a plurality of distracting stimuli, including stimuli that trigger unhealthy psychological responses.

FIG. 51 illustrates another screenshot of the game illustrated in the previous figure.

FIG. 52 illustrates another screenshot of the game illustrated in the previous figure.

FIG. 53 illustrates another screenshot of the game illustrated in the previous figure.

FIG. 54 illustrates another screenshot of the game illustrated in the previous figure.

FIG. 55 illustrates a screenshot of one embodiment of a game called "Name the Color," which challenges a game participant to respond to identify the font color of words that include words that trigger unhealthy psychological responses.

FIG. 56 illustrates a screenshot of one embodiment of a delay discounting game called "Now or Later," which scores a game participant's performance based upon the degree of self-control, including willingness to accept delayed gratification, that the game participant exhibits in selecting choices.

FIG. 57 illustrates another screenshot of the game illustrated in the previous figure.

FIG. 58 illustrates a screenshot of one embodiment of a game called "Scene That!" which challenges a game participant to indicate whether a target stimulus was contained within a set of distracting stimuli, including one or more stimuli that trigger unhealthy psychological responses.

FIG. 59 illustrates another screenshot of the game illustrated in the previous figure.

FIG. 60 illustrates another screenshot of the game illustrated in the previous figure.

FIG. 61 illustrates another screenshot of the game illustrated in the previous figure.

FIG. 62 illustrates a screenshot of one embodiment of a game called "Tick Tock," which displays an object and challenges the game participant to select the object after a user-perceived time interval.

FIG. 63 is a block diagram illustrating multiple embodiments of Tick Tock.

FIG. 64 illustrates a screenshot of one embodiment of a working memory game, called "The Matrix Recalled," that presents an ordered list of items—which occasionally includes an item that stimulates an unhealthy psychological response—and challenges the game participant to recall the items in the requested order.

FIG. 65 illustrates a screenshot of one embodiment of a facial cue processing speed game called "Gaze Cast," which presents a video clip of a person making a speeded glance shift in one of many possible directions followed by an array of peripheral objects and challenges the participant to select the peripheral object in the direction of the person's glance.

FIG. 118 illustrates another screenshot of the game illustrated in the previous figure.

FIG. 119 illustrates a screenshot of one embodiment of a social cue apprehension game called "Life Stories," which challenges game participants to listen to a story and apprehend social details in the story.

FIG. 120 illustrates another screenshot of the game illustrated in the previous figure.

FIG. 121 illustrates another screenshot of the game illustrated in the previous figure.

FIG. 122 illustrates another screenshot of the game illustrated in the previous figure.

FIG. 123 illustrates a screenshot of one embodiment of a vocal affect theory of mind game called "Say What?," which challenges game participants to apprehend a social situation and the meanings conveyed by voice inflection.

FIG. 124 illustrates another screenshot of the game illustrated in the previous figure.

FIG. 125 illustrates another screenshot of the game illustrated in the previous figure.

FIG. 126 illustrates a screenshot of one embodiment of a name memorization game called "Face and Name," which challenges game participants to associate a plurality of names with a plurality of faces.

FIG. 127 illustrates another screenshot of the game illustrated in the previous figure.

FIG. 128 illustrates another screenshot of the game illustrated in the previous figure.

FIG. 129 illustrates another screenshot of the game illustrated in the previous figure.

Figure 130:
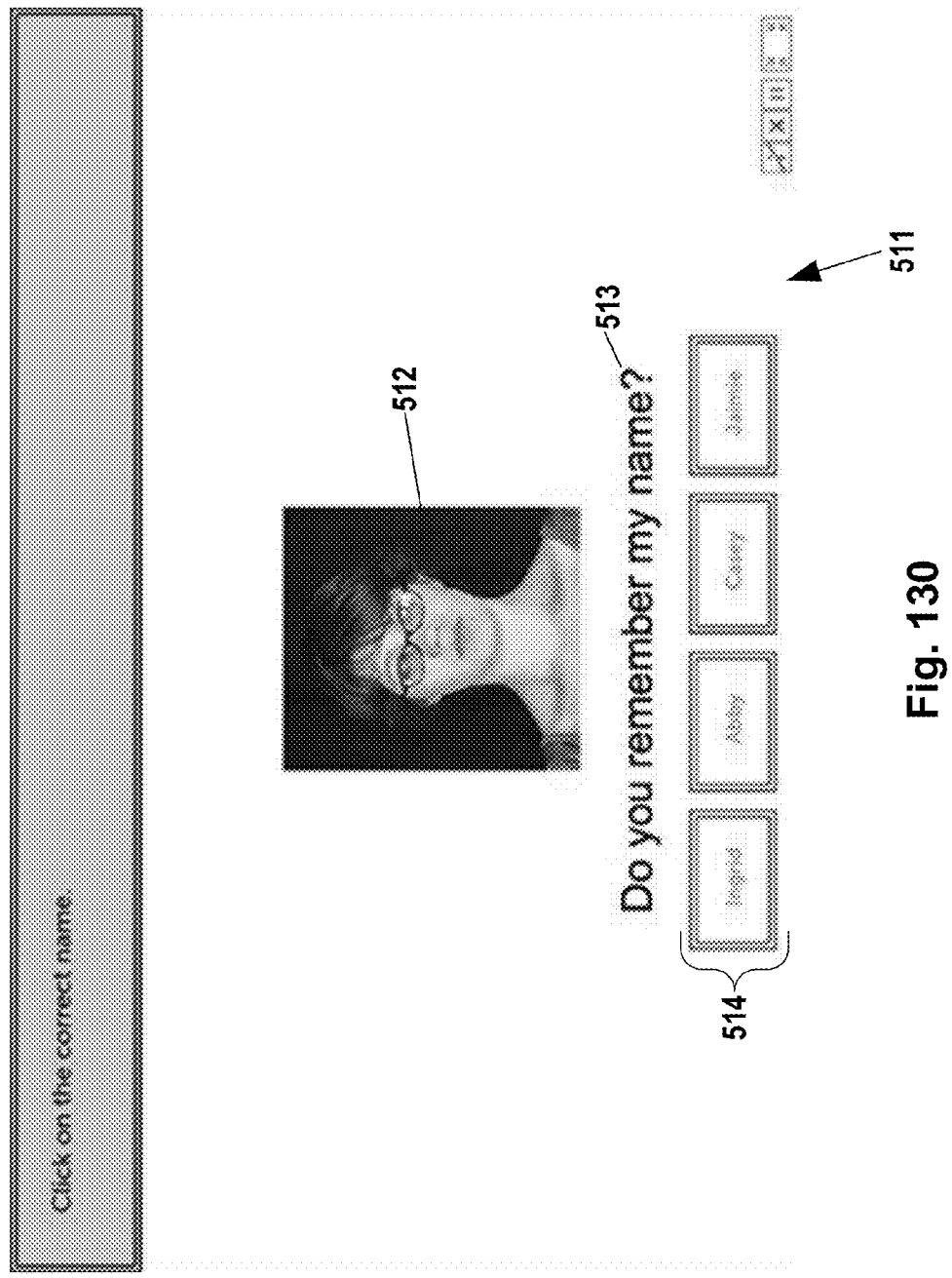

FIG. 130 illustrates another screenshot of the game illustrated in the previous figure.

Figure 131:
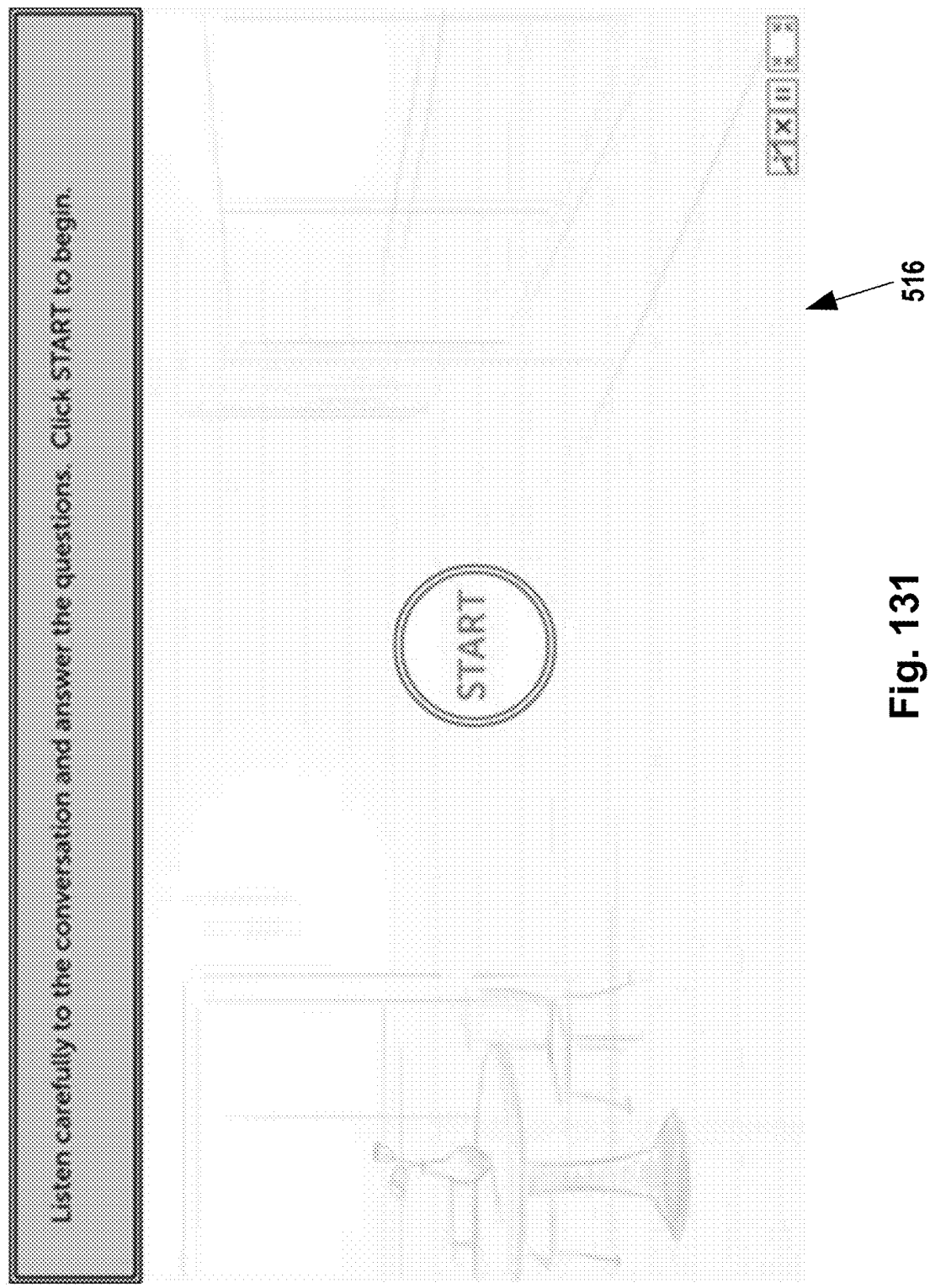

FIG. 131 illustrates a screenshot of one embodiment of a vocal emotional cue and theory of mind game called "Auditory Chatter," which challenges game participants to answer questions about persons discussed in a social conversation.

Figure 132:
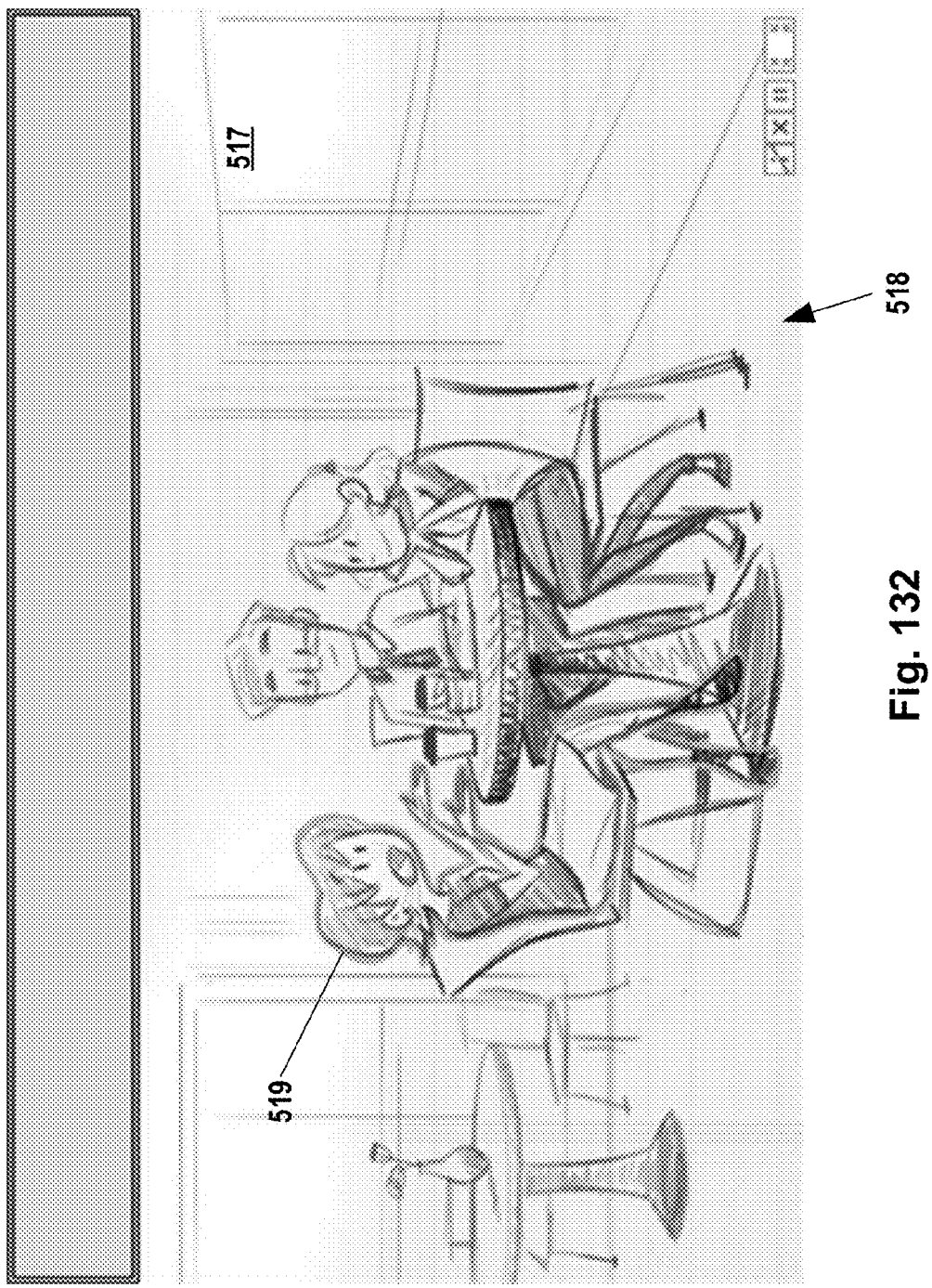

FIG. 132 illustrates another screenshot of the game illustrated in the previous figure.

Figure 133:
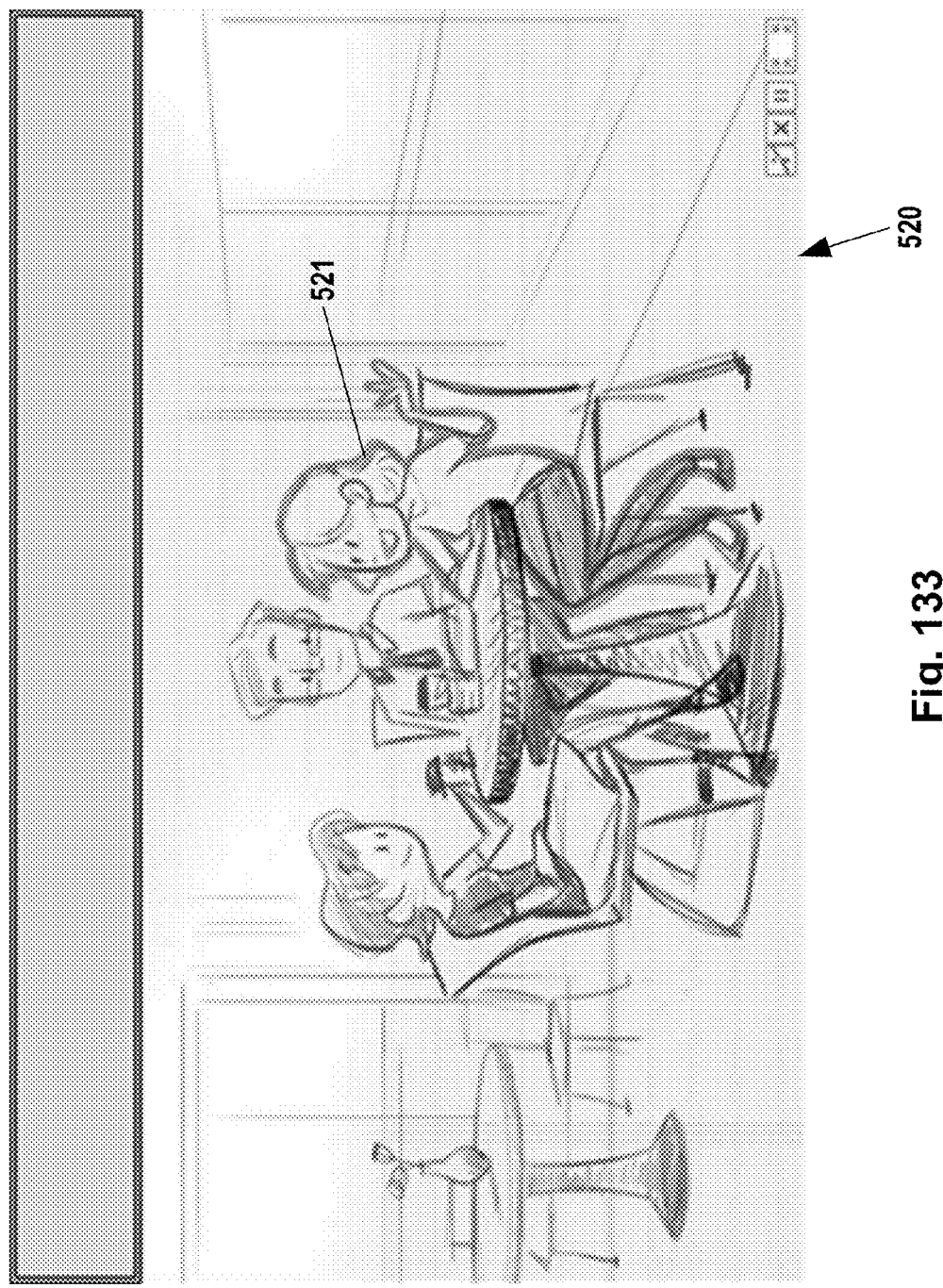

FIG. 133 illustrates another screenshot of the game illustrated in the previous figure.

Figure 134:
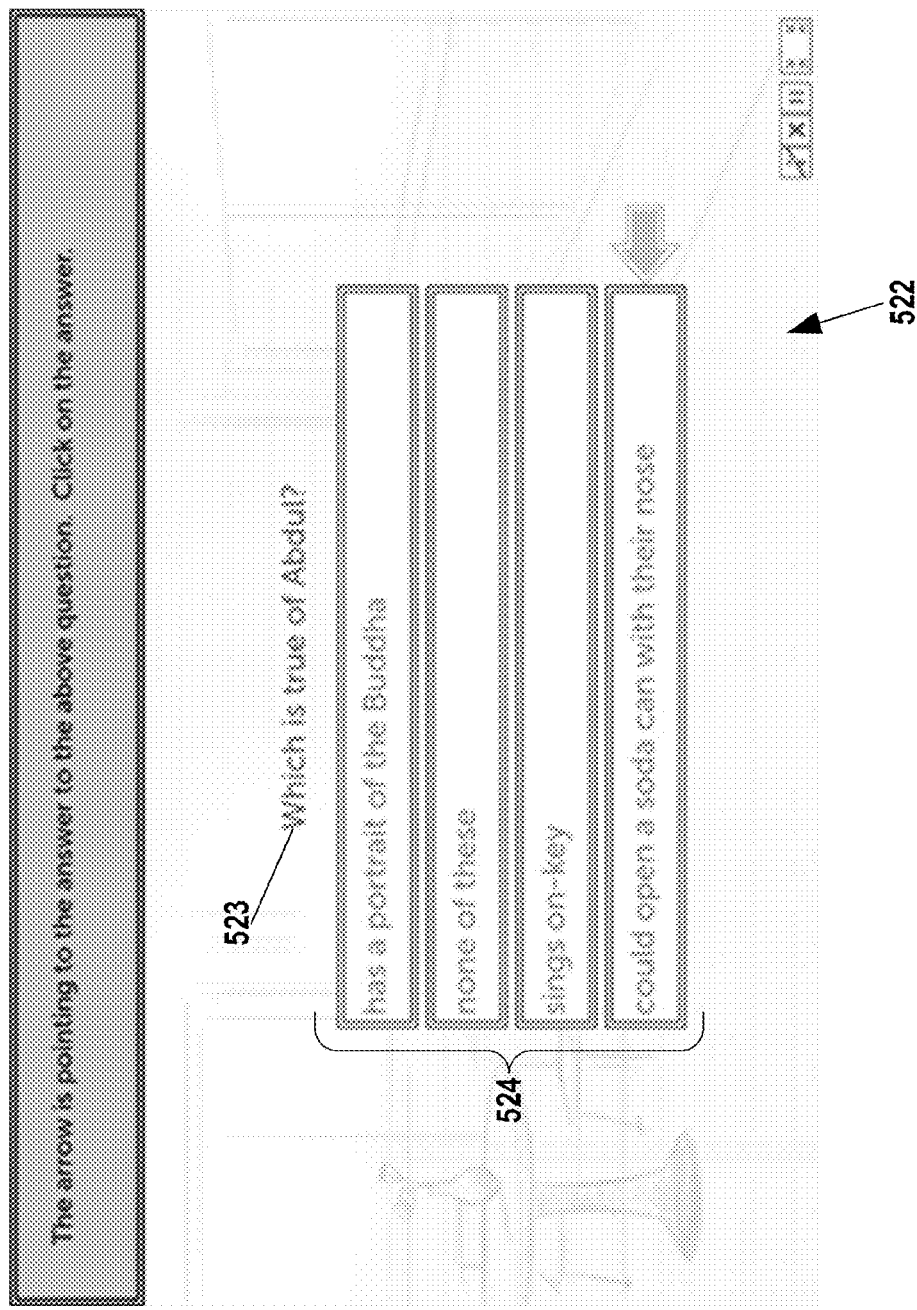

FIG. 134 illustrates another screenshot of the game illustrated in the previous figure.

Figure 135:
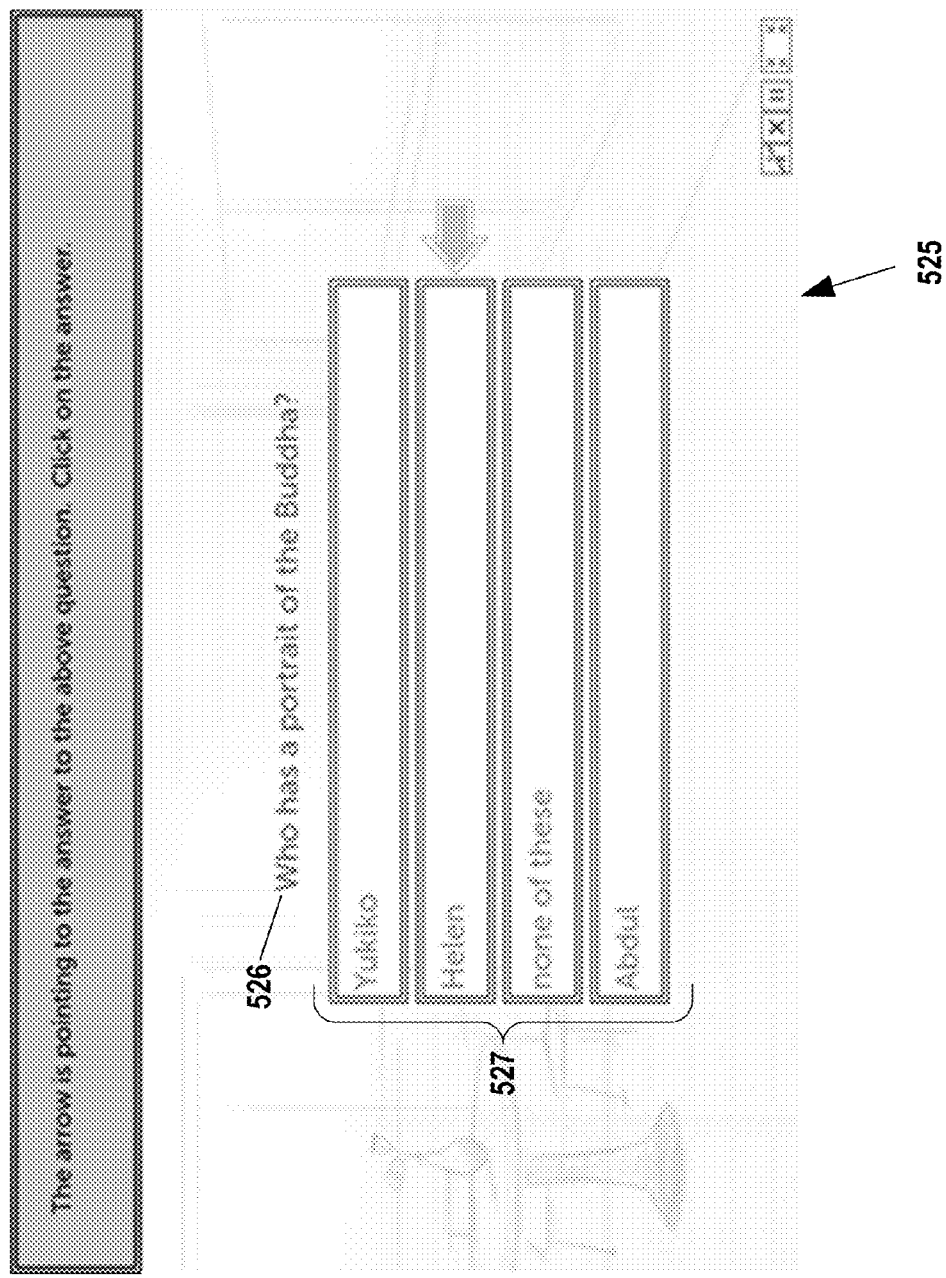

FIG. 135 illustrates another screenshot of the game illustrated in the previous figure.

Figure 136:
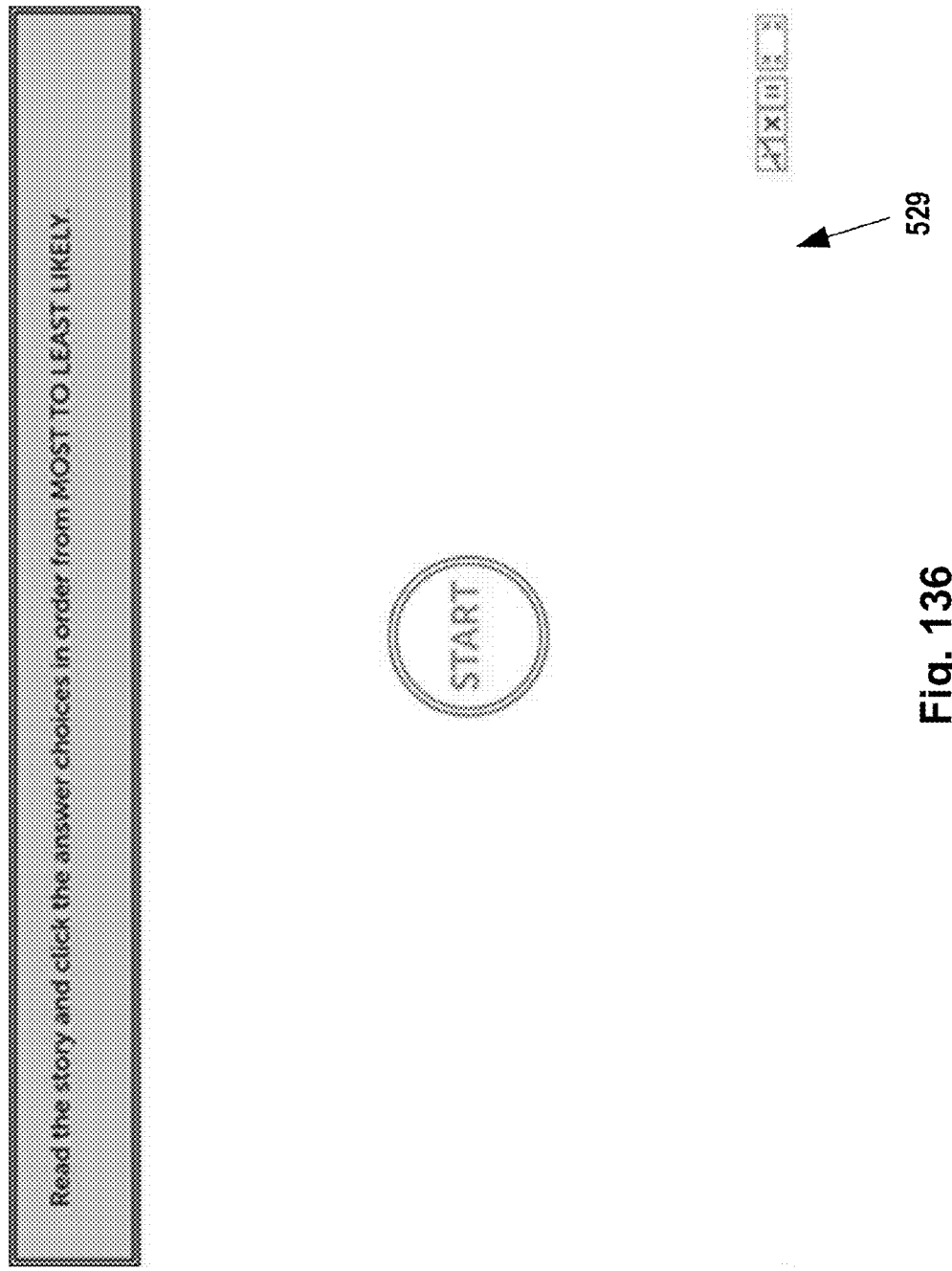

FIG. 136 illustrates a screenshot of one embodiment of a theory of mind game called "Social Scenes," which presents a short written narrative about a person and challenges the participant to infer what that person would have thought or felt based on the narrated circumstances.

FIG. 137 illustrates another screenshot of the game illustrated in the previous figure.

Figure 138:
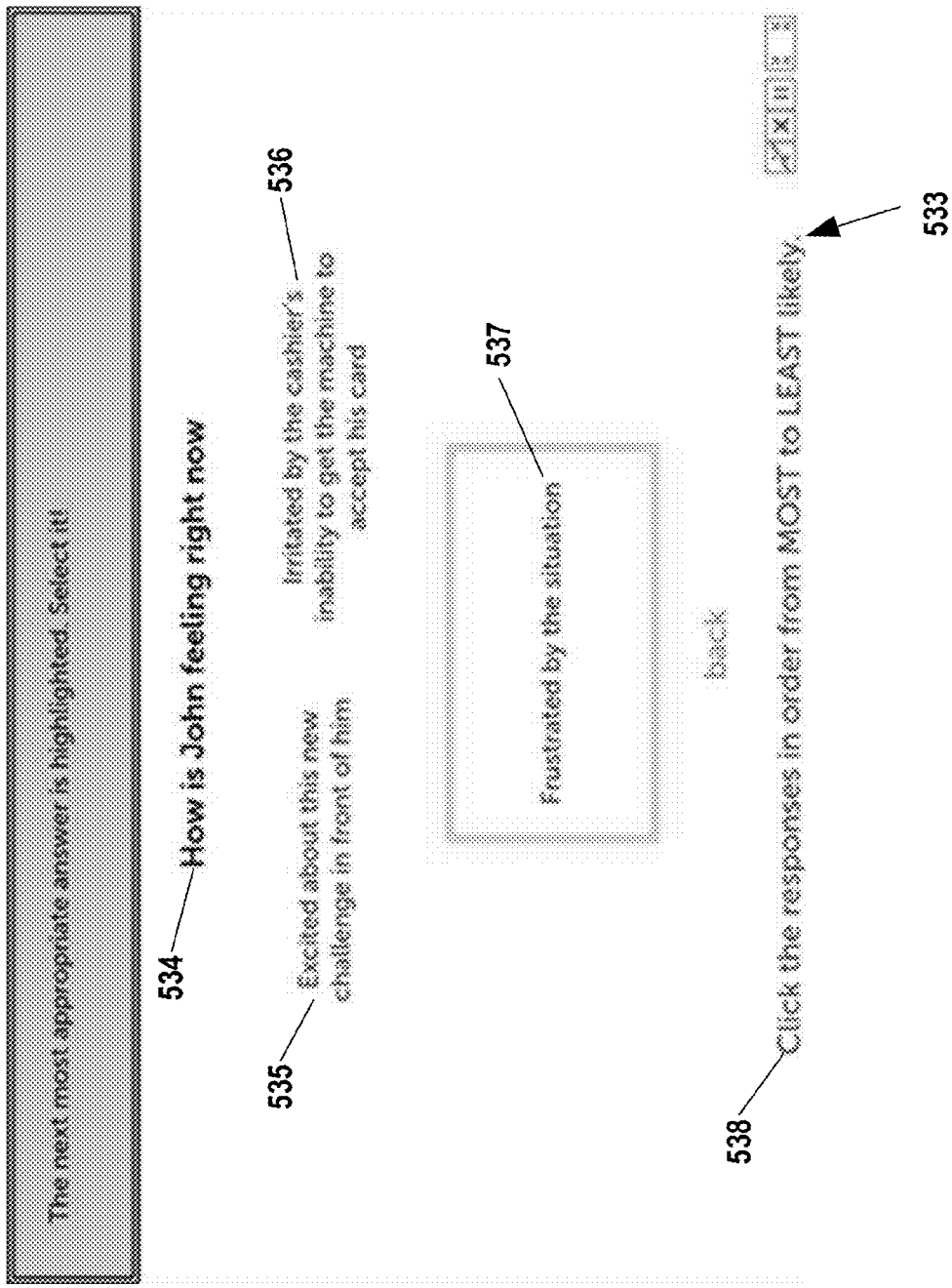

FIG. 138 illustrates another screenshot of the game illustrated in the previous figure.

Figure 139:
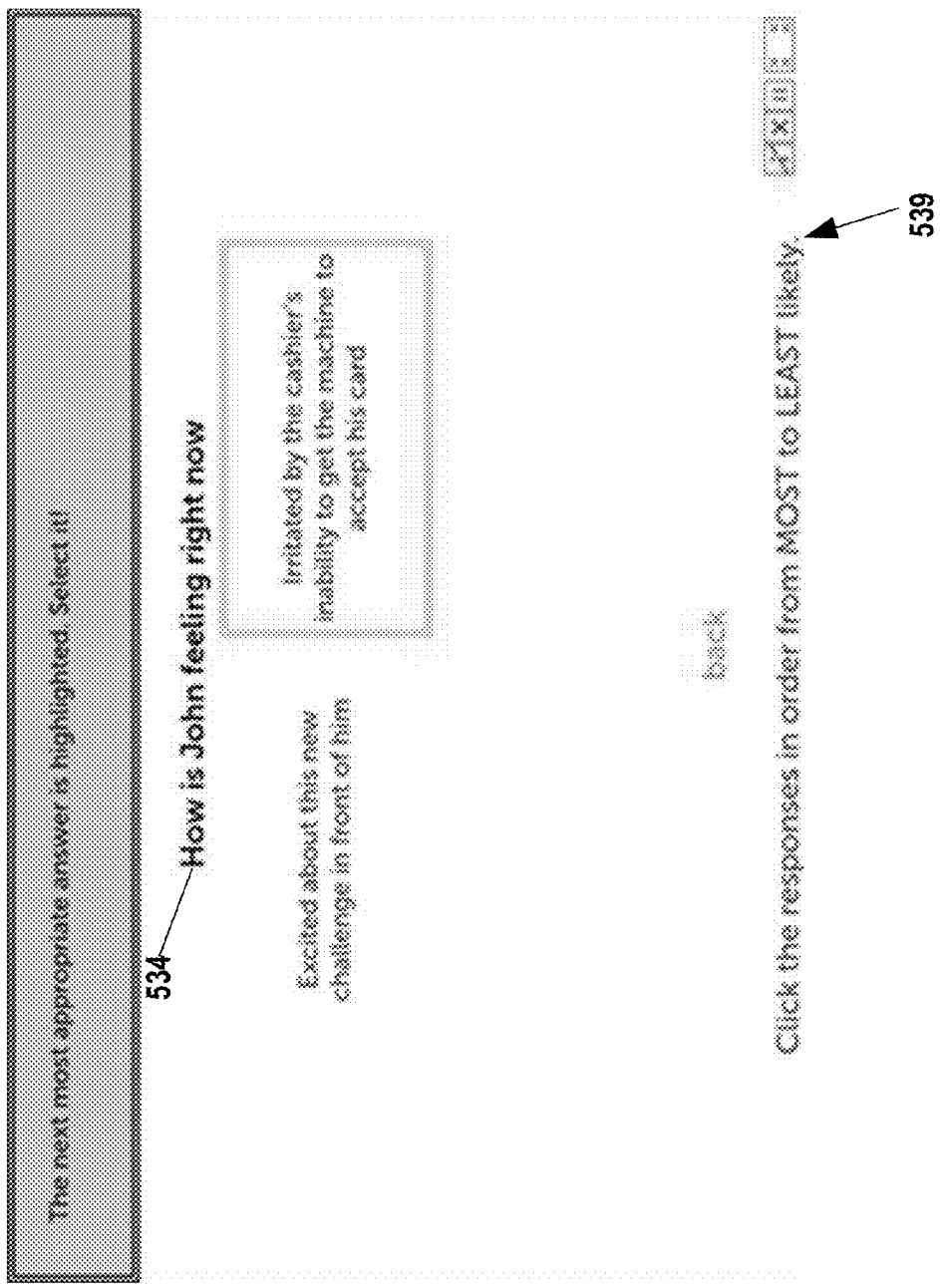

FIG. 139 illustrates another screenshot of the game illustrated in the previous figure.

Figure 140:
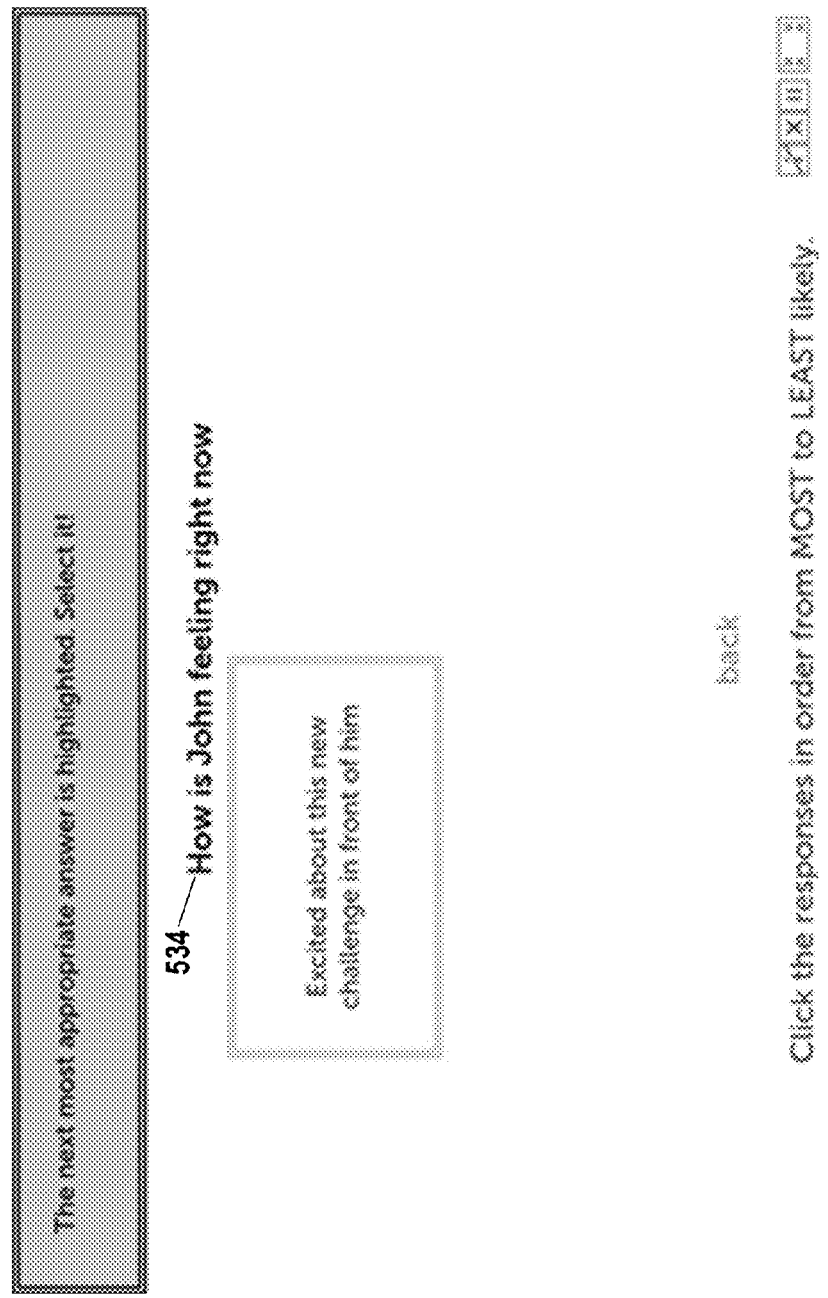

FIG. 140 illustrates another screenshot of the game illustrated in the previous figure.

Figure 141:
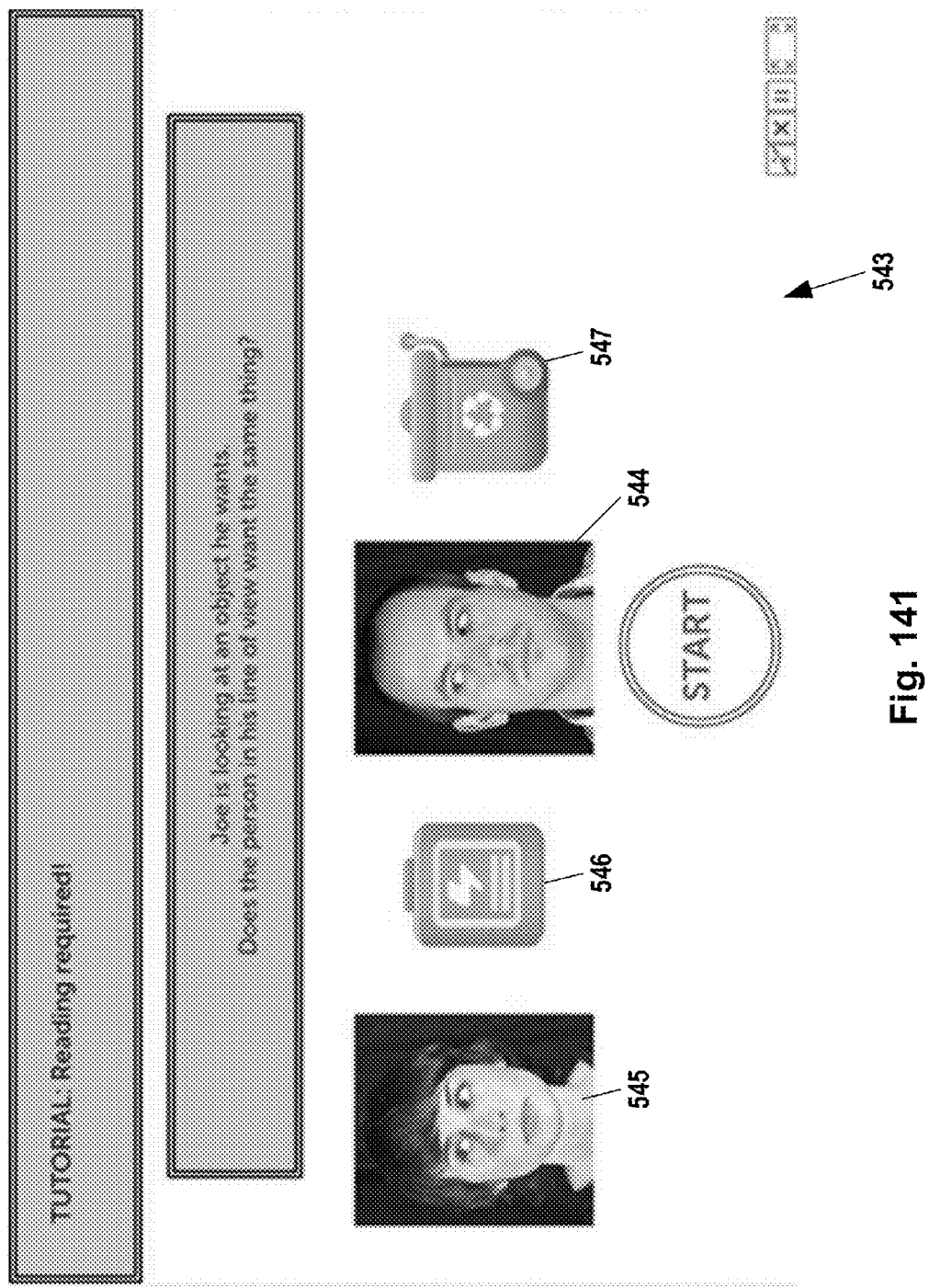

FIG. 141 illustrates a screenshot of one embodiment of a vocal cue theory of mind game called "What's Joe Thinking?" which challenges game participants to follow the direction of different people's eye gazes and interpret those gazes as denoting their thoughts.

Figure 142:
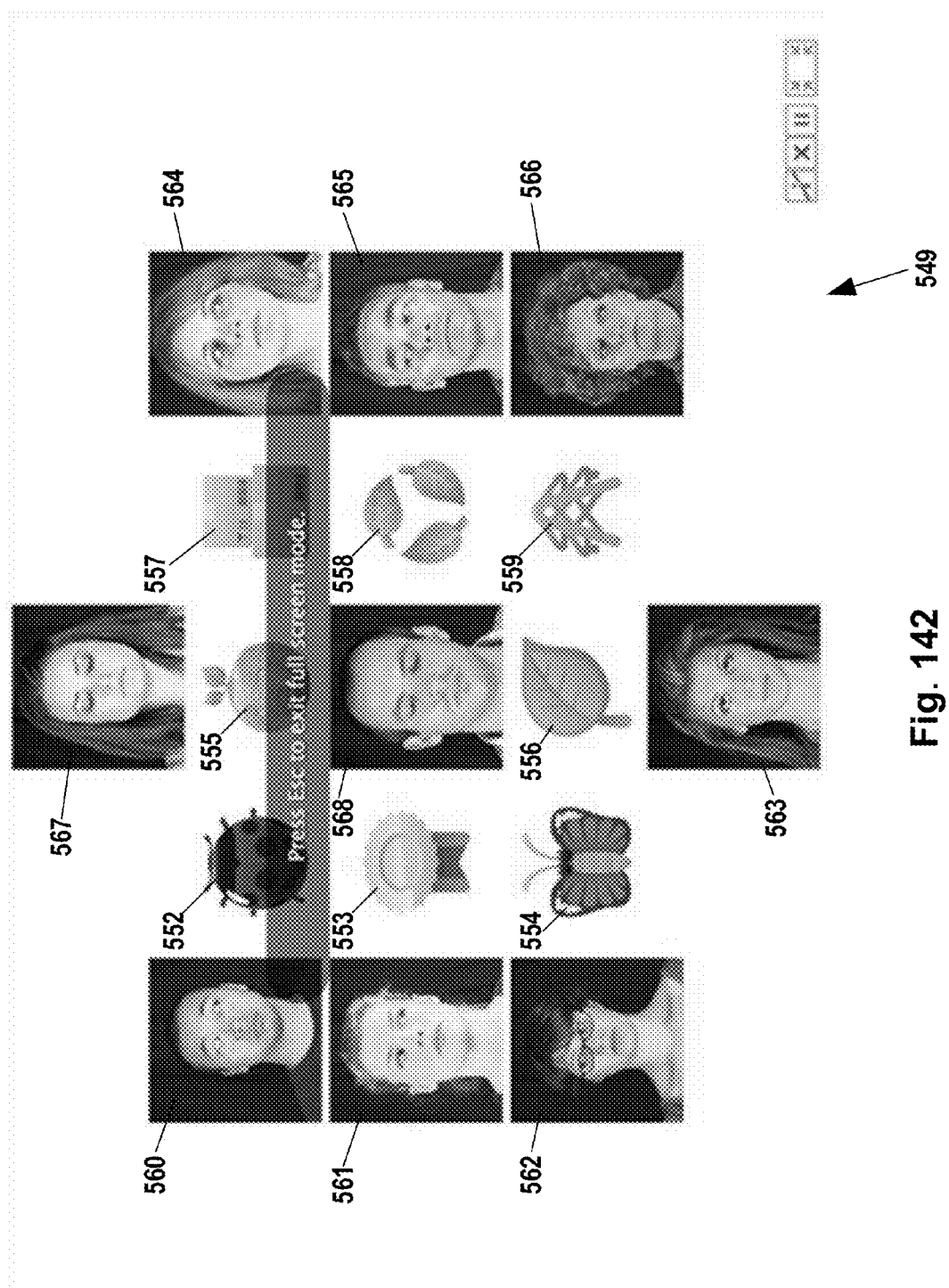

FIG. 142 illustrates another screenshot of the game illustrated in the previous figure.

Figure 143:
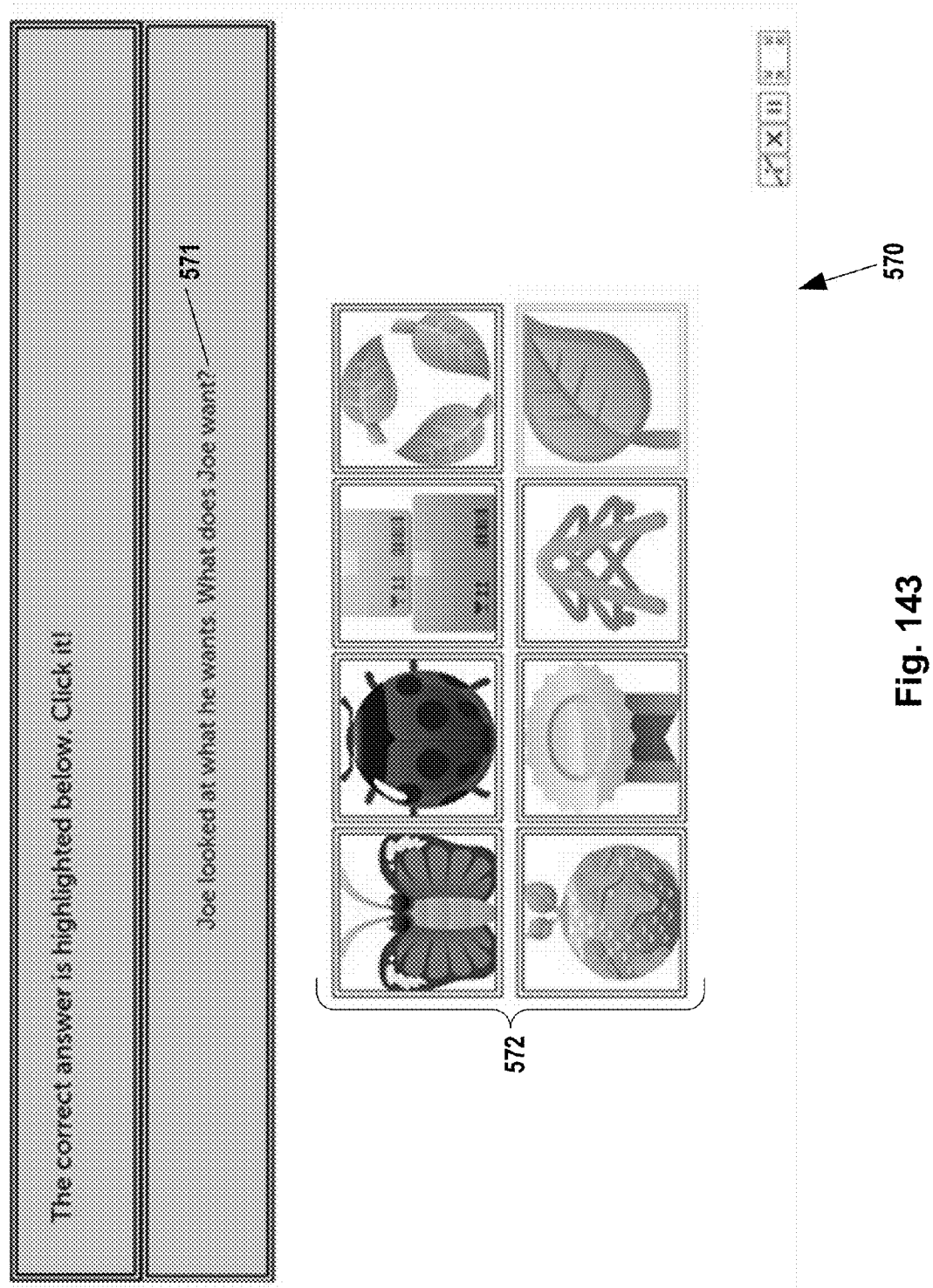

FIG. 143 illustrates another screenshot of the game illustrated in the previous figure.

DETAILED DESCRIPTION

Various embodiments of the present invention use a computer system and a computer network for executing one or more computer programs to train or retrain an individual to enhance cognition, where the term "cognition" refers to the speed, accuracy and reliability of processing of information, including filtering, recall, and manipulation of information, and attention and/or working memory.

A typical computer system (not shown) for use with the present invention will contain a computer, having a CPU, memory, hard disk, and various input and output devices. A display device, such as a monitor or digital display, provides visual prompting and feedback to the subject during execution of the computer program. Speakers or a pair of headphones or ear buds provide auditory prompting and feedback to the subject. A printer may be connected to the computer to enable a subject can print out reports associated with the computer program of the present invention. Input devices such as a keyboard, mouse, trackpad, touch screen, microphone, camera, or other sensor receive input from the subject. Although a number of different computer platforms are applicable to the present invention, embodiments of the present invention execute on either IBM compatible computers or Macintosh computers, or similarly configured computing devices such as set top boxes, PDA's, gaming consoles, etc.

A computer network (not shown) for use with the present invention contains multiple computers similar to that described above connected to a server. The connection between the computers and the server can be made via a local area network (LAN), a wide area network (WAN), or via modem connections, directly or through the Internet. The computer network allows information such as test scores, game statistics, and other subject information to flow from a subject's computer to a server. An administrator can review the information and can then download configuration and control information pertaining to a particular subject, back to the subject's computer.

I. General Characteristics

Figure 1:
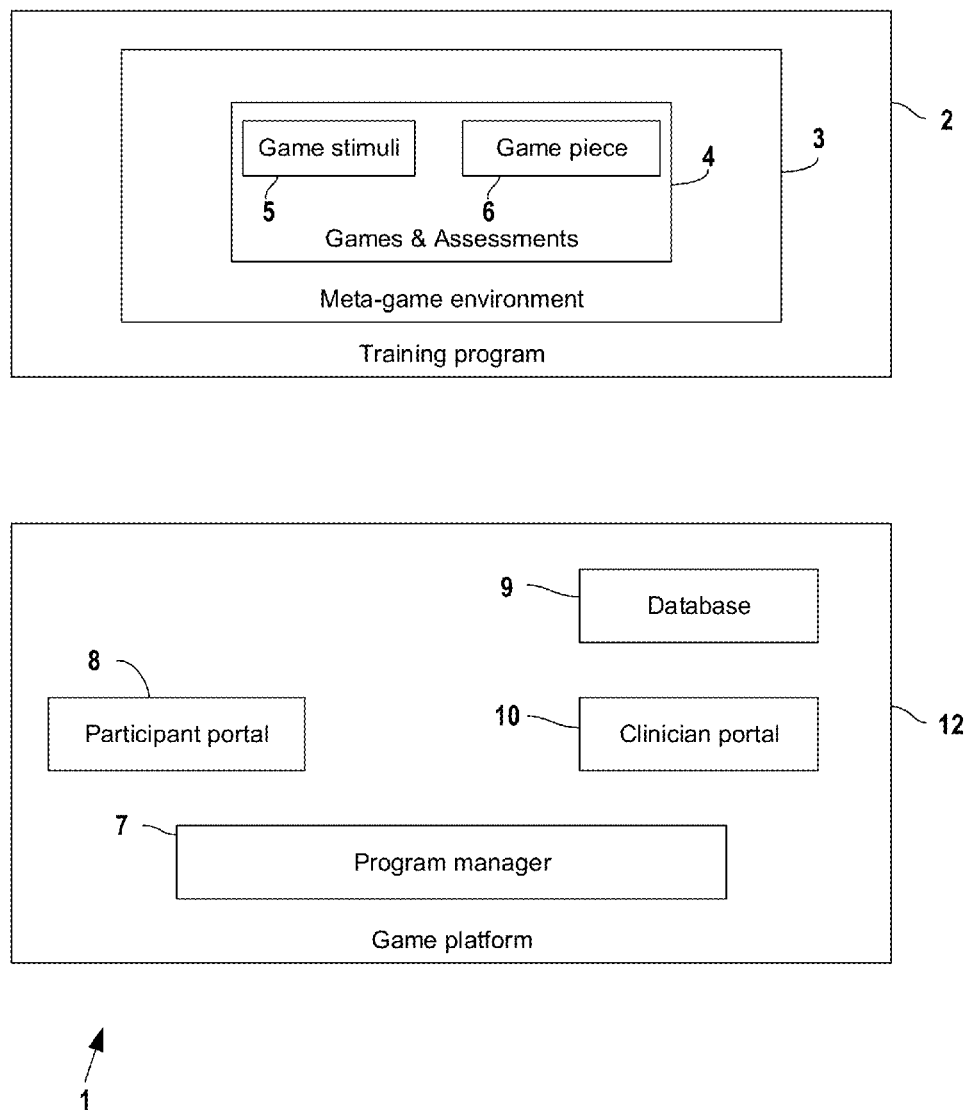
FIG. 1 is a block diagram of one embodiment of a multi-faceted, web-deliverable, and game-based neurological training system configured to treat one or more mental disorders or cognitive deficits.

FIG. 1 is a block diagram of one embodiment of a multi-faceted, web-deliverable, browser-playable and game-based neurological training system 1 configured to treat a cognitive deficit. The neurological training system 1 comprises a game platform 12 and training program 2. The game platform 12 controls exercise delivery and records all data on game play and performance progressions for exercise suites playable on Internet-connected computers and pads. It comprises a program manager 3, participant portal 8, clinician portal 10, and database 9. The program manager 3—also referred to herein as a game manager—is configured to administer the training program 2, manipulate a plurality of game stimuli 5, and receive input from at least one game piece 4.

The training program 2 comprises a plurality of games or exercises 4 targeting a plurality of cognitive domains and sensory modalities. Each training program 2 is customized and configured to address cognitive deficits that are associated with a neurological condition, such as addiction, depression, ADHD, or ASD, and its co-morbidities.

Each training program 2 exercises a range of cognitive domains, from foundational ones like processing speed to more complex ones like social cognition. Ordered from most foundational to most complex, the cognitive domains targeted comprise processing speed 26, attention 27, working memory 28, executive functioning 29, self-control 30, and social cognition 31.

In most embodiments, the game stimuli comprise images 23 displayed on a display device such as a computer monitor or digital screen and/or sounds 24 played through a speaker, ear buds or other auditory equipment. In other embodiments, the game stimuli comprise smells, tastes, or tactile (e.g., haptic) stimulation 25. The training program's stimulus set is designed to span the relevant dimensions of real-world stimuli to ensure that learning is never stimulus specific.

Early in training, the games use highly salient, emphasized (e.g., high contrast, temporally deliberate) stimuli 21 to drive strongly synchronized brain responses requisite for rapidly driving brain changes in a corrective way. The games then progressively move to more ecologically-relevant and valid stimuli 22 (e.g., real speech, complex realistic social stimuli with people showing emotions in context, social scenes, social interactions) to ensure generalization to real-world situations. However, in games to bias attention away from an unhealthy stimulus, the games progress the opposite direction, from low-salience 22 to high-salience stimuli 21.

The game piece 6 comprises a keyboard, computer mouse, track pad, touch screen, camera, remote sensing device (e.g., Microsoft Kinect®), microphone, or other input device.

The training program 2 provides the games through a portal 8 that is designed to be played in a social network environment, at a treatment center, or during a treatment class. In one embodiment, the training program 2 is designed to be platform-independent so that it can be delivered over the Web via any Internet-connected computer. In another embodiment, the training program 2 is provided through a hand-held computer (iPhone/Android phone/iPad/Android tablet/Amazon Fire) application.

The participant portal 8 provides access to game participants. Practically any patient on any computer located anywhere in the world can work on these programs as frequently as their time and schedule permit, under the supervision of a clinician who can (hypothetically) also be located anywhere. To use the program, a participant opens a standard web browser on a broadband connected computer and goes to a program web site. The participant then logs into the program using a screen name that contains no personally identifiable information.

In one embodiment, the portal 8 introduces the participant to a "meta-game wrapper" such as an image and map of a virtual social city that allows participants to visit locations, access games, view progress and results, and make or communicate with friends. The meta-game wrapper is characterized by simplicity, appealing graphics, a sense of control, and constant game rewards.

Figure 3:
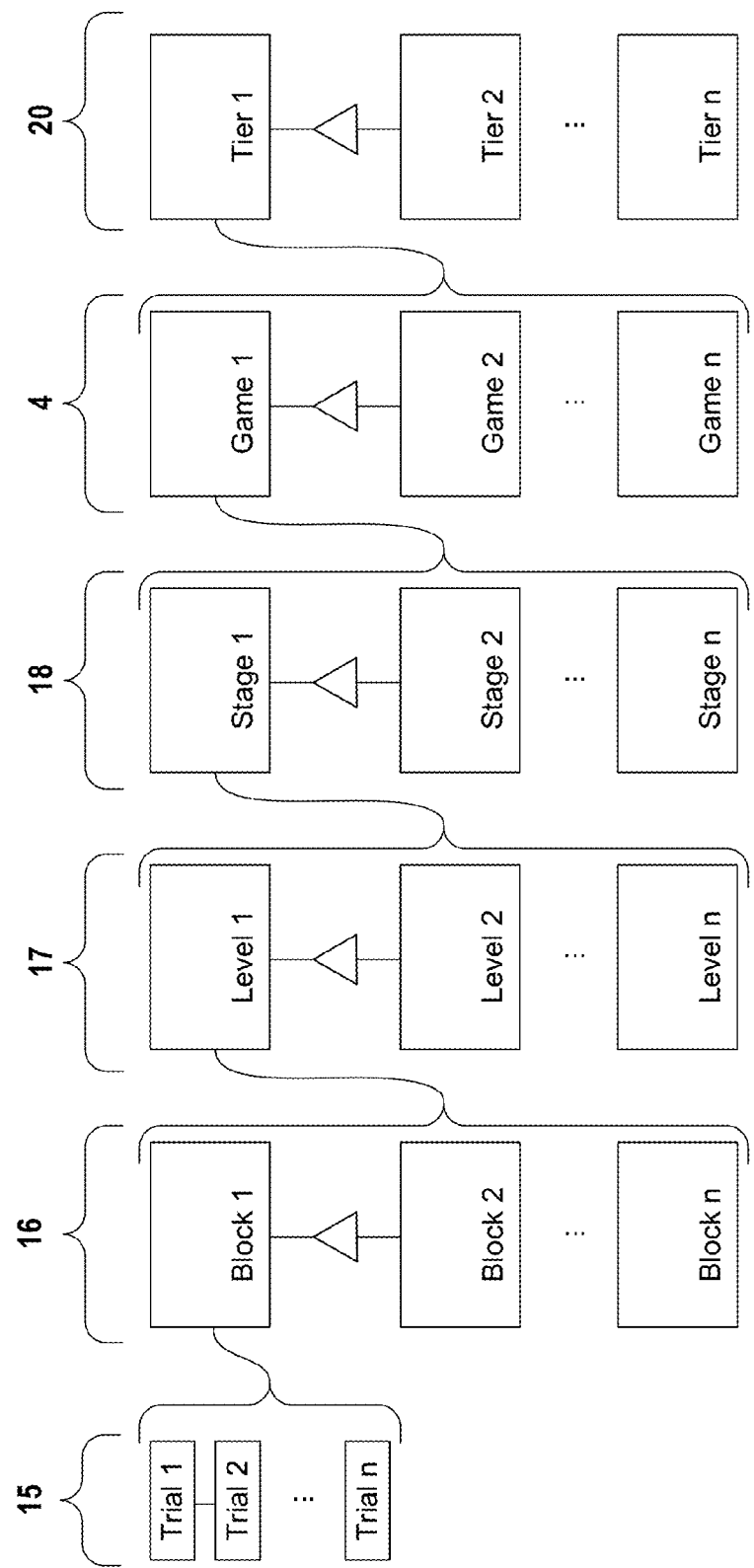
FIG. 3 is a block diagram of an embodiment of a hierarchical organization of games within the neurological training program.

The program manager 7 is configured to administer the games 4 to a game participant in a roughly hierarchical—but not purely linear—fashion. As illustrated in FIG. 3, each game comprises a plurality of blocks 16 of trials 15. Each game trial 15 presents a stimulus or stimuli 20, challenges the game participant to respond to the stimuli 20, receives the game participant's input through the game piece 4, and provides an indication or measure of the game participant's performance, accuracy, and/or aptness.

The program manager 7 applies a delivery strategy that subdivides each game 4 or training module into progressive 1.5-2 minute progressive training challenges (or trials 15). Initial task levels are achievable by every participant, but every participant is driven forward in performance to an asymptotic limit at the end of every short training cycle. The participant is then asked to repeat the cycle to beat their just-achieved score. Achievement is further marked by a "star" system in which five stars (the maximum) represents normal ability for a participant of the trainee's age at that specific task. In this exercise format, the participant is encouraged to replay subtasks in which their performance is still improvable, to get more and more "stars." Participants also work for rewards and achieving goals in an over-riding meta-game that has a structured reward economy.

Between blocks 16 of trials 15, the program manager adapts one or more parameters—such as the salience, duration, and number of target stimuli 20, the salience, duration, and number of distractor stimuli, and the time period between which the target stimuli are presented and the program manager 7 prompts the participant to answer questions that relate to the target stimuli—affecting a difficulty of the game 4 in response to the game participant's input.

Typically, games also include multiple levels 17 and multiple stages 18, each level 17 having a plurality of blocks 16 and each stage 18 having a plurality of levels 17. In a typical multilevel game 4, the game participant is required to achieve a certain threshold of performance in order to "unlock" another, more difficult level 17. Many of the games are also grouped into progressive (and optionally overlapping) tiers 20, requiring the game participant to satisfactorily complete all of the games 4 in a given tier 20, and a sufficient number of levels 17 within those games 4, before providing access to the games 4 of the next tier 20. Games 4 are grouped so that each progressive tier 20 includes games that span a variety of neurological target categories 32.

The program manager 7 administers a schedule that ensures that a participant progress through the games 4 in a defined order, generally moving from more simple (early sensory processing) games 4 to more complex (multimodal, working memory, memory span) games 4 over the course of a multi-week experience. At any point in time, the participant has access to a subset (for example, eight) of these games 4, and is challenged to perform at least a certain number (for example, six) of the games 4 per day. Each game 4 has specific criteria for completion or plateaued performance. After those criteria are met, the game 4 is removed from the active set and the next game 4 added to it. This mechanism ensures ongoing novelty and engagement for the participant, while ensuring that the participant progresses smoothly through the complete set over the program use period.

Within each game 4, a performance threshold, determined by an appropriate up-down procedure or a Zest algorithm, is derived for each block completed. The performance threshold provides performance and improvement data on the individual games. Game-based assessments, which are designated blocks 16 with medium difficulty of the specific games 4, are performed at various time points in the intervention to check progress.

The games 4 in the training program 2 are designed with a different objective than conventional games. Conventional games start at a fixed baseline and progress in a single direction, getting more difficult until the participant is unable to go any further, at which point the game typically terminates. Conventional multilevel games also require completion of one level to progress to the next, more difficult, level, terminating mid-level if the participant is unable to complete a given level.

The games 4 of the training program 2, by contrast, are adaptive and threshold-based. Learning rules are relaxed in initial training to assure near-errorless learning. Error rates are slowly increased to achieve challenge conditions known to be optimal for normal individuals by the end of the training epoch. Likewise, 'rewards' for performance gains are initially amplified, in comparison with those applied for training in other patient populations. The games 4 increase in difficulty when the participant exceeds a threshold of success, and they decrease in difficulty when the participant's performance drops below another threshold. Many of the games 4 enable a participant to "unlock" a new level merely by beating the participant's previous best score. By measuring success in metrics of personal improvement rather than fixed performance requirements, both participants with relatively high cognitive abilities and participants with relatively significant cognitive deficits can progress through the entire training program 2.

After logging in, a game-like experience begins in which the participant is encouraged to earn points and in-game rewards to further advance in each game 4. To do so, the participant selects one of the games 4 scheduled for the day, and performs that game for 5-10 minutes. The game 4 itself contains the core science stimuli and task built into a game-like experience. Performing the game 4 resembles practice on a skill akin to learning to play an instrument or learning to ride a bicycle.

Participants perform tens to hundreds of trials 15 over the course of the ten-minute session. Each trial 15 provides auditory and visual feedback and rewards to indicate if the trial 15 was performed correctly or incorrectly. After each trial 15, the difficulty of the next trial 15 is updated to ensure that within each session, the participant gets ~85% of trials correct. Maintaining a relatively high level of success helps prevent frustration and minimizes the possibility of potential drop-out from the program. Summary screens including game metrics (points, levels) and game metrics (usage, progress) are shown to the participant at the end of each session.

To progress through a game 4, the participant performs increasingly difficult discrimination, recognition, memorization or sequencing tasks under conditions of assured focused attention. Each game 4 employs adaptive tracking methods to continuously adjust one or two adaptive dimensions of the task to the sensory and cognitive capabilities of the participant. This process is based on a statistically optimal Bayesian approach that allows the games 4 to rapidly adjust to an individual's performance level, and maintain the difficulty of the stimulus sets at an optimal level for driving most-efficient learning.

This continuously-adjusted adaptivity operates from trial 15 to trial 15, to sustain an individual's performance success at a challenging (80-90%), since subject is not correct all the time, yet engaging and rewarding (since subject is correct most of the time) level of performance success. This continuously-adjusted adaptivity is also adjusted across sessions to ensure that the games 4 become more challenging at exactly the appropriate rate for a specific individual's rate of learning. This adaptivity also allows the game 4 to adapt to an individual's variable performance across days depending on their overall mood, attention, and health.

By this strategy, training is individualized. A trainee rapidly progresses across training landscapes for which impairments are mild or insignificant but must work hard to improve domains of substantial impairment—always working on the edge of their achievable performance abilities to drive positive, corrective changes at an optimized day-by-day rate, to address the specific neurological problems that most specifically frustrate their higher functioning.

If a game 4 is used as a training module, it is presented as stages 18 that last about ten minutes. During those ten minutes, the participant plays the stage 18 two times: first to set a baseline, and second to beat or match that baseline. This repetition is intentional, because the targeted strengthen of certain neural pathways achieved in the games requires repeated activation of those neural pathways. Stages 18 generally have one level 17 (block of trials intended to be played straight through), but they can have more.

The program manager 7 delivers all patient performance data in encrypted forms to a cloud-located database, which are provided, with appropriate informed consents, to one or more treatment program professionals, who access the relevant patient data through a clinician portal 10 in order to supervise patient treatment and assure enrollment, compliance, and monitored and guided patient progress.

Every aspect of a patient's compliance and progress is recorded in training and can be provided via a cloud-based database 9 (with appropriate permissions) to supervising training monitors or professionals. No personally identifiable information (including Internet protocol addresses) is stored on the server. The server makes the data available for review by the clinician(s) supervising patient care, the site trainer, site coordinator, and site investigator through a secure web portal 10, which requires a complex password to secure the identification of these individuals. Only data from participants in a particular clinic can be viewed by that clinic's staff. The site trainer, in particular, uses the secure web portal 10 to regularly check on usage and progress of each active participant to customize their weekly phone/in-person/social network discussions to provide helpful guidance and coaching.

By solving the treatment access problem and by providing a basis for intensive and extensive remotely-supervised treatment at low cost, substantially improved overall medical outcomes in this population can be achieved.

II. Assessments

Each training program 2 utilizes assessments to personalize the types of games, types of stimuli, and levels of difficulty to the participant. Each game 4 can be used as an assessment or a training module. If a game 4 is used as an assessment, it is played once through before the participant advances to the next game.

Playing an assessment typically lasts five or fewer minutes. Assessments are used sparingly to avoid inducing learning/practice effects. In assessments, progressive variables that change an exercise's difficulty may be removed to provide a static reading of performance. Visual and/or auditory feedback and rewards may also be removed to reduce effects related to trial-by-trial learning or motivation.

The training program 2 uses two general forms of assessments to calibrate the games 4, providing objective measures like reaction times and accuracy or subjective measures like self-reported abilities. Assessments provide a range of information regarding within exercise improvements (is the participant improving on the task at hand?), near-transfer effects (is training on a processing speed task going to lead to improvements on other processing speed tasks?), far-transfer effects (is training on an attention task going to lead to improvements on a memory task?), and clinical and real world measures (is our training program going to improve depressive symptoms or quality of life?)

The training program 2 also uses standard clinical and neuropsychological assessments. The training program 2 uses the Trail Making Test and Wechsler Adult Intelligence Scale (WAIS-IV) Symbol Coding to assess processing speed. The training program 2 uses the WAIS-IV Digit Span and Arithmetic to assess working memory, the Hopkins Verbal Learning Test to assess delayed memory, and the Brief Visuospatial Memory Test to assess visuospatial memory. The training program 2 uses the Trail Making Test and Wisconsin Card Sorting Test to assess executive functioning. The training program 2 uses the Iowa Gambling Task, Balloon Analog Risk Task (BART), and Barratt Impulsiveness Scale (BIS) to assess impulse control. An embodiment of the training program 2 used for treating alcoholism uses the Penn Alcohol Craving Scale (PACS) to quantify alcohol cravings in alcoholic participants and Hopkins Verbal Learning Test-Revised (HVLT-R) to quantify verbal learning and memory, respectively. These assessments are administered to participants before they begin training.

In training programs for children, surveys are provided to the children's guardians before and after training to assess behavior related to ADHD, social abilities, conduct, and other dimensions of development.

Assessments are embedded in the training program 2 in form of surveys and exercises of varying similarity to those selected for training. Assessments are placed before and after training and often during checkpoints within training.

The training program 2 calibrates the games 4 based on pre-training assessment results to select games 4 and certain stages or levels within the games to present as part of the training program. The assessment-based calibration also includes adjusting the proportion of training exercises related to each cognitive domain (e.g., processing speed, attention, theory of mind, impulse control). Calibration is also used to adjust parameters within an exercise like the start point of the progressive variable or the number of trials in a block. Such parameters tend to be calibrated for adults with moderately high cognitive abilities. Young children and individuals suffering from cognitive impairments often require specialized settings.

Checkpoints generally occur every 10 to 14 days of training and can be spaced further apart for longer training programs.

III. Specific Training Programs

1. Autism

Figure 4:
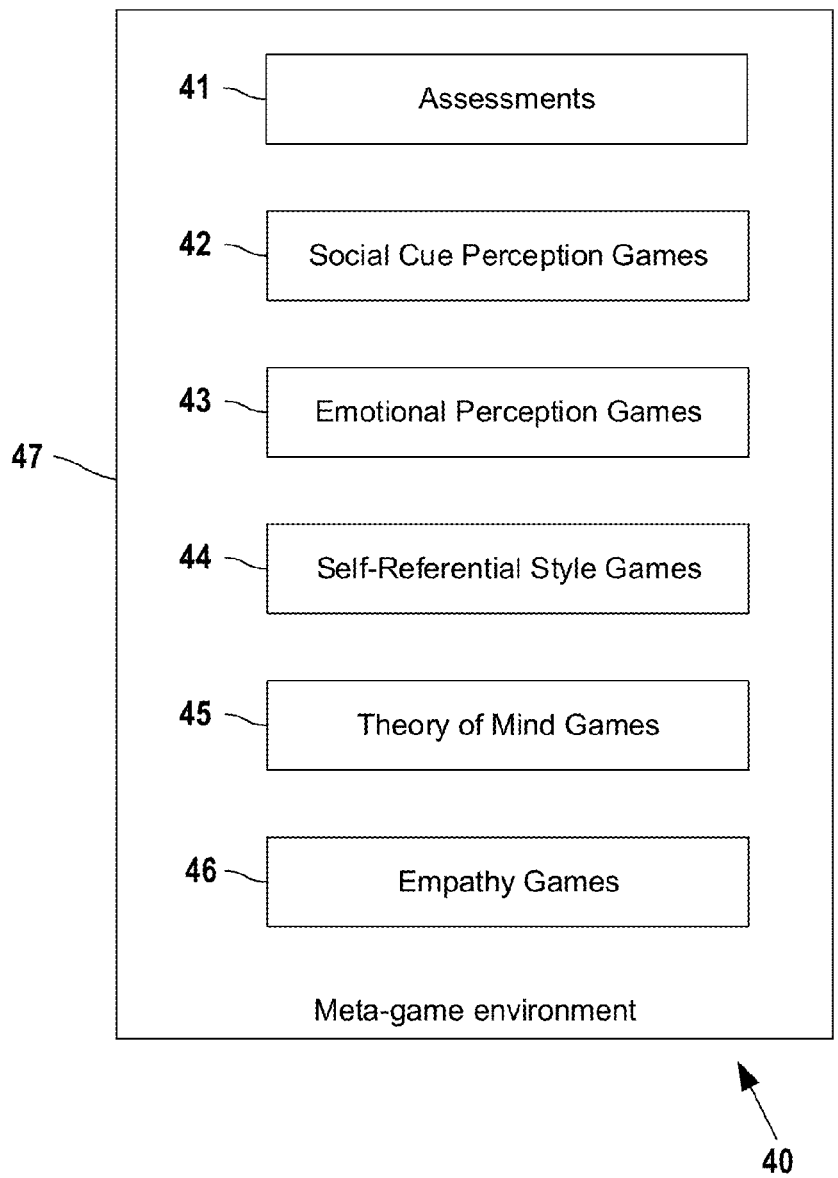
FIG. 4 is block diagram of one embodiment of a computer-based cognitive training program that addresses several of the dimensions of abnormal neurology that limit individuals with autism or social cognition deficits.

FIG. 4 is a block diagram of one embodiment of a computer-based cognitive training program 40 called "TARA" (for Training Approach to Remediate Autism) that addresses several of the dimensions of abnormal neurology that limit individuals with autism. TARA targets universal deficits in social cognition and social control deficits in ASD individuals.

TARA comprises a plurality of games administered through a many-faceted, web-deliverable, browser-playable SC training program suite specifically designed to overcome at least most of the shortcomings that have limited earlier therapeutic tool designs.

One embodiment of TARA includes twenty-two different SC games focusing on each of five SC domains: social cue perception 42, emotional perception 43, self-referential 44, theory of mind 45, and empathy 46, which are described in Table 1 below. Many of these games are described in further detail in this specification.

TABLE 1

Suite of games incorporated into one embodiment of an autism-treatment training program

| Domain | Game Name | Modality | Task |
|---|---|---|---|
| Social Cue perception | Looky Lou | Visual | Find the face with the same gaze direction as the target face |
| | Gaze Cast | Visual | Select the peripheral object which the target face looks at |

TABLE 1-continued

Suite of games incorporated into one embodiment
of an autism-treatment training program

| Domain | Game Name | Modality | Task |
|---|---|---|---|
| | Face It! | Visual | Match the same face from different angles |
| | Face It: Flashback | Visual | Reconstruct the sequence of faces that you have just seen |
| | Face Facts | Auditory & visual | Memorize social details about sequentially presented faces |
| | Bright Whites | Visual | Keep tracking the person who is nicer to you (i.e. keeps smiling at you when clicking on it) |
| Emotion perception | Poke that Feeling | Visual | Find a face expressing the same facial emotion as the target |
| | Emotion Motion | Visual | Name the facial expression shown in a video clip showing a person featuring an emotion |
| | Second That Emotion | Visual | Match pairs of similar facial expressions in a memory-like game |
| | Emotions Memory | Visual | Match pairs of emotion clips and emotion labels |
| | Emotion Replay | Visual | Reconstruct the sequence of emotion clips |
| | Voice Choice | Auditory | Identify the emotional prosody of progressively shorter sentences |
| | Second That Intonation | Auditory | Match pairs of emotional sentences and emotional tags |
| Self-referential Style | Self-source memory | Auditory | Generate attributes to auditory word lists and identify the self-generated ones following longer and longer time intervals |
| | Affective Picture Rating | Visual | Rate the affect of a given picture and match it to the normalized overall rating for longer and longer time intervals |
| | Maintain the Affect | Visual & Auditory | Self-select an affective category and maintain the affect over the time period of the block |
| Theory of Mind (ToM) | What Just Happened? | Visual & Auditory | Match the emotion shown in a video clip with the right social scenario |
| | Life Stories | Auditory | Answer questions about ToM and social interactions in stories comprised of twenty segments each |
| | Say What? | Auditory | Decide how a person should sound in a given social scenario |
| | Social Scene Interpretation | Visual & Auditory | Understand and interpret gradually more complex social scenes and situations (presented by real actors in video clips) |
| Empathy | Mutual Mood Matching | Visual | Score more points if your affective rating/mood in response to a given picture/clip matches that of all your mutual game partners |
| | Cooperative Teamwork | Visual & Auditory | Work with your game partners to solve social problems (increasingly complex social narratives) that emphasize cooperation, empathy and compassion |

The training program 40 provides participants continuous feedback about treatment progress, expressed directly and symbolically in an engaging meta-game 47. Frequent reward screens are presented, with game-like rewards marking the achievement of training benchmarks. Social network capabilities are mounted in the training program model. Participants are encouraged (with their clinician's Internet-delivered help) to form training "teams" in which all participants can work together on a "mission." The training program 40 also includes a set of assessment tools 41 that provide a basis for evaluating key default-system components in any participant. Based upon those assessments, the training program 40 provides a customized set of games to drive corrective improvements.

TARA addresses 1) attention, cognition and cognitive control deficits; 2) receptive and expressive deficits in aural language, reading and related abilities; and 3) the hypersensitivities that can plague individuals in the spectrum. TARA's games heavily engage the neuromodulatory control machinery that governs attention, arousal, and reward processes to establish and strengthen and in other ways normalize their control of learning and memory processes. Each of the TARA games implements principles of brain plasticity-based therapeutics in a specific and unique way to target a different aspect of SC functionality. The suite of games work synergistically to improve the speed, perceptual accuracy and interpretive powers of information processing in the brain's SC systems and SC function all across the SC brain machinery. Also, each game deploys a carefully designed stimulus set that allows progressive training to improve speed and accuracy within the SC sub-domain targeted by that game.

Clusters of component TARA training modules addressing different aspects of SC deficits were applied in preliminary studies by research teams at UCSF, the San Francisco VA Medical Center, UNC, Harvard, UCLA, and Haifa domains: social cue perception 42, emotional perception 43, self-referential style 44, theory of mind 45, and empathy 46. Different constructed tasks sets are applied to help different populations of SC-impaired individuals. For example, Table 2 below shows a suite of fourteen games targeted to the Asperger's population.

TABLE 2

Suite of games incorporated into one embodiment of an Asperger's-treatment training program

| Domain | Game Name | Modality | Task |
| --- | --- | --- | --- |
| Social Cue perception | Looky Lou | Visual | Find the face with the same gaze direction as the target face |
| | All Aboard | Visual | Arrange the people in order of presentation as they board the social train |
| | Face It! | Visual | Match the same face from different angles |
| Emotion perception | Poke that Feeling | Visual | Find a face expressing the same facial emotion as the target |
| | Emotion Motion | Visual | Name the facial expression shown in a video clip showing a person featuring an emotion |
| | Second That Emotion | Visual | Match pairs of similar facial expressions in a memory-like game |
| | Voice Choice | Auditory | Identify the emotional prosody of progressively shorter sentences |
| Self-referential Style | TAPAT | Auditory | Make the correct self-attributions implicitly by responding to 'self' vs. 'other' |
| | The Self Monitor | Visual | How do I feel about and how well do I understand what I have just seen |
| | Who Did That? | Visual & Auditory | Trains self-source memory implicitly by shifting attention to the 'self' generated items |
| Theory of Mind (ToM) | What Just Happened? | Visual & Auditory | Match the emotion shown in a video clip with the right social scenario |
| | Life Stories | Auditory | Answer questions about ToM and social interactions in stories comprised of twenty segments each |
| Empathy | Mutual Mood Matching | Visual | Score more points if your affective rating/mood in response to a given picture/clip matches that of all your mutual game partners |
| | The Empathy Hub | Visual & Auditory | Learn to put yourself in the position of another person (story character) |

University. Pilot data derived from these initial studies demonstrate that: a) patients can comply with proposed schedules of program use; b) TARA programs drive improvements in the SC abilities targeted by its specific training modules; c) benefits extend to real-world SC improvements and quality of life; and d) neurological distortions in the brains of trained subject populations are driven normal-ward by TARA program training.

Different versions of TARA are provided for different populations, including one for pre-schoolers, another for elementary students, and another for older students and adults.

2. Social Cognition

A similar embodiment of a computer-based cognitive training program 40 addresses several of the dimensions of abnormal neurology that limit other people with social cognition deficits, including individuals with Asperger's and individuals with schizophrenia. The training program 40 is automatically adaptive and applicable to children or adults with mild to severe functional deficit levels (including non-verbal individuals).

This program 40 also includes multiple SC games 4, described in Table 2 below, focusing on each of five SC In contrast to prior art approaches, the training program 40 targets all levels of the dysfunctional SC systems in the socially dysfunctional brain. All of its games quickly establish and maintain an engaging-yet challenging task difficulty level, where the most rapid brain changes are known to be achieved. Also, all games 4 advance progressively in speed and accuracy challenges. Gradual progressions in games 4 from basic, lower-level SC tasking to naturalistic, real life settings assure broad recovery and extension to 'real-life' operations. Constant rewards and feedback are provided, specifically designed to up-regulate also-commonly deficient attention, reward and learning processes in the SC systems of the brain.

The training program 40 also includes games that challenge implicit, low-level, perceptual learning processes that are generally intact but severely deficient in SC-impaired populations. Importantly, the training program 40 addresses these implicit processes before strongly challenging executive control abilities. Gradual progressions in exercises from basic, lower-level SC tasking to naturalistic, real life settings assure broad recovery and extension to 'real-life' operations.

The training program 40 restores the brain's capacity to process and utilize socially-relevant information with high accuracy and efficiency, in a way that is distinct from existing educational or training-based approaches. Thereby, the program 40 provides a relatively complete remediation approach that can be expected to drive strong generalization to everyday social functioning.

3. ADHD

Figure 5:
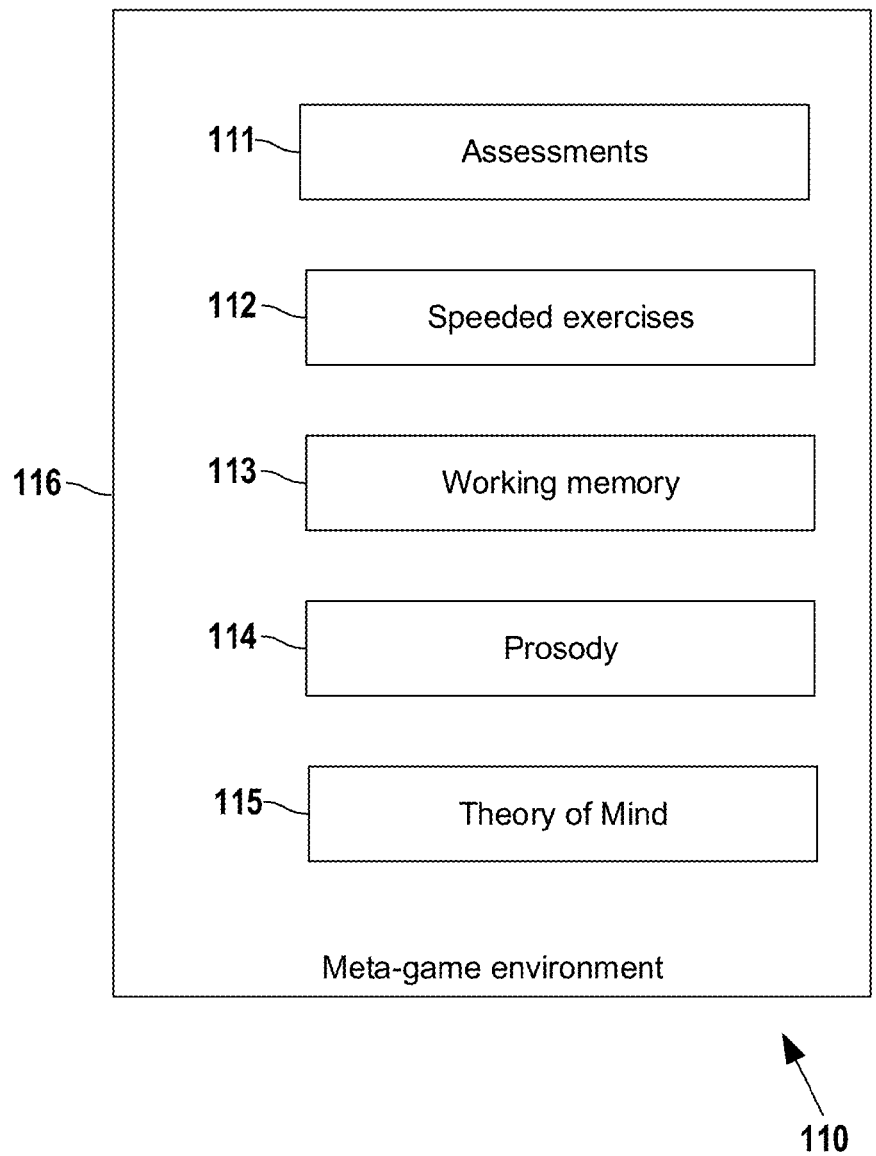
FIG. 5 is a block diagram of one embodiment of a computer-based cognitive training program that is configured to treat schizophrenia.

FIG. 5 is a block diagram of one embodiment of a computer-based cognitive training program 50 that is configured to address the many dimensions of abnormal neurology that limits the child with ADHD.

The program 50 comprises arousal-stimulating games 52 designed to increase the level of arousal-stimulating neurotransmitters, including noradrenaline and dopamine, in the ADHD's child's brain. The current standard of treatment is to prescribe stimulant drugs to increase these "brightening" chemicals. In contrast to drug treatment, program 52 provides training games that stimulate the brain's own production of these agents, and also improve the brain machinery controlling the patient's levels of arousal.

The program 50 also comprises decoding games 53 designed to re-normalize decoding abilities in aural language in the framework of very closely attended tasking. These games 53 act to broadly normalize decoding abilities, recover brain speed in the trained (in this case, hearing) domain, and completely recover the selective neurological amplification of closely-selectively-attended inputs in ADHD individuals. Trained individuals' listening accuracy is much less strongly affected by environmental acoustic noise.

The program 50 also comprises selective attention control games 54 that target the recovery of decoding and related selective attention control abilities for visual behaviors. This training results in sharp improvements in decoding abilities, brain speed and working memory.

The program 50 further comprises games 55 that challenge the participant to exhibit highly flexible attention-shifting in a multi-tasking format. This leads to large-scale improvements in the ability of a child or adult to keep track of information all across a broad visual field of view, while accurately continuously and persistently monitoring important information arising from key sources or locations. This form of training also drives strong improvements in visual speed of processing. Very positive corrective changes in frontal cortex responses in attention networks parallel behavioral improvements in these key visual attention abilities.

The program 50 additionally includes behavioral tasks and games 56 motivated by mindfulness practices that require subjects to sustain attention in a divided attention environment for progressively longer epochs of time. The training promotes attentional system "stabilization," a weakening of the disruptive effects of intrusive mental thoughts, and large-scale improvements in the trained subjects' control of persistent attention.

The program 50 includes intensive language and visual training games 56. This training substantially re-normalizes behavioral and neurological distortions in impulsivity in attentionally-impaired patient populations.

The training program 50 also includes novel distractor-suppression training components. Training is designed in an extended working memory challenge setting, where individuals are required to seek out specific low probability target stimuli amidst many related but irrelevant, distracting stimuli. The task is to maintain the target stimulus in working memory over extended time periods aided by trial-by-trial performance feedback, while simultaneously suppressing the distractions.

In other working memory tasks the trainee is cued to the identity of the working memory target trial by trial, or the task is designed with multiple possible targets held in working memory, or the working memory target itself changes trial by trial. In the training program 50, attentional focus is directed at a specific stimulus target over stimulus blocks lasting multiple minutes. With longer working memory spans, the subject literally perceives the crystallization and sharpening of the target, and essentially requires the suppression of the domain of distractors for successful task completion. Learning rates are accelerated by using a constant, unchanging anchor stimulus (i.e., target) held in working memory over long epochs.

Second, distractors are not background noise, which induce negative plasticity and degrade sensory signals. In the training program 50, distractors differ only in identity from the target but share all other features, e.g. identifying a tone target amidst tone distractors, phoneme targets amidst phoneme distractors, shape targets amidst shape distractors. As targets and distractors are in the same feature domain, distractors generate high sensory competition with the targets.

Third, with time, the training program 50 adaptively modulates only the distractors—not the targets—based on the individual's performance. Thus, correct discrimination performance leads to new distractions that resemble the target more closely. Incorrect performance leads to easier distractions that resemble the target less closely. This strategy effectively maintains a constant level of challenge and requires individuals to resolve progressively more similar stimuli, and as a consequence, simultaneously drives implicit improvements in perceptual resolution via successful distractor suppression.

The training program 50 provides participants continuous feedback about treatment progress, expressed directly and symbolically in an engaging meta-game 58. Frequent reward screens are presented, with game-like rewards marking the achievement of training benchmarks. Social network capabilities are mounted in the training program model. Participants are encouraged (with their clinician's Internet-delivered help) to form training "teams" in which all participants can work together on a "mission." The training program 50 also includes a set of assessment tools 51 that provide a basis for evaluating key default-system components in any participant. Based upon those assessments, the training program 50 provides a customized set of games to drive corrective improvements.

One embodiment of an ADHD training program suite 50 was conducted on 140 impaired children in a special school in New Delhi. This program suite embodied 28 game-like tasks designed to address arousal, decoding, brain speed, working memory, impulsivity, selective attention control and distraction suppression dimensions of ADHD. All games were playable on any Internet-connected computer with a moderate- to high-speed Internet connection. The program took about thirty hours of "game play" to complete.

The program suite 50 was constructed on a platform that fed all child compliance and performance outcome data via the Internet 'cloud' to a central database. With this architecture, the child could complete their training on any combination of Internet-connected computers. Information from this database could also be fed back via a 'clinician/parent portal' to support professionals and/or parents, as appropriate, to assure effective program use for every child.

4. Schizophrenia

Figure 11:
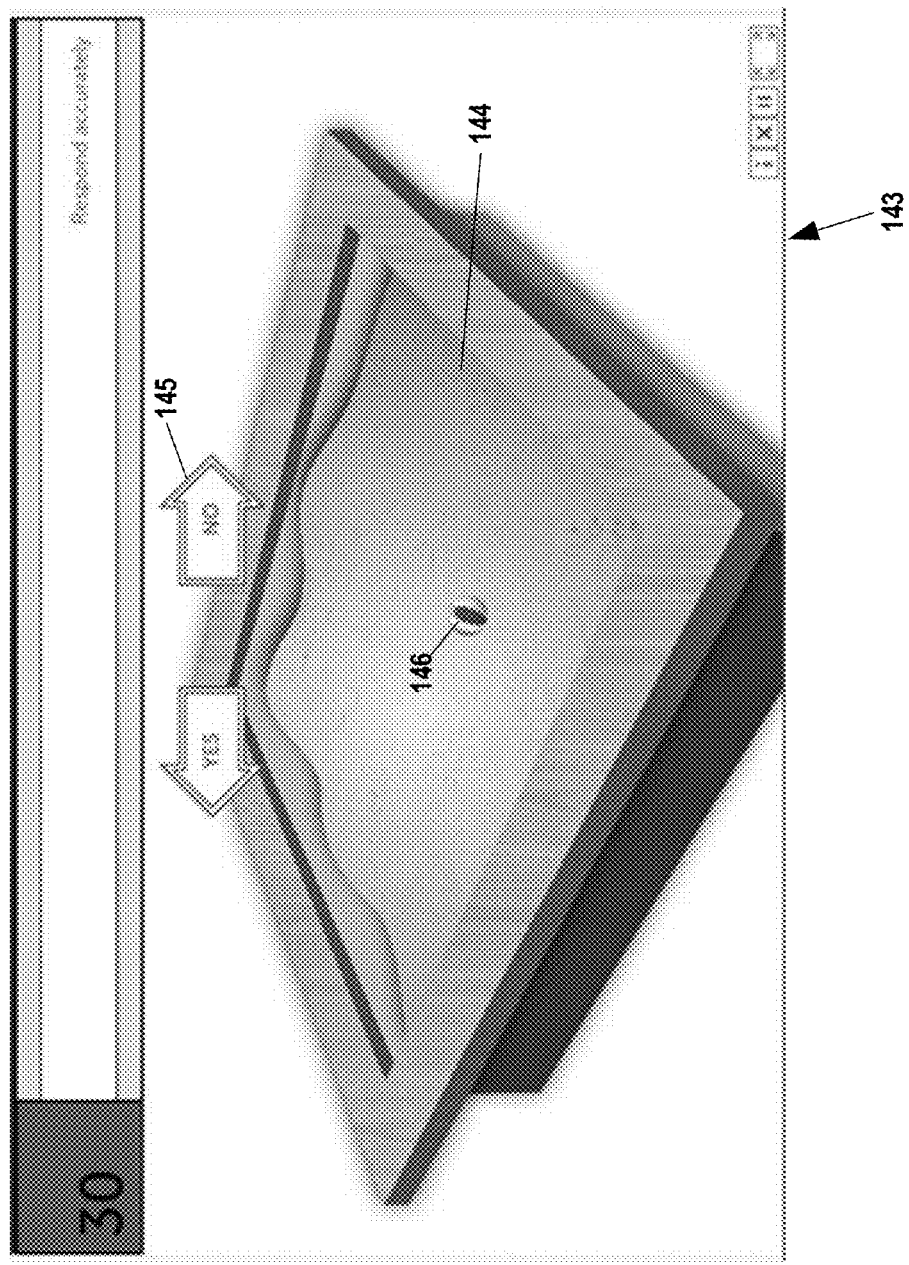
FIG. 11 illustrates another screenshot of the game illustrated in the previous figure.

Pervasive social cognition deficits are evident early in the course of schizophrenia and are directly linked to functional outcome, making them an important target for intervention. Here, we tested the feasibility of use, and initiated the evaluation of efficacy, of a novel, neuroplasticity-based online training program 110 called "SocialVille" in young adults with schizophrenia. As illustrated in FIG. 11, SocialVille comprises a set of processing speed games 112, working memory games 113, prosody detection games 114 and theory of mind games 115.

The training program 110 provides participants continuous feedback about treatment progress, expressed directly and symbolically in the engaging meta-game 116 called "SocialVille." Frequent reward screens are presented, with game-like rewards marking the achievement of training benchmarks. Social network capabilities are mounted in the training program model. Participants are encouraged (with their clinician's Internet-delivered help) to form training "teams" in which all participants can work together on a "mission." The training program 110 also includes a set of assessment tools 111 that provide a basis for evaluating key default-system components in any participant. Based upon those assessments, the training program 110 provides a customized set of games to drive corrective improvements.

exercises aim to improve efficiency of stimulus representation and processing speed in the specific neural systems that underlie social cognition, and have been shown to function abnormally in schizophrenia.

Table 3 below lists 19 computerized SocialVille exercises, most of which are described in further detail later in the specification. These exercises target speed and accuracy of neural functions dedicated to processing of social information. Specifically, the SocialVille exercises target the social cognitive domains of affect perception (both visual and vocal), social cue perception, ToM and self-referential processing. Using a computerized setting and speeded tasks, the participant is required to make hundreds of speeded, accurate, and increasingly more challenging discriminations of socially-relevant information (e.g., emotional faces, eye gazes, voices, social situations). Further, the exposure to socially relevant stimuli in SocialVille is systematic, targeted and progressive: training of each important sub-skill starts with very basic stimuli (e.g. front-facing faces, basic emotions, simple social interactions) and gradually becomes more complex, multi-modal, and ecologically-valid (e.g., complex social scenarios).

TABLE 3

Suite of games incorporated into one embodiment of a schizophrenia-treatment training program
SocialVille Exercises

| Domain | Game Name | Modality | Task |
| --- | --- | --- | --- |
| Speeded Exercises | Gaze Cast | Visual | Select the peripheral object |
| | Looky Lou | Visual | Match gaze direction of face |
| | Face It! | Visual | Match the same face from different angles |
| | Name That Feeling | Visual | Identify emotion that best expresses emotion of target face in still image |
| | Emotion Motion | Visual | Identify emotion that best expresses emotion of target face in video clip |
| | Poke That Feeling | Visual | Match faces with similar implicit emotions |
| | Mass Affect | Visual | Delayed match of the valence of a target picture |
| | TAPAT MDD | Visual | Withhold response for neutral faces, press for emotional faces |
| | Bright Whites | Visual | Select the smiling face when the faces keep changing |
| | What Just Happened? | Visual | Select the correct affective (facial) response in a given situation |
| Working Memory | Second That Emotion | Visual | Match pairs of facial emotion cards in a working memory task |
| | WM Facial Emotion - Clips | Visual | Match pairs of facial emotions and labels in a working memory task |
| | Second That Intonation | Auditory | Match pairs of vocal emotion cards in a working-memory task |
| | Face It: Flashback | Visual | Arrange the faces in the order they were presented |
| | Facial Emotion Span | Visual | Arrange the facial emotions in the order they were presented |
| | Face Facts | Visual | Memorize sequences of faces and personal facts on the faces |
| Other | Voice Choice | Auditory | Identify the emotional prosody of progressively shorter sentences that are intrinsically neutral. |
| | Life Stories | Auditory | Answer questions about ToM and social interactions in stories comprised of twenty segments each |
| | Say What? | Auditory | Select the correct prosody response in a given situation. |

SocialVille aims to treat social cognition deficits using the principles of neuroplasticity-based learning, by targeting the impaired brain systems underlying social cognition rather than the impaired social behaviors per-se that are targeted by molar social skills training approaches. The SocialVille The rationale behind this approach was applied to address general cognitive deficits in chronic schizophrenia, on the hypothesis that directly strengthening the fidelity of representations of socially-relevant information in the brain should improve an individual's social behavior. The exercises employ psychophysical principles of training and exploit implicit learning mechanisms. They continuously adapt in difficulty, based on individual performance. The participant learns through tasks that involve many socially-relevant stimulus examples while given feedback on correct and incorrect discriminations. These neuroplasticity-based principles provided the basis for the construction of SocialVille.

To assess feasibility, we predicted that at least 75% of enrolled participants would complete the training and that they would report satisfaction with the exercises with ratings of at least 4 on the 7-point Likert scale items. We measured learning rates by assessing improvement on the SocialVille exercises. We hypothesized that participants would show improvements on the trained exercises, as well as learning generalization to proximal social cognition measures. We explored whether more distal measures of functioning and motivation would improve with this form of computerized training.

Schizophrenia patients (n=17) completed twenty-four hours of online SocialVille game play either from home or at a clinic, over a six to ten week period. Subjects were instructed to complete six exercises per training day, each taking about ten minutes to complete. We examined training feasibility, gains on the SocialVille exercises relative to matched healthy controls (n=17), and changes on measures of social cognition, social functioning, global functioning and motivation.

SZ subjects met the following inclusion/exclusion criteria: diagnosis of schizophrenia, schizophreniform, or schizoaffective disorder via the Structured Clinical Interview for DSM-IV (SCID-IV); good general physical health; age eighteen to thirty-one years; premorbid IQ≥70 (estimated using WTAR); no neurological disorder or history of traumatic brain injury; and no substance dependence or serious substance use in the past six months. SZ Symptom severity at baseline was assessed using the Positive and Negative Syndrome Scale. Nine subjects were within two years of psychosis onset, seven more within five years, and that only one was more than five years from onset (7.2 years). All subjects had achieved clinical stability (outpatient status for at least three months prior to study participation) and were stable on psychiatric medications for at least one month prior to study onset.

Ten of the SZ participants, at a university-based early psychosis program at the University of California at San Francisco (UCSF) were either active or former patients at the early psychosis clinic (EPC), which provides medication management and some psychotherapy; for the duration of the study, four were receiving no treatment, three were receiving outside treatment, and three were seen at the EPC.

Seven of the SZ participants completed the study protocol at UCLA. They were enrolled in the Aftercare Program protocol, and all were receiving psychosocial treatment, medication, and case management there. None of the UCLA participants were in other cognitive remediation training during their SocialVille training.

Healthy control (HC) subjects (status verified through the SCID-Nonpatient edition) were recruited to match the SZ cohort at a group level in terms of age, gender and education.

Following informed consent, eligible SZ participants underwent baseline assessments. Subjects from the UCSF clinic (n=10) were then loaned laptop computers, given logins and asked to complete the intervention from home. The UCLA clinic subjects (n=7) came into the clinic twice a week to complete the intervention there, as they were already coming to the clinic twice each week anyway. Subjects from both sites were asked to complete twenty-four hours of training with the SocialVille online program (one to two hours per day, two to five days per week for six to twelve weeks). Following training completion, subjects completed the post-training assessment battery.

Following consent and initial screening, HC participants completed the SocialVille exercise-based assessments only, i.e. one block of every SocialVille social cognitive exercise. Subjects received monetary compensation for participating in the study. Assessments were conducted by psychology practicum graduate students (UCSF site) or by case managers and research assistants (UCLA site).

To evaluate SocialVille's training program feasibility and ease of use, we evaluated the attrition rate (the percentage of subjects who actually completed the twenty-four hours of training); adherence to training schedules (the number of training sessions/week); and the SocialVille program rating (upon completion of training, SZ subjects were asked to complete a questionnaire in which they rated enjoyment, satisfaction, ease of use, program attractiveness, frustration level and program security concerns using a seven-point Likert scale (1=strongly disagree through 7=strongly agree; 4=undecided).

To evaluate SocialVille's treatment effectiveness, performance levels on the SocialVille exercises (i.e. social cognition abilities) were assessed at baseline (SZ and HC participants) and post-training (SZ only) using the exercise-based assessments embedded in the SocialVille program. Each assessment is a single 'block' of each exercise (except for two exercises), for which performance threshold is determined using an adaptive staircase algorithm within 5-15 minutes. For each exercise-based assessment, we derived normalized (Z) scores relative to the mean score of the HC group on that assessment. This was done to allow the creation of composite scores by summing assessment scores across domains, and to more easily visually depict test scores across a variety of scales (e.g. reaction time in ms, number of correct items, % correct, etc.).

To further evaluate SocialVille's treatment effectiveness, social cognition outcome measures, functioning measures, and self-report motivation measures were obtained from the SZ group. The performance-based Penn Facial Memory Test assessed immediate and delayed (following thirty minutes) memory of neutral faces. The performance-based Prosody Identification Test assessed subjects' accuracy and reaction time in identifying the emotional prosody in a series of sentences. We also assessed the subjects' ability to perceive emotions and manage emotions using the performance-based Mayer-Salovey-Caruso Emotional Intelligence Test battery. Functioning was measured using the clinician-rated Global Functioning: Social and Role Scales assessed social and occupational functioning assessment. Social functioning was also assessed with the self-report Social Functioning Scale. Quality of life was evaluated using the clinician-rated Quality of Life Scale-Abbreviated. The self-report Behavioral Inhibition Scale/Behavioral Activation Scale was used to assess two motivational systems, each with a unique neural signature, that regulate approach and withdrawal behavior. Reward sensitivity was assessed with the self-report Temporal Experience Q4 of Pleasure Scale (TEPS; Gard et al., 2006), which assesses anticipatory pleasure and consummatory pleasure. Anticipatory pleasure is closely linked to motivation and goal-directed behavior while consummatory pleasure is associated with satiation (i.e. wanting versus liking). Research indicates that schizophrenia patients have a deficit in anticipatory pleasure, but normal consummatory pleasure.

All variables were screened and normally distributed after winsorising of outlying values. Group differences in gender were tested using a chi-square test. Independent Samples t-tests tested for group differences in age, education level, IQ and the exercise-based assessments. Paired samples two-tailed t-tests were used to examine whether SZ participants made significant gains on the training exercises and to test changes from baseline to post-training on all other outcome measures. Two-tailed tests with no correction for multiple comparisons were used because gains were hypothesized and because of the preliminary nature of the study.

Results. The HC and SZ groups did not differ significantly in gender or education. As is typical with this population, the groups differed slightly in IQ, with the difference approaching statistical significance ($F(1,32)=-1.95$; $p=0.06$).

Attrition Rate. Twenty-two (22) SZ participants were recruited (UCSF: n=13; UCLA: n=9). Seventeen completed the study. Five subjects (three from UCSF and two from UCLA) dropped out at initial phases (four before being given the training laptop and one after completing two training sessions). The reasons provided for dropping out were as follows: due to increased stress at work/school (n=2), hospitalization (n=1), boredom (n=1) and unknown reason (n=1). The attrition rate was not different for the two sites (23% and 22% at UCSF and 296

Compliance. Subjects were asked to complete two to five one-hour sessions of training per week for six to twelve weeks (twenty-four sessions total). On average, subjects took 8.1±2.5 weeks to complete training (range: five to twelve weeks), with only four subjects taking more than ten weeks to complete the program. The average number of weekly sessions completed was 3.15±0.8.

Satisfaction. Following training, subjects rated their satisfaction in playing SocialVille on a seven-point Likert scale. The following averaged ratings were obtained: (a) Satisfaction rating ('I felt satisfied after the training') of 5±1.9 (5 corresponds to 'somewhat agree'); (b) Program clarity rating ('the exercise instructions and tutorials were easy to understand') of 6±1 (6 corresponds to 'mostly agree'); (c) Ease of navigation rating ('the program was easy to navigate') of 5.8±1.3; (d) Ease of use rating ('the program makes it quick and easy for me to start playing each day') of 4.7±2 and ease of fit into daily schedule ('the program easily fits into my daily schedule') of 4.5±1.8; (e) Attractiveness rating ('the program graphics were attractive') of 4.5±1.9; (f) Program usage difficulty ("the program was difficult to use") was rated as 3.06±2.1 ('somewhat disagree'); (g) Security concerns of using the online program ('I was worried about the security of my log-in account') were 2.3±1.9 (corresponding to 'mostly disagree' with the statement).

Figure 2:
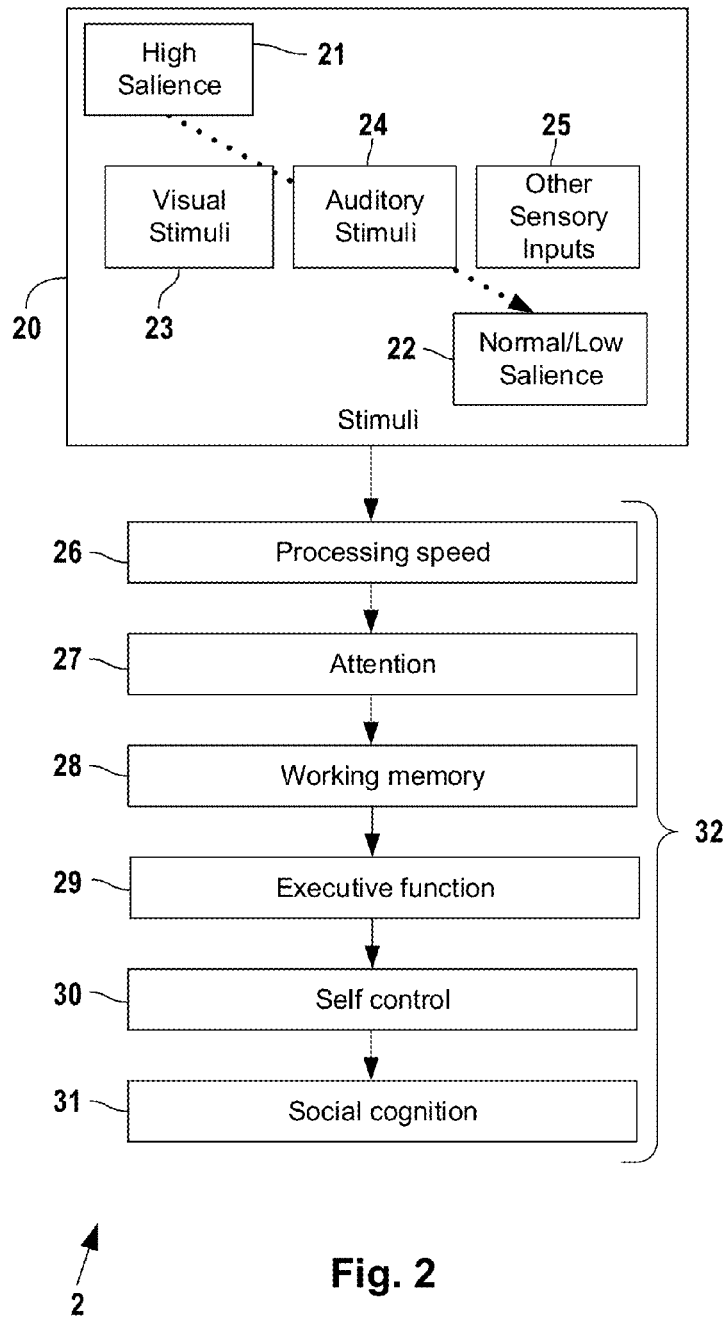
FIG. 2 is a block diagram of one embodiment of a curriculum of a neurological training program configured to treat one or more mental disorders or cognitive deficits.

Exercise-Based Assessments. For 17 of the 19 SocialVille exercises, we calculated a normalized z-score for the SZ group relative to the HC baseline performance on each exercise. On the 'speeded' SocialVille exercises (i.e. tasks that required speeded processing of stimulus on every trial, significant z-score changes from baseline to post-training were evident on all but one of the exercises (two were at trend-level). Following training, patients' performance on these tasks was similar to that of the initial performance of the HC group. On the six "working memory"-based SocialVille exercises, improvements were evident on five of the exercises, however only one of these reached statistical significance (FIG. 2B). We further derived composite scores for the speeded tasks, the WM tasks and a total composite score. Significant z-score changes were seen on all composite scores (speeded: $t(16)=-6.9$, p b 0.0001; WM: $t(16)=-2.6$, p b 0.02; Total: $t(16)=-7.4$, p b 0.0001). The pre- to post-test gain on the speeded task composite score was large (1.15 SD), while the gain in the WM composite score was small to moderate (0.45 SD).

Social Cognition Outcome Measures. The median RT for correct responses of the Penn Facial Memory test significantly decreased for both immediate and delayed recall. Following training, prosody identification accuracy showed a non-significant tendency to increase and median RT significantly decreased. No significant changes were seen on the perceiving emotions or managing emotions subscales of the MSCEIT test.

Functioning. Subjects showed a significant increase in GFS's social functioning, and no significant change in role functioning. On the SFS there was a trend-level increase on the interpersonal communication subscale, and no significant change on the other SFS subscales. There were no significant changes on the Quality of Life Scale.

Motivation/Reward Sensitivity. We found a significant decrease on the Behavioral Inhibition Total scale and a trend-level increase in the Behavioral Activation-Drive subscale. Changes on the two other BIS/BAS subscales were non-significant. We found an increase on the TEPS Anticipatory Pleasure subscale and no significant change on the Consummatory Pleasure subscale.

Discussion

We tested the feasibility and preliminary efficacy of SocialVille, a new online training program targeting deficits in social cognitive processing speed and working memory (WM) in young adults with schizophrenia. Following twenty-four hours of training performed over a six to twelve week period, we found: relatively high adherence with the training requirements; satisfaction with the exercises; significant pre- to post-training improvements on the SocialVille social cognition exercise composite scores; significant improvements on proximal measures of social cognition (prosody identification and facial memory); and significant improvements on social functioning, motivation and reward sensitivity. These findings suggest that an online training approach is feasible in early psychosis, and that social cognitive deficits may be addressed early in the course of schizophrenia. Given the importance of early intervention, and the link between social cognition and functional outcome in schizophrenia, this study provides an initial scalable way of targeting a set of critical core deficits. Although promising, the results are preliminary and not case-controlled. An appropriately powered, randomized controlled trial is required to determine whether these effects are replicable.

To the best of our knowledge, our study is the first to demonstrate the feasibility of online social cognitive training in young adults with schizophrenia. Two other studies tested the feasibility of social cognitive training in early psychosis, both using group-based interventions administered in clinic. CET uses computerized 'cold' cognition training with group-based social skills training. SCIT is a group-based therapy as well, comprised of 18 sessions focused on three phases of understanding emotions, social cognitive biases, and integration, in which trainees practice the acquired social skills in everyday situations. These two interventions, although including some computer-assisted parts, are administered in a therapist-instructed group format.

Here, we show the feasibility of a fully-computerized intervention, which can be completed either at home or at the clinic, using internet-connected computers. Gains were obtained after a relatively short period of treatment (less than twelve weeks). The attrition rate in our study is similar to other training studies in young clinical populations. Moreover, the high compliance with the training schedule indicates that this form of individual online training is feasible with young adults, comparable to clinic-based group training. We note that at-home participants needed weekly phone-calls and/or emails to reliably adhere to training requirements, thus clinical staff involvement in the form of solution-focused conversations was still required. Future studies will determine whether combining our computer-based training with psychosocial interventions (e.g. social skills groups) enhances generalization. Still, our study provides the first demonstration of a potentially highly-scalable form of treatment that could be easily used in practically every household or clinical facility equipped with an internet connection, thus providing treatment options to under-resourced areas and to patients who are unable or unwilling to come in to the clinic.

Study participants made larger gains on the 'speeded' SocialVille composite (i.e. processing speed of social information), whereas improvements on the 'WM' composite (i.e. WM manipulations of social information) were smaller. The fact that large pre-post gains were found in processing speed is encouraging: recent 'cold cognition' studies consider speed of processing deficits among the largest cognitive impairments in recent-onset schizophrenia and hence an important target for early intervention. While speed of processing during "cold cognition" tasks and social cognitive tasks may be quite different, our results suggest that speed-of-processing deficits of social information are evident in early psychosis, and that training drives improvements in this fundamental ability.

Although there are currently no rigorous studies of computerized social cognition training in early schizophrenia, our outcomes are comparable to recent reports of social cognition training in chronic schizophrenia, and further strengthen the notion that social cognition is linked to social functioning and functional outcome in schizophrenia. Interestingly, while SocialVille includes training on facial affect, we did not find significant changes on the MSCEIT emotion perception and management subscales. However, our findings still suggest that subjects improved on emotion recognition abilities, as is evident by improvements on SocialVille emotion exercises and on vocal affect recognition. We hypothesize that this negative result is likely due to the focus of SocialVille on processing speed, while affect perception and management is measured differently in the MSCEIT. The short duration of training relative to that included in other studies might have also contributed to the lack of improvement on the MSCEIT.

Following training, participants improved on motivation and reward sensitivity: participants showed decreased behavioral inhibition and increased drive, as well as increased anticipatory pleasure. To our knowledge, this is the first demonstration of changes in motivation following cognitive training in early schizophrenia. Interestingly, motivation is generally considered a stable trait in healthy individuals, not subject to change. A few recent reports have shown that motivation plays a significant and mediating role between neurocognition, social cognition and functional outcome. Our preliminary finding that motivation can be enhanced with social cognitive training provides strong support for this model, and further stresses the importance of targeting social cognition in schizophrenia.

Our study had several limitations. These include the small sample size, the lack of a control group, and the fact that participants were provided remuneration for participation in the study. Further, we cannot rule out practice effects or non-specific effects of study participation. These factors all limit our ability to attribute improvements to the SocialVille training itself. Furthermore, since the main goal of the study was to establish feasibility in early schizophrenia patients, no general cognition and symptom outcome measures were included.

Future, well-controlled studies are required to further establish the efficacy of computerized social cognitive training administered with no additional neurocognitive training. Also, the results of our pilot study do not rule out the possibility that improvements are driven by non-specific effects of training such as increased attention span or general improved processing speed. Still, results from several recent studies imply that non-social cognitive training does not improve social cognition and social function. Finally, we note that there is currently no consensus on the best social cognition outcome measures to be used in intervention studies, as many of them are considered to have poor psychometric characteristics. Future studies should consider applying additional or different outcome measures, given new psychometric information on outcome measures.

Other Studies. Another independent study at Harvard included fourteen young (age: 21.9±4) participants at clinical high risk for schizophrenia who completed SocialVille training and cognitive training over four to eight weeks. fMRI scans were conducted before and after training, during which participants performed an emotion identification task. These scans revealed group-level increases in activation in the fusiform gyrus and SRC following training. Both of these areas are known to be critically involved in emotion perception. Furthermore, changes in fusiform activation were correlated with changes in SC and predicted changes in social function, supporting the notion that training induced these positive changes. These data support SocialVille's efficacy in young individuals at high risk, and provide evidence for the neural-level changes at underlying SC brain areas, brought-about with training.

Yet another independent study at UCSF involves in an ongoing double-blind RCT of chronic schizophrenia patients that received SocialVille+cognitive training (TCT; n=17). This study shows gains compared to an active computer games control (CG; n=10) in emotion management (TCT: $p=0.06$; CG: $p=0.52$), emotion perception (MSCEIT; TCT: $p=0.07$; CG: $p=0.26$), ToM (interaction: $p=0.03$), and functional outcome (UPSA-B communication subscale83; TCT: $p=0.08$; CG: $p=0.52$). A subset of participants performed a Monetary Incentive Delay task to assess motivation for upcoming reward pre- and post-training. At baseline, patients showed no activation in ventral striatum (VS) and medial prefrontal cortex (mPFC) during reward anticipation, unlike healthy controls (HCs). Following training, activation increased in VS and mPFC during reward anticipation, similar to HCs. Thus, SocialVille training induced recruitment of relevant brain regions mediating motivation for an upcoming reward.

We conclude that SocialVille is a promising intervention which is feasible and resulted in initial positive outcomes in social cognition, social functioning, and motivation in young individuals with schizophrenia. Given the importance of early intervention, and the lack of effective treatment options, there is a clear need for effective, scalable treatments. Future randomized controlled trials will determine whether these preliminary findings are replicable and are needed to discover the 'active ingredients' of training that allow for learning to transfer to everyday functioning.

5. Distorted Time Tracking

Distorted time perception is seen in various neurological and psychiatric disorders, including addiction, attention deficit hyperactivity disorder (ADHD), autism, schizophrenia, traumatic brain injury, and Parkinson's disease. It is also seen in normal aging elderly adults. People who tend to perceive time passing more quickly also tend to discount the future more heavily, preferring small rewards delivered sooner over bigger rewards delivered later. Abnormal time perception involves a range of brain areas—basal ganglia, prefrontal cortex, inferior parietal cortex, premotor cortex, pre-supplementary motor area, supplementary motor area, and cerebellum. Further, many of these areas operate in networks.

Damage to the prefrontal-inferior parietal network in the right hemisphere, but not the left, results in temporal distortions. Patients with lesions to the right hemispherical network also have difficulty switching their nonspatial attention, though patients with lesions in either hemisphere had attention deficits overall. Attention and working memory contribute to time perception even in healthy subjects.

Focusing on the timing of visual stimuli increases metabolic activity in the corticostriatal network involving basal ganglia, pre-supplementary motor areas, among other areas. Focusing on the color of the stimuli increases activity in area V4. Hence, we hypothesize that attending and training on temporal properties of stimuli should consequently exercise these networked brain areas by inducing plastic changes to them.

Subjective duration of stimuli is influenced by information coming from different sensory systems. An auditory event can appear shorter or longer when presented simultaneously with conflicting visual information. Thus, we hypothesize that cognitive training of time may benefit from first training single sensory modalities, and then training across modalities.

IV. Processing Speed Games

Each training program 2 includes, and begins with, a set of processing speed games. These games train the participant to pick up on details or changes in visual and auditory stimuli as quickly as possible. For example, in a sensorimotor reaction time game (not shown) called "Spotted," the participant is challenged to press the spacebar as soon as they see a green circle appear on the screen.

V. Attention Games

Each training program 502 also includes a set of attention and sensory discrimination games. These games train the participant to focus on certain objects or features of objects, while ignoring other objects (suppressing irrelevant stimuli). Characteristic games suitable for the training program 502 include the Odd Beep and Beep Seeker games described in WO 2012009117 A1 and WO 2012005953 A1, which are herein incorporated by reference.

A. Sensory Discrimination

In one embodiment, the training program 2 comprises twenty-five games in three groups: 1) Odd Out 2) Recall 3) Seeker. All three groups of games have at least eight variants, of which four are visual and four are auditory. Visual variants use the following stimuli: (i) orientation lines (ii) shapes of different colors and patterns (iii) directional motion and (iv) scenic images. Auditory variants use the following stimuli: (i) pure tones (ii) sound sweeps (iii) phonemes and (iv) words. These stimuli sets train different hierarchical aspects of the visual and auditory sensory systems. A ninth type of Odd Out variant uses both auditory and visual stimuli.

The "Odd Out" games train enhancement of a deviant signal amidst a constant background of distractions. The game challenge increases with correct performance as the deviant signal becomes weaker and weaker and starts blending with the background distractions and becomes more difficult to discriminate.

The first "Odd Out" variant is "Odd Lines," which requires the participant to discriminate a deviant line pattern on each trial amongst a constant background of lines. The second "Odd Out" variant is "Odd Shapes," which requires the participant to discriminate a deviant shape on each trial amongst a constant background of shapes. Other odd out variants require the participant to discriminate deviant directions of motion, scenes, beeps, sweeps, sounds, and words amongst constant backgrounds of the same type of stimuli. The "Odd Duo" variant requires the participant to discriminate an audiovisual mismatch on each trial amongst a constant background of matched sounds and visuals.

Generally, each "Odd Out" game presents a set of stimuli, all belonging to a common stimulus category, wherein one of the stimuli deviates from the rest of the stimuli; and challenges the game participant to indicate whether any of the patterns displayed was incongruous with the other presented stimuli. After receiving the participant's response, the "Odd Out" game indicates to the participant whether the participant's response was accurate and repeats the preceding steps over multiple repetitions. The game adapts to the participant's performance by changing the number of objects or stimuli and speed at which the objects or stimuli are presented during the game.

The "Recall" games train suppression of explicit distractions that appear during the memory period of a delayed working memory task; hence these games also explicitly train working memory. As the participant's performance improves, the game challenge increases by increasing the number of distracting signals and decreasing their differentiability from the remembered targets.

The first "Recall" variant is "Line Recall," which requires the participant to remember a target line pattern while ignoring various line distractors. The second "Recall" variant is "Shape Recall," which requires the participant to remember a target shape pattern while ignoring various shape distractors. Other "Recall" variants require the participant to remember a target motion direction, scene image, beep, sound sweep, phonemic sound, or word while ignoring distractors of the same type of stimuli.

In general, each "Recall" game presents a first stimulus or set of stimuli belonging to a stimulus category during a first interval of time; ceases presentation of the first stimulus or set of stimuli; presents a series of distractor stimuli belonging to the same stimulus category during a second interval of time; challenges a game participant to ignore the distractor stimuli; prompts the game participant that a challenge stimulus or set of stimuli is about to be presented; presents the challenge stimulus or set of stimuli; and challenges the participant to respond by identifying whether the challenge stimulus or set of stimuli matches the first stimulus or set of stimuli. After receiving the participant's response, the game indicates to the participant whether the participant's response was accurate. The game repeats the preceding steps over multiple repetitions using progressively longer second intervals of time. The games adapt to the participant's performance by changing the number of objects or stimuli and speed at which the objects or stimuli are presented during the game.

The "Seeker" games train suppression of implicit distractions as the participant discriminates a pre-defined target from all other stimuli. All stimuli other than the target form the implicit distractions. These distractions are implicit as opposed to explicit, as the participant continually decides whether a stimulus is or isn't a distractor. The longer the participant can discriminate targets from distractors, the better. The game challenge increases with correct performance as the distracting signals become more similar to the target.

One "Seeker" variant is "Beep Seeker," which requires the participant to discriminate a pre-defined target beep in each trial amidst other beep distractors. Another "Seeker" variant is "Sweep Seeker," which requires the participant to discriminate a pre-defined sound sweep in each trial amidst other sound sweep distractors. Other "Seeker" variants require the participant to remember a line, shape, motion direction, scene image, phonemic sound, or word while ignoring distractors of the same type of stimuli.

In general, each "Seeker" game presents a first stimulus or set of stimuli belonging to a stimulus category during a first interval of time; ceases presentation of the first stimulus or set of stimuli; presents a second stimulus or set of stimuli belonging to the same stimulus category during a second interval of time; and challenges the game participant to indicate whether the target stimulus or set of stimuli was present in the second stimulus or set of stimuli. After receiving the participant's response, the "Seeker" game indicates to the participant whether the participant's response was accurate. The "Seeker" games repeat the preceding steps over multiple repetitions using progressively longer second intervals of time. The games adapt to the participant's performance by changing the number of objects or stimuli and speed at which the objects or stimuli are presented during the game.

B. Divided Attention Games

Figure 6:
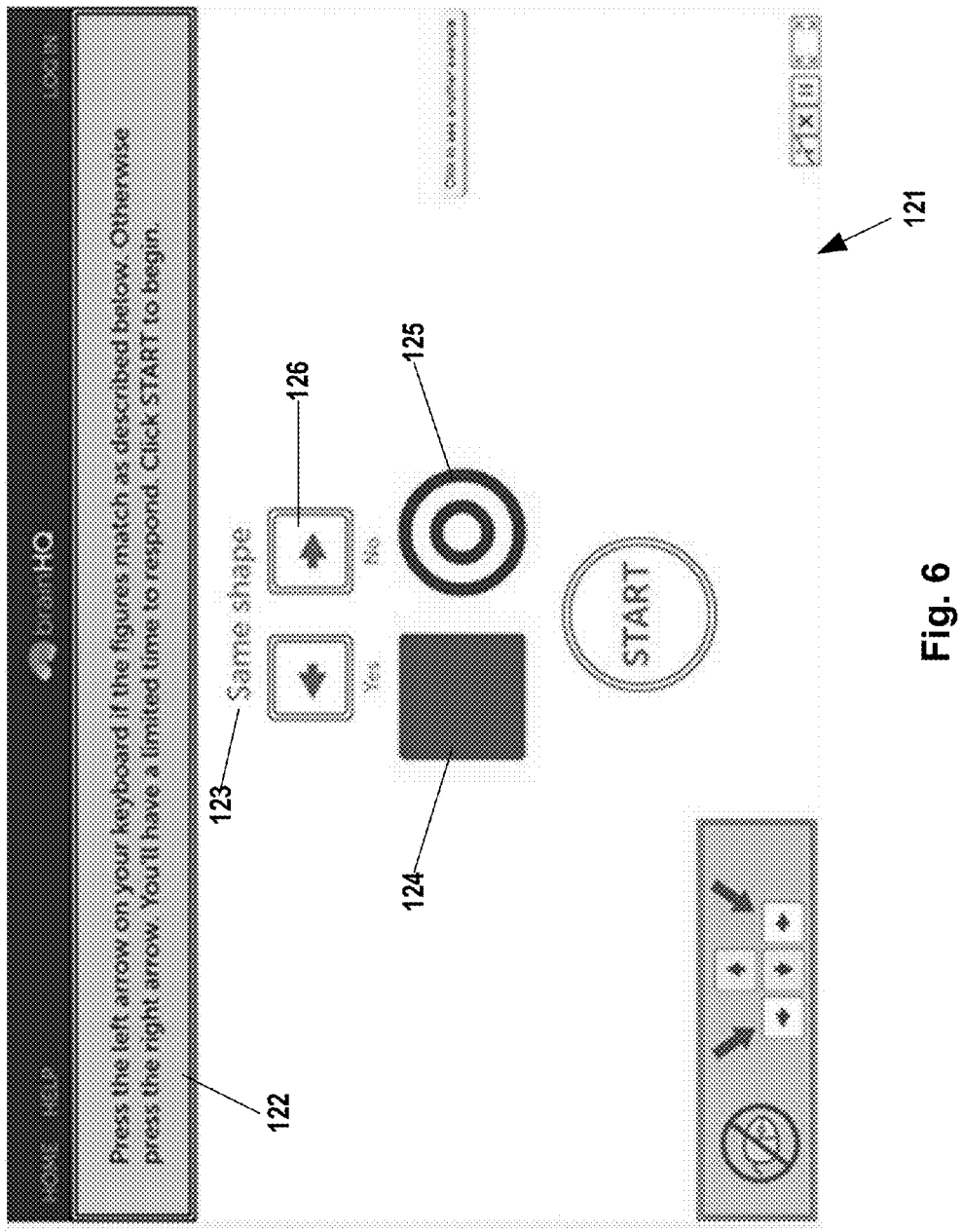
FIG. 6 illustrates a screenshot of one embodiment of a divided attention game called "Task Switcher," which challenges a game participant to identify whether two objects share a target characteristic, wherein the target characteristics change unpredictably.
Figure 7:
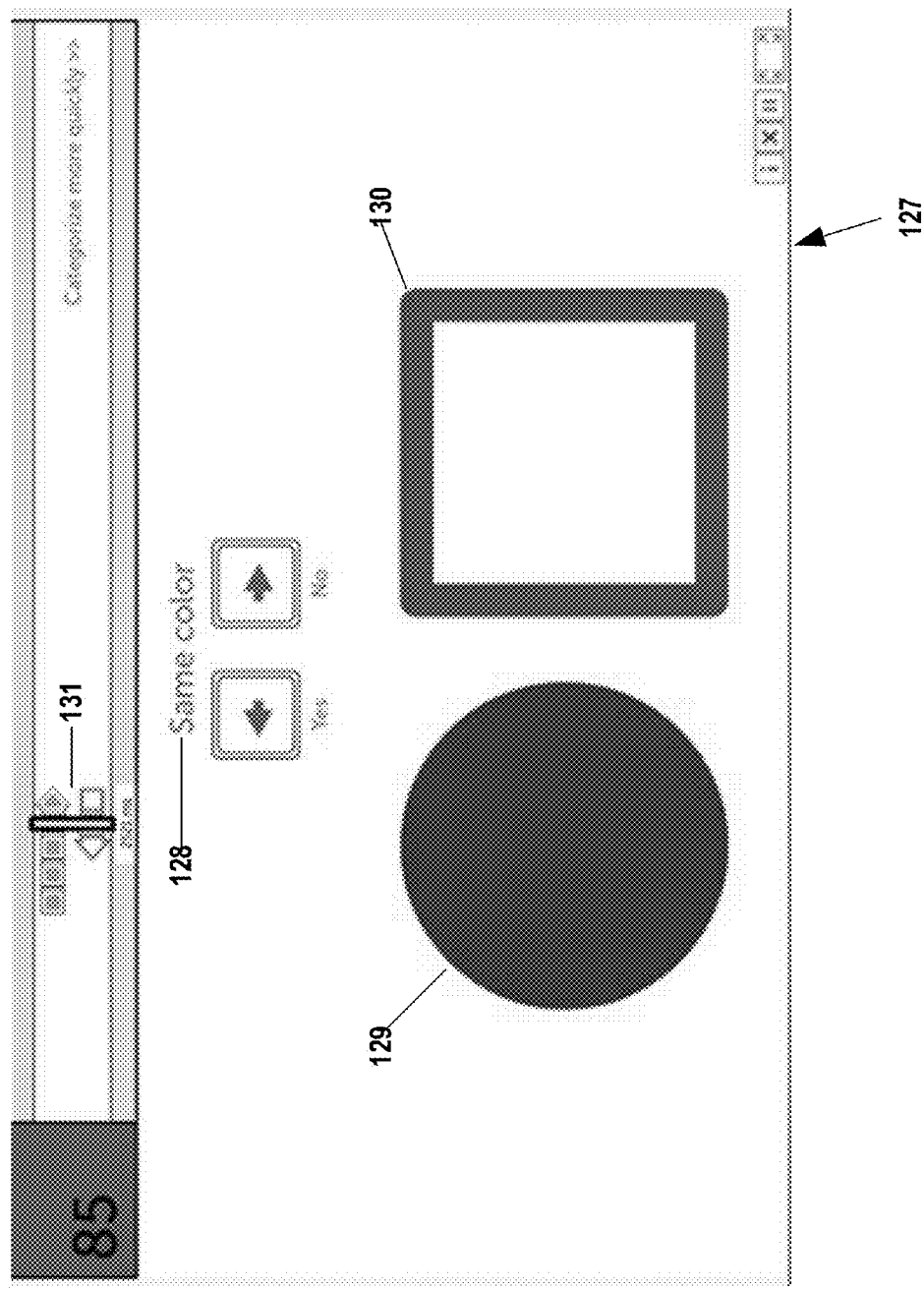
FIG. 7 illustrates another screenshot of the game illustrated in the previous figure.

In another embodiment, the training program 392 comprises one or more divided attention games. FIGS. 6 and 7 illustrate two screenshots 121, 127 of one embodiment of a divided attention game and game called "Task Switcher," which challenges a game participant to identify whether two stimuli share a target characteristic, wherein the target characteristics change unpredictably.

The game gives the participant a general instruction 122 and a specific rule 123, 128 to follow, like matching objects based on shape or color or pattern. The game presents two stimuli 124, 125 and challenges the participant to indicate— for example, by selecting an appropriate arrow button 126— if they match based on the current rule. The game presents a new set of stimuli 129, 130 with each trial. Also, the rules 123, 128 change—for example, from "same shape" to "same color"—after a block of trials or in an unpredictable manner between trials. The participant must respond quickly, because the trials keep proceeding even without participant input. The game registers an accurate response with a pleasant sound such as a "ding" and an inaccurate response with an unpleasant sound such as a "thunk." To prod the participant to respond more quickly, the game presents an indication 131 of the participant's speed (which may be a moving average) or speed category.

This cognitive training game and game improves executive function, attention, and working memory. It also improves overall speed and accuracy of audio and/or visual processing, audio and/or visual working memory retention and retrieval, and attention.

It should be noted that the particular game disclosed herein is meant to be exemplary, and that other repetition-based cognitive training games using audio/visual stimuli with multiple stimulus sets may be used, singly or in combination. The game described herein is but one example of a cognitive training game using a computing system to present audio/visual stimuli to a participant, record the participant's responses, and modify some aspect of the stimuli or its presentation based on these responses, where these method elements are repeated in an iterative manner using multiple sets of stimuli to improve the executive function, attention, and working memory of the participant. Such cognitive training may include a variety of such audio/visual stimulus-based games, including in a coordinated manner.

B. Sensorimotor Impulse Suppression

Figure 8:
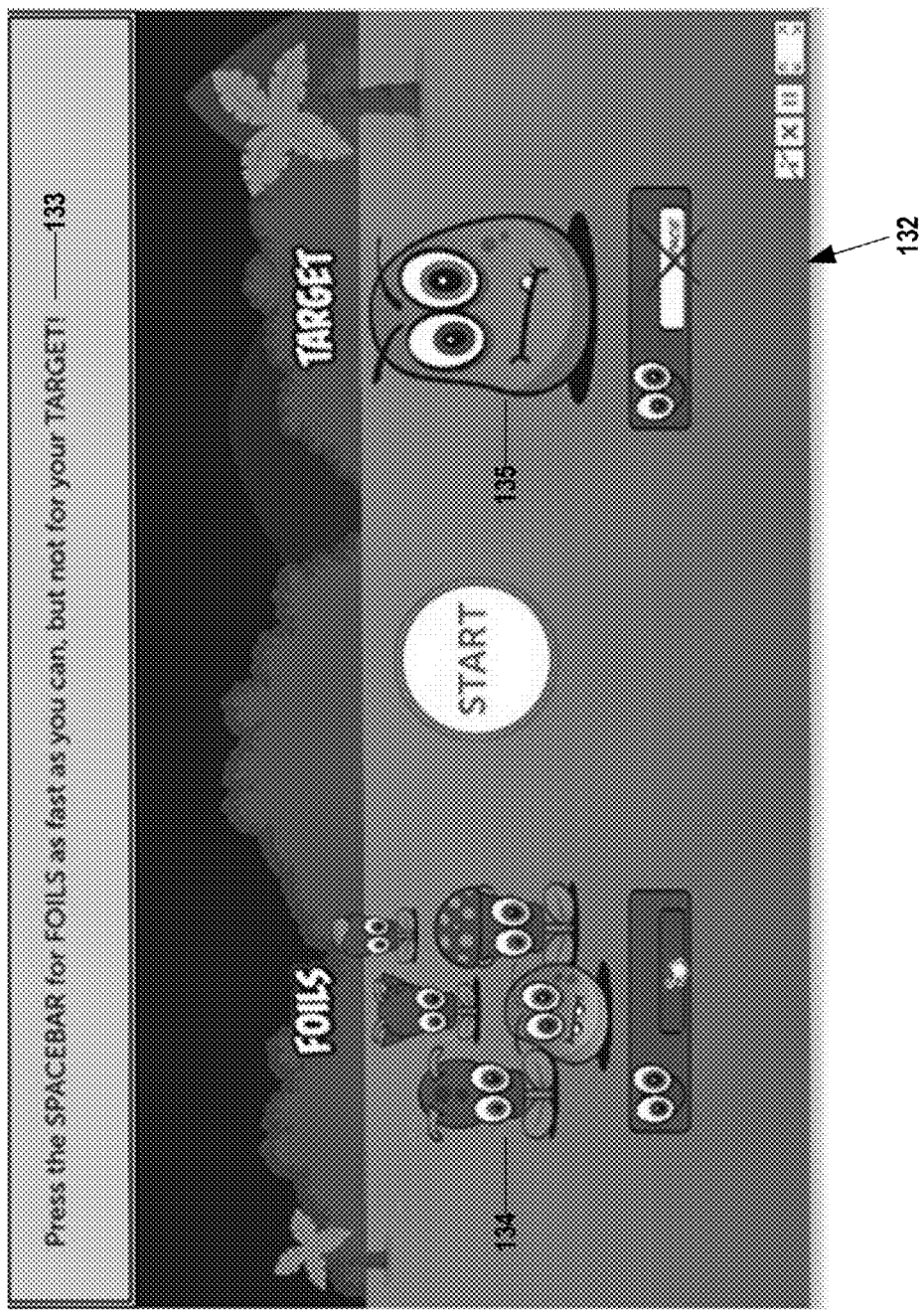
FIG. 8 illustrates a screenshot of one embodiment of a game called "Wango Mango," which challenges a game participant to press the spacebar whenever an image appears that is not the target, but to withhold pressing the spacebar if the image appears.
Figure 9:
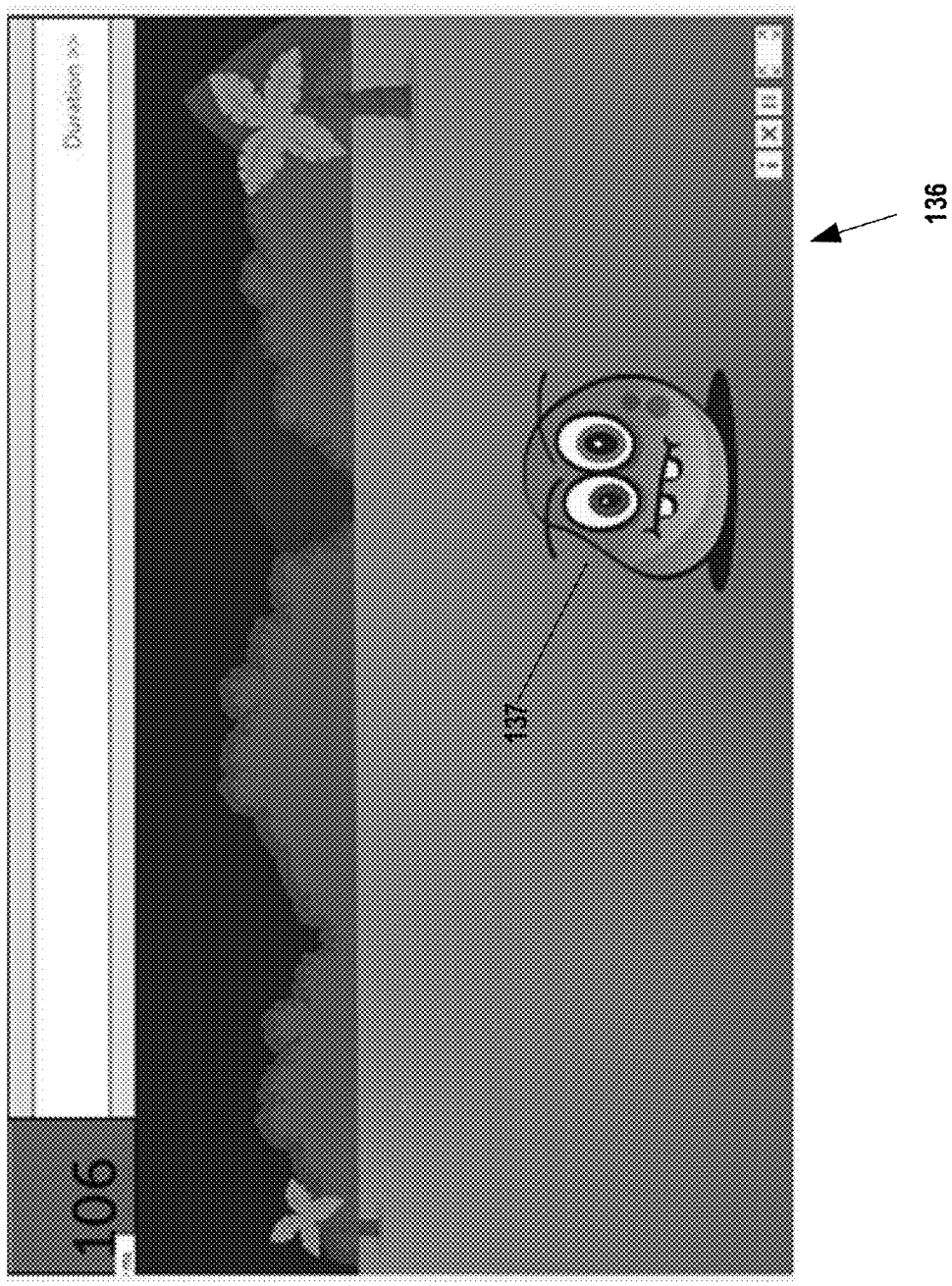
FIG. 9 illustrates another screenshot of the game illustrated in the previous figure.

In another embodiment, the training program 2 comprises one or more sensorimotor impulse suppression games. FIGS. 8 and 9 illustrate two screenshots 132, 136 of a visuospatial information assessment task called "Wango Mango," which challenges a game participant to press the spacebar whenever an image appears that is not the target, but to withhold pressing the spacebar if the image appears.

Wango Mango displays a target stimulus 135 and examples of a plurality of foil stimuli 134 and prompts 135 the game participant to respond as quickly as possible (for example, by pressing the space bar) to foil stimuli while refraining from responding to the target stimulus.

VI. Working Memory Games

Each training program 2 also includes a plurality of working memory games. These games train the participant to remember details in short-term memory. The details can be visual or auditory stimuli, and they can relate to objects or people. As the participant improves, the number of items to remember increases. The participant may also need to manipulate the items like reorder them to produce the correct response on a trial. In embodiments of the training program 2 configured for addicts, participant-specific distractors may appear within the games.

1. Spatial Memory

Figure 10:
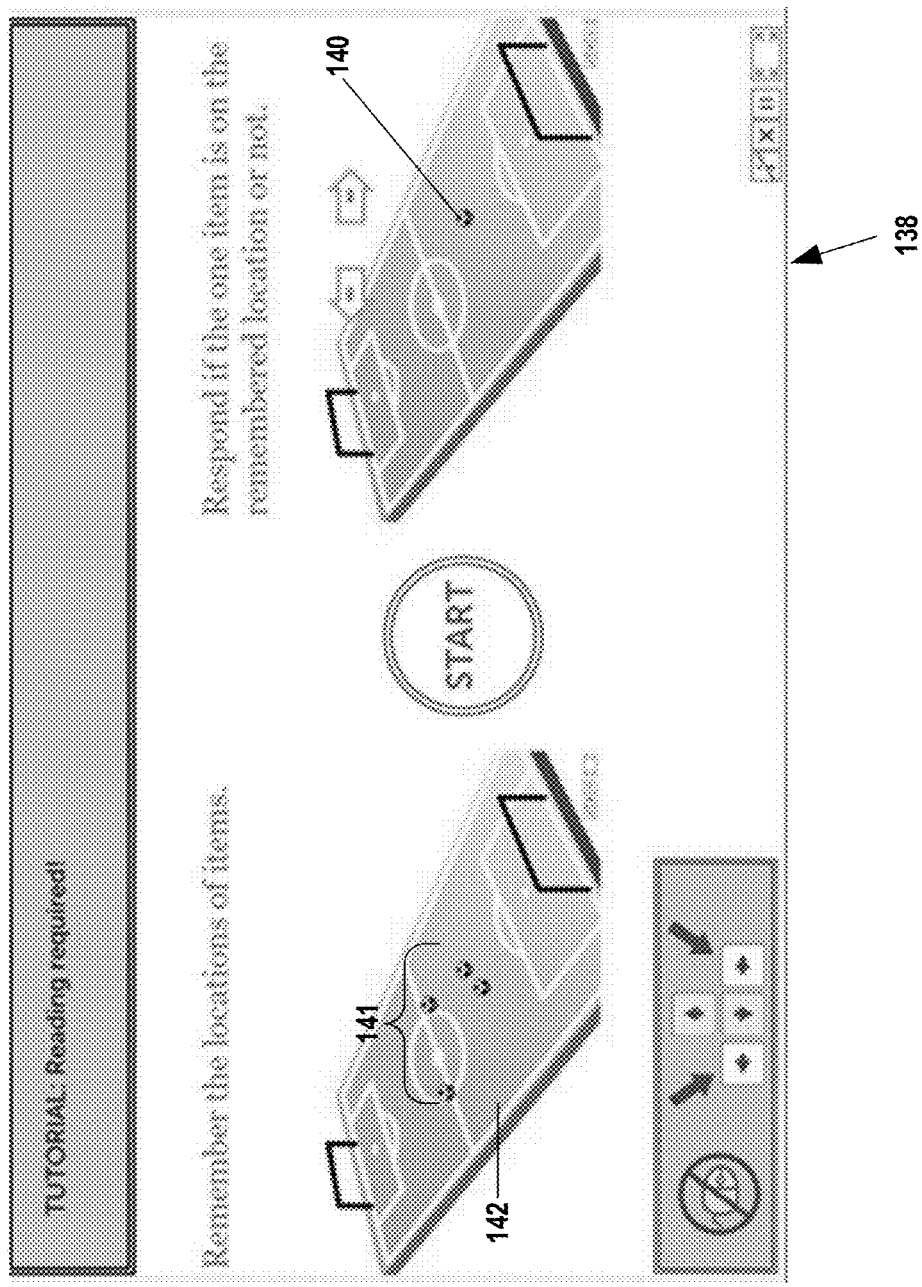
FIG. 10 illustrates a screenshot of one embodiment of a working memory game called "Spatial Memory," which challenges a game participant to memorize the locations of several objects and thereafter respond if the object is at a remembered location.

FIGS. 10 and 11 illustrate screenshots 138, 143 of one embodiment of a visuospatial working memory game called "Spatial Memory," which challenges a game participant to memorize the locations of several objects and thereafter respond if the object is at a remembered location.

Spatial Memory displays a first set of spatially distributed elements—for example, a plurality of balls 141 superimposed on a representation of a boundary-marked playing area such as a soccer field 142 or sandbox 144—on a physical display for a first time interval. Spatial Memory then clears the first set of spatially distributed elements from the physical display, replacing it with a visual mask. Next, Spatial Memory displays the challenge element 140, 146 on the physical display for a second interval of time. Spatial Memory prompts 145 the participant to indicate whether the challenge element is located in the same position as one of the first set of spatially distributed elements. After receiving the participant's response, Spatial Memory indicates whether the participant's response was accurate. Spatial Memory repeats the preceding steps over multiple repetitions. As the participant's performance improves, Spatial Memory uses progressively larger first sets of elements and progressively shorter first and second time intervals.

2. Brainville

FIGS. 12-23 illustrate screenshots 147, 150, 153, 156, 159, 161, 164, 167, 170, 173, 176 and 179 of one embodiment of a sequential visual memory game called "Brainville," which challenges a game participant to recall the progression of a journey, the objects seen along that journey, and the order in which those objects were seen.

Figure 12:
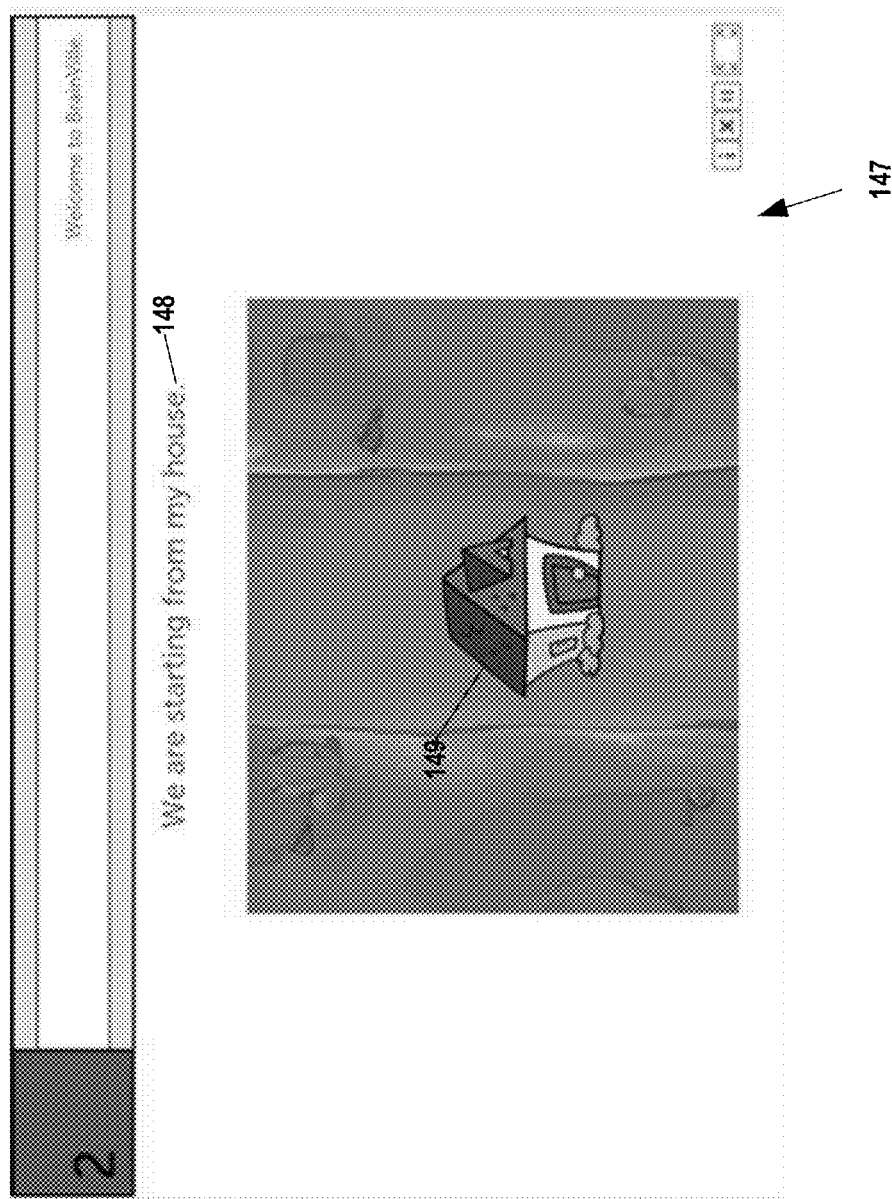
FIG. 12 illustrates a screenshot of one embodiment of a navigation game called "Brainville," which challenges a game participant to recall the progression of a journey, the objects seen along that journey, and the order in which those objects were seen.
Figure 13:
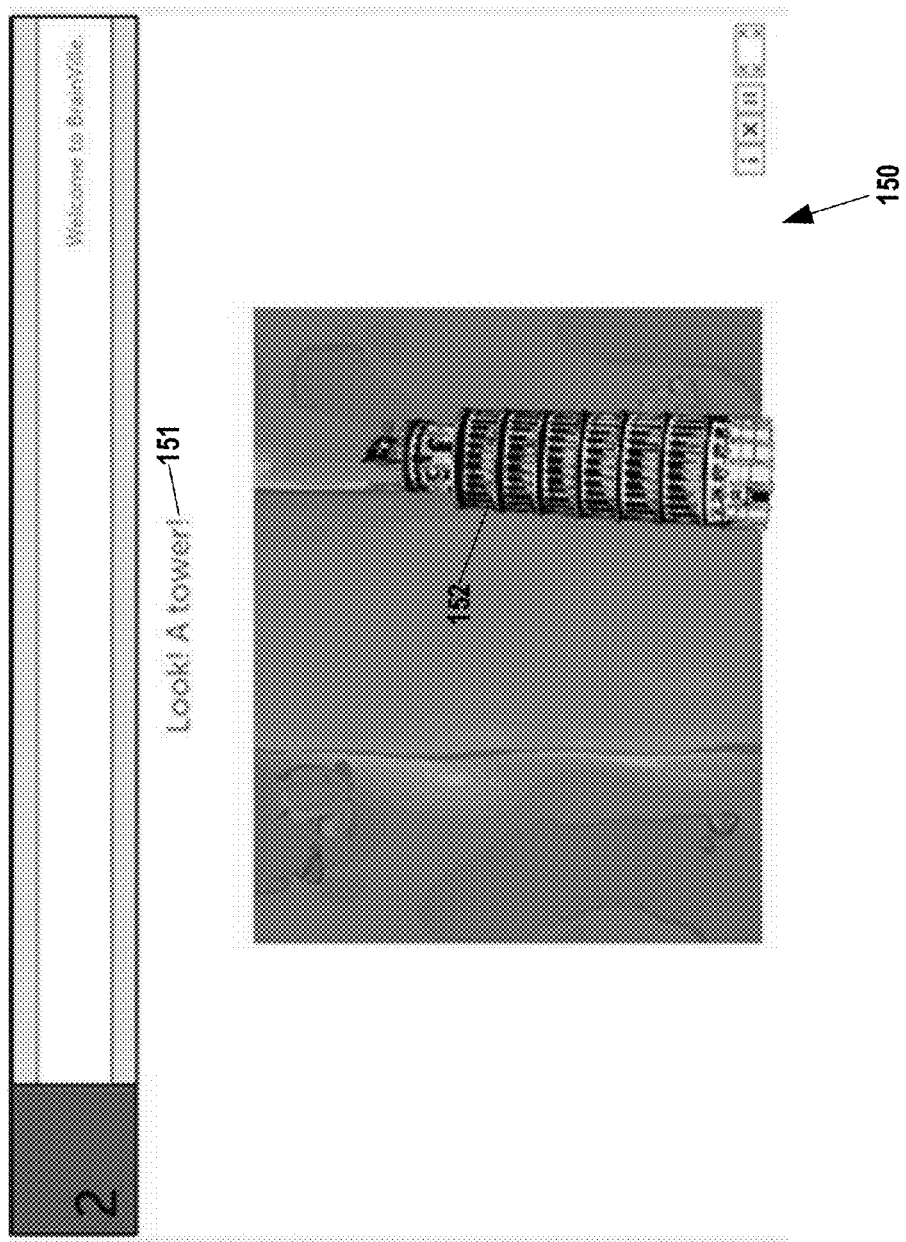
FIG. 13 illustrates another screenshot of the game illustrated in the previous figure.
Figure 14:
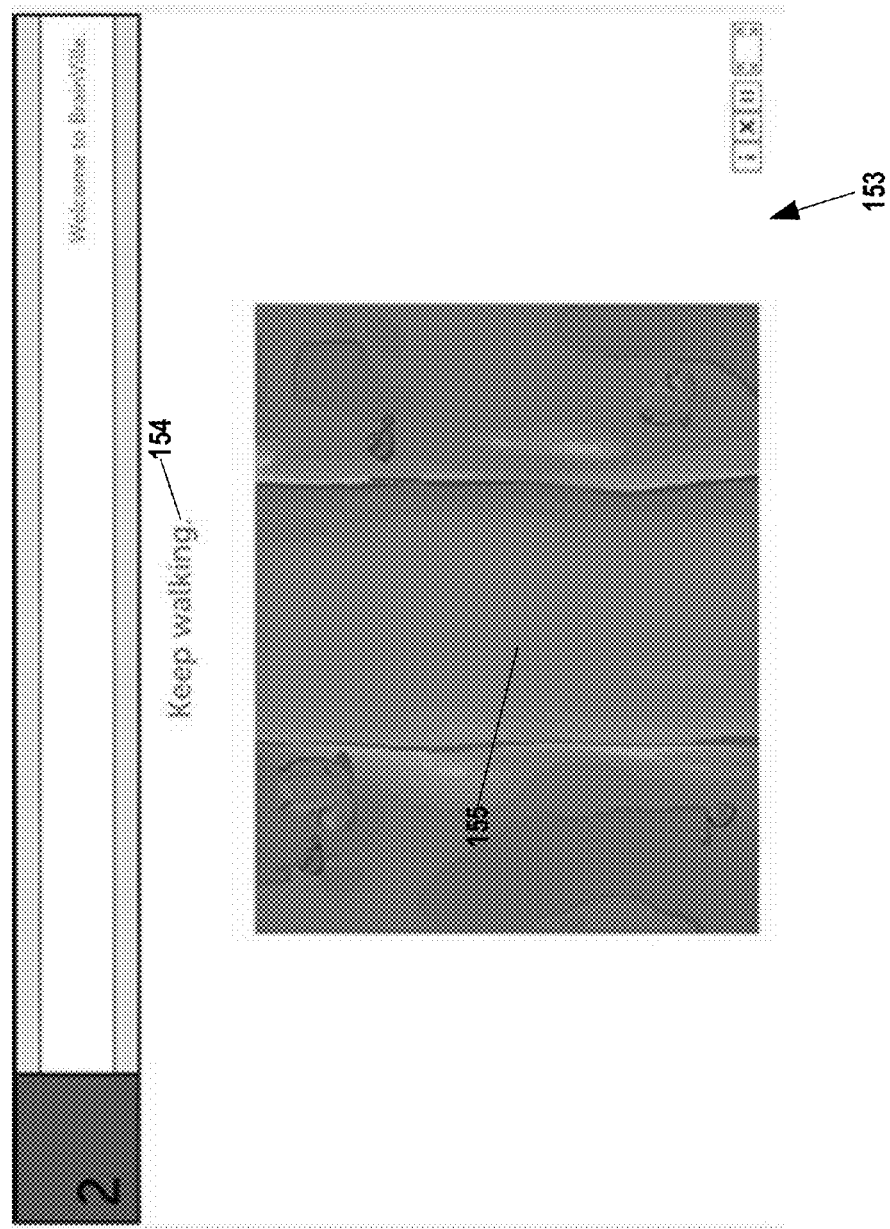
FIG. 14 illustrates another screenshot of the game illustrated in the previous figure.
Figure 15:
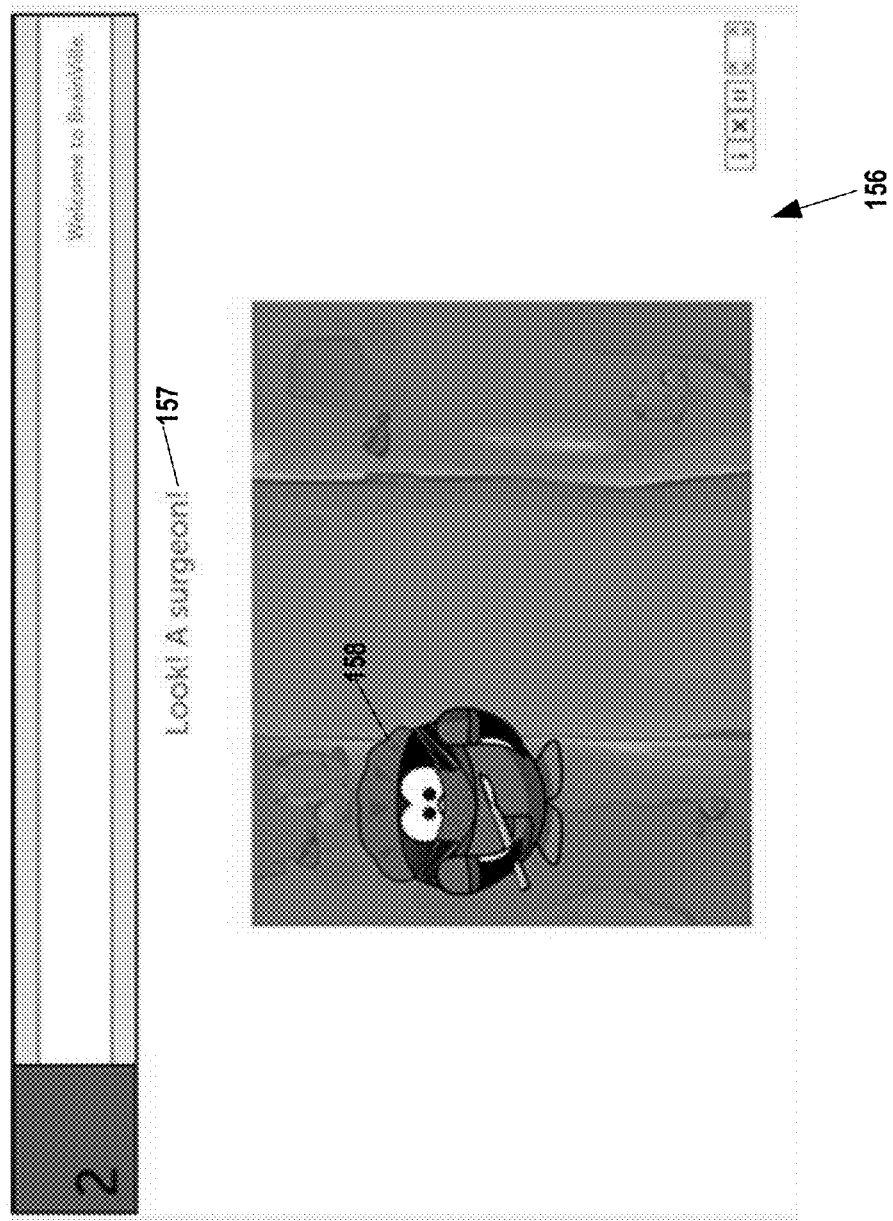
FIG. 15 illustrates another screenshot of the game illustrated in the previous figure.
Figure 16:
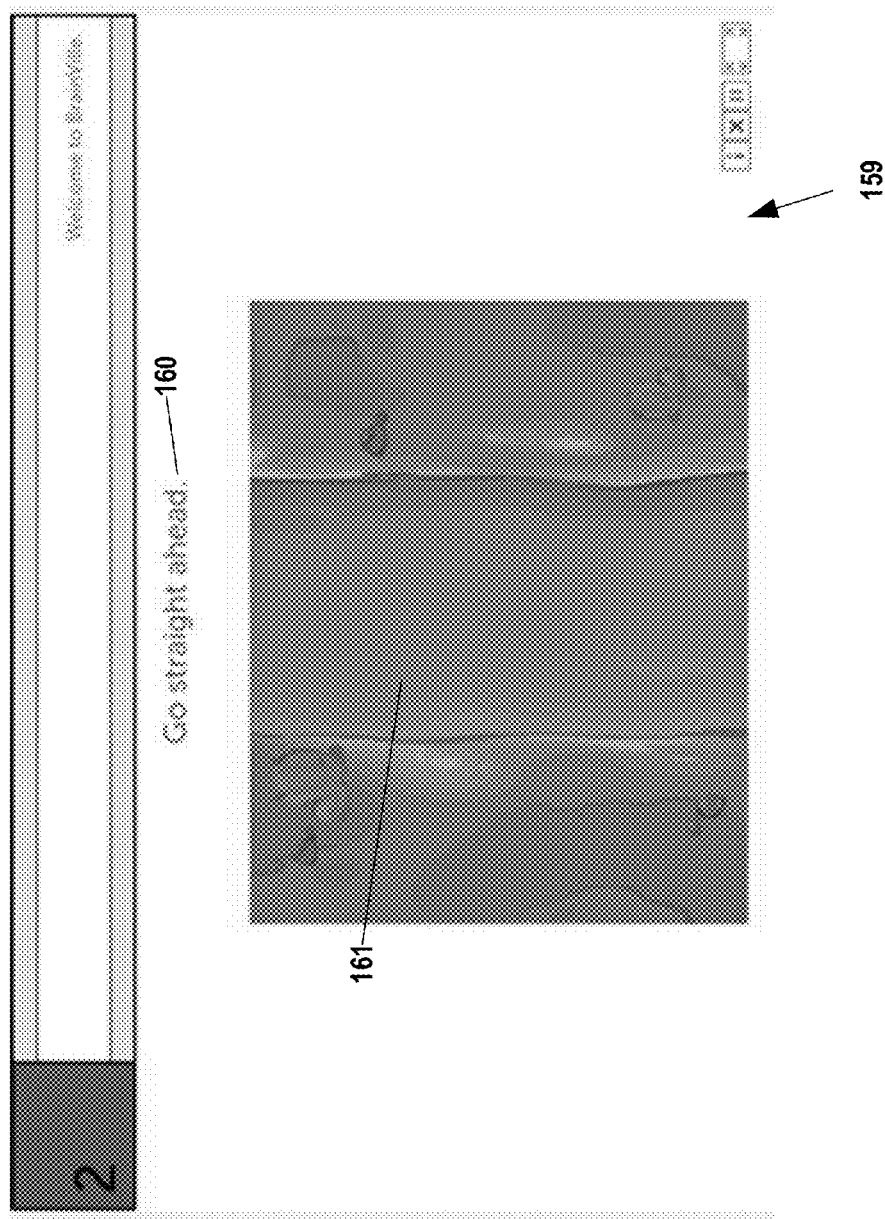
FIG. 16 illustrates another screenshot of the game illustrated in the previous figure.
Figure 17:
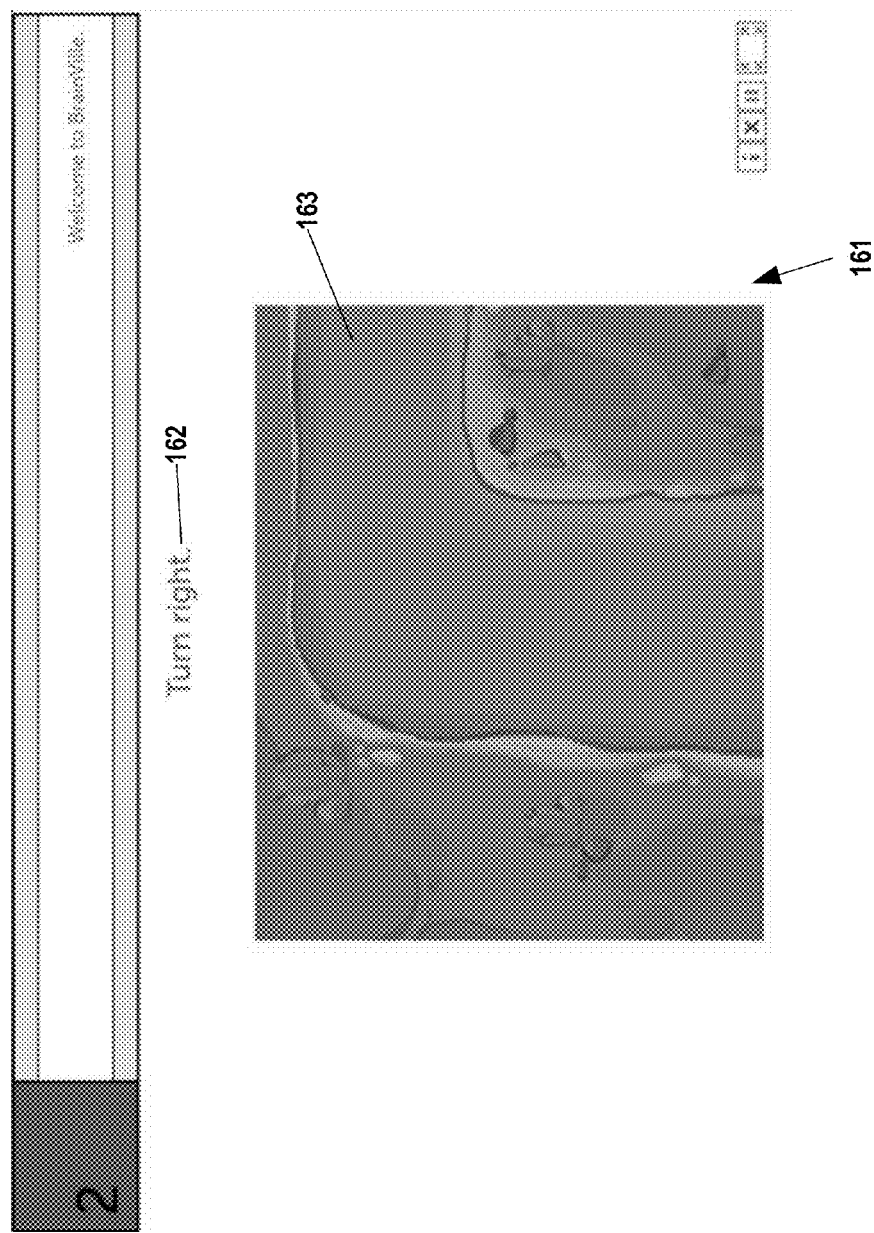
FIG. 17 illustrates another screenshot of the game illustrated in the previous figure.
Figure 18:
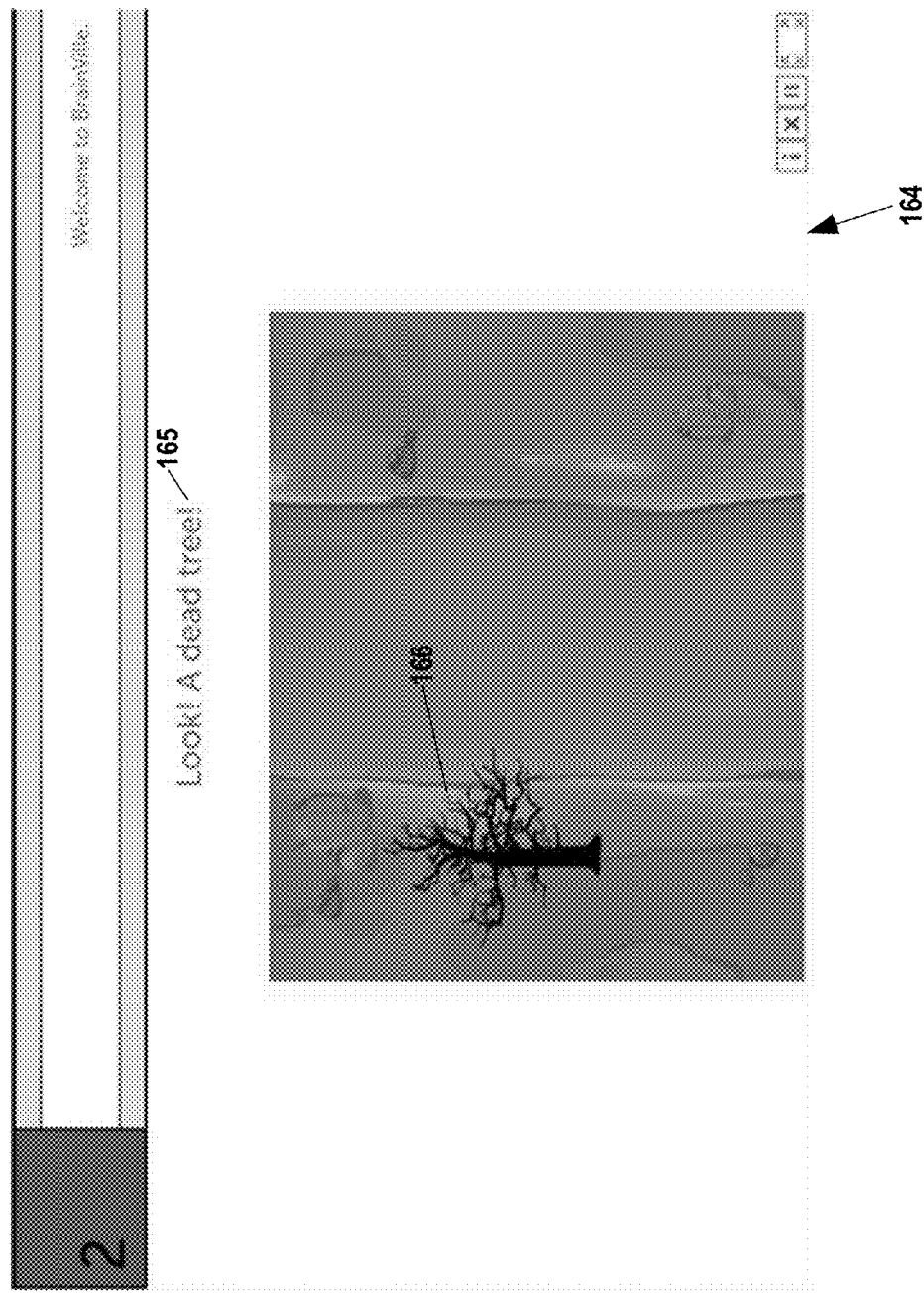
FIG. 18 illustrates another screenshot of the game illustrated in the previous figure.
Figure 19:
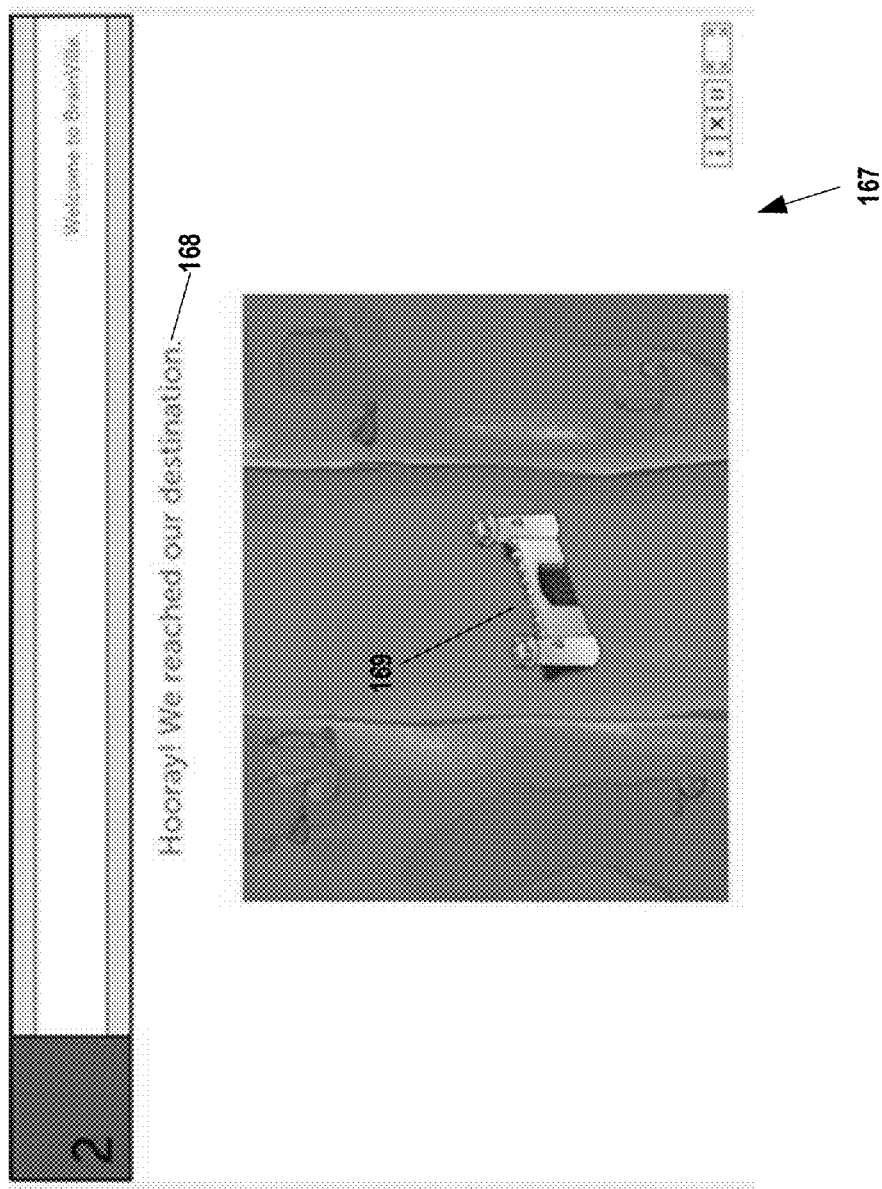
FIG. 19 illustrates another screenshot of the game illustrated in the previous figure.
Figure 20:
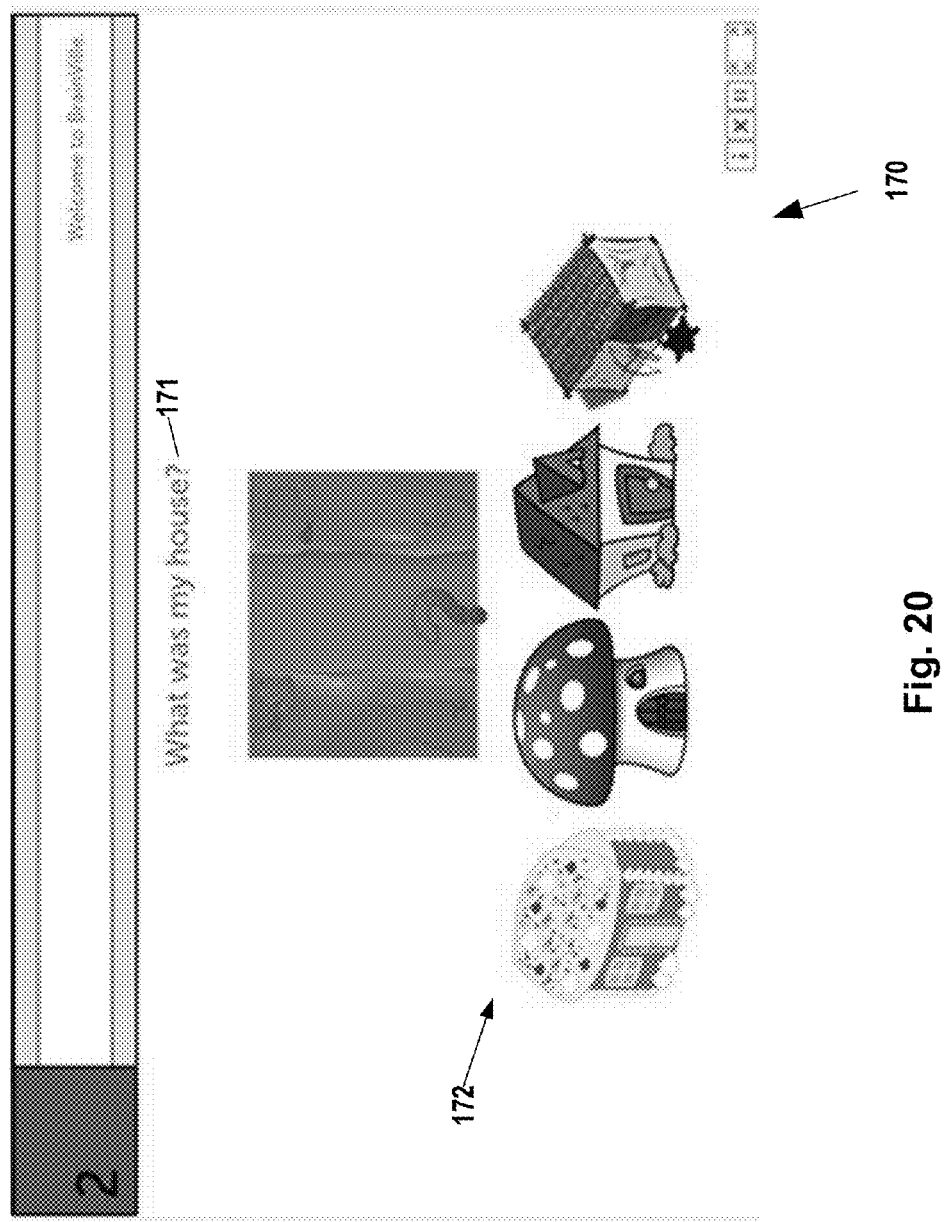
FIG. 20 illustrates another screenshot of the game illustrated in the previous figure.

For example, FIG. 12 depicts the journey beginning at a narrator's house 149. Brainville notifies 148 the participant that "We are starting from my house." Next, Brainville exclaims 151 "Look! A tower!" and displays an image of the tower 152. This is followed by the statement 154 "Keep walking," along with an image 155 of a road and sounds of walking. Next, Brainville exclaims 157 "Look! A surgeon V" together with an image 158 of a penguin dressed as a surgeon. This is followed by the statement 160 "Keep walking," and the statement 162 "Turn right," each with an image 161, 163 of a straight road or a road with a bend accompanied by sounds of walking. Next, Brainville exclaims 165 "Look! A dead tree!" together with an image 166 of a dead tree. Finally, Brainville announces 168 "Hooray! We reached our destination" and displays an image 169 of a castle entrance.

Figure 21:
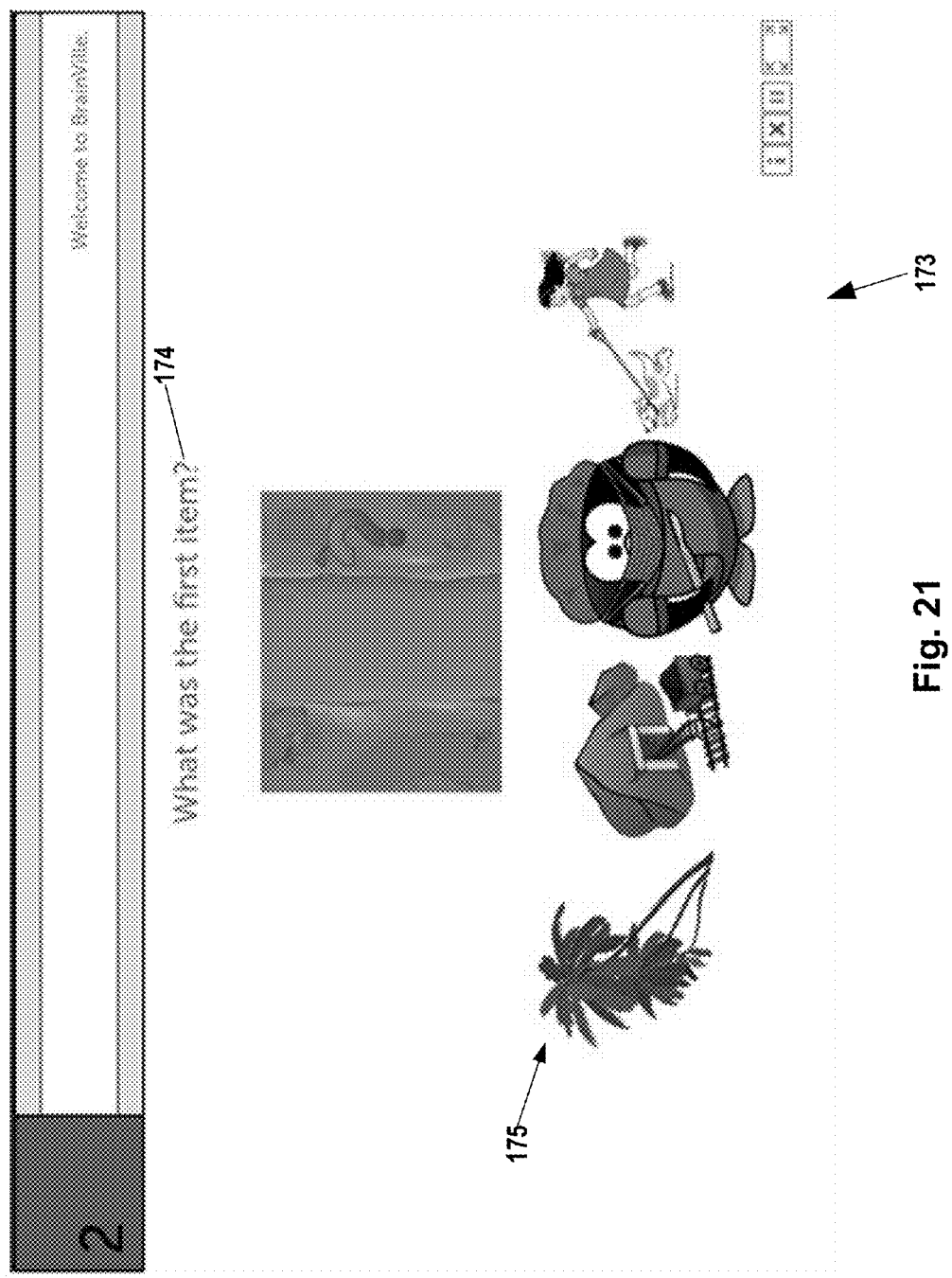
FIG. 21 illustrates another screenshot of the game illustrated in the previous figure.
Figure 22:
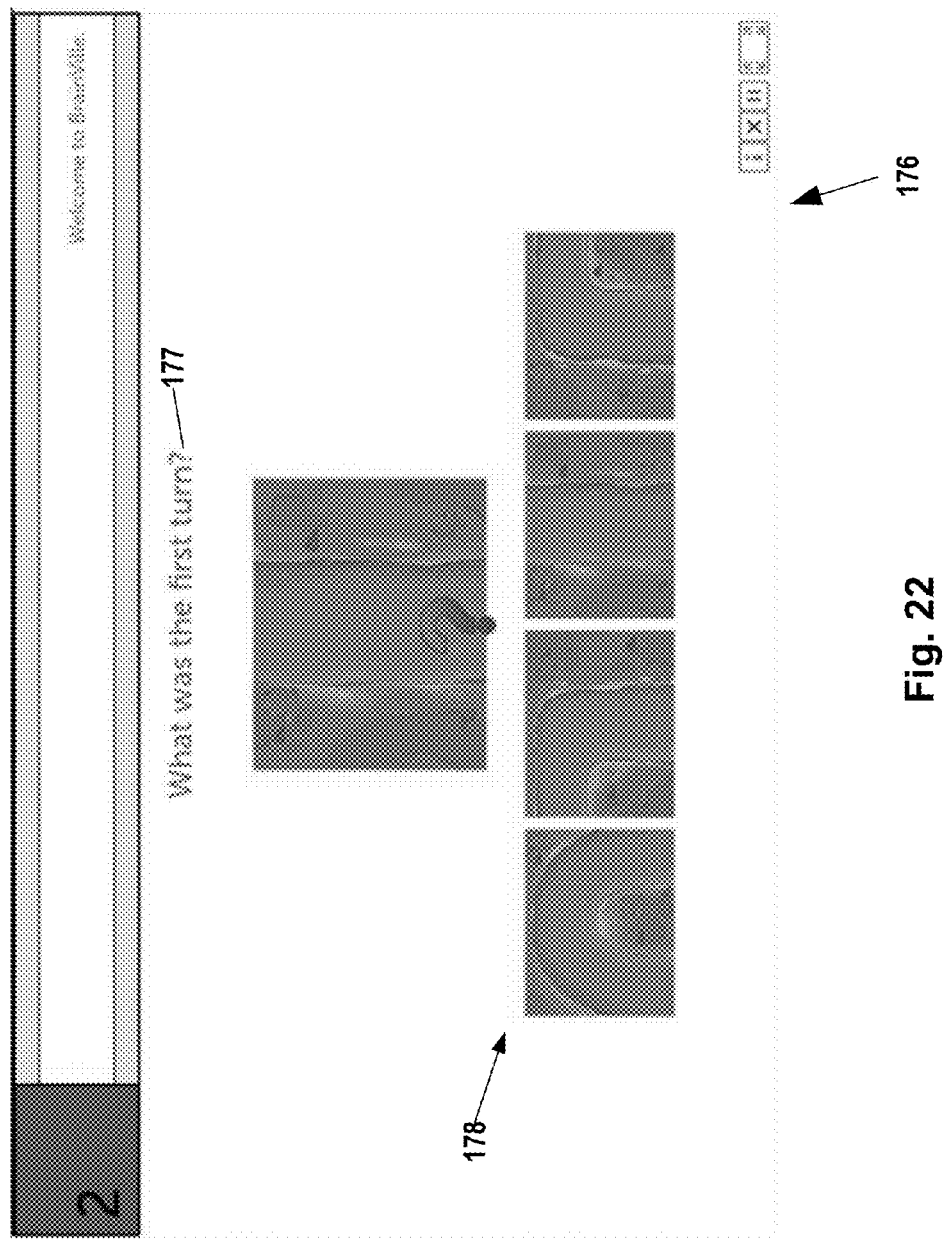
FIG. 22 illustrates another screenshot of the game illustrated in the previous figure.
Figure 23:
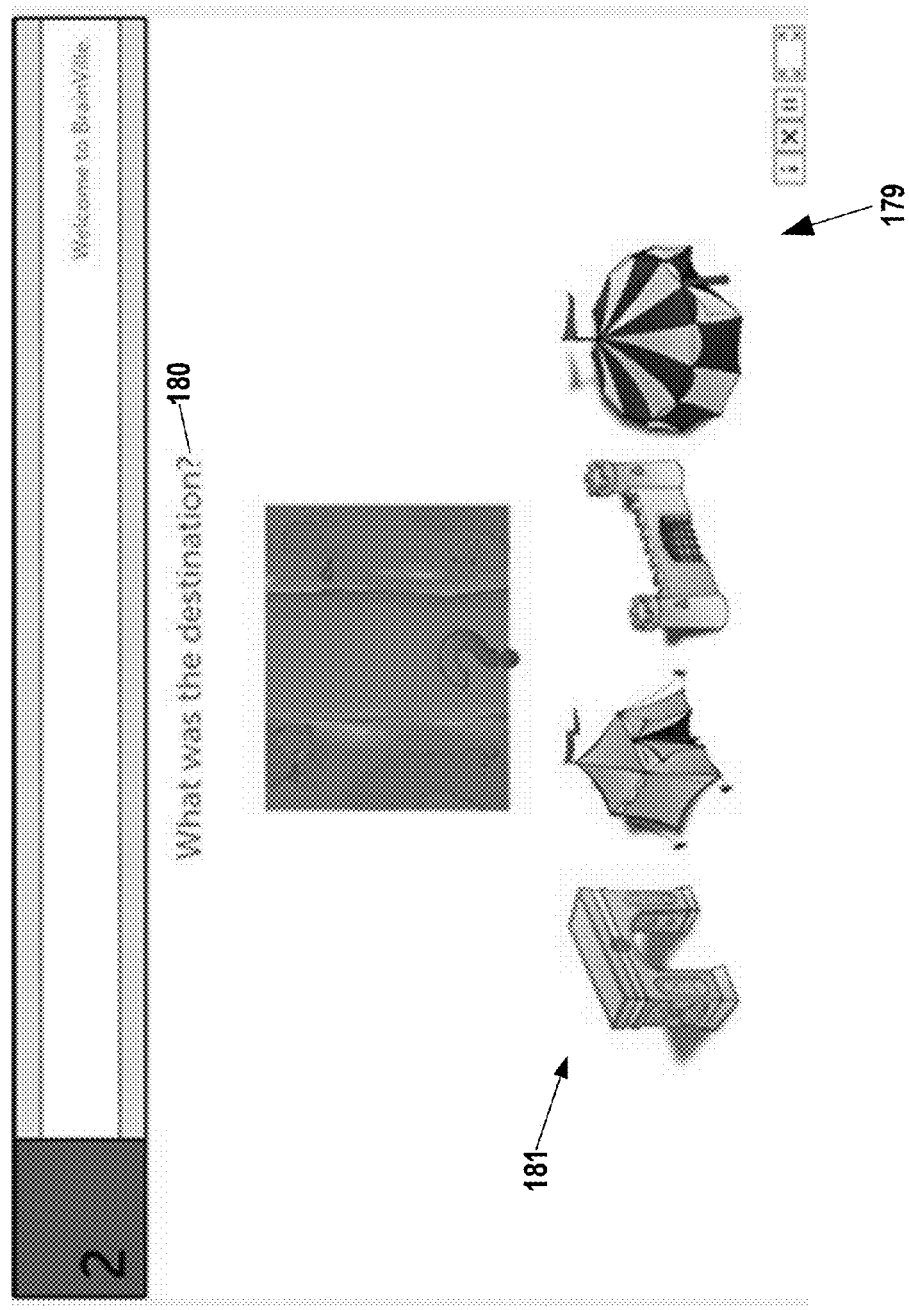
FIG. 23 illustrates another screenshot of the game illustrated in the previous figure.

Following this narrative, Brainville quizzes the participant about the journey. For example, in FIG. 20, Brainville asks 171 "What was my house?" and displays a set of answer choices 172 constituting images, one of which is the house 149 displayed at the beginning of the journey. In FIG. 21, Brainville asks 174 "What was the first item?" and displays another set of answer choices 175 constituting images, one of which is the image 158 of a penguin dressed as a surgeon. In FIG. 22, Brainville asks 177 "What was the first turn?" and displays a set of answer choices 178 constituting images of roads, one of which is straight, one of which turns left, one of which turns right, and one of which turns a full half-circle. In FIG. 144, Brainville asks 180 "What was the destination?" constituting images, one of which is the castle entrance image 169 displayed at the end of the journey.

More generally, Brainville presents a series of stimuli in sequential fashion, with each stimulus separated by a representation of progression, navigation, or traversal away from the previous stimulus. Brainville challenges the game participant to identify one or more of the stimuli based upon the order in which the stimulus was presented. Brainville also challenges the game participant to identify a characteristic of each of at least one of the representations of progression away from a stimulus.

3. Visual Memory

Figure 24:
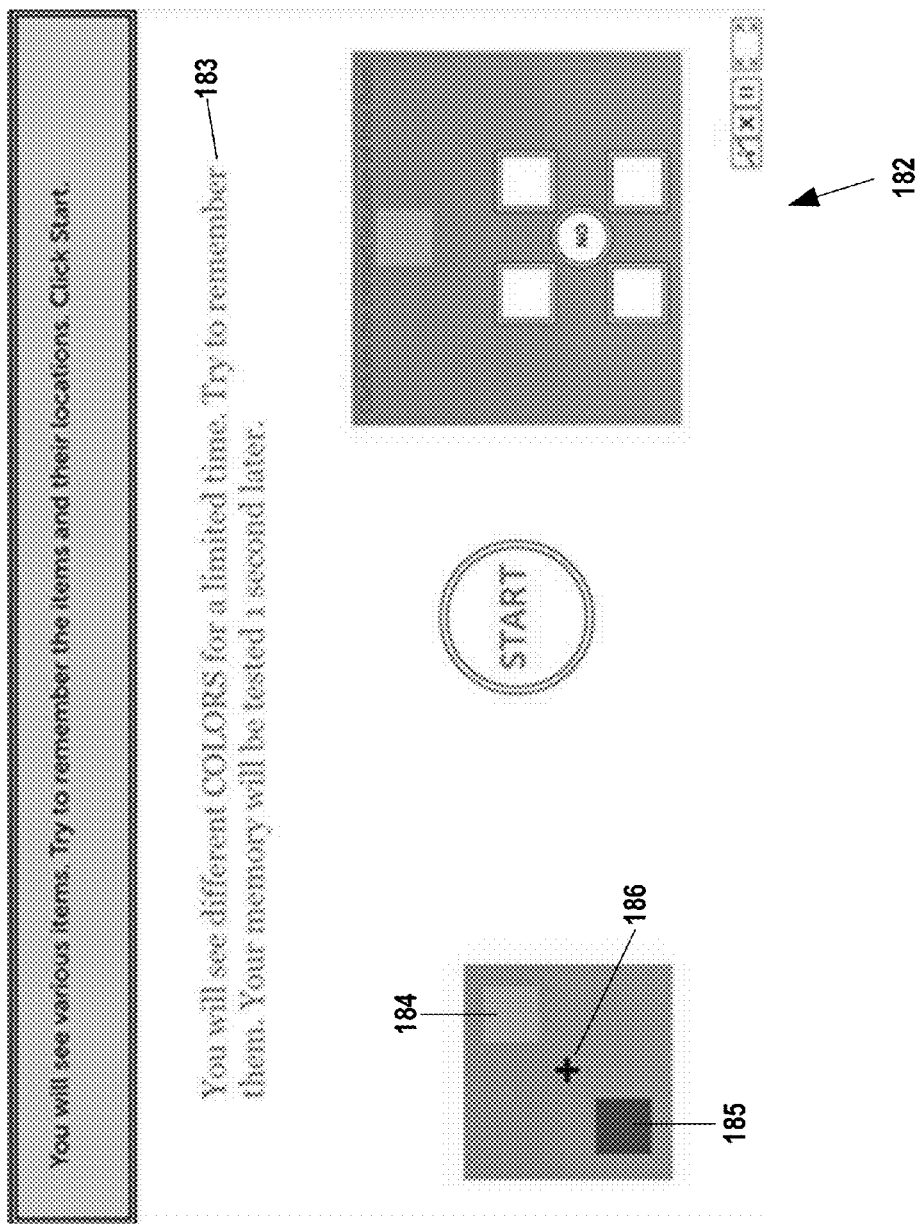
FIG. 24 illustrates a screenshot of one embodiment of a visuospatial memory game called "Visual Memory," which challenges a game participant to remember objects shown at different spatial locations across a time delay.
Figure 25:
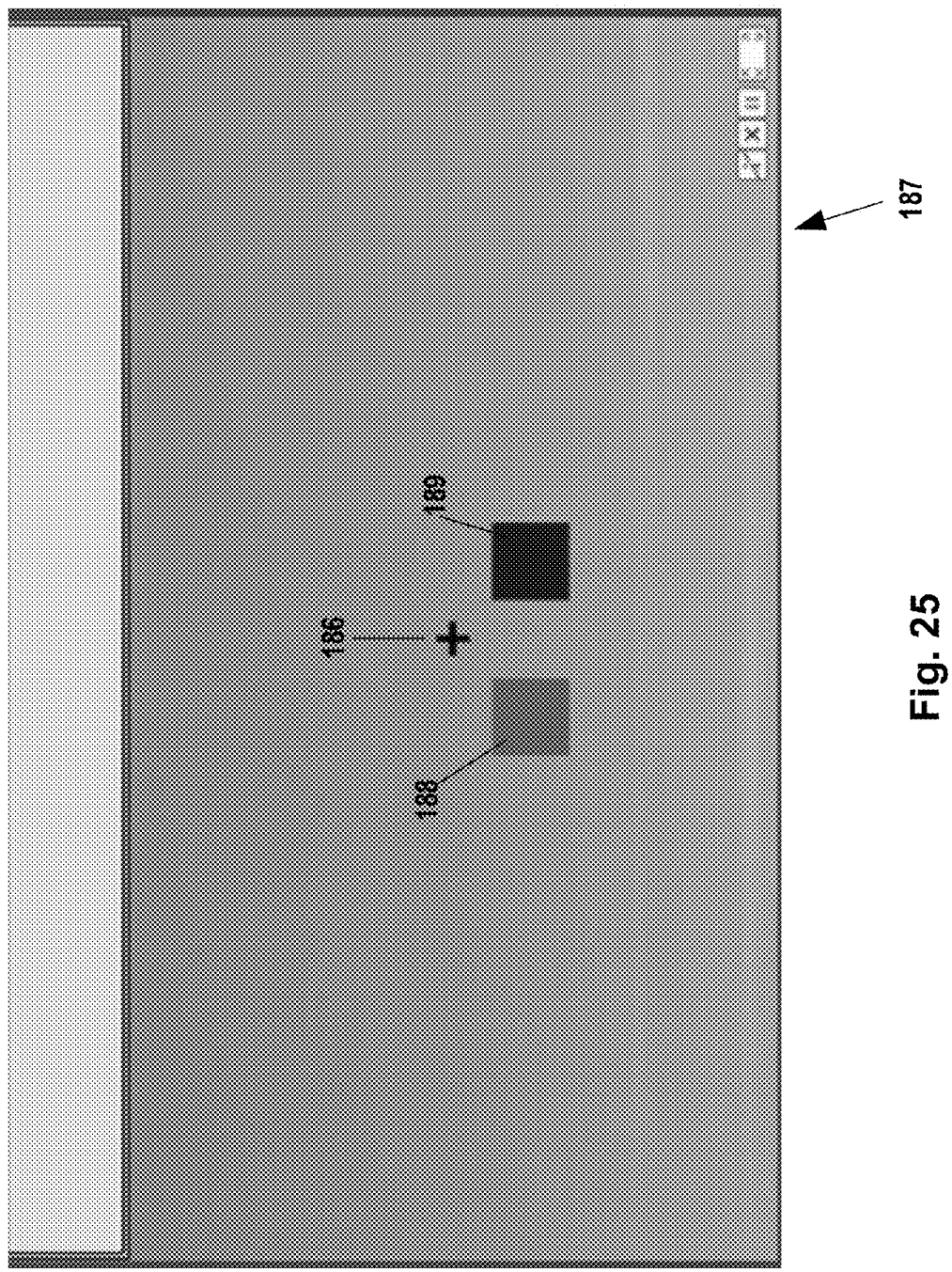
FIG. 25 illustrates another screenshot of the game illustrated in the previous figure.
Figure 26:
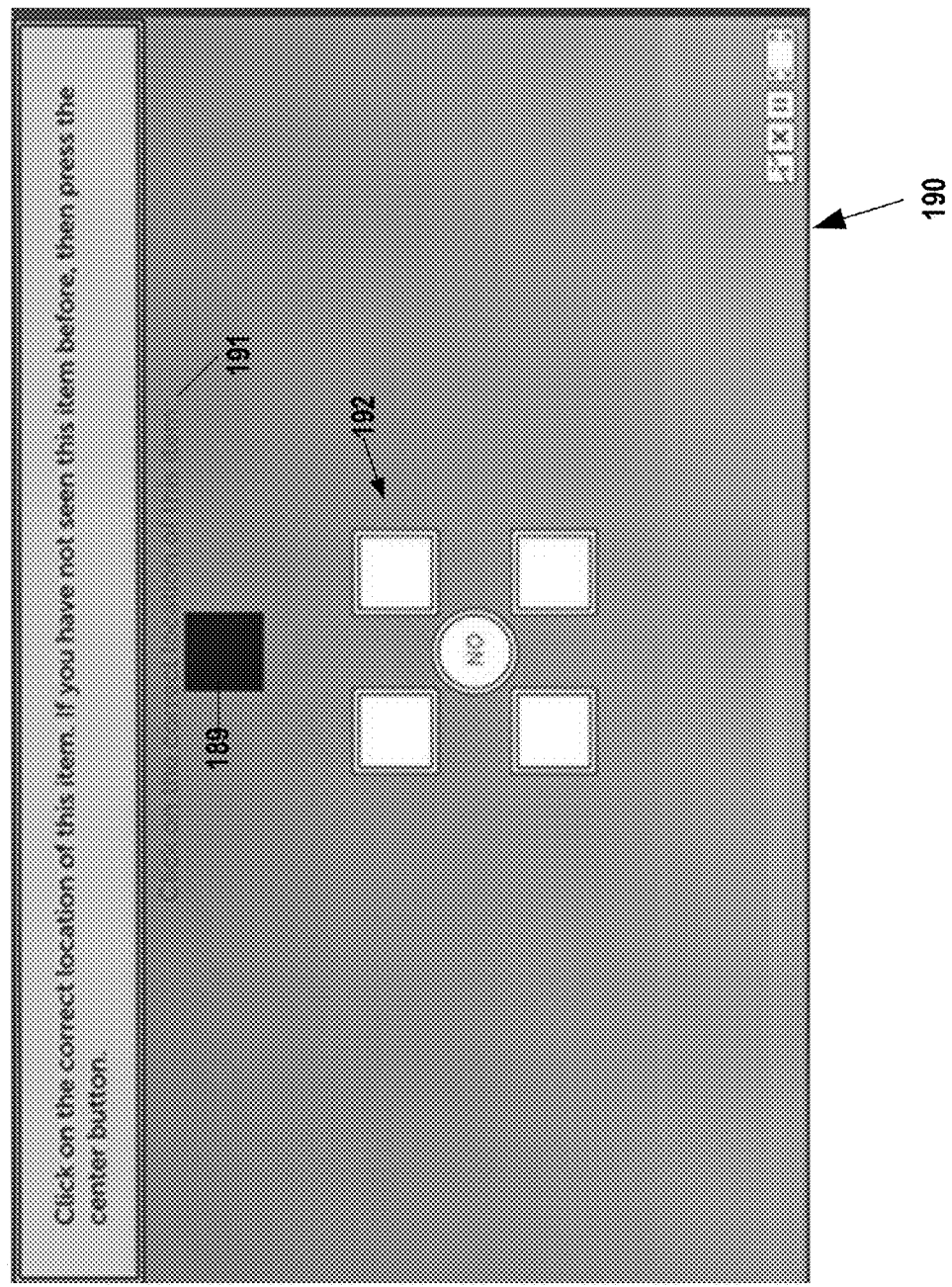
FIG. 26 illustrates another screenshot of the game illustrated in the previous figure.

FIGS. 24-26 illustrate screenshots 182, 187 and 190 of one embodiment of a visuospatial memory game called "Visual Memory," which challenges a game participant to remember objects shown at different spatial locations across a time delay.

In FIG. 24, Visual Memory prompts 183 the participant that it will briefly present multiple colors 184, 185 at different locations around a central object of fixation 186. For example, in FIG. 25, Visual Memory displays a purple-colored box 68 to the lower left of a "+" symbol 186 and a blue-colored box 189 to the lower right of the "+" symbol 186. After a first time interval, Visual Memory clears the boxes 188, 189 from the display, replacing it with a visual mask that lasts for a second time interval. Then, Visual Memory displays a selectable set of spatial locations 192 and prompts 191 the participant to indicate the location that the blue-colored box 189 had appeared.

The second time interval begins at 1 second and increases as training progresses. Also, as training progresses, the set of possible locations increases and details in the objects become more similar. To ensure generalizability, the details about the objects change across blocks of trials, from color hue to overall shapes to minor details in the shape.

4. Musical Games

The training program 2 also includes games that use musically structured stimuli to integrate auditory, visual and motor sequencing and develop hand and voice control. The participant hears a melodic sequence and plays it back from memory by tapping the spacebar, typing the appropriate keys, or singing. Their accuracy is determined by one or more of three measures: 1) rhythm, 2) duration and 3) pitch.

FIGS. 27-30 illustrate screenshots 193, 195, 198 and 201 of one embodiment of an auditory and spatial memory game called "Look, Listen, and Repeat," which challenges a game participant to press buttons he sees and hears in the remembered order. The game is similar to how one learns to play the piano. The participant hears a musical sequence and plays it back on multiple keyboard keys. The task trains the participant to retain an accurate mental model of the rhythm and pitch of a musical sequence, and to convert it into an appropriate motor response sequence by playing it back on multiple keys.

Figure 27:
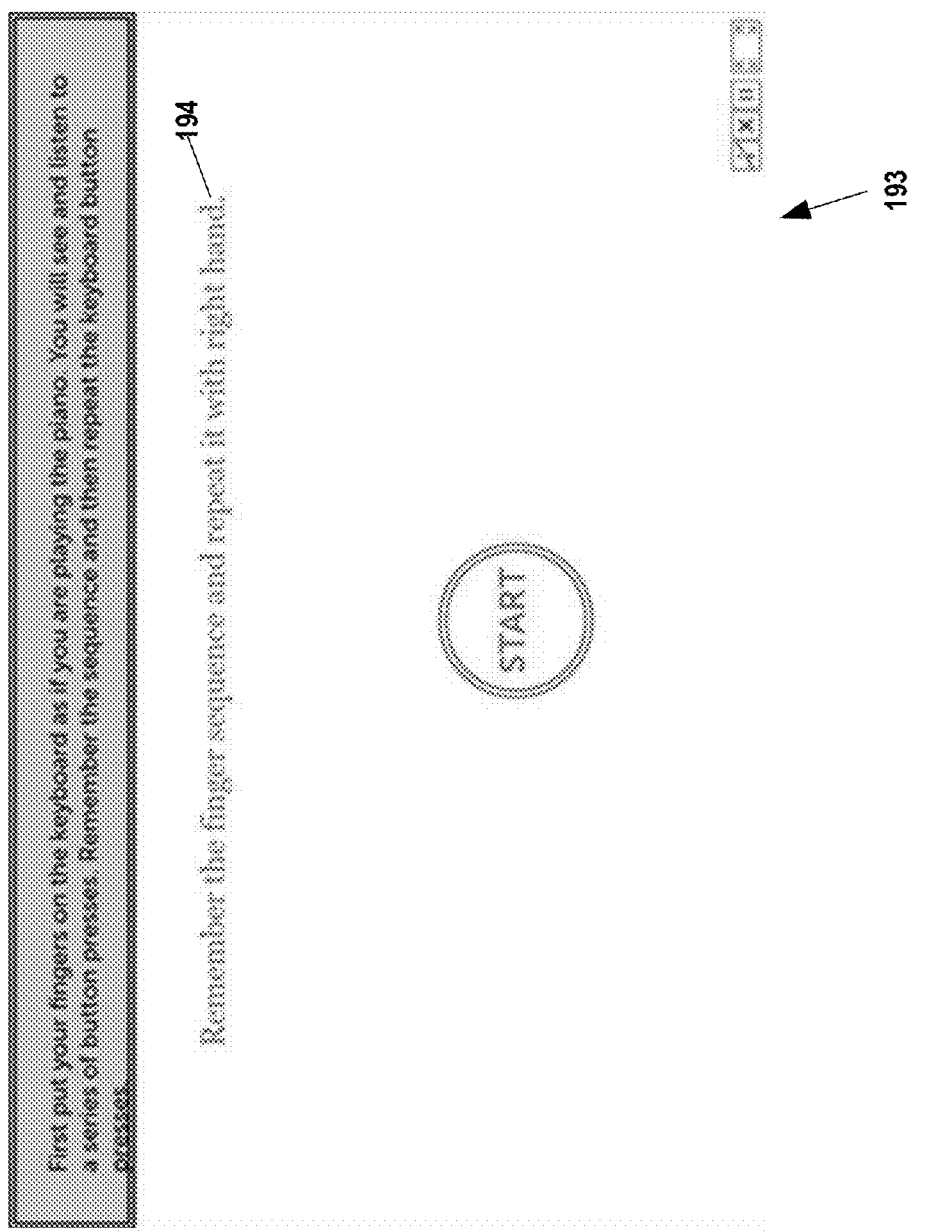
FIG. 27 illustrates a screenshot of one embodiment of an auditory and spatial memory game called "Look, Listen, and Repeat," which challenges a game participant to press buttons he sees and hears in the remembered order.
Figure 28:
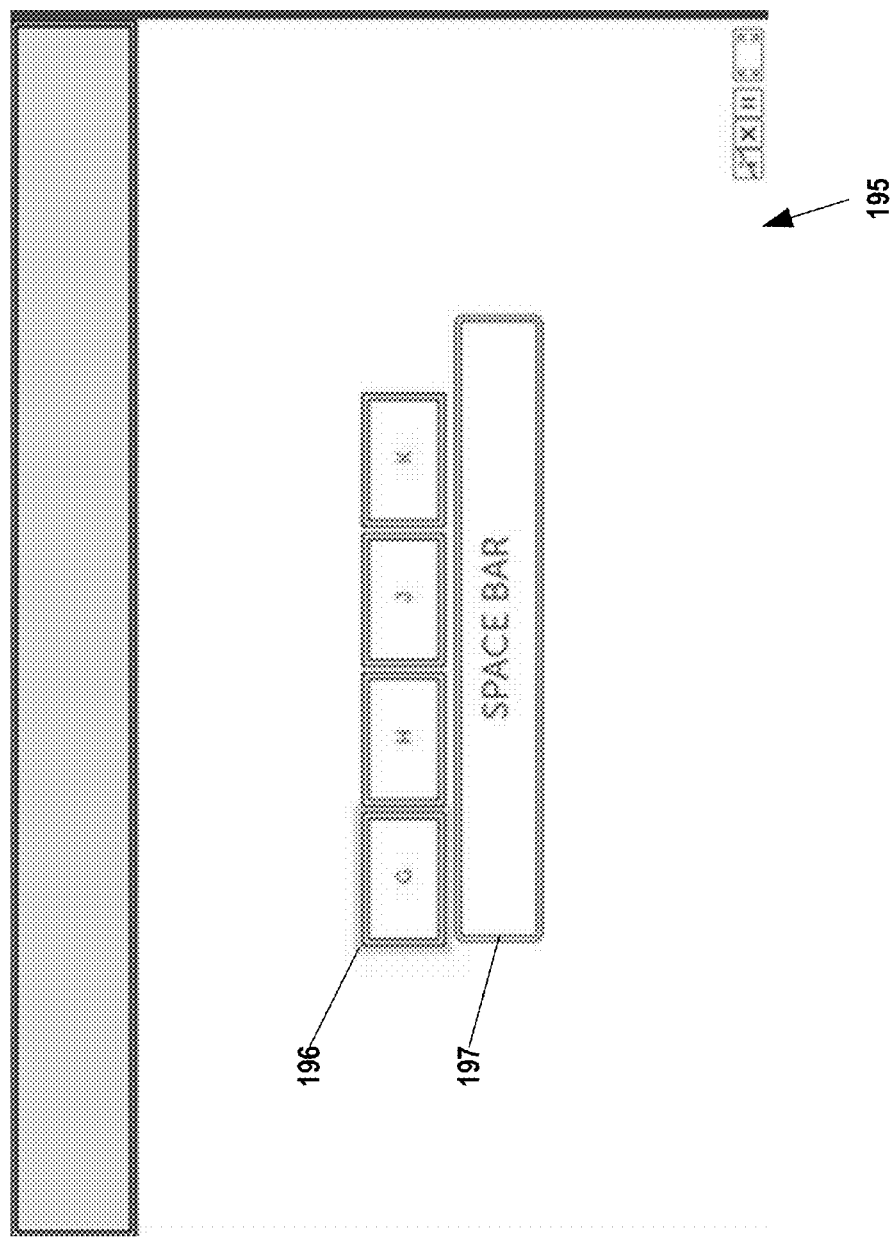
FIG. 28 illustrates another screenshot of the game illustrated in the previous figure.
Figure 29:
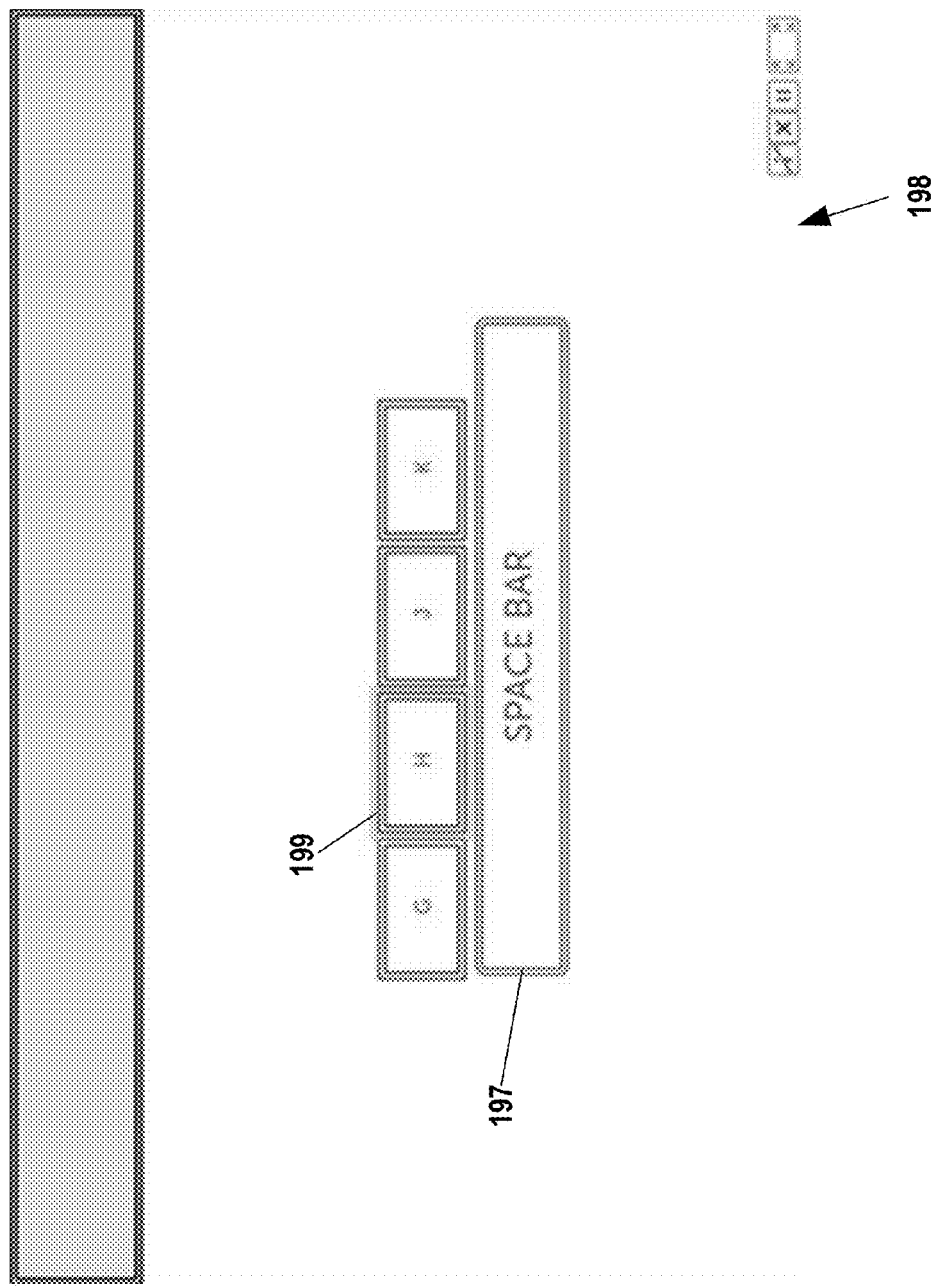
FIG. 29 illustrates another screenshot of the game illustrated in the previous figure.
Figure 30:
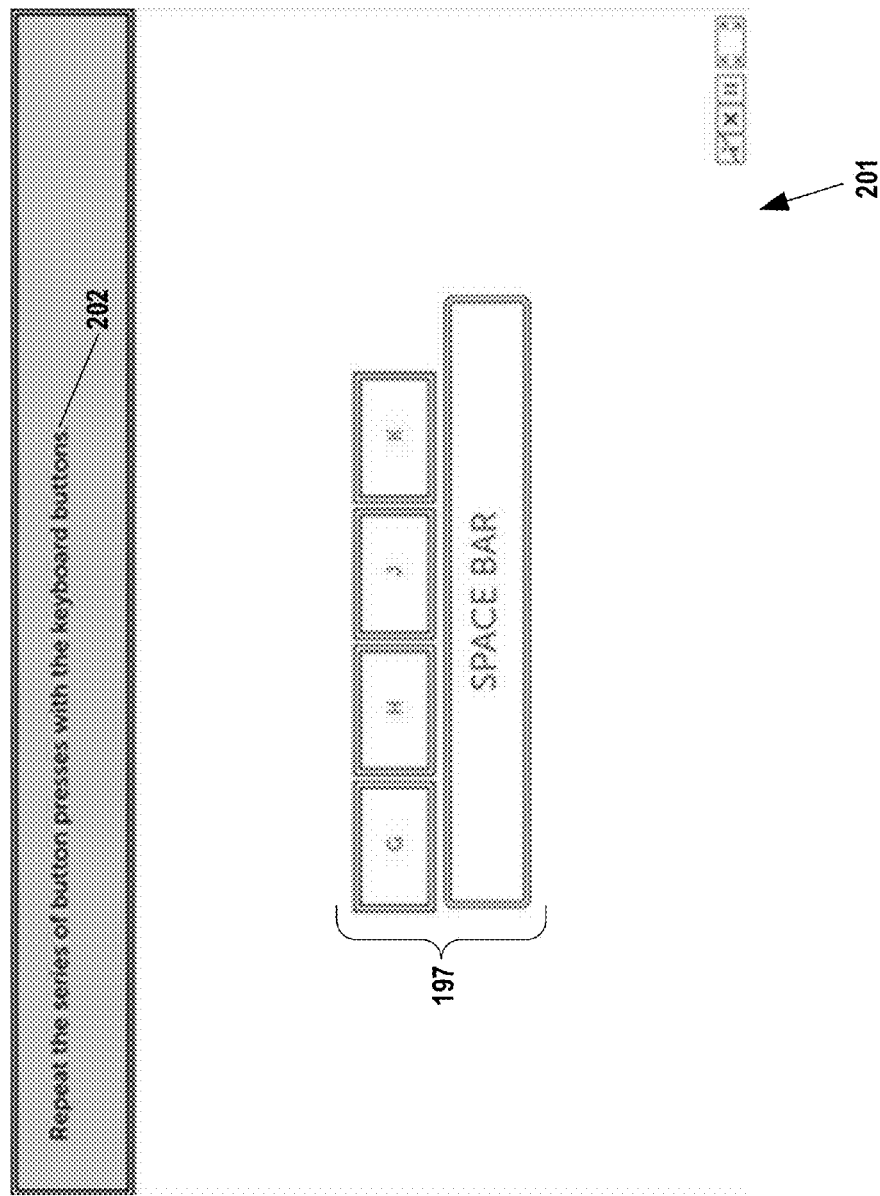
FIG. 30 illustrates another screenshot of the game illustrated in the previous figure.

In FIG. 27, the game instructs 194 the participant to place their fingers on the keyboard as if they are playing the piano, watch and listen to a series of button presses, and remember and repeat the sequence they saw and heard. FIGS. 28 and 29 illustrate a QWERTY keyboard portion 197 and two successively highlighted keys 196 and 199. After a predetermined delay, in FIG. 30, the game illustrates the same QWERTY keyboard portion 197 and prompts 202 the participant to repeat the series of button presses with the keyboard buttons.

As training increases in difficulty, the sequence of played keys gets longer and is played more quickly. The game also presents more button options and increases the predetermined delay.

FIGS. 31-34 illustrate screenshots 204, 206, 209 and 212 of one embodiment of such a game called "Keyboard: Timing," which challenges a game participant to recall the rhythm of a musical sequence by playing it back on the spacebar. Keyboard: Training trains the participant to retain an accurate mental model of the rhythm of a musical sequence, and to convert it into an appropriate motor response sequence by playing it back on the spacebar.

Figure 31:
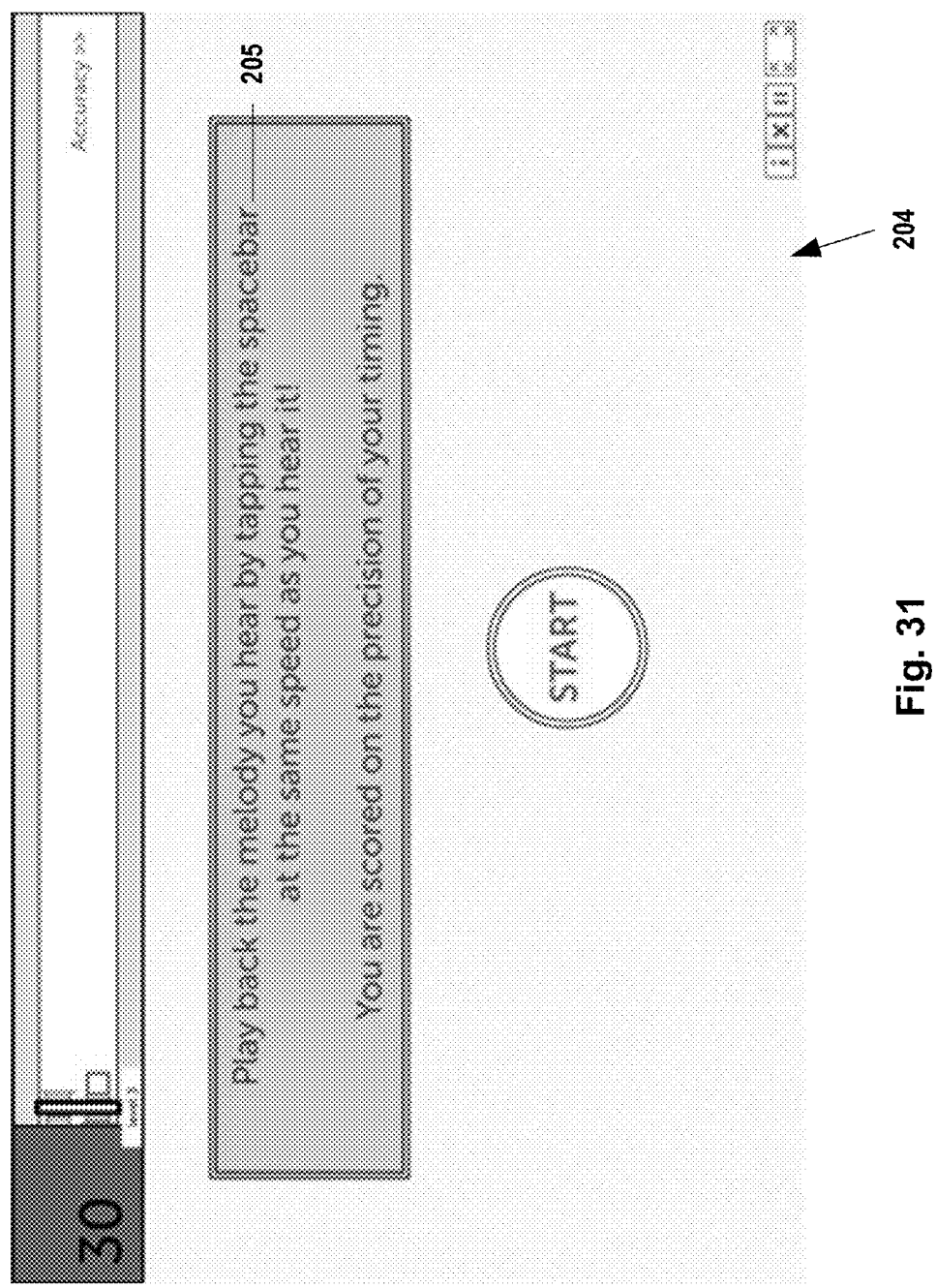
FIG. 31 illustrates a screenshot of one embodiment of a sequencing and multimodal integration game called "Keyboard: Timing," which challenges a game participant to recall the rhythm of a musical sequence by playing it back on the spacebar.
Figure 32:
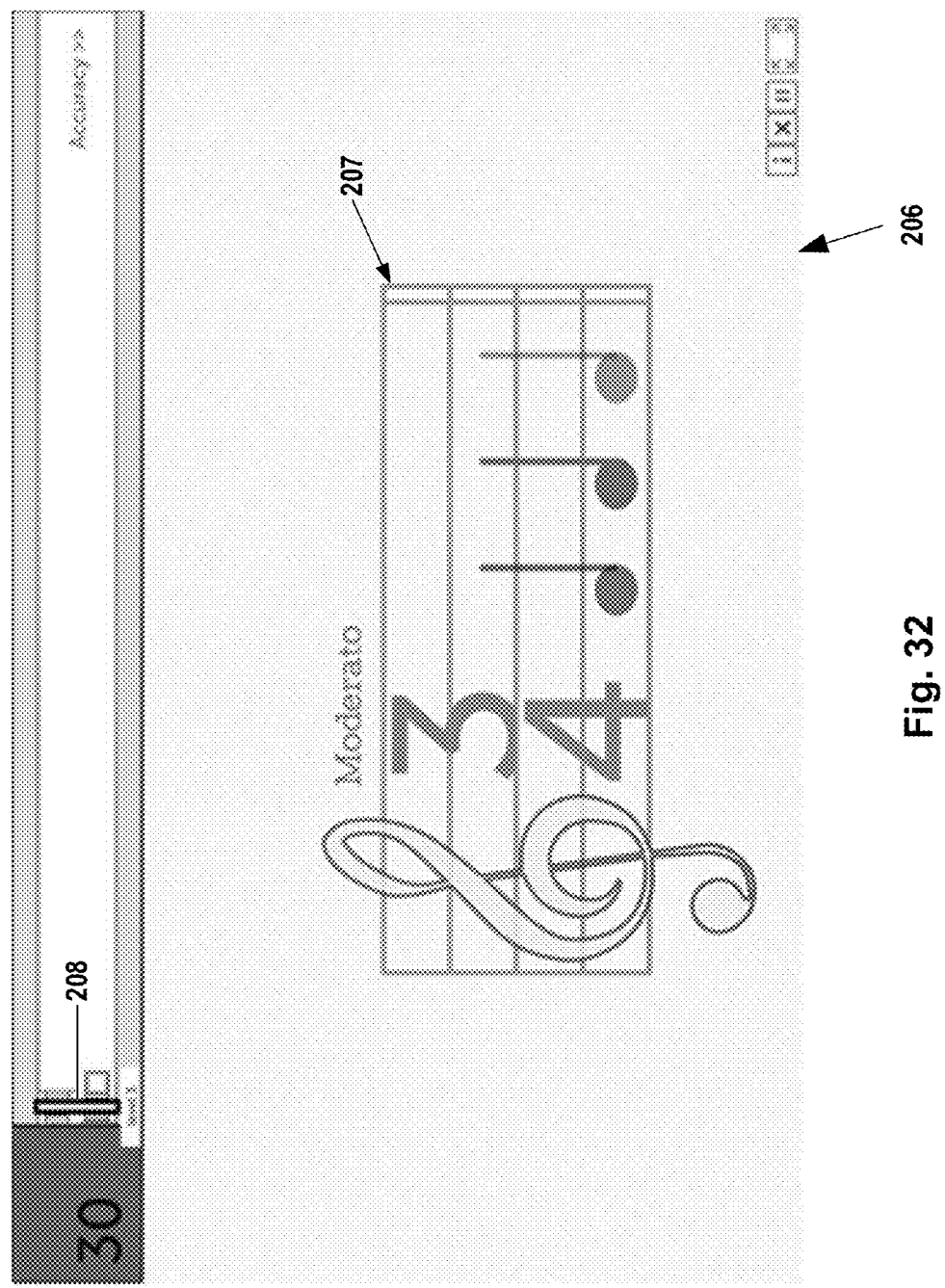
FIG. 32 illustrates another screenshot of the game illustrated in the previous figure.
Figure 33:
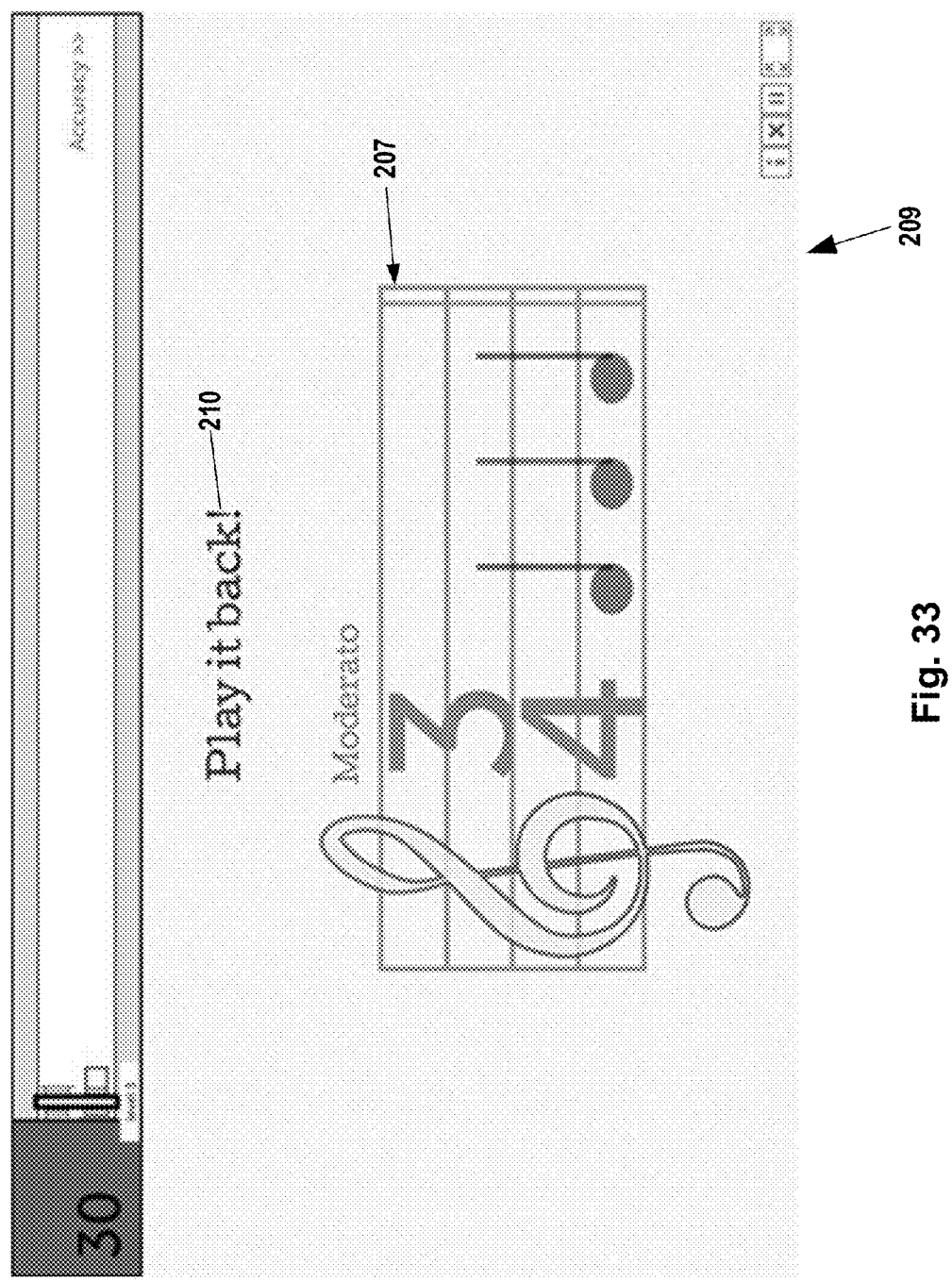
FIG. 33 illustrates another screenshot of the game illustrated in the previous figure.
Figure 34:
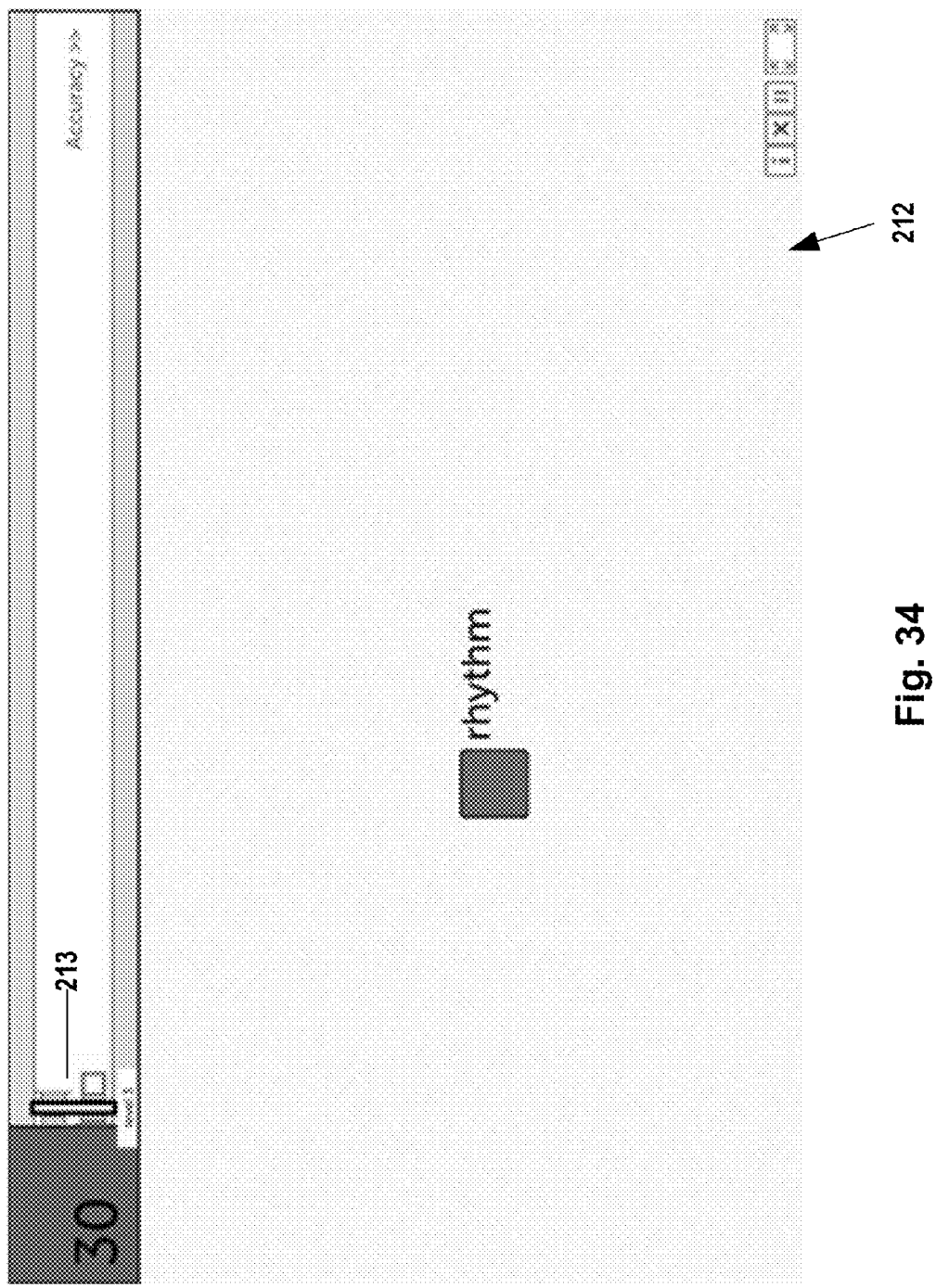
FIG. 34 illustrates another screenshot of the game illustrated in the previous figure.

In FIG. 31, Keyboard: Timing challenges 205 the participant to play back the melody by tapping a single input device (such as the spacebar) at the same speed as they hear it. In FIG. 32, Keyboard: Timing displays musical notation 207 while playing the melody. In FIG. 34, Keyboard: Timing prompts 210 the participant to play the melody back. Keyboard: Timing also grades the participant's response, provides an indication of whether their rhythm and/or pitch was correct, and displays a multi-trial measure 213 of the participant's progress. In one embodiment, not shown, Keyboard: Timing provides a display that graphically compares the participant's response with the correct stimulus sequence.

Figure 35:
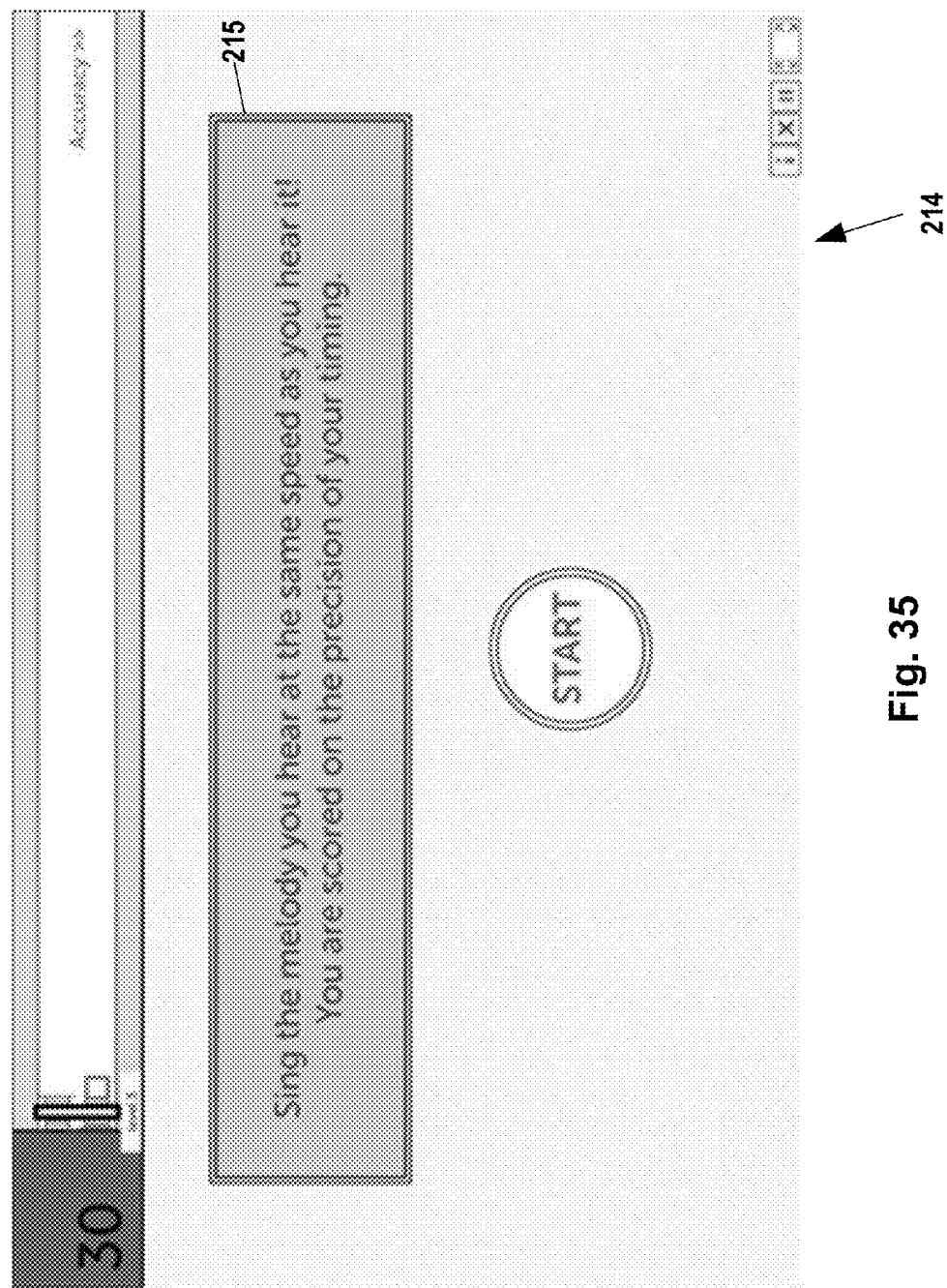
FIG. 35 illustrates a screenshot of one embodiment of a sequencing and multimodal integration game called "Voice: Timing," which challenges a game participant to recall the rhythm of a musical sequence by singing the melody back.
Figure 36:
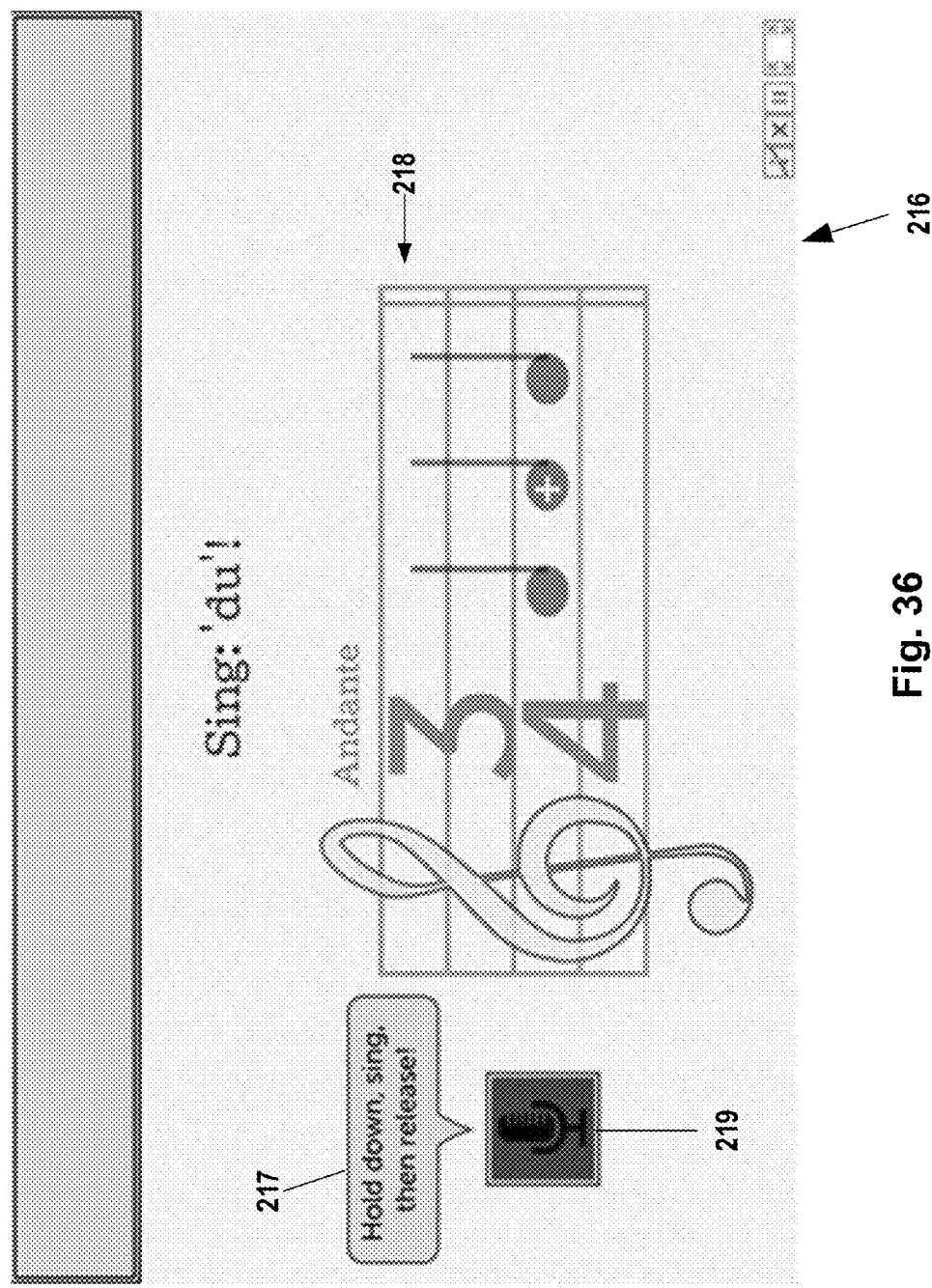
FIG. 36 illustrates another screenshot of the game illustrated in the previous figure.

FIGS. 35 and 36 illustrate screenshots 214, 216 of another embodiment of a game called "Voice: Timing," which challenges a game participant to recall the rhythm of a musical sequence by singing the melody back. The participant hears a musical sequence and sings it back. The task trains the participant to retain an accurate mental model of the rhythm of a musical sequence, and to convert it into an appropriate vocal motor response sequence.

Voice: Timing prompts 215 the participant to sing the melody they hear at the same speed as they hear it. In FIG. 36, Voice: Timing displays musical notation 218 and a microphone button 219, while prompting 217 the participant to hold the microphone button, sing, and release. Voice:

Timing receives the participant's audio input from a microphone, parses it into a rhythmic sequence, and measures the similarity of the participant's timing to that of the played melody.

Figure 37:
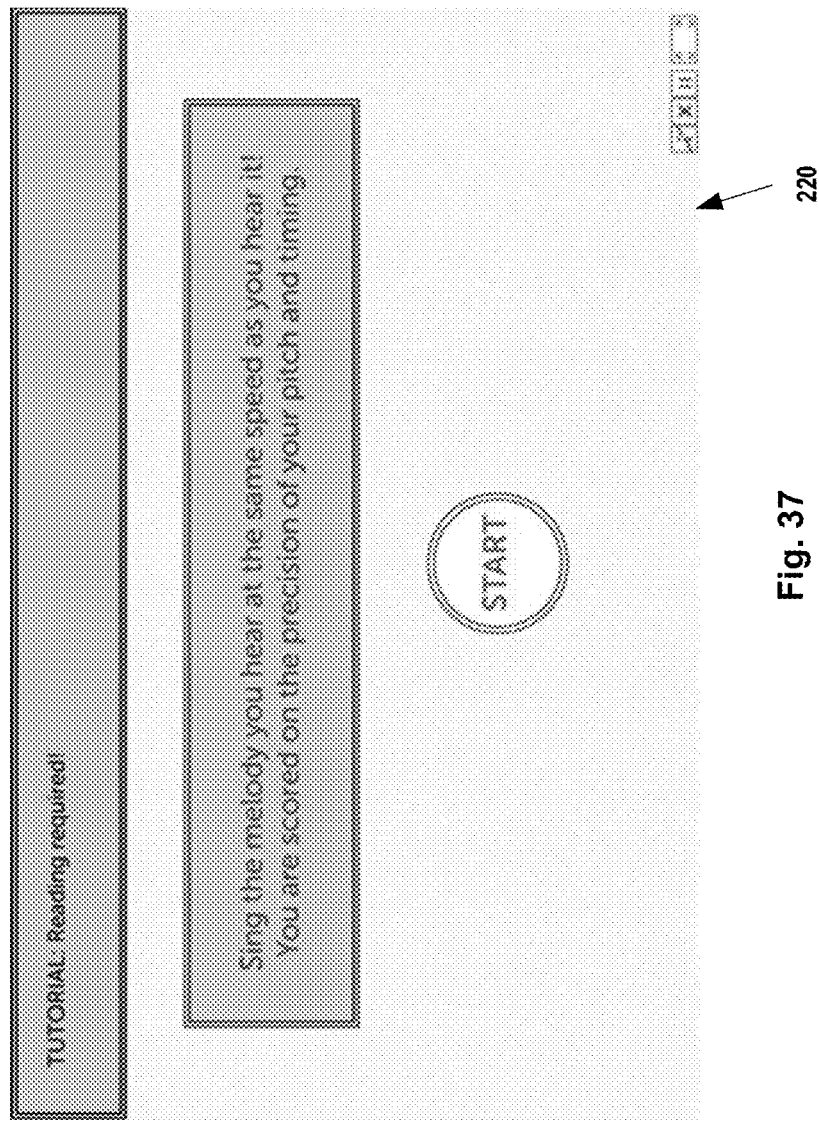
FIG. 37 illustrates a screenshot of one embodiment of a sequencing and multimodal integration game called "Voice: Timing & Pitch," which challenges a game participant to recall the rhythm and pitch of a musical sequence by singing the melody back.

FIG. 37 illustrates a screenshot 220 of a sequencing and multimodal integration game called "Voice: Timing & Pitch," which challenges a game participant to recall the rhythm and pitch of a musical sequence by singing the melody back. The participant hears a musical sequence and sings it back. The task trains the participant to retain an accurate mental model of the rhythm and pitch of a musical sequence, and to convert it into an appropriate vocal motor response sequence. Instructions are provided at the beginning of the task.

VII. Executing Functioning

1. Rule Change

Figure 38:
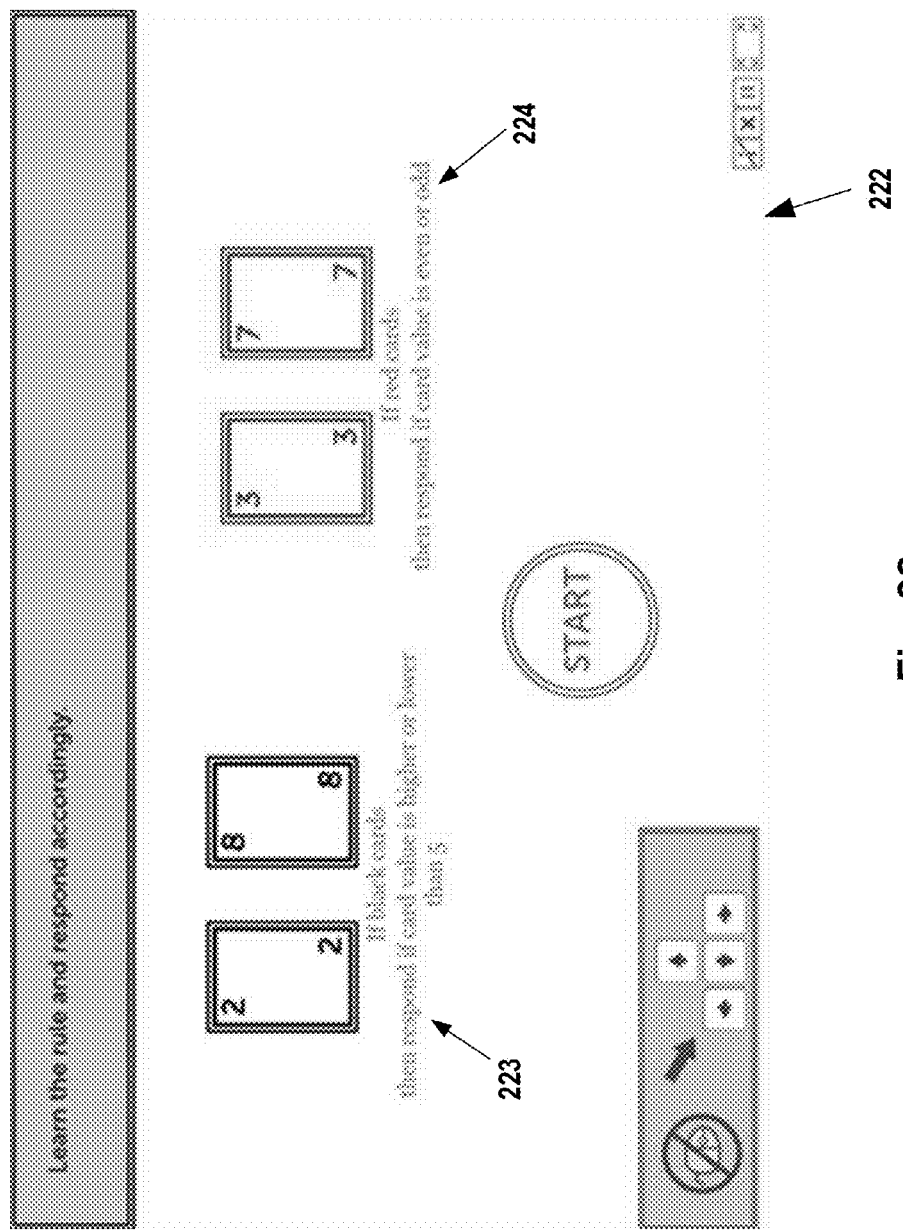
FIG. 38 illustrates a screenshot of one embodiment of an executive functioning game called "Rule Change," which challenges a game participant to categorize cards based on conditional rules.
Figure 39:
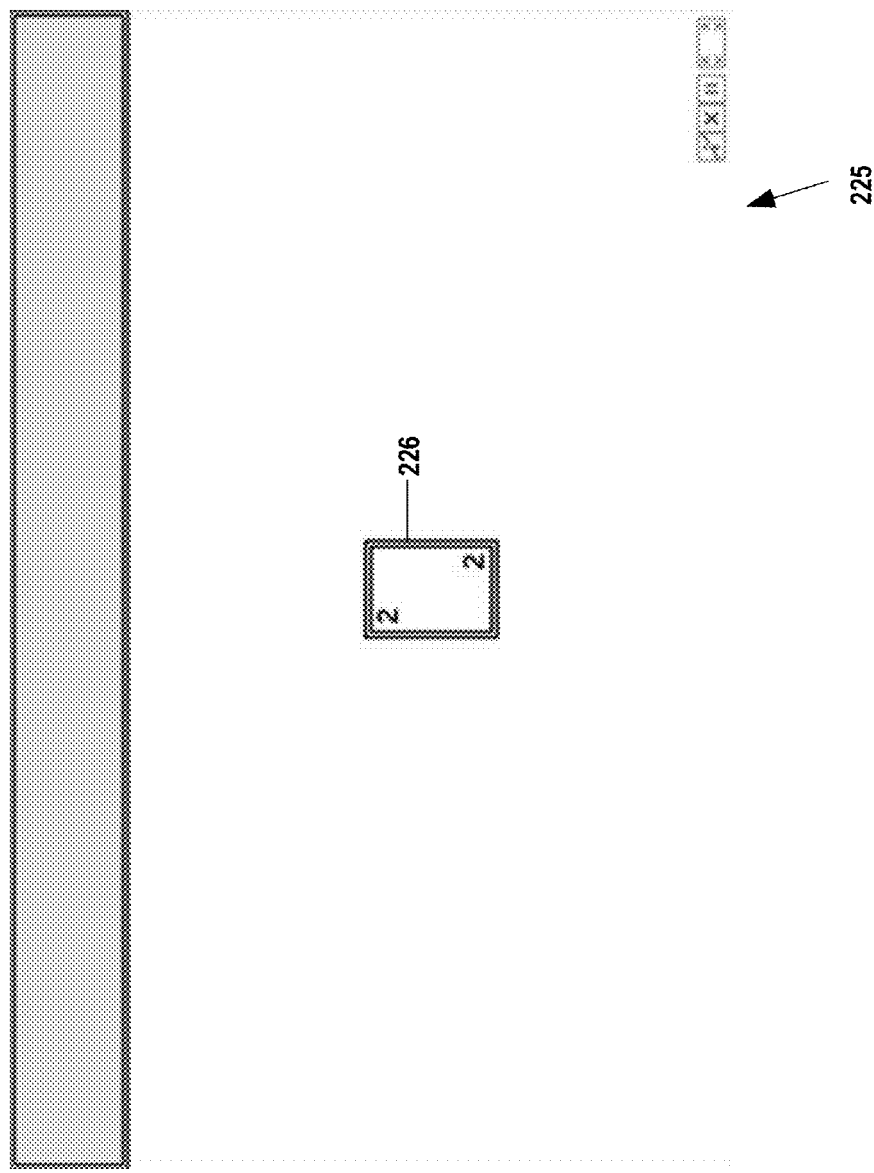
FIG. 39 illustrates another screenshot of the game illustrated in the previous figure.
Figure 40:
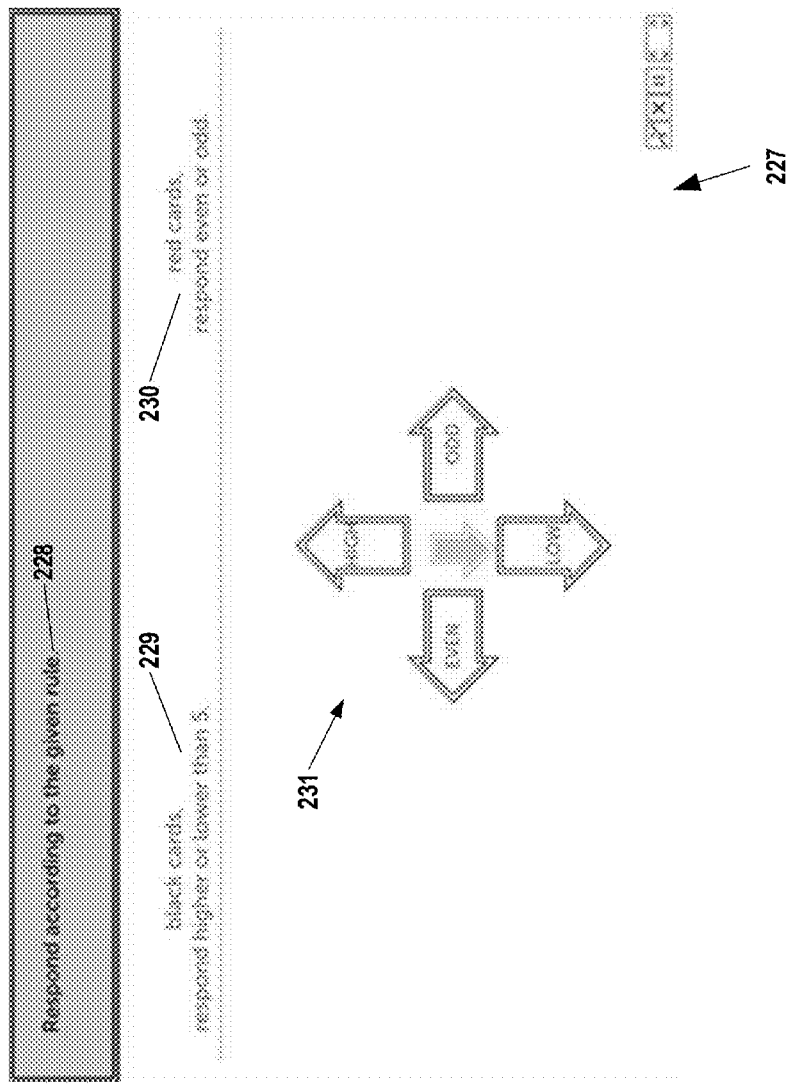
FIG. 40 illustrates another screenshot of the game illustrated in the previous figure.

FIGS. 38-40 illustrate screenshots 222, 225 and 227 of one embodiment of an executive functioning game called "Rule Change," which challenges a game participant to categorize cards based on conditional rules.

For example, in FIG. 38, Rule Change gives two instructions to the game participant. The first instruction 223 is to respond to a black card if the card value is higher or lower than five. The second instruction 224 is to respond to a red card if the value is even or odd. In FIG. 39, Rule Change displays a card 226 drawn from a normal desk of cards. The participant is challenged to initially differentiate the card 226 based on the color of the card (black vs red). Then, in FIG. 40, Rule Change ceases displaying the card 226 and prompts 229-231 the participant to follow the appropriate rule that involves the number on the card. The participant is challenged to respond as quickly as possible. As training progresses, the rules change more frequently.

2. Mental Rotation

Figure 41:
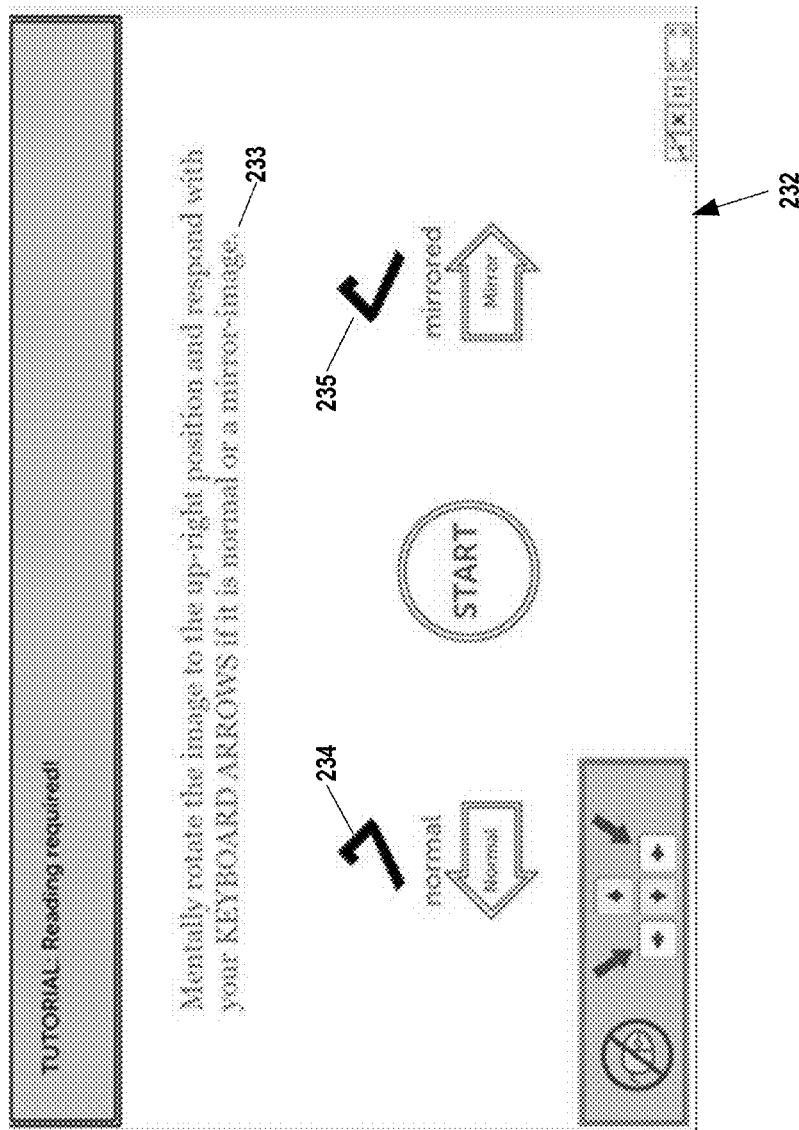
FIG. 41 illustrates a screenshot of one embodiment of another executive functioning game called "Mental Rotation," which challenges a game participant to mentally rotate a letter or number to its right-side up position and indicate whether it is a normal or mirrored image.
Figure 42:
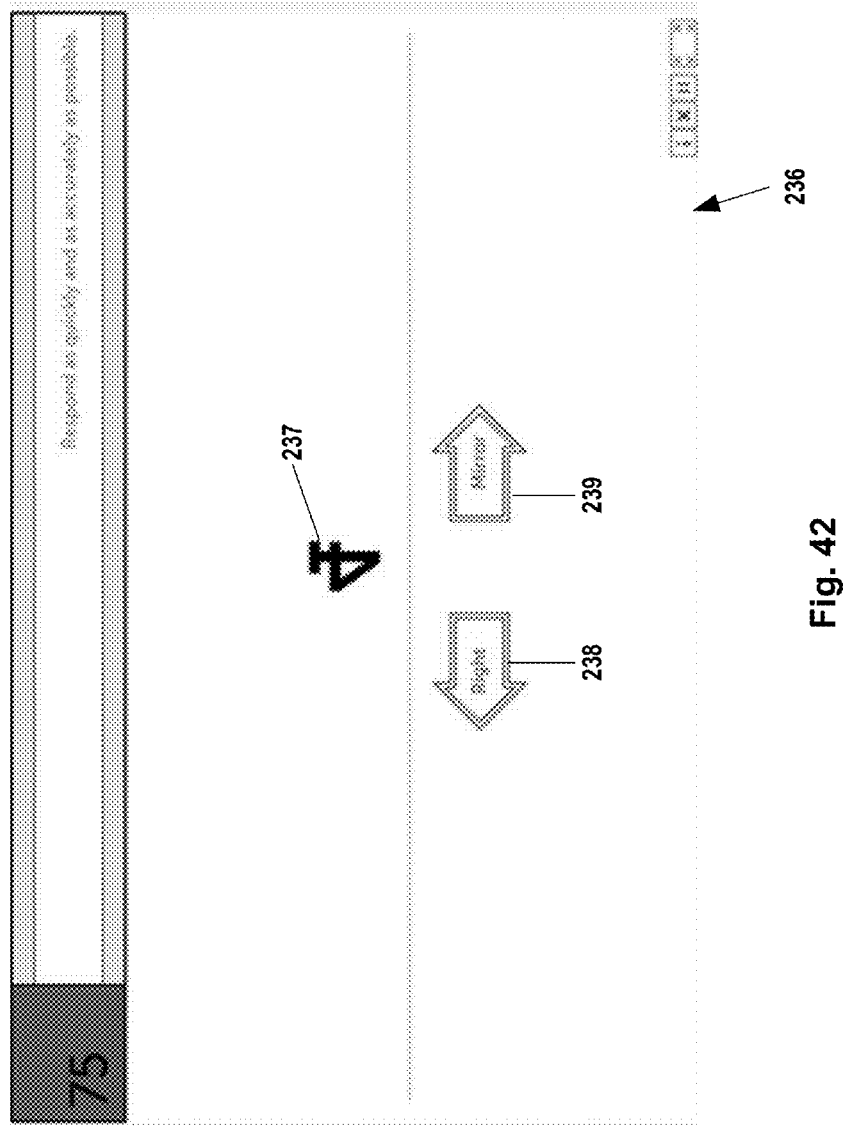
FIG. 42 illustrates another screenshot of the game illustrated in the previous figure.

FIGS. 41 and 42 illustrate screenshots 232, 236 of one embodiment of another executive functioning game called "Mental Rotation," which challenges a game participant to mentally rotate a letter or number to its right-side up position and indicate whether it is a normal or mirrored image. For example, FIG. 41 illustrates rotated "7" 234 and a rotated-and-mirrored "7" 235. Mental Rotation instructs 233 the participant to mentally rotate each target image to its upright position and indicate, using keyboard arrows, whether the target image is a normal or mirror-image. In FIG. 42, the target image 237 is a rotated-and-mirrored "4." The participant is prompted to indicate whether the target image 237 is a normal or mirrored "4" using the left arrow key 238 or the right arrow key 239, respectively.

VIII. Self Control and Reward Processing

The training program 2 also includes games 4 that address various aspects of self-control and reward processing. Games 4 that strengthen self-control utilize techniques like meta-cognition (metric on how impulsive the user is in comparison to healthy peers who are more patient), speeding up inhibition processes, manipulation of attention, and control over one's internal state. Games 4 that renormalize reward values train the user to shift their attention towards rewards that healthy peers consider rewarding (like scenes of family, friends, life milestones). More advanced games 4 require the participant to track and manipulate the rewarding values to perform memory tasks or decision-making tasks.

Some games 4 train the participant to divert attention away from salient addiction-related or obsession-triggering stimuli that they should be paying less attention to, e.g., drugs, fattening food, source of anxiety or negativity (Grin Hunting, Name the Color, The Matrix Recalled). Other games 4 train through tracking measures of impulsivity in oneself like warped time perception (Tick Tock) and discounting of future monetary rewards before and after seeing distracting stimuli (Now or Later). These measures of impulsivity are provided to the participant to gain self-awareness and training tends to focus on metacognition. Aside from external distractions, self-control must also work on internal distractions. Training to let thoughts and feelings pass by is dealt with in the mindful breathing exercise (Air Control). Self-control can also be expressed as poor motor control or "pulling the trigger too quickly", so there is one game addressing motor impulsivity (Category Click).

In particular, Self-control games train the participant to suppress automatic processes like reading words, particularly if they relate to substances (Stroop task with trigger words), and attending to external stimuli (Mindfulness task). Participants are also trained to observe and alter their choice behavior to be more consistent with their healthy peers (Temporal choice game that provides self-awareness). Other games deal with time perception and motor control, which are typically less controlled in individuals with SUD. Distractors across the games are drug-related triggers spanning people, places, things, and actions associated with drug use. These distractors are never part of a correct response, and so the participant should implicitly shift attention away from them. By having such distractors be irrelevant throughout training, we are dampening the encoding of stimulus-outcome associations in the brain that pair drug-related triggers with positive outcomes by rendering the positive outcome obsolete.

Reward processing games renormalize reward processing, by having the participant focus more on rewards normally considered rewarding, e.g., family, friends, life milestones, helping others, symbols of happiness and success. The participant not only focuses on such rewards during the games, but also discovers through implicit training that these rewards lead them to the correct responses. Since reading of social cues is necessary for deriving reward from them, games in this domain also train the participant to notice more details in social cues and accurately classify them based on their emotional properties. Games become more difficult by requiring the participant to manipulate reward attributes in the task or remembering the attributes against distractors and time delays. Again, the distractors are tailored to the participant. By requiring fast and/or attentive responses to rewarding and emotional stimuli, these games attempt to strengthen Pavlovian approach responding towards people, places, things, or actions normally considered rewarding.

The stimuli described here are for alcoholism. However, they can be modified to address other forms of addiction (like food or drugs), anxiety, or negativity.

1. Air Control

Figure 43:
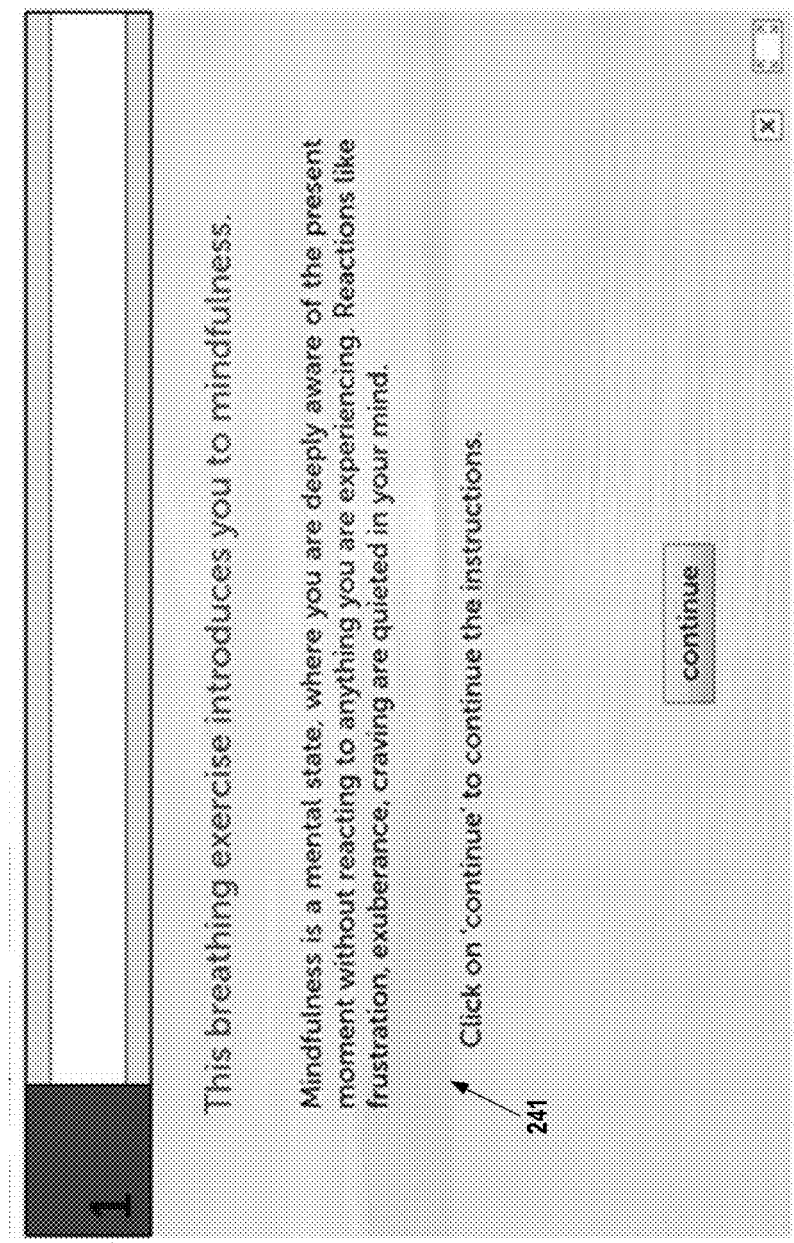
FIG. 43 illustrates a screenshot of one embodiment of a mindfulness exercise called "Air Control," which challenges a participant to practice mindful breathing.
Figure 44:
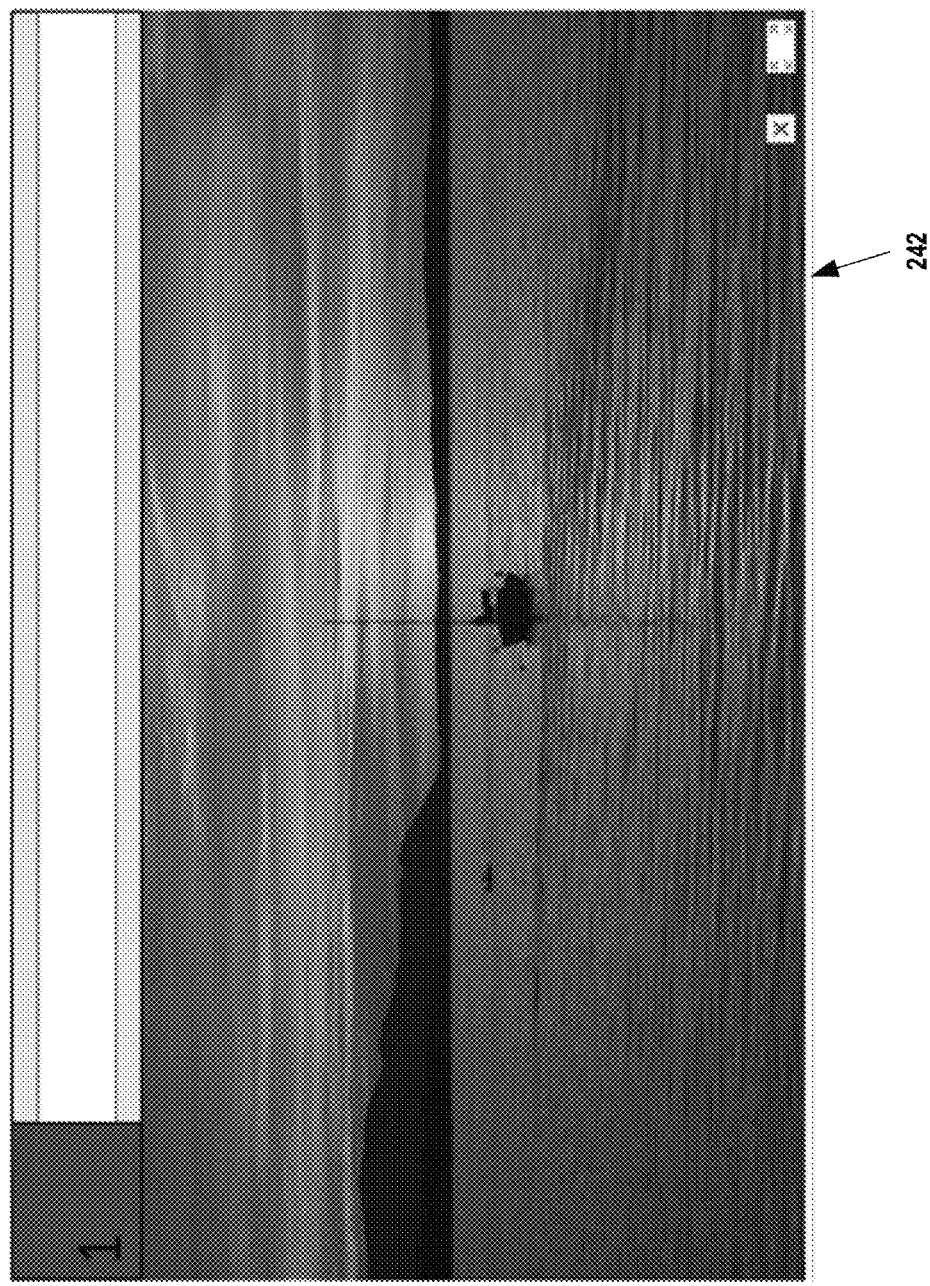
FIG. 44 illustrates another screenshot of the exercise illustrated in the previous figure.

FIGS. 43 and 44 illustrate screenshots 240, 242 of one embodiment of a mindfulness game called "Air Control," which challenges a participant to practice mindful breathing. Air Control provides instructions 241 at the beginning of the task. As shown in screenshot 242, Air Control displays a peaceful nature scene to facilitate mindfulness. The duration of the mindfulness period starts at two minutes and increases by thirty seconds increments up to five minutes.

2. Grin Hunting

Figure 45:
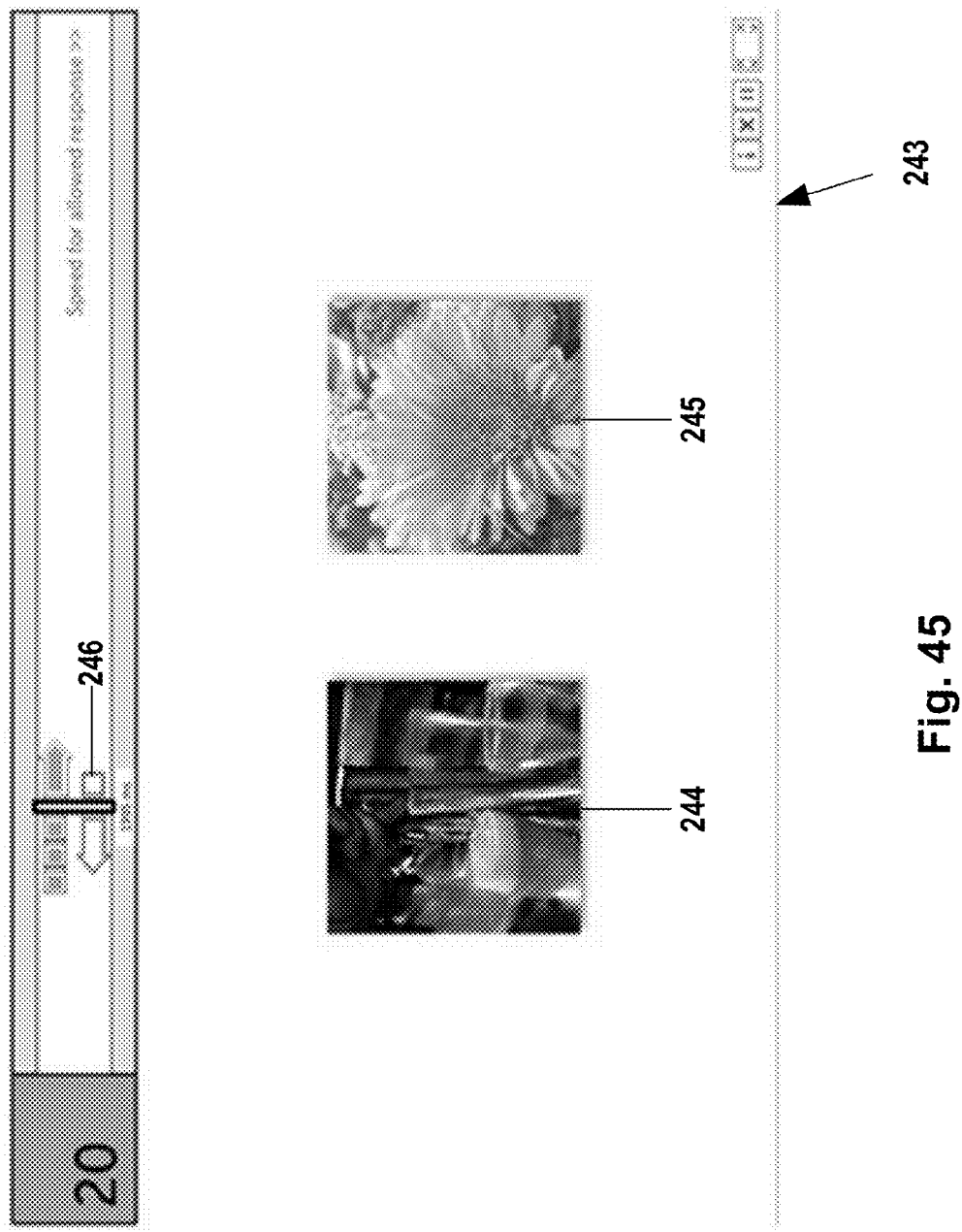
FIGS. 45-64 illustrate various embodiments of attentional bias modification games that challenge the game participant to suppress responses to stimuli to which the game participant is prone toward an unhealthy psychological response, such as craving, trauma, or depression.
Figure 46:
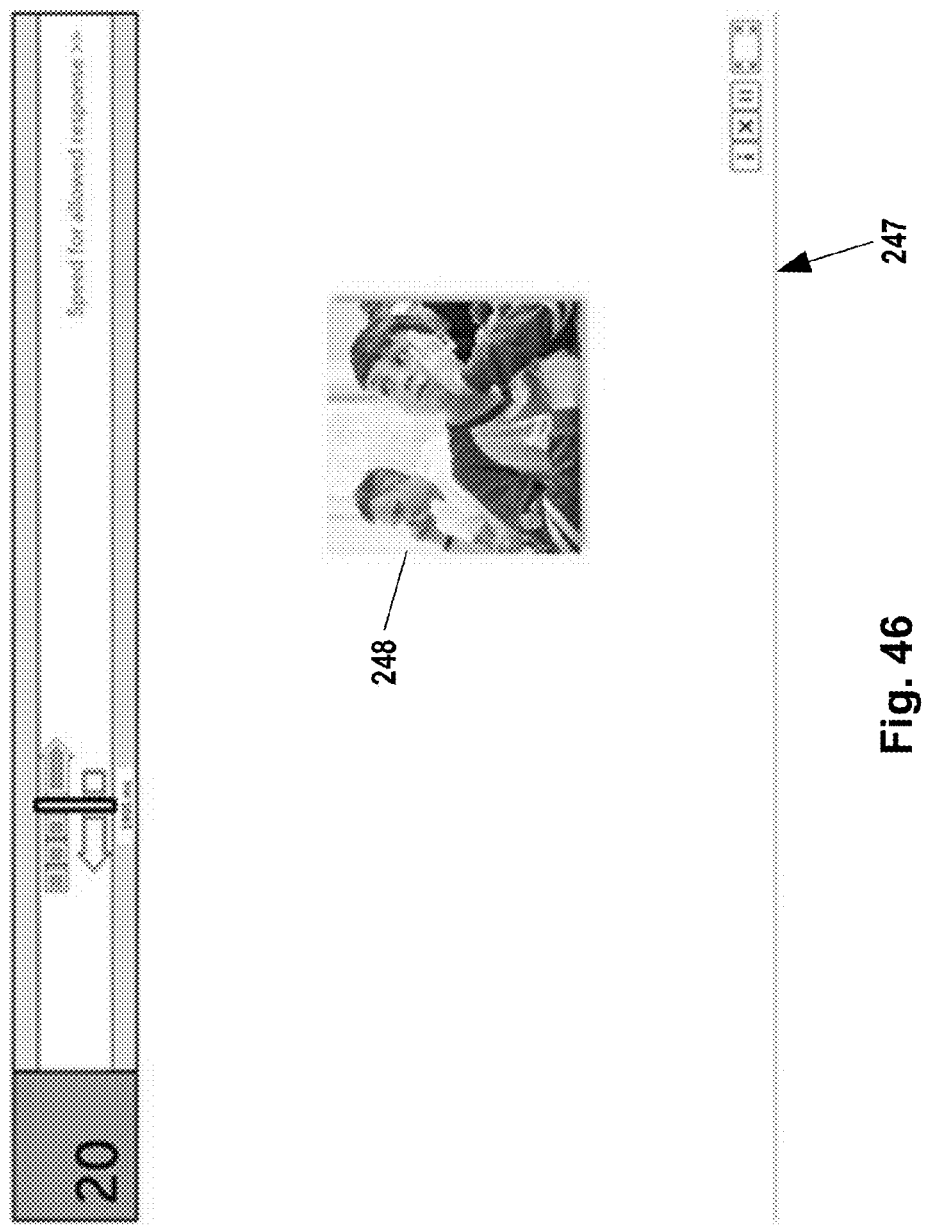

FIGS. 45 and 46 illustrate screenshots 243, 247 of one embodiment of an attentional bias modification game called "Grin Hunting." In an addict, images, sounds, and smells of objects of their addiction frequently trigger craving. Depressed individuals tend to linger on depressing images and sounds longer than healthy individuals. In PTSD individuals, certain images, sounds, and smells can trigger trauma. Grin Hunting challenges and trains a game participant—such as an addict or a depressed or traumatized individual—to ignore stimuli that trigger unhealthy psychological responses and/or selectively respond to healthy stimuli.

Grin Hunting displays sets of spatially distributed images 244, 245. Each set of images 244, 245 is displayed for a brief time interval, after which the images are cleared from the screen and replaced with a single image in the position where the image with a positive valence was located.

In each set, one of the images—such as of a flower 245 or a smiling face—has a positive valence. The other image in the set tends to initially trigger or evoke an unhealthy psychological response, such as craving, anger, or obsession.

In a version or configuration tailored for addicts, Grin Hunting includes objects—such as a picture 244 of an alcoholic beverage—that triggers craving in an addict. In a version or configuration tailored for depressed individuals, Grin Hunting shows depressing pictures—such as pictures of a sad facial expression—upon which depressed individuals are more prone to dwell. In a version or configuration tailored for traumatized individuals, Grin Hunting shows images related to their trauma.

The set of positive and negative valence images stimuli remain presented for a short duration. Afterwards, they disappear (they are cleared from the screen), and a replacement image is displayed in the position where the positively valenced image was. The replacement image may have a positive valence, such as a smile, or a neutral valence, such as the image 248 of an emotionally neutral expression shown in FIG. 46. The replacement image is not one that would reinforce the game participant's addiction, trauma, depression, or vice. If the stimulus contains a smile, the user is to locate and click on the smile to get the trial correct. Otherwise, the user waits to continue onto the next trial.

The game receives and times the game participant's selections, providing an indication or measure 246 of the speed of the game participant's response. In a competitive embodiment, Grin Hunting ranks the game participant's selections against those of other game participants after the game participant completes a block of trials.

In general, a Grin Hunting trial has two steps, an attention biasing step and a smile detection step. In the attentional biasing step, two or more spatially distinct stimuli are presented to the participant, of which one (or a subset) is to be ignored. The rest are all effectively positive stimuli. For example, two visual stimuli appear briefly to the left and right of the center of a digital display (e.g., on a computer monitor, tablet, or phone). One is an image that prompts the undesirable behavior (for example, the craving for eating or for drinking an addictive food or beverage). The other is an emotionally positive image that does not prompt the undesirable behavior.

The stimuli remain presented for a short duration, then disappear and initiate the smile detection step. In this step, the previous stimulus not associated with the undesirable behavior is replaced with another emotionally positive image, which may or may not contain a smile in it. If the stimulus contains a smile, the participant is to locate and click on the smile to get the trial correct. Otherwise, the participant waits to continue onto the next trial. While the participant performs the training, data is collected and analyzed to compute measures of how well the participant is in disengaging cues triggering the undesirable behavior. These measures enable the participant to see regular improvement, which could increase their motivation to continue with their training and behavior modification. Data can also be shared with clinicians and other medical professionals.

Selection of the stimuli is designed for specific behavior modification. Stimuli that draw unwanted exaggerated attention can be used for those that are to be ignored in the task and final corrected behavior. Example images would feature cigarettes and lighters for smokers, spider webs and daddy longlegs for spider phobics, and bloodshed for soldiers with post-traumatic stress disorder. Emotionally positive stimuli that do not prompt the behavior to be corrected would feature images of sunsets and tranquil scenery, family and friends, and representations of inspirational goals and success (which can be personalized). Those stimuli are then divided for use in the two steps of the trial. Through net positive framing of the training stimuli, this cognitive training method can additionally increase happiness and wellbeing.

Another example of stimuli to be ignored could be images of fattening food, from which a dieter trains to divert attention away. The dieter instead would attend to other stimuli like images of delicious, healthy foods and positive images of exercise, which predict where the subsequent image with a smile will be. The task design reduces attention and value of the stimuli that are to be ignored, while enhancing attention and value of the stimuli that are motivating in correcting behavior and promoting positive emotions. By focusing on fundamental mechanisms that guide behavior, Grin Hunting has board applications beyond attention and social cognition training. It can address addictive behaviors like drug abuse and overeating, depression and other mood disorders, anxiety and phobias, as well as overall happiness. Further, data collected during the training can serve as assessments of progress.

Eradicating a bad habit requires dissolving neural mechanisms that encode associations between stimuli that trigger the cascade of undesirable behavior and actions that make up the undesirable behavior. Meanwhile, it is complemented by strengthening favorable behavior and weakening associates between habit-triggering cues and memories and their expectancies and outcomes. The approach of Grin Hunting is to divert attention away from any cue that prompts the undesirable behavior. For alcoholics, successful training that reduces relapse involves disengaging attention towards images related to alcohol. Similar training can be applied to ameliorate other forms of addiction like smoking, other drugs, or gambling, as well as the treatment of phobias. Shifts of attention can also be coupled with actions that antagonize and eventually replace bad habits and abnormal behavior. For instance, if a bad habit involves gravitating towards particular items, training would require movements away from said items. Grin Hunting reduces attention to cues that trigger an undesirable behavior, while making them irrelevant to decision-making processes; promotes and rehearses actions that replace the undesirable behavior; and reinforces positive, pro-social emotions (in the form of smiles) for executing good behavior. Instilling positive emotions in the training serves as an analogue to the release of endorphins after intense physical exercise (i.e., for a dieter) in that good behavior is implicitly reinforced and broadly represented on a neuronal level in the brain.

In one embodiment, Grin Hunting uses randomized trials, wherein a selected percentage (such as 50%) of the images are followed by smiles. As the participant's accuracy improves or the levels advance, the sets of images are presented at a faster pace, and the presentation duration decreases. The possible locations of the images also increase as the game progresses. The stimuli also change in salience or visual properties like luminance, making diversion of attention away from the cue associated with an undesirable behavior, i.e., image of cigarettes for breaking the habit of smoking, harder. For example, in a Grin Hunting game configured for alcohol addicts, alcohol-related images appear progressively brighter and more distracting compared to non-alcohol-related images. The stimuli also increases in realism, going from cartoon to high-resolution photos to the participant's personal collection of stimuli. These changes drive bottom-up attentional processes that must then be regulated by top-down attentional processes and strengthened cognitive control. The collective changes affecting attentional bias also scale with how well the participant performs in the training across trials and days.

While the user performs the training, data is collected and analyzed to compute measures of how well the user is in disengaging cues triggering the undesirable behavior. These measures enable the user to see regular improvement, which could increase their motivation to continue with their training and behavior modification. Data can also be shared with clinicians and other medical professionals.

In one embodiment of an attentional bias modification program, one stage of the Grin Hunting game is used in the assessment phase, and five stages are used in the training phase.

3. Category Click

Figure 47:
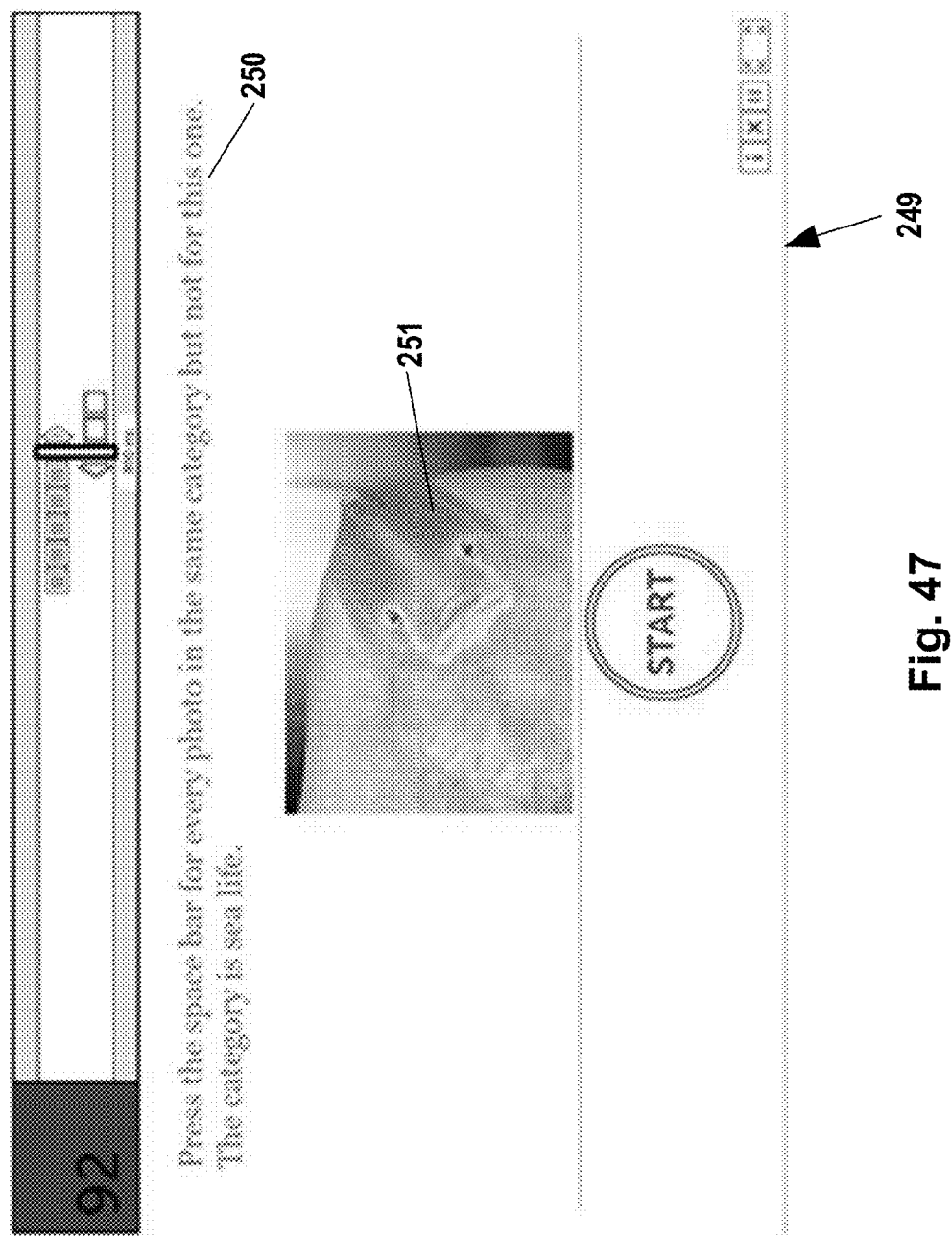
Figure 48:
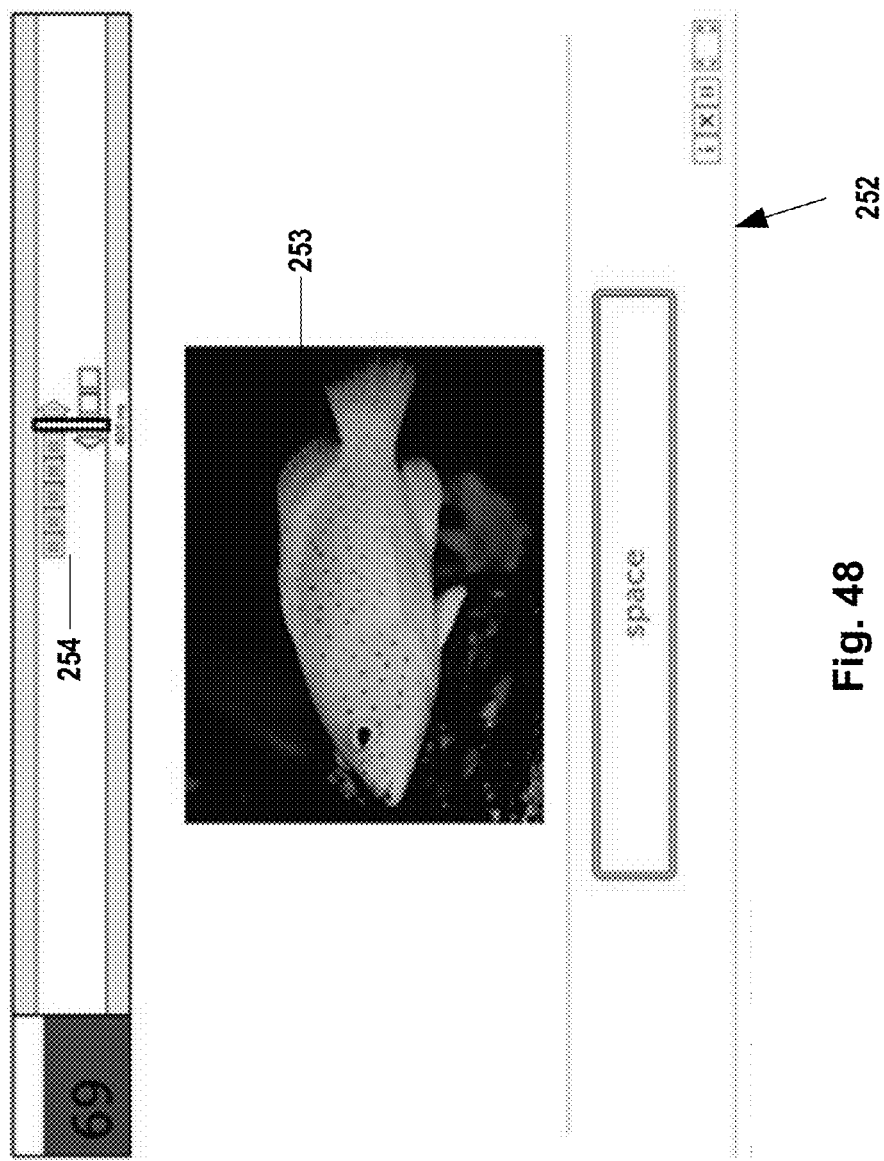
Figure 49:
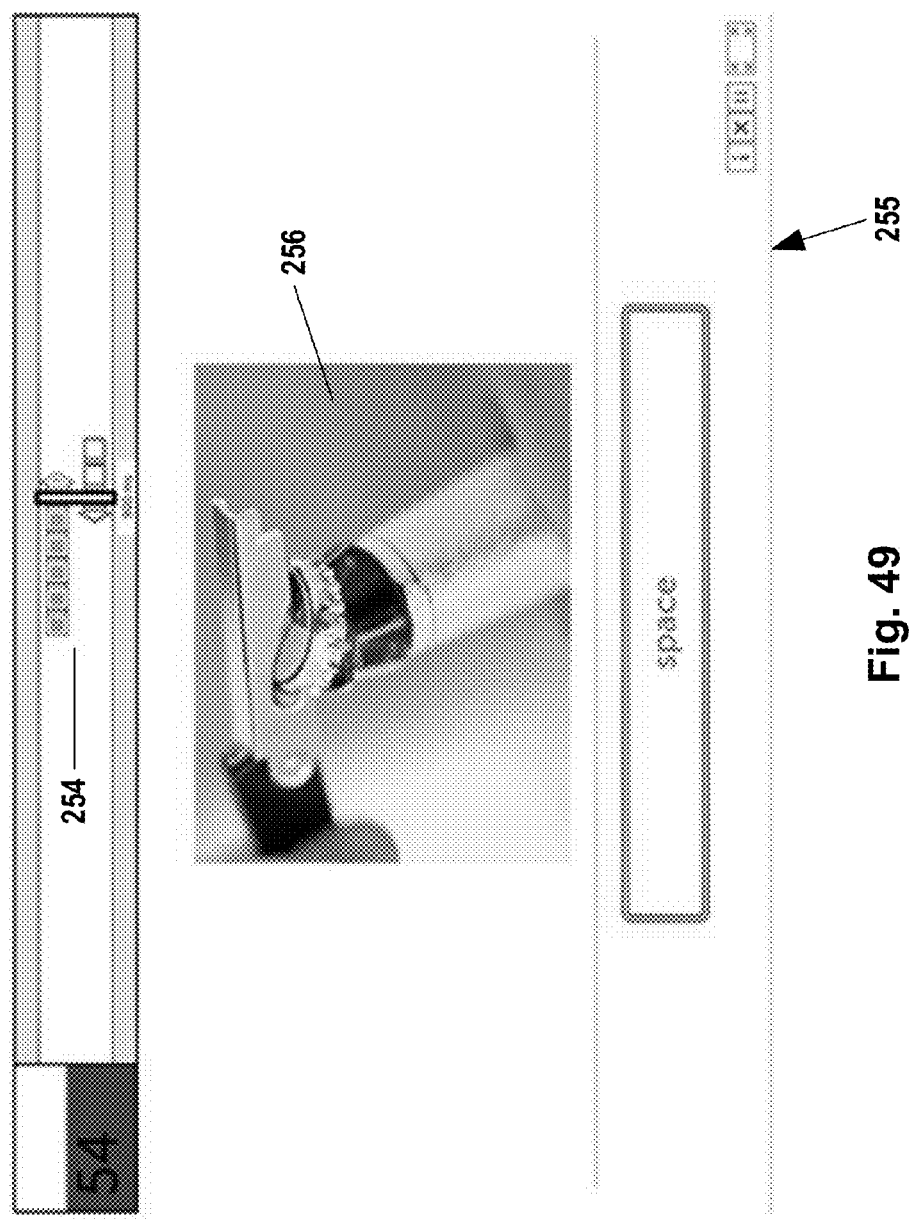
Figure 50:
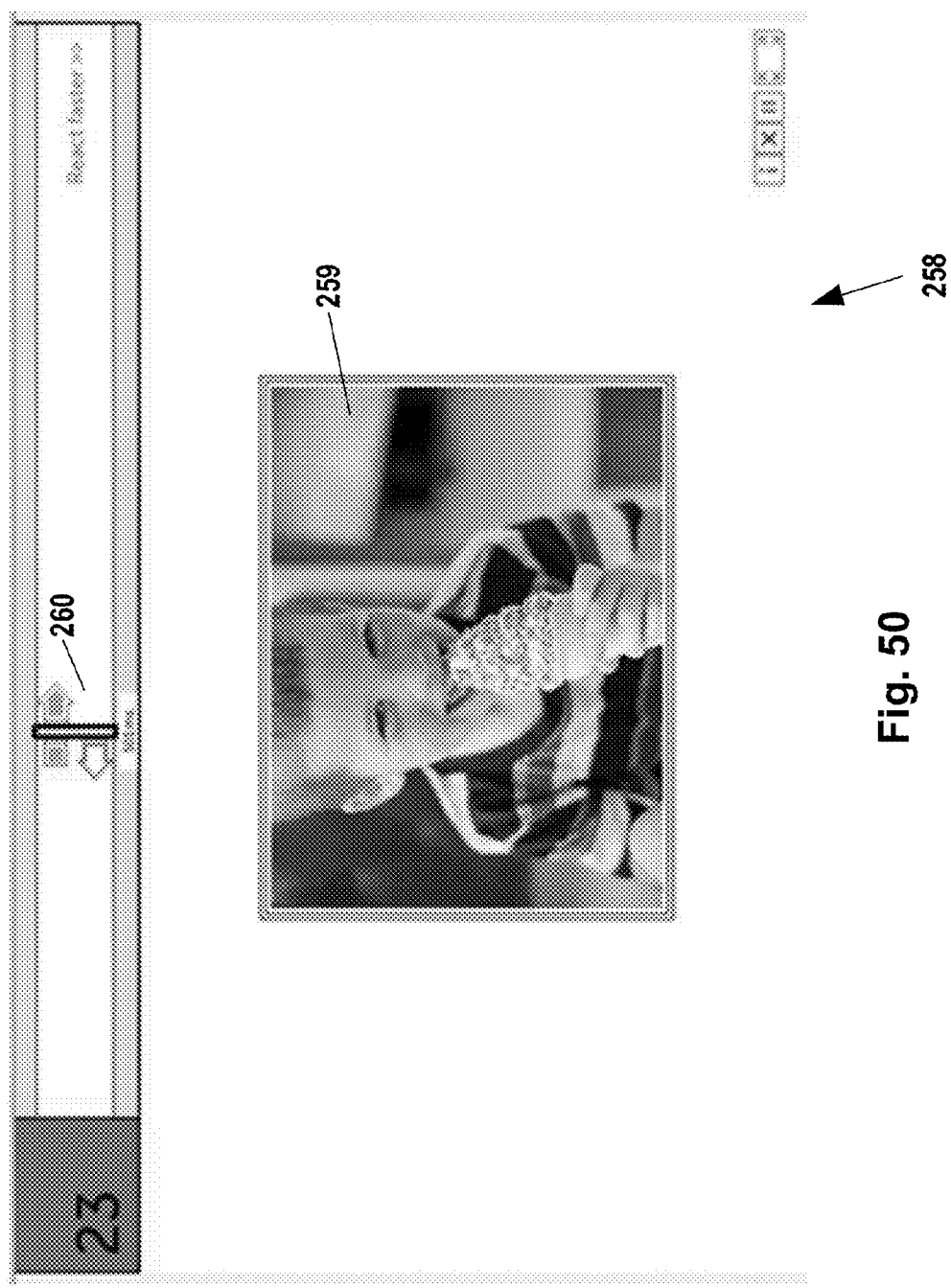
Figure 51:
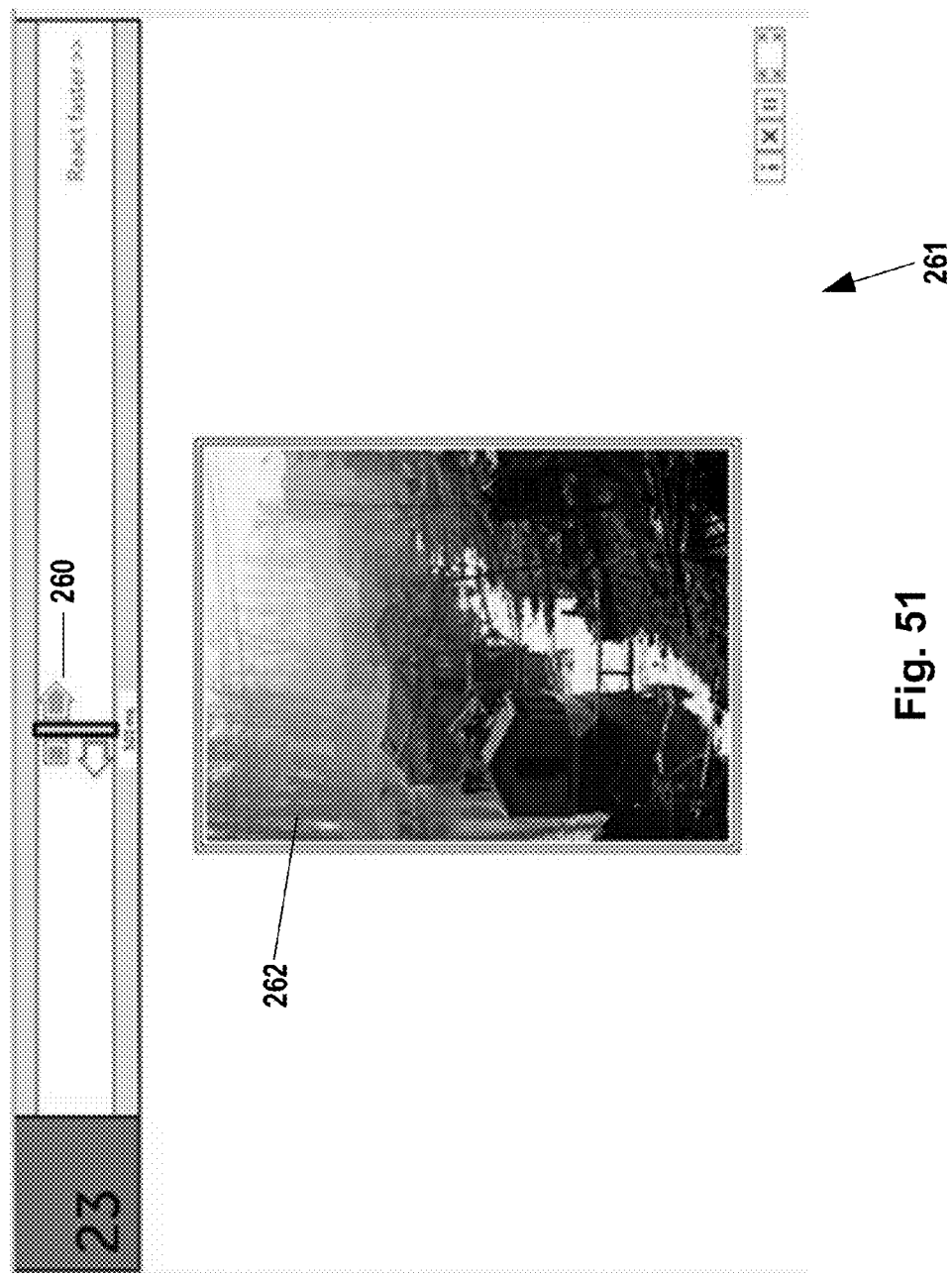
Figure 52:
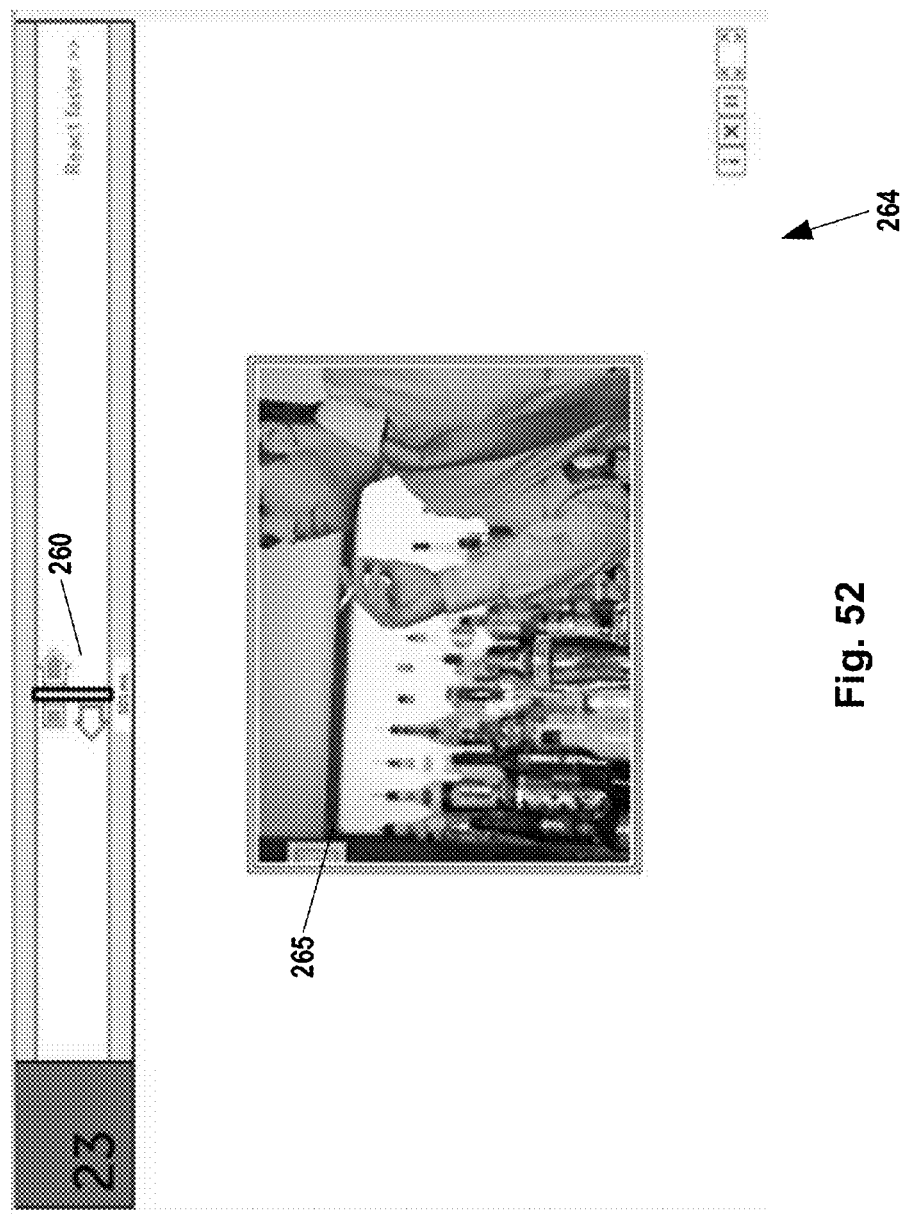
Figure 53:
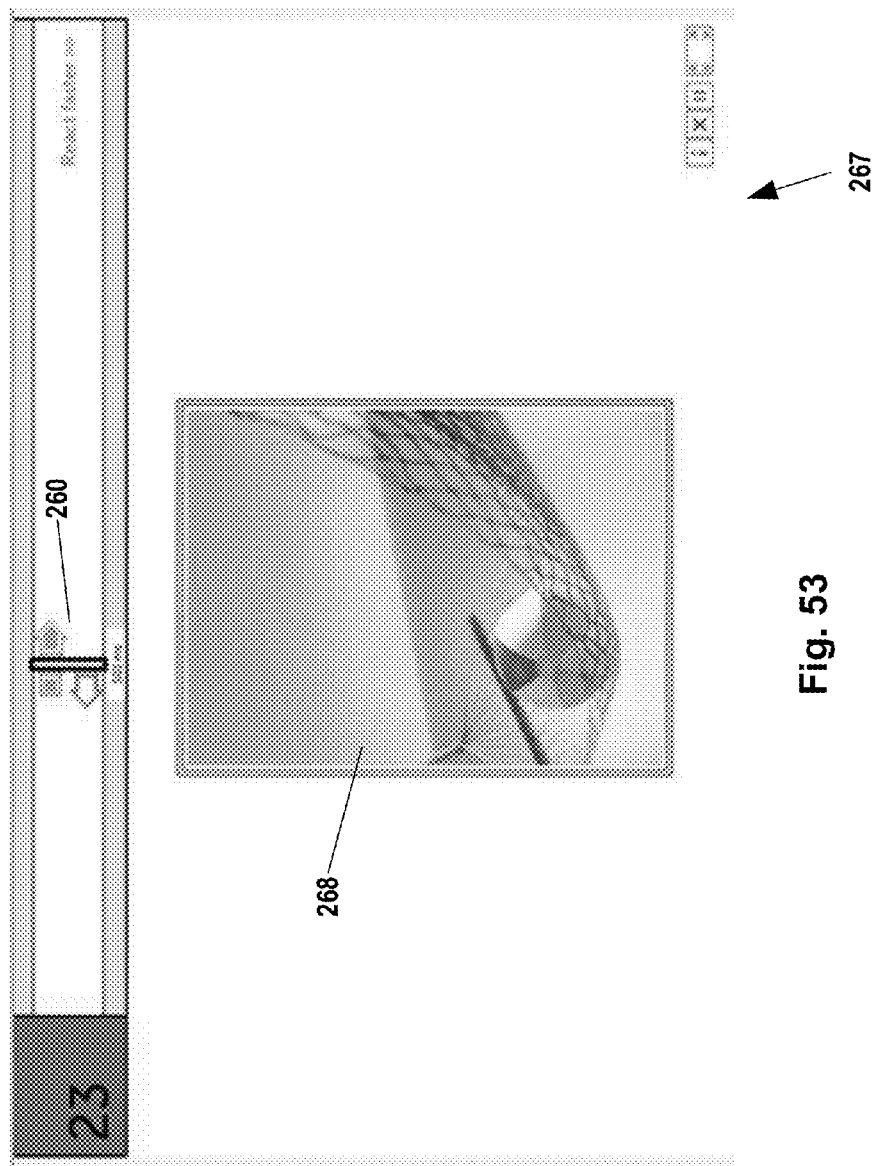
Figure 54:
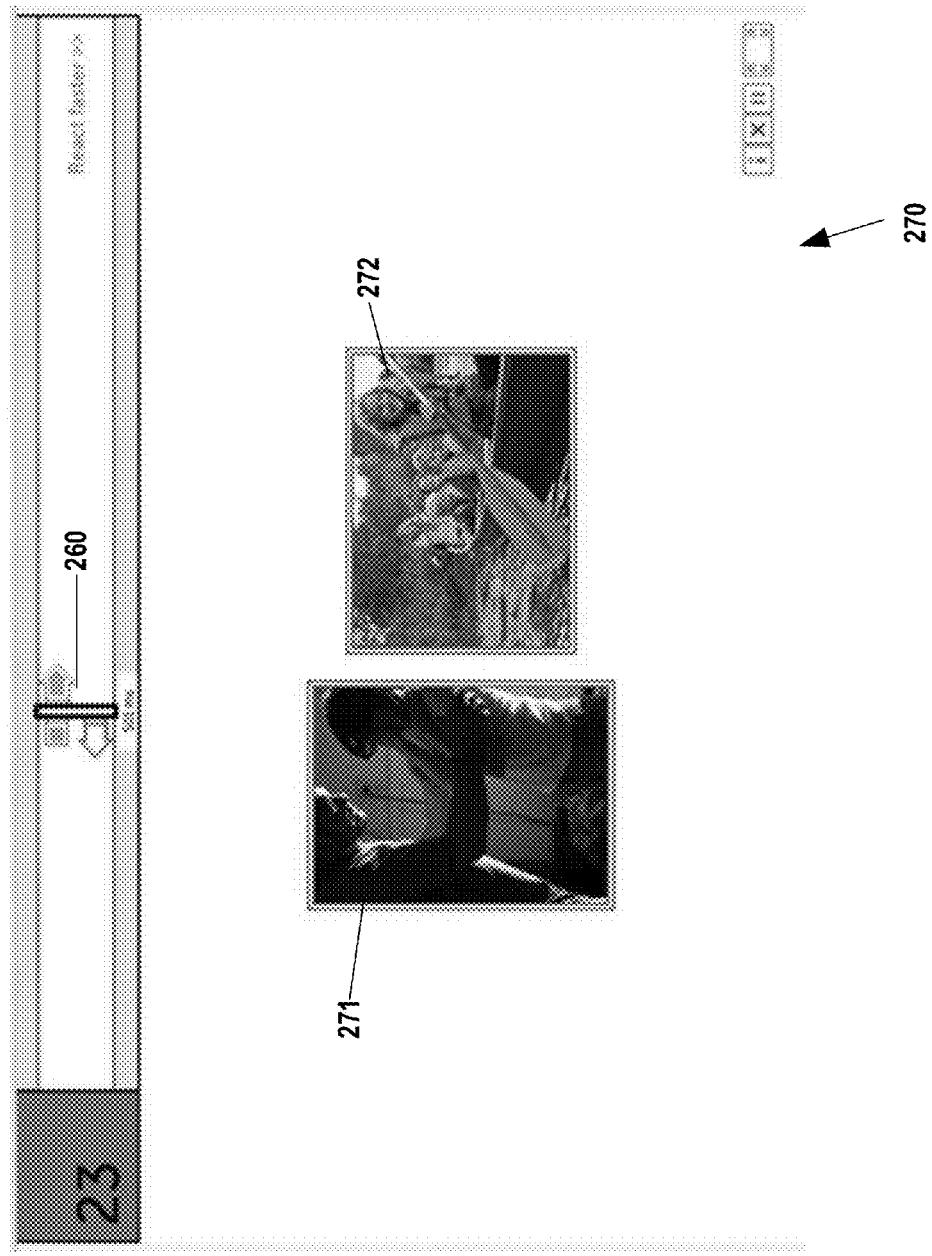

FIGS. 47-49 illustrate screenshots 249, 252, and 255 of one embodiment of a game called "Category Click," which challenges a game participant to selectively respond to stimuli that fall within a target category except for one or more pre-identified "freeze" stimuli that fall within that category.

Category Click presents a target category and a freeze stimulus that belongs to that category. FIG. 47 illustrates an instruction 250 that identifies the category as "sea life" and illustrates a freeze stimulus 251 constituting a stingray image.

After the game participant selects "Start," Category Click displays a sequence of stimuli on the screen. A plurality of the stimuli—for example, the fish 253 shown in FIG. 48—belong to the target category. A plurality of the stimuli do not belong to the target category. At least one of the stimuli includes the freeze stimulus. Furthermore, a plurality of the stimuli—for example, the image 256 of a bottle cap being removed on FIG. 49—are distractor stimuli, for example, images and/or sounds that arouse addictive craving or trigger negative feelings.

Category Click challenges the game participant to respond to every stimulus that belongs to the category except for the reference stimulus. Category Click also challenges the game participant to withhold providing any response to any distractor stimuli. For example, the participant may be challenged to click a mouse button or press a spacebar every time he or she sees an image within an instructed category, but to withhold responding to either the freeze image or any alcohol-related lures that may appear.

Category Click receives and times the game participant's selections and displays a measure 254 of the participant's speed on the screen. At the end of a block of trials, Category Click ranks the game participant's performance against those of other game participants.

In one embodiment of an attentional bias modification program, one stage of the Category Click game is used in the assessment phase, and twenty stages are used in the training phase. As the game progresses, Category Click alternates between various categories of images. Also, as the game progresses toward advanced levels, the freeze image becomes harder to differentiate from the rest of the images in the category.

4. Mood Matchmaker

FIGS. 50-54 illustrate screenshots 258, 261, 264, 267, and 270 of one embodiment of an affective working memory game called "Mood Matchmaker." Mood Matchmaker challenges a game participant to match a challenge stimulus to a target stimulus in a context that includes a plurality of distracting stimuli, including stimuli that trigger unhealthy psychological responses.

This game is also designed to promote empathy, for which severe problems are noted for individuals with ASD, and to further strengthen ToM elements in the social cognition system. Trainees are required to label social images based on what "the other person" playing the game at the same time would rate it (the other person is actually a normative rating obtained from hundreds of image raters). Participants score points only if their tags match those of the normative rating.

In this task, Mood Matchmaker presents an image 259 evoking a certain affective value (emotion/mood)—for example, of a boy smiling while eating an ice cream cone—and challenges the game participant to remember it across some time period. During that time period, Mood Matchmaker presents a sequence of images 262, 265, 268 that can interfere with their memory retention.

In embodiments of Mood Matchmaker configured for addicts or depressed individuals, the sequence of images 262, 265, 268 may include one or more distracting images 262 or 265 to the game participant. For example, for a game participant struggling with a smoking addiction, the distractions are related to the game participant's "vice," such as an image 265 of cigarette smoking that is highly salient to that game participant. For a game participant struggling with depression, the distractions have a negative affective value, such as a depressing image 262 of a shantytown.

After presenting the sequence of distractor images 262, 265, 268, Mood Matchmaker presents a set of images 271, 272 and prompts the participant to pick the one with the most similar affective value as the first image 259.

Mood Matchmaker receives and times the game participant's selections and displays a measure 134 of the participant's speed on the screen. At the end of a block of trials, Category Click ranks the game participant's performance against those of other game participants.

In one embodiment of an attentional bias modification program, one stage of the Mood Matchmaker game is used in the assessment phase, and twelve stages are used in the training phase.

5. Name the Color

Figure 55:
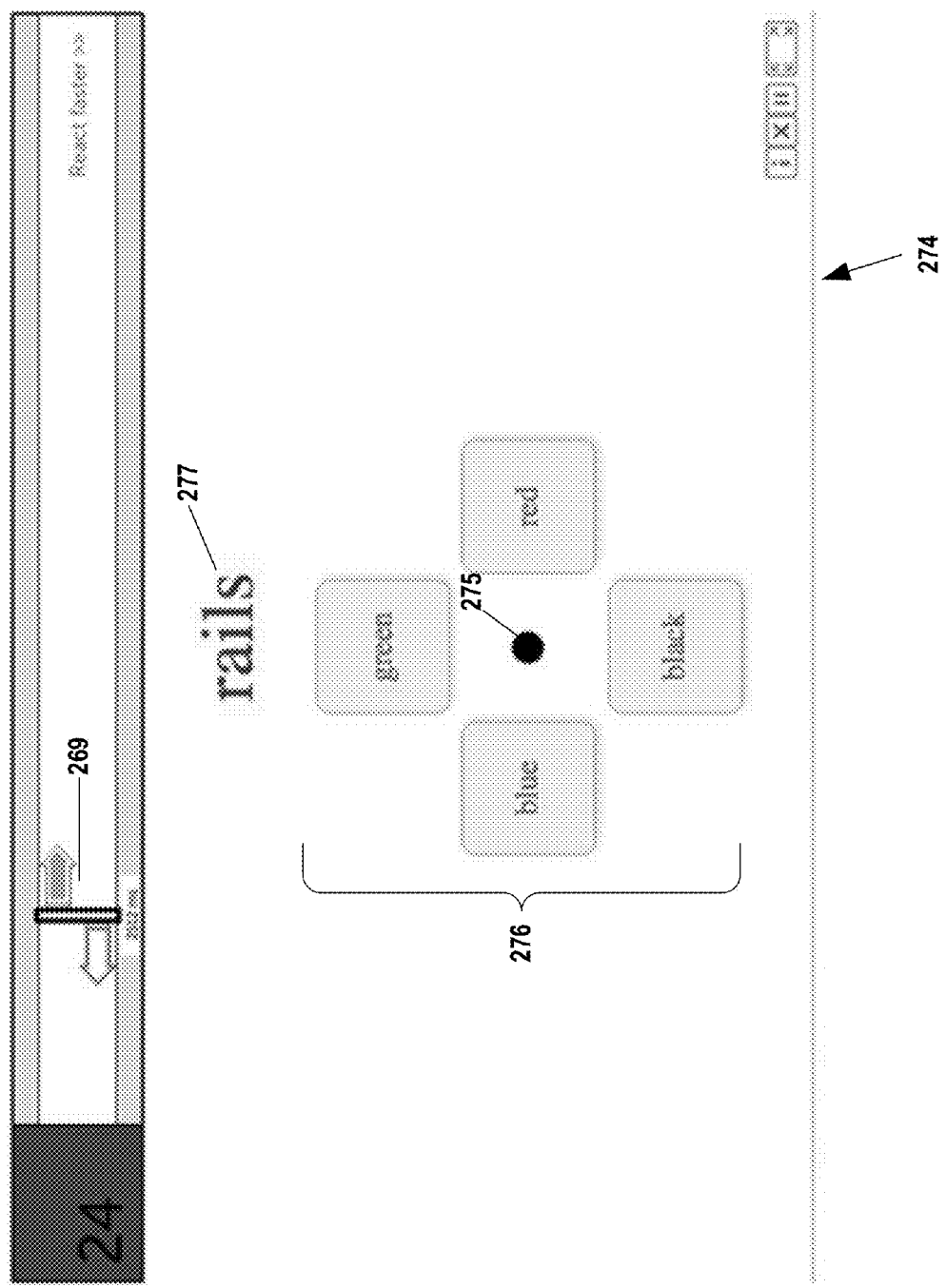

FIG. 55 illustrates a screenshot 274 of one embodiment of a game called "Name the Color." Name that Color challenges a game participant to identify the font color of words that include words that trigger unhealthy psychological responses.

Name that Color presents a central dot 275 and a plurality of selectable buttons 276 around the central dot 275, each selectable button 276 being labeled with a name of a color, such as "red", "blue", "green," and "black." The game instructs the game participant to move a cursor over the dot 275. As soon as the cursor is moved over the dot 275, Name that Color displays a colored challenge word 277 on the screen.

The challenge word 277 is not a name of the color of the word. The challenge words are either neutral words or trigger words related to an addiction or emotional impairment. For example, in FIG. 55, the neutral challenge word "rails" is presented in a red-colored font. Examples of trigger words related to alcoholism include "beer," "bar," and "happy hour." Examples of trigger words related to depression include "bad," "failure" and "dying." Name that Color challenges the game participant to ignore the semantic content of the challenge word 277 and select the button 276 whose label matches the color of the challenge word 277.

Name that Color measures and tracks the game participant's response time to each challenge word 277 and provides an indication or measure 269 of the game participant's speed. Between some of the trials, Name that Color rearranges and/or relabels the selectable buttons, requiring the game participant to continue reading the words on the buttons 276, while attempting to ignore the semantic content of the challenge words 277, as the game goes on.

At the end of a block of trials, Name that Color ranks the game participant's performance against those of other game participants. In one embodiment of an attentional bias modification program, one stage of the Name that Color game is used in the assessment phase, and ten stages are used in the training phase.

The words come from one of two categories—alcohol-related or neutral words. The categories alternate across blocks within the task, and the block size decreases across levels. Colors are red, green, blue, or black.

6. Now or Later

Figure 56:
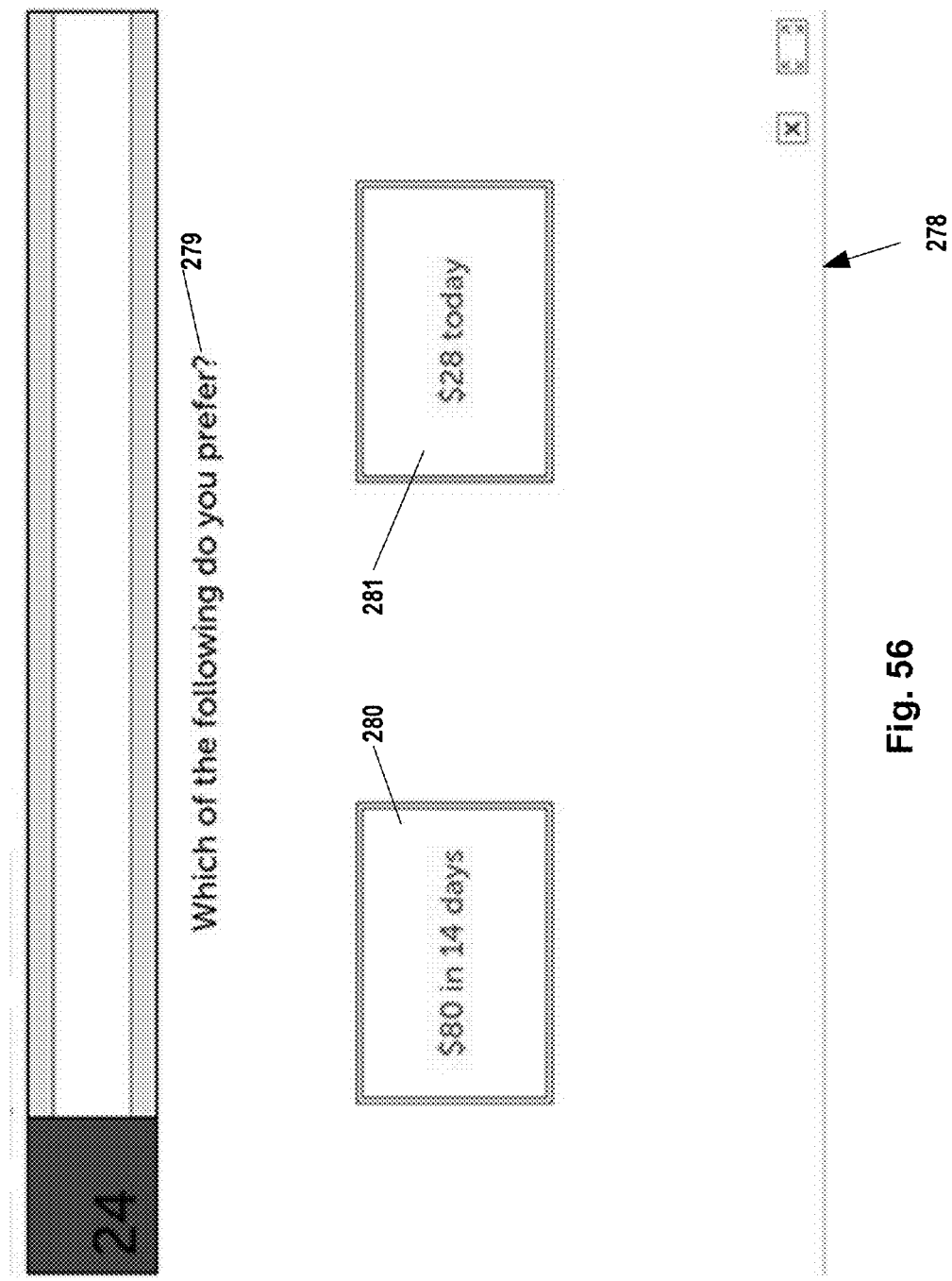
Figure 57:
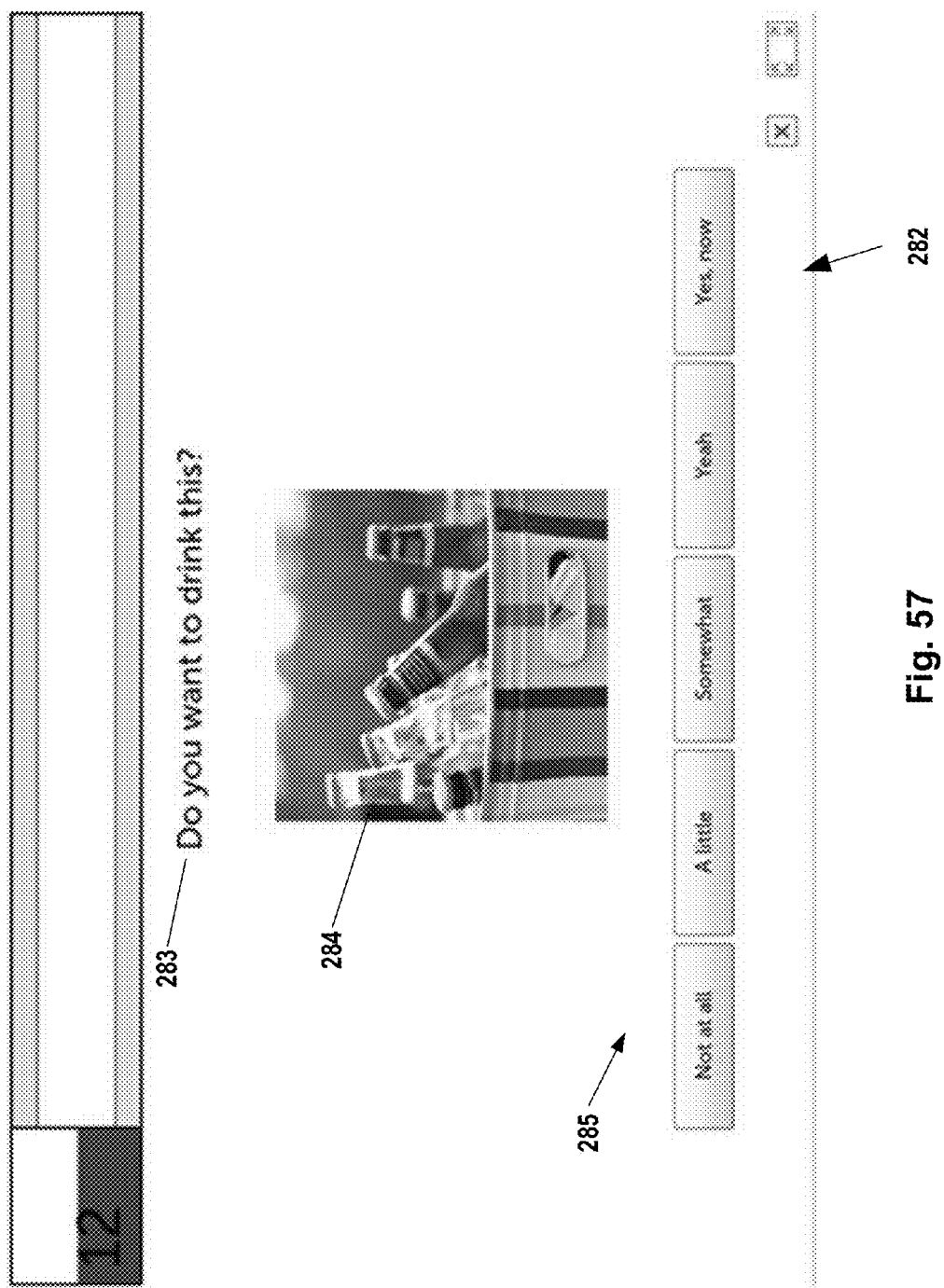
Figure 58:
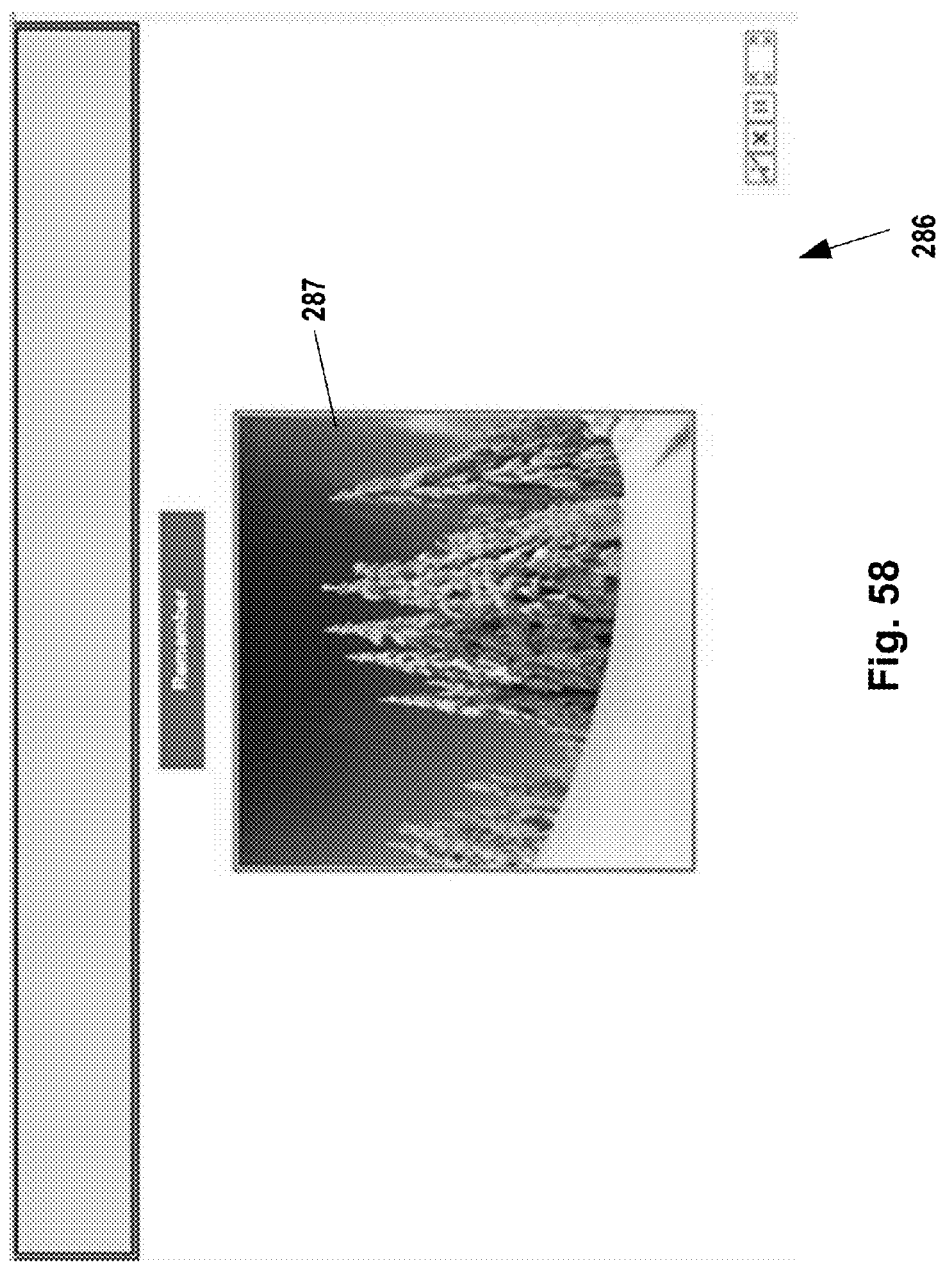
Figure 59:
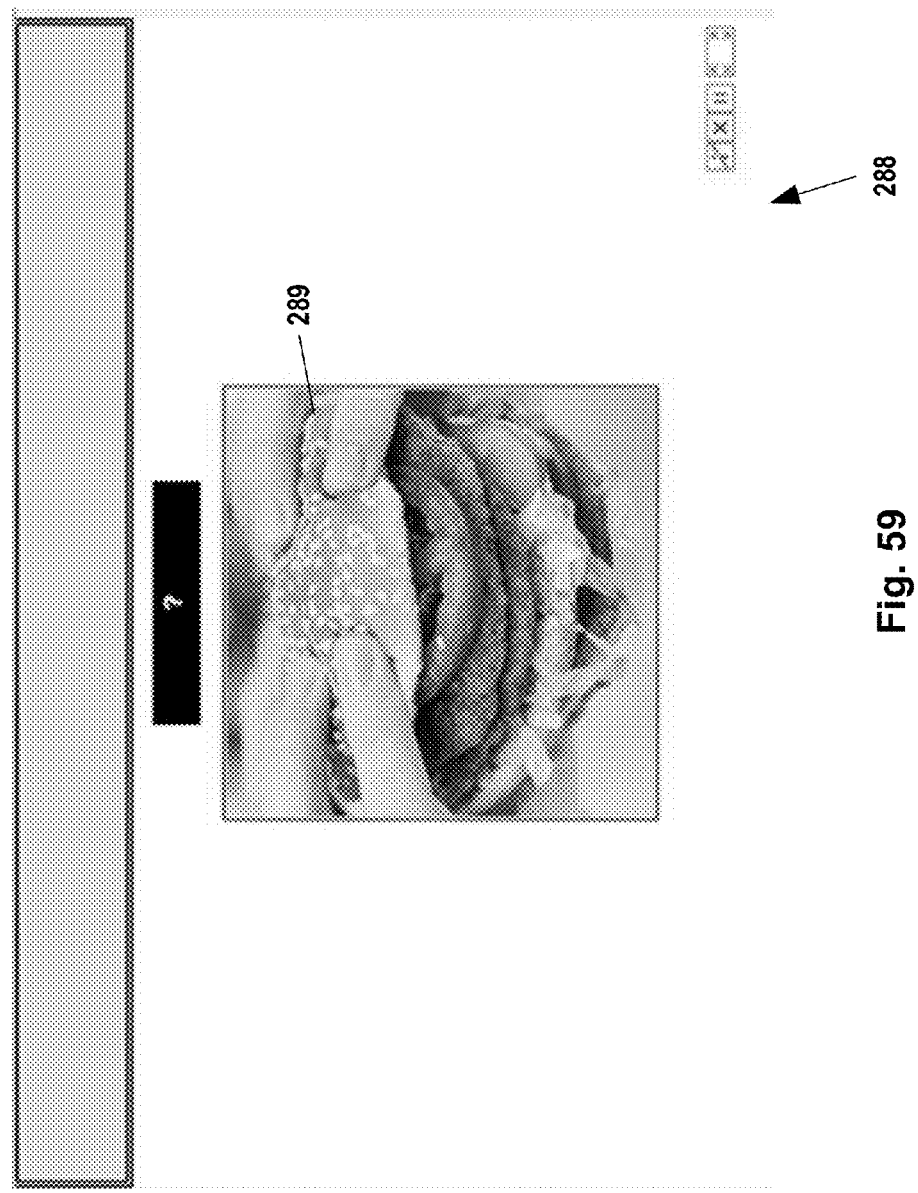
Figure 60:
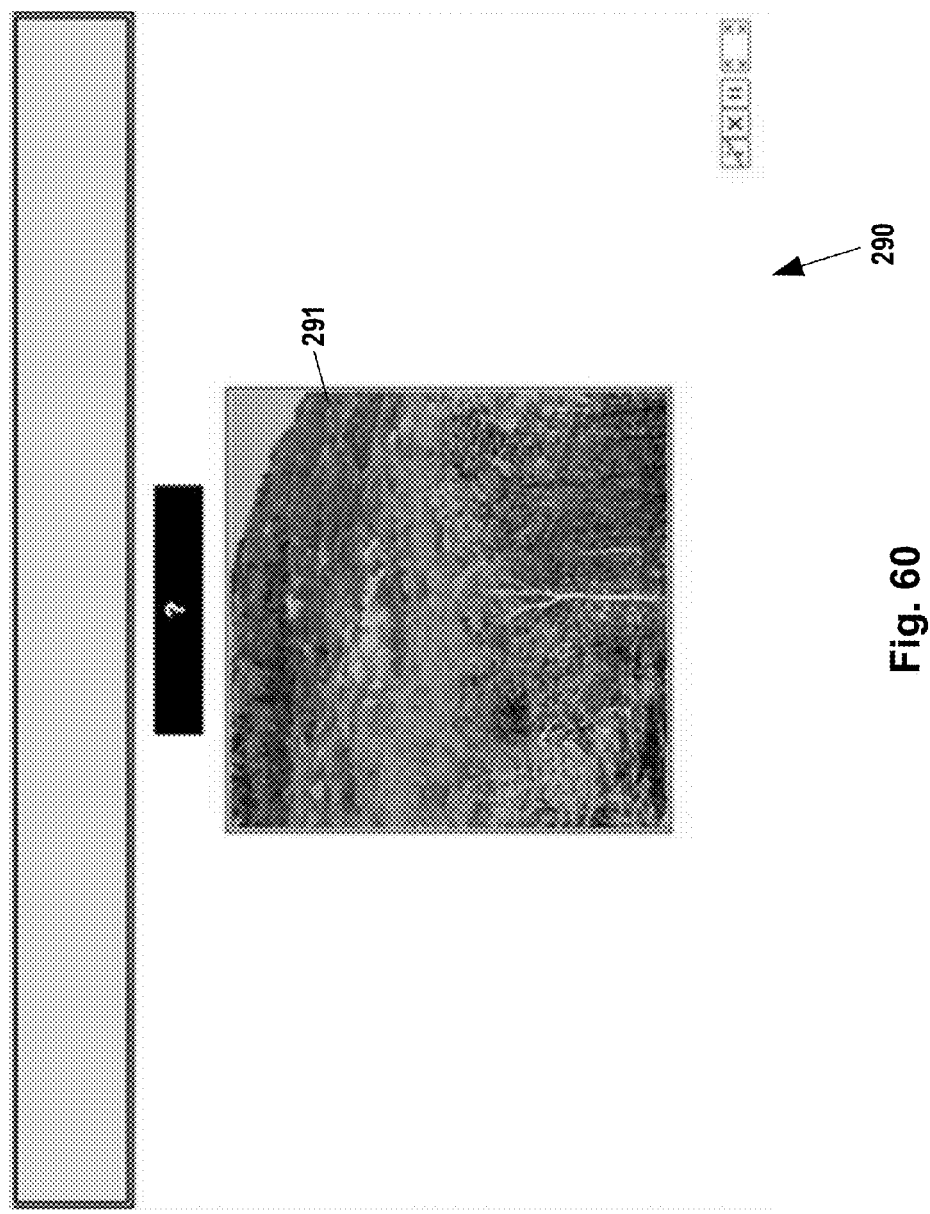
Figure 61:
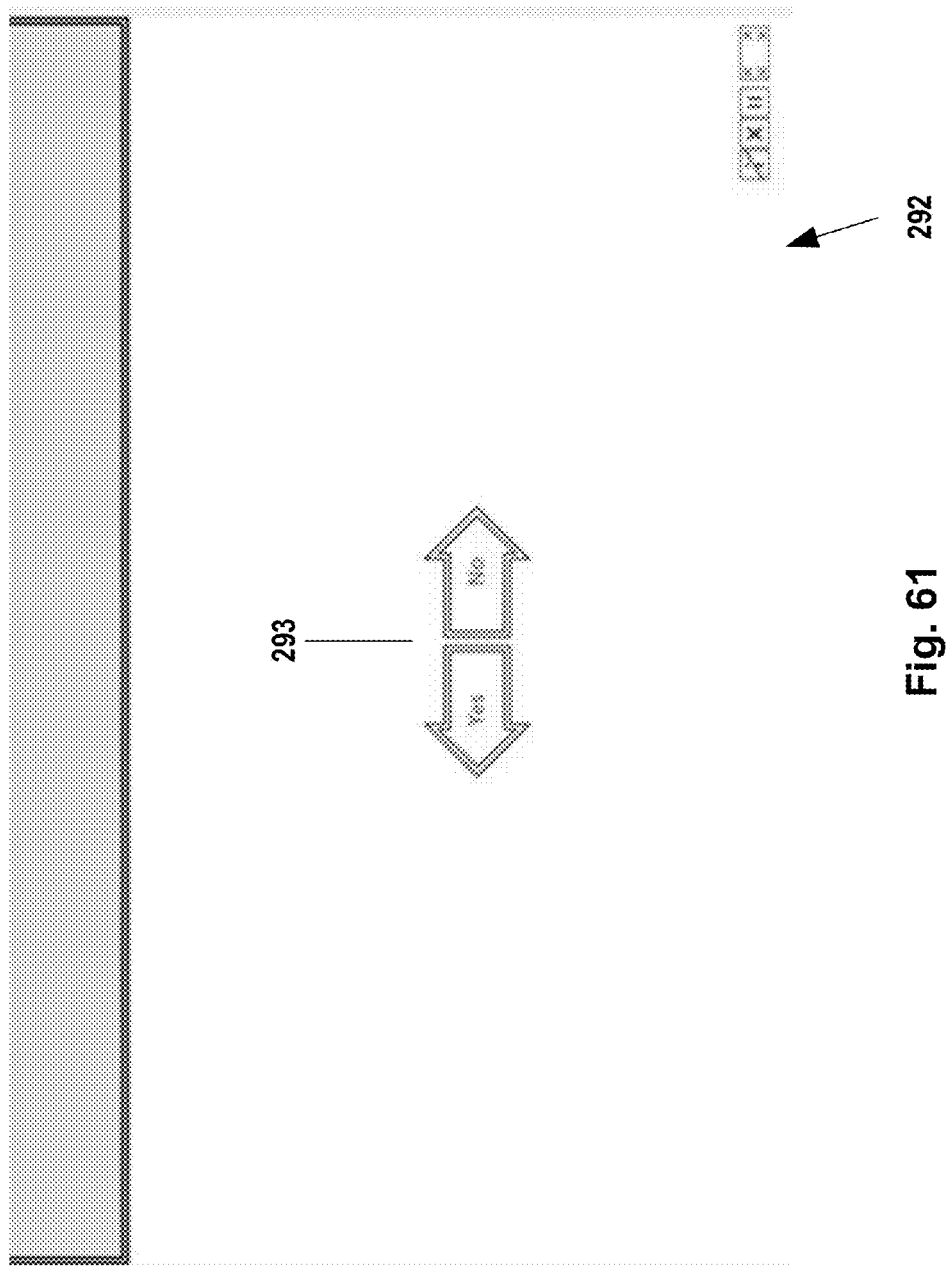

FIGS. 56 and 57 illustrate screenshots 278, 282 of one embodiment of a delay discounting assessment and training module called "Now or Later." Now or Later is one example of a game targeting reward processing and self-control, others of which include attention bias modification, mindful breathing, and a daily survey for meta-cognition and self-awareness. An important purpose of such exercises is to significantly less craving from baseline.

Now or Later measures a game participant's self-control as indicated by the participant's degree of craving and willingness to accept delayed gratification. Now or Later initially challenges the game participant with sets of delay discounting choices between an immediate monetary reward or a delayed but relatively larger monetary reward. Subsequently, Now or Later presents images of objects of addiction (such as alcoholic beverages) and asks the game participant to subjectively rate how significantly they desire that object. Now or Later then returns to more delay discounting choices.

For example, in FIG. 56, Now or Later presents a challenge question 279 that asks the game participant to select between two monetary rewards, $80 in fourteen days (box 280), or $28 today (box 281). Based on the participant's choices across trials, Now or Later approximates how impulsive the participant is in regards to delaying gratification.

In FIG. 57, Now or Later illustrates an image 284 of an ice bucket filled with alcoholic beverages, along with the challenge question 283, "Do you want to drink this?" The participant selects a rating 285 of how desirable the image of the particular "vice" is. Applicants have observed that arousal can weaken a game participant's ability to delay gratification. Therefore, by comparing the game participant's choices before and after the vice images, Now or Later assesses the severity of the game participant's addiction.

After the game participant has made twenty choices, Now or Later displays a bar graph showing how much self-control the participant exhibited based on his choices during the level. Now or Later then challenges the game participant to correctly answer a question related to his performance to finish the level.

The first level of the Now or Later game presents images of non-alcoholic beverages. Subsequent levels depict images of alcoholic beverages.

One embodiment of an attentional bias modification program uses the Now or Later task to select stimuli to incorporate into the other attentional bias modification games, thereby personalizing the modules to specific game participants.

Now or Later is useful in assessing and training schizophrenia patients, alcoholics, smokers, methamphetamine abusers, pathological gamblers, and obese individuals, all of whom show higher discount rates in that they prefer smaller, immediate rewards.

7. Scene That!

FIGS. 58-61 illustrate screenshots 286, 288, 290, and 292 of one embodiment of a game called "Scene That!" Scene That! challenges a game participant to indicate whether a target stimulus was contained within a set of distracting stimuli, including one or more stimuli that trigger unhealthy psychological responses.

Scene That briefly presents a target scene 287 and challenges the game participant to remember it. Then, Scene That! presents a stream of scenes 289, 291 one by one, including highly salient images—such as an image of a large hamburger 289—that stimulates a "vice" such as overeating, alcohol or drug addiction. In some of the trials, Scene That also presents the target scene 287 in the stream of images. After the stream of images passes, Scene That!, in screen 292, presents a prompt 293 for the game participant to indicate whether the target scene 287 was in the stream.

8. Tick Tock

Figure 62:
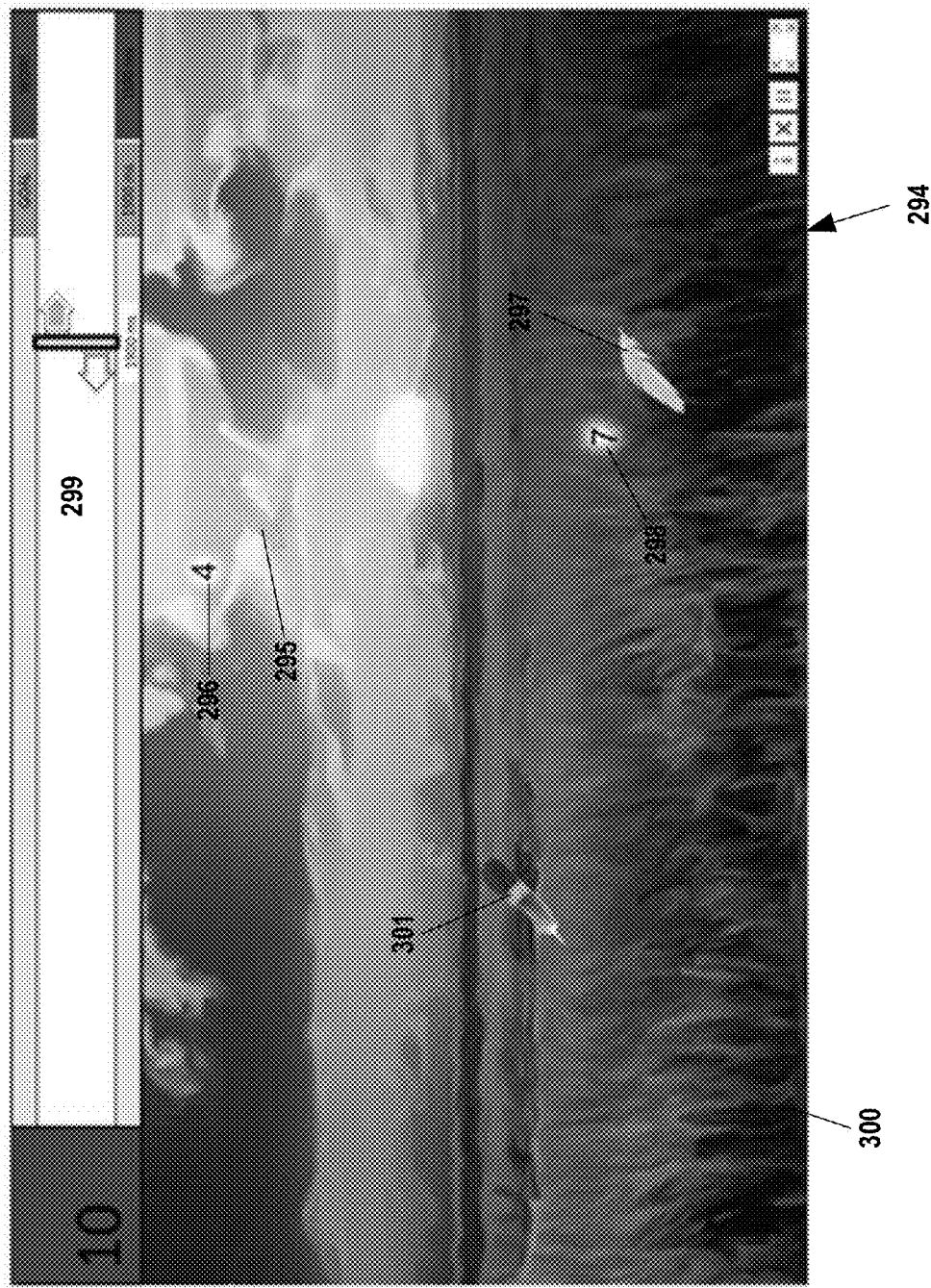

FIG. 62 illustrates a screenshot 294 of one embodiment of a time tracking game called "Tick Tock," which displays one or more objects and challenges the game participant to select the object(s) after the indicated time interval(s). Tick Tock is a time tracking task with n-back and dual-n-back working memory components.

Tick Tock aims to tune up the brain networks involved in time perception by training the participant to have more accurate time perception. While Tick Tock uses visual stimuli, stimuli can be visual, auditory, tactile, or any combination thereof.

Tick Tock first displays a background scene 300. After a brief delay, Tick Tock superimposes images of one or more objects—such as feathers 295 and 297—on the background scene 300. Tick Tock also displays one or more numbers 296, 298 to accompany those objects. Tick Tock also presents distractor stimuli 301, which the participant is challenged to ignore.

Tick Tock challenges the participant to count the indicated number of seconds, whenever an image appears paired with a number, and then click on the image. Tick Tock treats the response as correct if the participant-perceived time interval is close enough to the instructed time interval. That is, if the participant clicks the image within a given buffer of time around the target time, the participant's response is treated as correct. The buffer is the allowed temporal error in a response to be scored as "correct".

FIG. 62 shows a trial in which the participant is challenged to concurrently track two time intervals: four seconds and seven seconds. These intervals may have started at different times in the past. The participant is also challenged to ignore all stimuli that are not paired with numbers.

Tick Tock provides the participant with visual and auditory feedback, so the participant knows if they clicked too soon or too late, or if they clicked within a given buffer of time around the target time.

As the Tick Tock game progresses into more advanced stages, the number of time intervals the game participant is required to track increases, as does the set of possible time intervals. Tick Tock advances in difficulty in other dimensions, too, including the number of distractors (images that do not require time tracking), the similarity of distractors to target images, the salience of the target images compared to the background, and the number of possible locations at which the target images appear (thus expanding the field of view to which the participant must pay attention). Also, as the participant becomes more accurate in tracking time intervals, the buffer of time (bounds of allowed temporal error) around the target time decreases.

In an auditory form of Tick Tock (not shown), instructions, targets, and distractors are sound clips. The participant may hear something like this: "In exactly one second after you start hearing this beep <insert beep sound here>, click on the button labeled "first interval completed" . . . . <beep sound plays now>". Sounds can come from different locations if the participant wears binaural headphones. As training becomes harder, the number of targets and distractors increases. Further, targets and distractors will become more similar in sound, while the background becomes noisier. The background starts off silent though. Each target has its own corresponding button, so that the computer can give correct feedback based on which specific time interval the participant is responding to. Visual and auditory feedback is given on the participant's accuracy as described above.

A third, cross-modal version of Tick Tock (also not shown) uses more than one sensory domain, like combining visual and auditory domains. In the case of auditory targets, instructions at the beginning of the session would dictate what the target sound is. The time interval, on the other hand, would be set during gameplay from the number that is onscreen when the participant hears the target sound. After the target's time interval has past, the participant clicks on a button corresponding to which interval had completed, e.g., "first interval completed." Increasing the difficulty in gameplay uses strategies described above: increase the number of targets and distractors, display visual stimuli across a larger area, play background sounds simultaneously with target sounds, and overlay target images on a distracting background (e.g., gray text on black background; or graphic background with characters resembling the target, but are not identical to it). The roles of visual and auditory stimuli in this use case can be reversed.

Tactile stimuli can also replace one modality or augment this cross-modal version of time-tracking-based cognitive training. In the haptic form, targets and distractors are tactile stimuli like vibrations. A controller device containing the gameplay software provides instructions either visually or aurally. The haptic interfacing component or separate device gets commands from the controller device and generates a range of tactile sensations. This component or separate device can be either touched or worn by the participant in such a manner that responses from the device are easily communicated to the participant. The participant indicates when time intervals have completed through the controller device or another device that communicates responses back to the controller. If sensations are delivered as a single point, targets and distractors are differentiated by frequency and amplitude of vibrations. However, if sensations are delivered across many spatial positions, then position serves as the third parameter for differentiating targets and distractors. Increasing the difficulty in gameplay uses strategies described in the previous cross-modal sample use case. Tactile stimuli can be made more similar and span more spatial locations.

In a retrospective time estimation version of Tick Tock, the participant estimates how much time has past between different events, where one or both events happened in the past. Feedback is given as to how accurate the participant's estimate was in the manner described above. The participant sees a background scene, over which images appear. If the image is a target, at a later point in time, the participant will be asked how much time has past since the target had appeared. There is also an auditory version of this, where stimuli are sound clips. In either version, the participant can be instructed beforehand what the target looks like or sounds like. Some images or sounds serve as distractors and are to be ignored. The first level starts with only one target, and the levels progress in difficulty as described above.

In a time reproduction version of Tick Tock, the participant is asked to reproduce time intervals. At the start of a trial, the participant is informed what the target(s) is. Then during an observation period, one or more target images appear onscreen and then disappear after different amount of times. Distractors will do the same thing, but are to be ignored. After the observation period ends, the participant is asked to reproduce when, where, and for how long each target image appeared. Visual and auditory feedback about accuracy will be given for each target image. Levels progress in difficulty in the same manner described in "Use case 1A". For other use cases, replace visual stimuli with auditory or tactile stimuli, or any combination thereof.

In a time manipulation version of Tick Tock, the participant is asked to manipulate temporal information like determining which time interval is longest, ranking time intervals from shortest to longest, or matching time intervals. At the start of a trial, the participant selects an image and observes how much time it animates for. Then the participant selects a different image and observes how much time it animates for. Afterward, the participant is asked to find the image with the shorter or longer animation. Multiple images can be presented, in which case the participant is later asked 1) which image had the shortest or longest animation, or 2) to rank the images based on their animation durations, or 3) to provide numeric estimates on the animation durations. Visual and auditory feedback is given on the participant's accuracy. To increase difficulty of gameplay, these techniques are used: 1) adding more target images, 2) adding distracting animations that are to be ignored, 3) allowing target images to span more onscreen area, and 4) having animation durations become more similar.

In yet another version, the participant sees images one by one, each appearing for a different amount of time. Then the participant is presented with all images side by side and asked which one animated for some inquired number of seconds. The participant clicks on the image that they think had appeared for the inquired number of seconds. Visual and auditory feedback is provided as described above. More images can be chained together, and their appearance durations can be made more similar to increase task difficulty. Additionally, the images' content can be made more distracting by being more emotionally salient and/or cognitively engaging.

In one version of a goal-directed decision-making implementation, the participant tries to find an image that will yield the biggest reward. Reward amounts are associated with different time intervals, as are the images to choose from. Hence to obtain the biggest reward, the participant must estimate the animation duration associated with the biggest reward. Then the participant observes the animation duration of different images until they find the one whose duration matches that of the biggest reward. The training can be made more difficult with more choice options and more similar animation durations.

Figure 63:
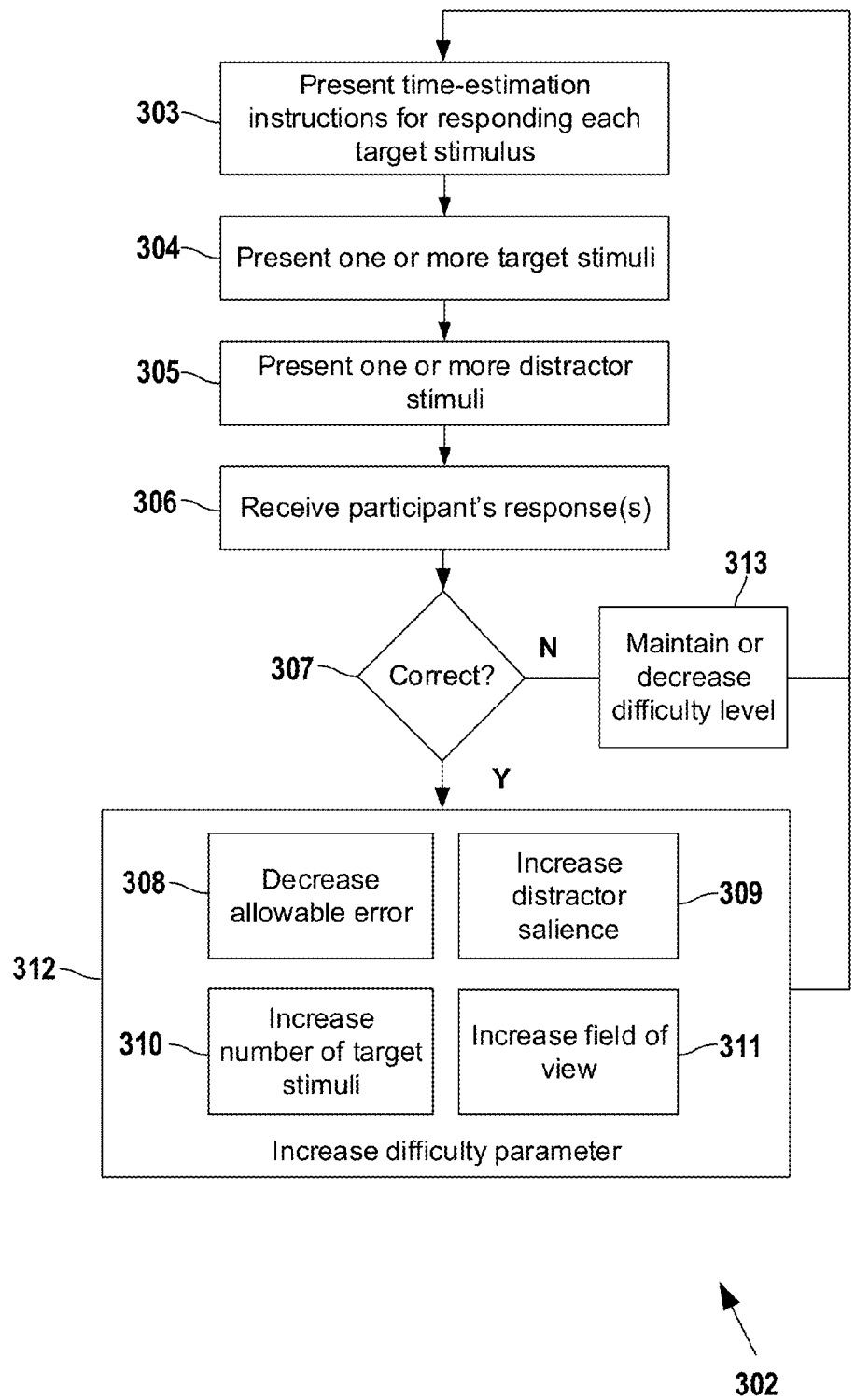

In all use cases, visual stimuli can be switched for auditory or tactile stimuli, and cross-modal versions can be implemented. FIG. 63 is a functional block diagram that summarizes the Tick Tock exercise. In block 303, Tick Tock presents time-estimation instructions for responding to each target stimulus. As discussed in one embodiment above, the instruction may comprise a number associated with a target stimulus. Or, as discussed in other embodiments above, the instruction may comprise being told to wait a number of seconds after a target stimulus is presented, to estimate the length of time a target stimulus is presented, to estimate the length of time between the presentation of two target stimuli, to compare how long different stimuli were presented, to identify which stimulus was presented the shortest or the longest, or to rank the stimuli based on the durations they were presented.

In blocks 304 and 305, Tick Tock presents the target stimulus or target stimuli and distractor stimulus or distractor stimuli. The target stimuli may be presented before, after, or at the same time as the distractor stimuli. In block 306, Tick Tock receives the participant's response(s). If correct, Tick Tock may in step increase a difficulty parameter using the adaptivity procedure discussed earlier by, for example, decreasing the allowable time estimation error (block), increase the distractor salience (block), increase the number of target stimuli that the participant is required to track (block), or increase the field of view (block). If incorrect, Tick Tock may in step maintain or decrease the difficulty level using the adaptivity procedure discussed earlier.

9. The Matrix Recalled

Figure 64:
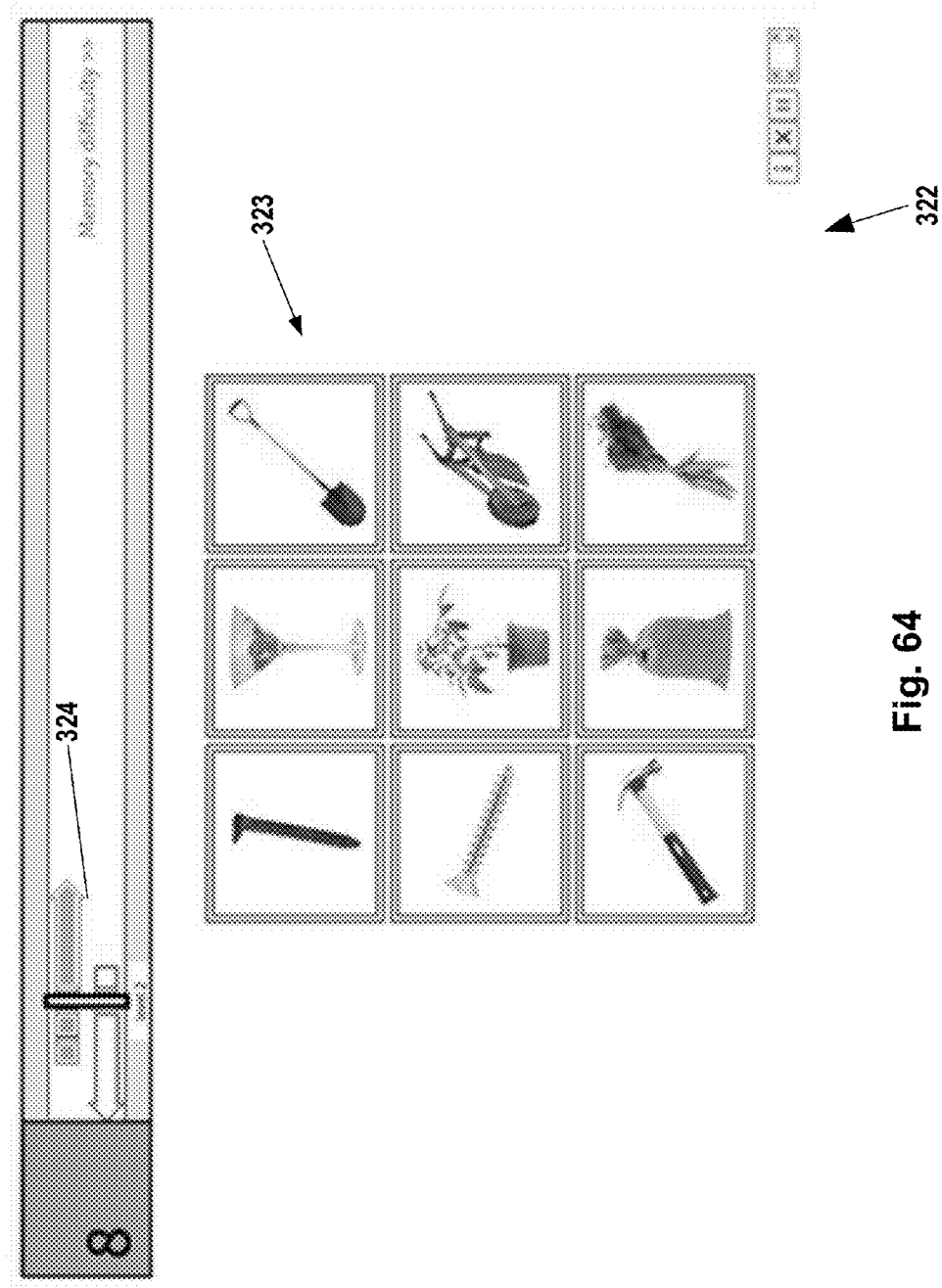

FIG. 64 illustrates a screenshot 322 of one embodiment of a working memory game called "The Matrix Recalled." The Matrix Recalled presents an ordered list of items in audible form. In some trials, the ordered list of items includes a distractor, such as an image of alcohol, that stimulates an unhealthy psychological response. After presenting the list, The Matrix Recalled presents a grid 323 and challenges the game participant to recall the items in the requested order.

The participant hears an ordered list of items. Then they must recall those items in the requested order by clicking on them from a grid. On occasion, items in the grid will be distracting images of alcohol. The distracting images can be changed to be from other categories.

The Matrix Recalled receives and times the game participant's selections and displays a measure 324 of the participant's speed on the screen. At the end of a block of trials, Category Click ranks the game participant's performance against those of other game participants.

IX. Social Cognition

Another suite of games are designed to assess and train social cognition abilities, emphasizing improvement in speed of processing of basic social cognitive abilities through repetitive practice and implicit learning. In one embodiment, a suite of games called "SocialVille" provides nineteen different games that collectively target the various social cognition domains of social cue perception, visual and vocal emotion perception, self-referential processing and theory of mind (ToM). The games can be characterized as being one of three types: (1) "speeded" tasks that challenge processing speed by requiring the participant to make fast perceptual discriminations; (2) "working memory" tasks that require the participant to make working memory manipulations; and (3) "other" games that do not have a particular emphasis on either processing speed or working memory.

1. Speeded Gaze Direction Identification

Figure 65:
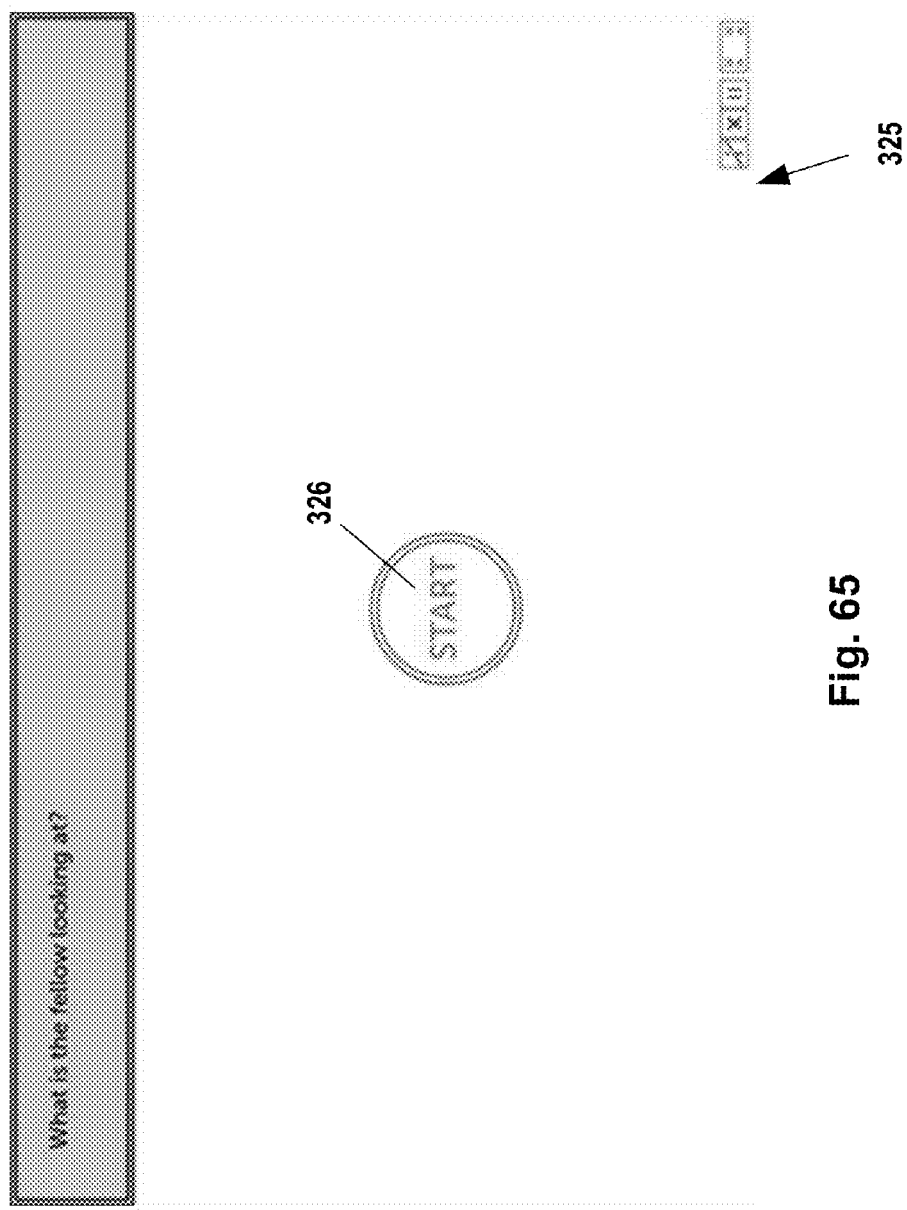
FIGS. 65-142 illustrate various embodiments of social cognition games that challenge game participant with social impairments to recognize, understand, and respond to social, visual, and auditory cues.
Figure 66:
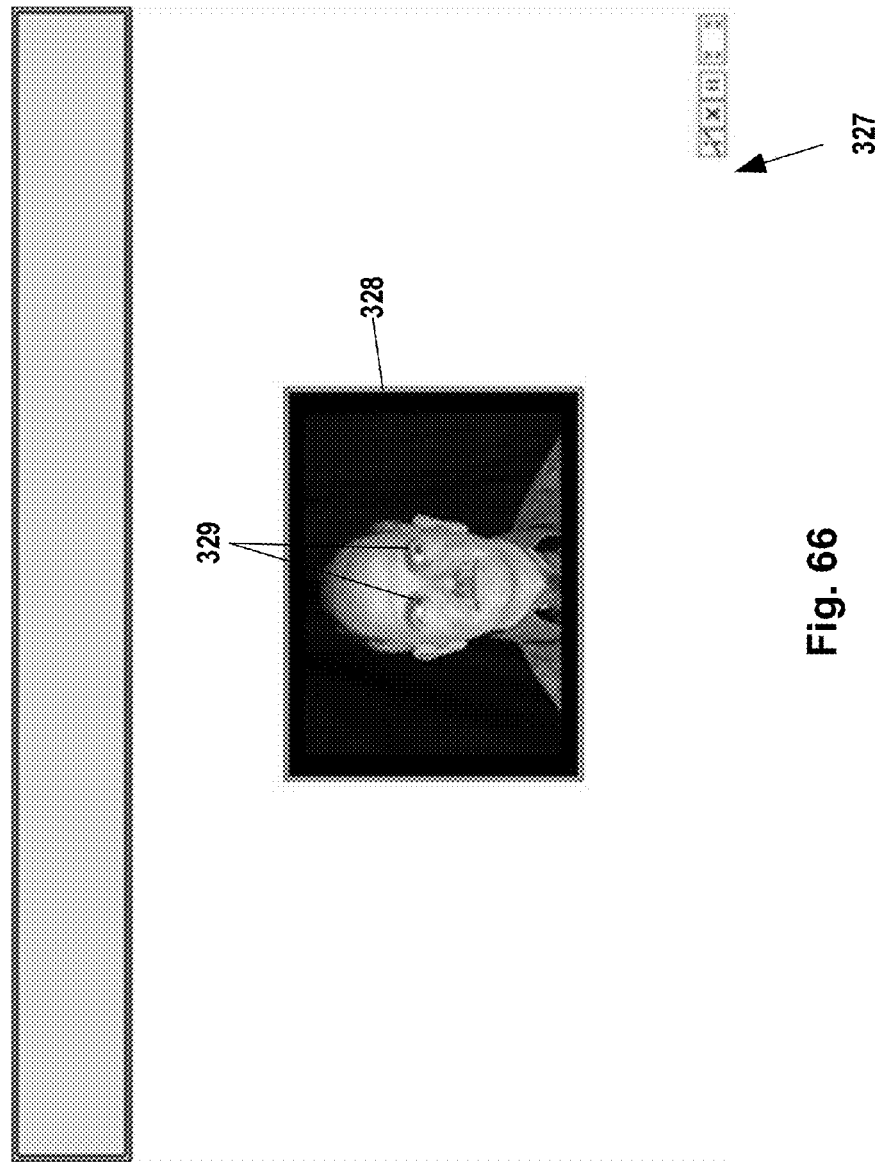
FIG. 66 illustrates another screenshot of the game illustrated in the previous figure.
Figure 67:
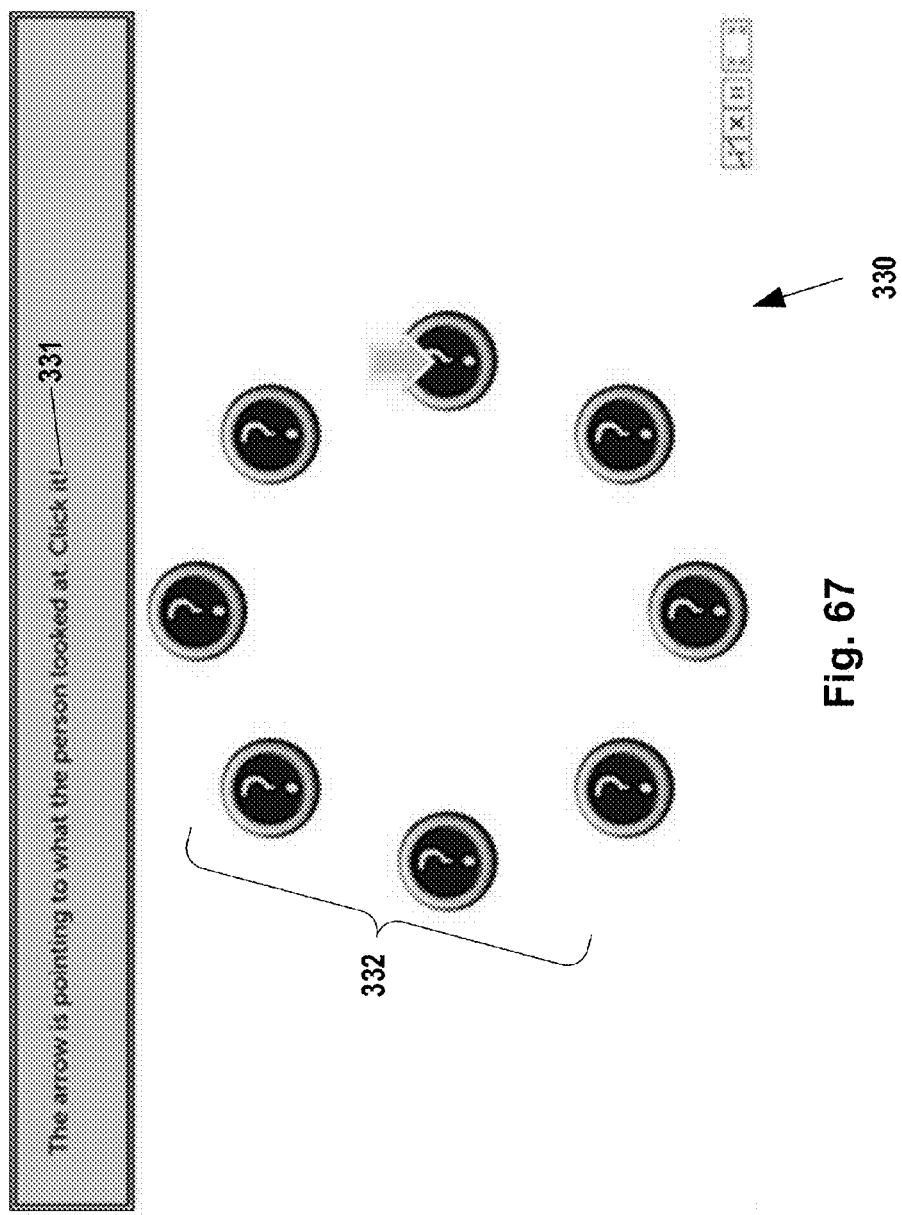
FIG. 67 illustrates another screenshot of the game illustrated in the previous figure.

FIGS. 65-67 illustrate screenshots 325, 327 and 330 of one embodiment of a facial cue processing speed game called "Gaze Cast." The goals of this game are to: (1) improve the SC system's ability to track other's gaze direction; (2) strengthen the mirror neuron system by 'forcing' the tracking of the gaze direction of others, and; (3) improve the trainee's ability to hold gaze direction in memory.

Each trial of Gaze Cast starts with a central "start" button 326. Once the participant clicks on the start button, Gaze Cast presents a video clip 328 of a person. The person makes a speeded glance shift 329 in one of many possible directions. Next, the video clip then stops and disappears. Gaze Cast then presents an array of between two and nine peripheral objects 332 (depending on the level in training) and prompts 331 the participant to select the peripheral object in the direction of the person's glance.

Gaze Cast provides auditory feedback for both correct and incorrect responses. The next trial begins three seconds after the participant's response. In Gaze Cast, the duration speed of the video clip is adaptively varied (on a scale from one being slowest to ten being fastest) based on participant's responses using an up-down adaptive algorithm. Also, in some embodiments, the speed of the gaze shift adaptively shortens and the number of peripheral objects adaptively increases as the subject gets better at the task.

2. Speeded Same Gaze Direction Match

Figure 68:
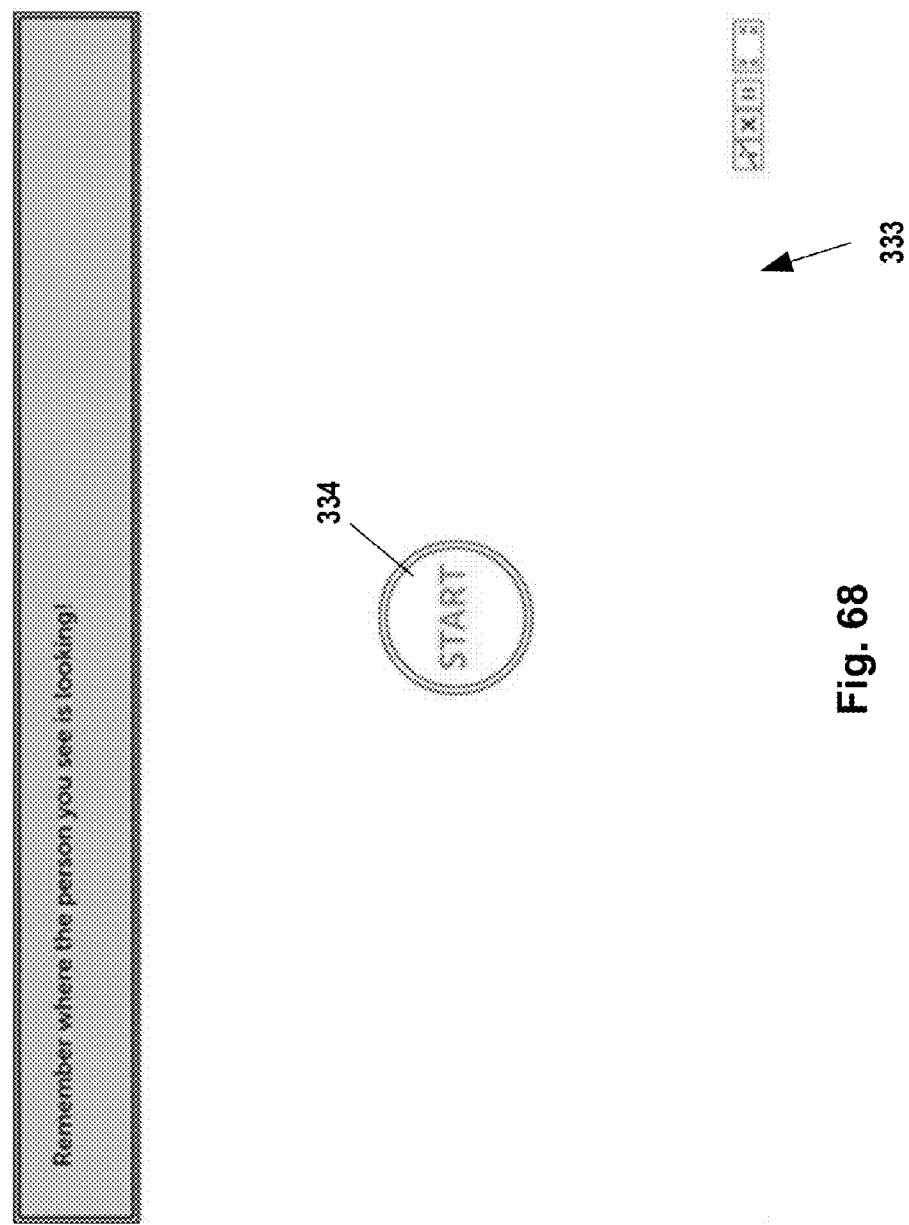
FIG. 68 illustrates a screenshot of another embodiment of a facial cue processing speed game called "Looky Lou," which presents a target face for a brief interval of time, followed by a visual mask, followed by a subsequent set of faces, and challenges the participant to select the face whose eyes are gazing in the same direction as the target face.
Figure 69:
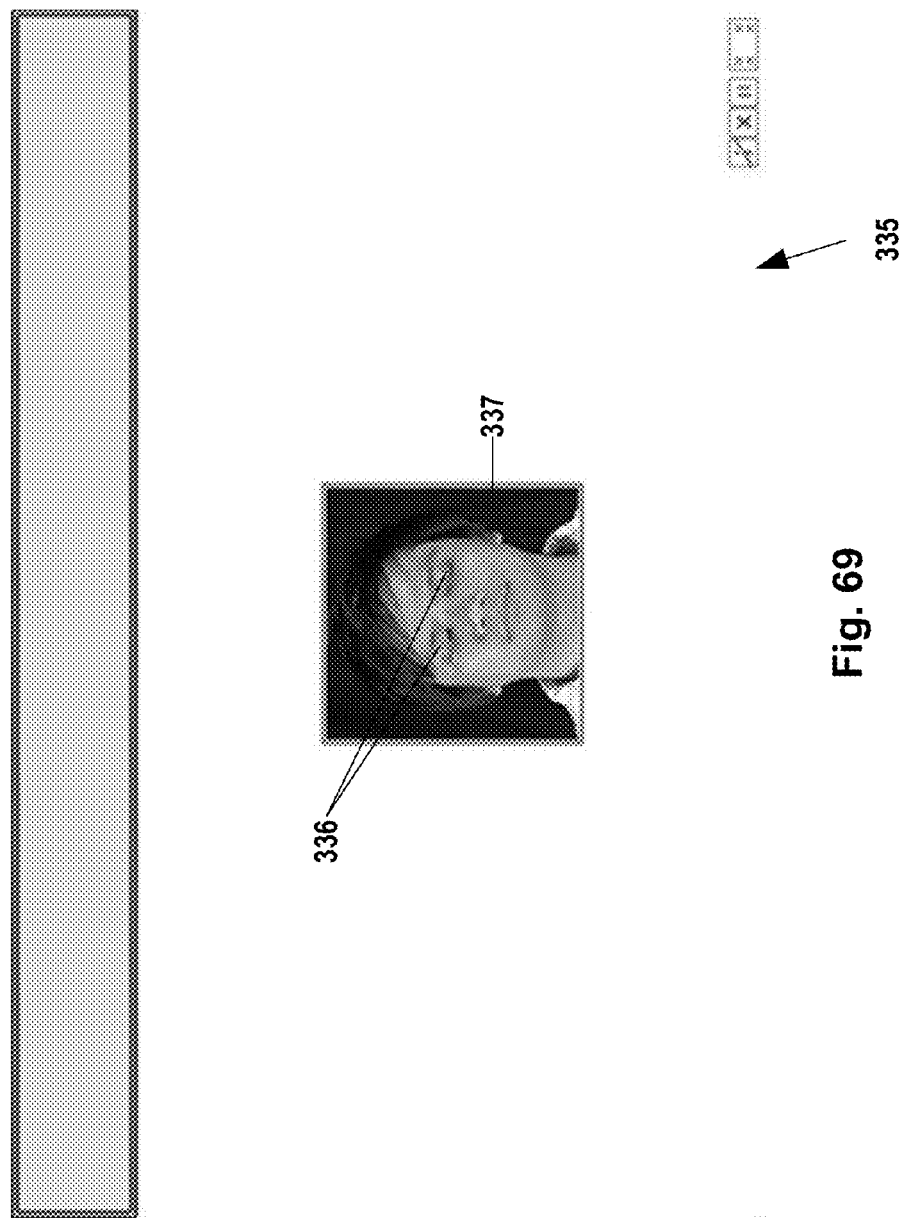
FIG. 69 illustrates another screenshot of the game illustrated in the previous figure.
Figure 70:
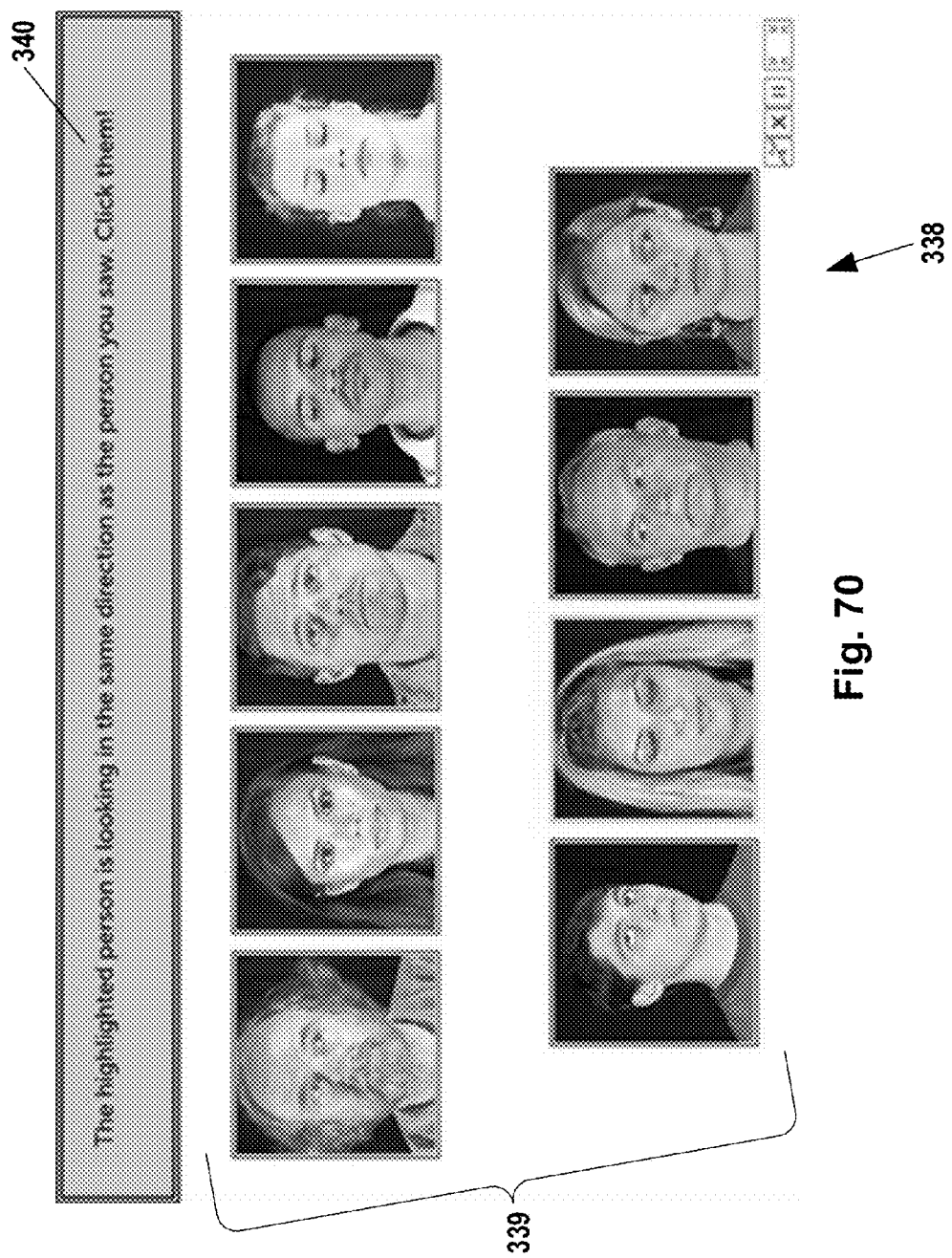
FIG. 70 illustrates another screenshot of the game illustrated in the previous figure.

FIGS. 68-70 illustrate screenshots 333, 335 and 338 of another embodiment of a facial cue processing speed game called "Looky Lou." Looky Lou presents a target face for a brief interval of time, followed by a visual mask, followed by a subsequent set of faces. Looky Lou then challenges the participant to select the face whose eyes are gazing in the same direction as the target face.

The goal of this game is to improve the subject's implicit ability to focus attention on the region of the eyes, which has been shown to convey key social information. Individuals with ASD are known to have severe difficulties focusing on the eye region or in inferring information from the eyes. In this game, Looky Lou presents images of individuals looking in various directions, and prompts participants to select the individual that looks in the same direction as the target individual.

Each trial of Looky Lou starts with a central 'start' button 334. Once the participant clicks on the start button 334, a target face 337 is presented for a brief period of time. The target face's eyes 336 are depicted looking at one of nine potential directions (randomly selected with equal probability) followed by a visual mask for 500 ms, and then an array of between two and nine faces 339.

Participants are required to select the face 339 whose eyes are gazing in the same direction as the target face 337 (regardless of face identity) by clicking on it with the computer mouse. Auditory feedback is provided for both correct and incorrect responses, and the next trial begins three seconds after the participant's response.

In this game, the duration of presentation of the target face 337 is adaptively varied based on participant's responses using a Zest algorithm, which is a Bayesian adaptive psychometric method that uses maximum likelihood procedure for threshold estimation. That is, images are presented for shorter and shorter time durations (as little as a few milliseconds) as subjects' performances improve through a training block. The number of gazes to select from also gets larger as participants progress with training.

3. Speeded Facial Image Match

Figure 71:
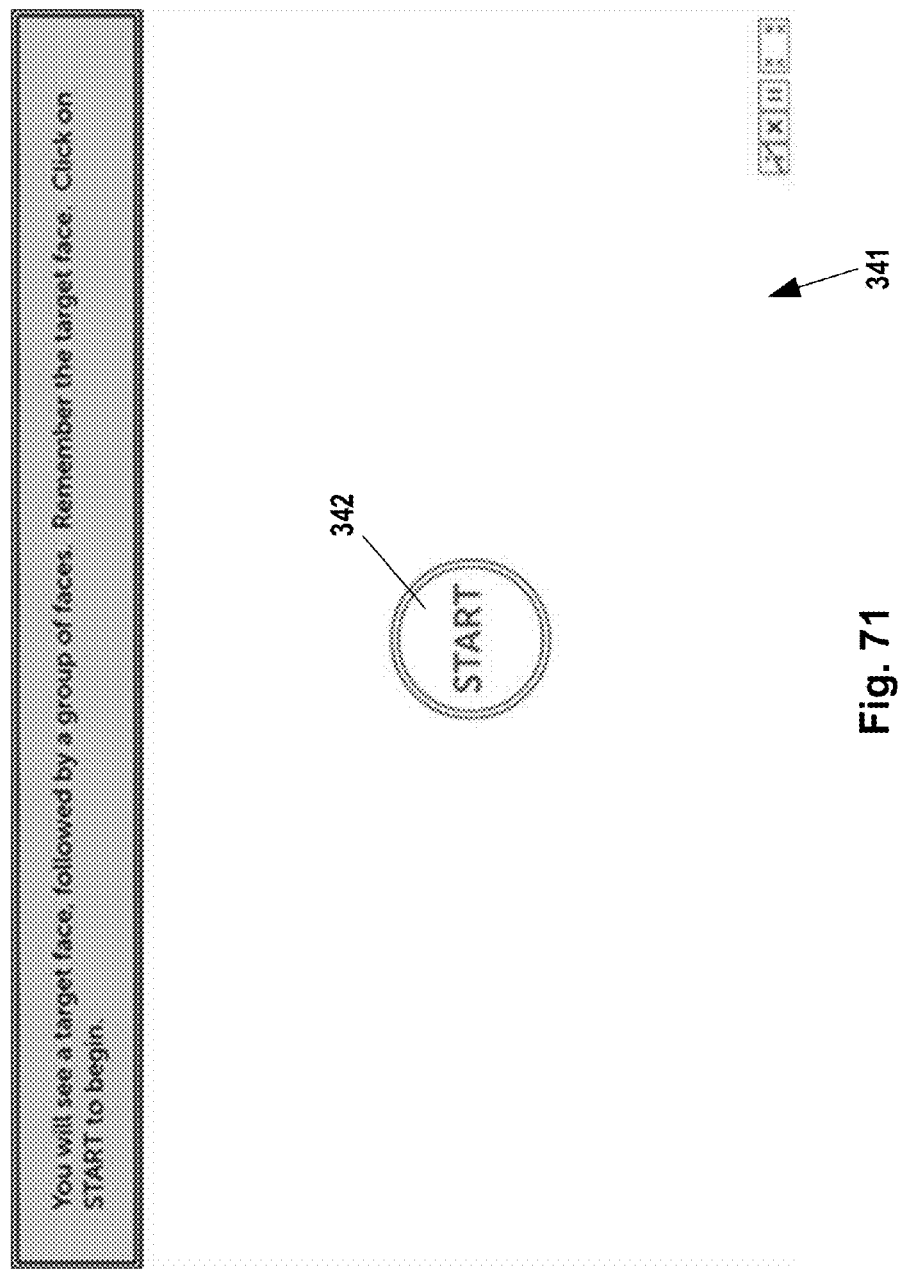
FIG. 71 illustrates a screenshot of yet another embodiment of a facial cue processing speed game called "Face It," which presents a target face from the front, side, or an angle, followed by a visual mask, followed by a subsequent set of faces, and challenges the participant to identify the target face in the array.
Figure 72:
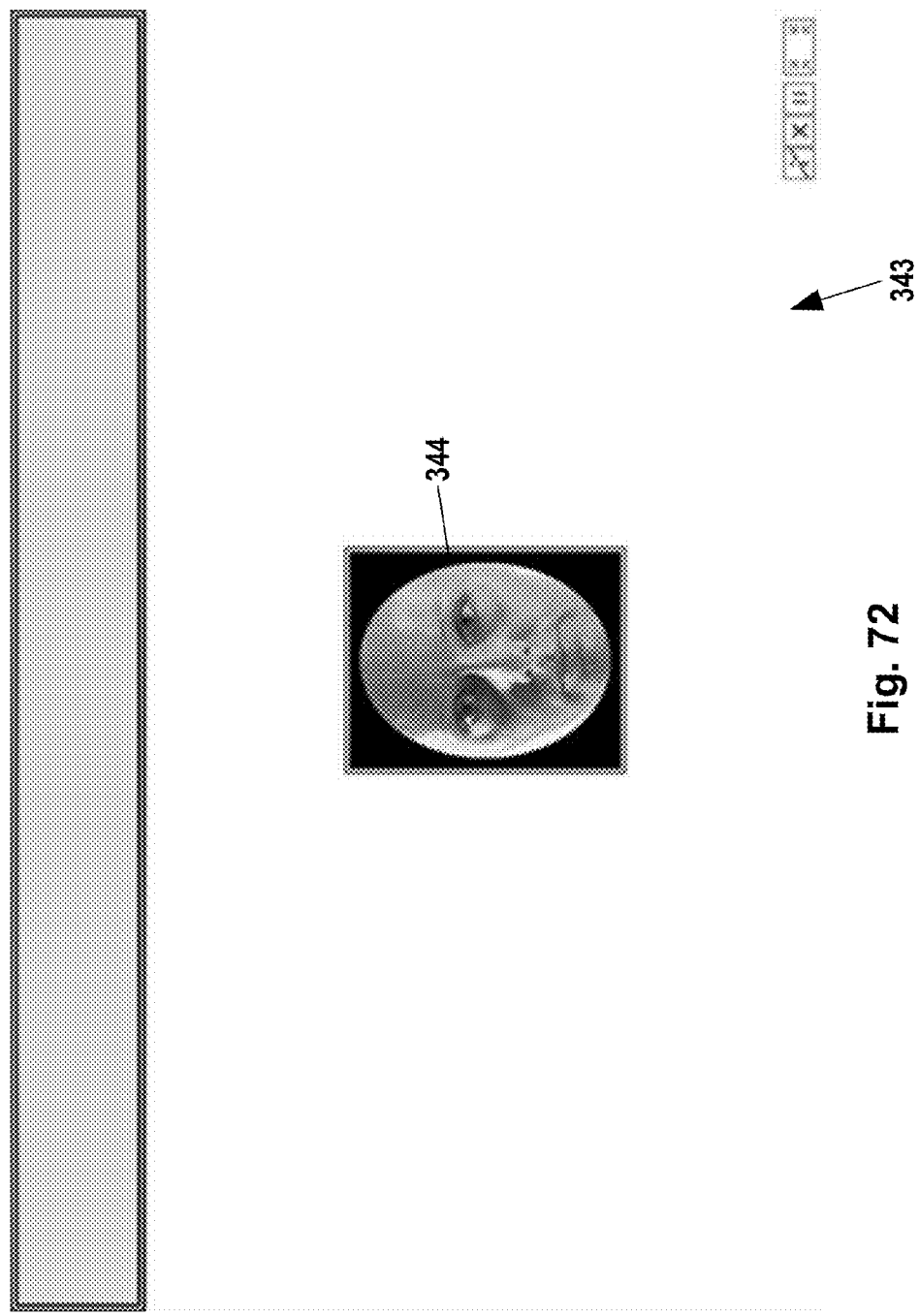
FIG. 72 illustrates another screenshot of the game illustrated in the previous figure.
Figure 73:
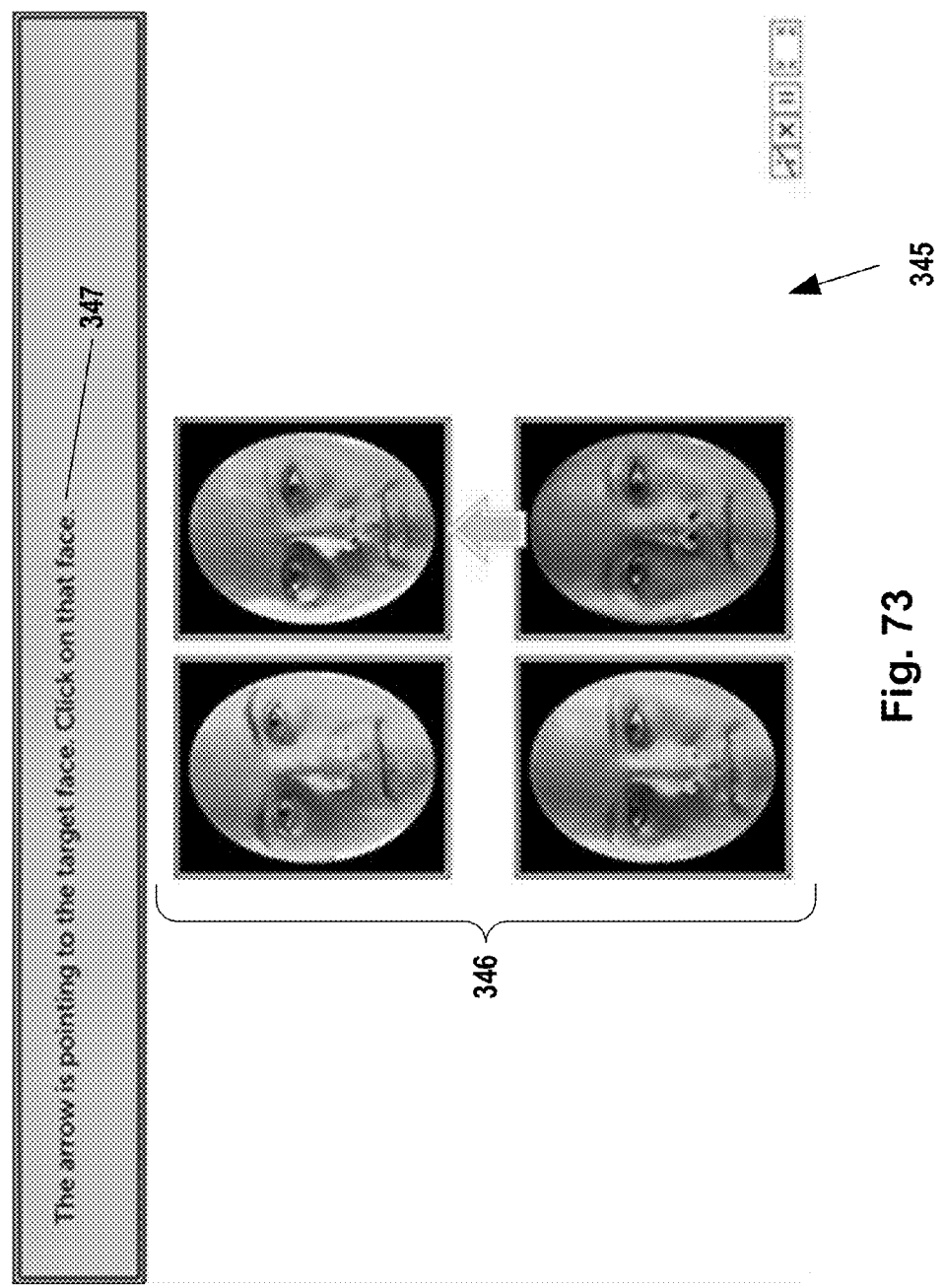
FIG. 73 illustrates another screenshot of the game illustrated in the previous figure.

FIGS. 71-73 illustrate screenshots 341, 343 and 345 of another embodiment of a facial cue processing speed game called "Face It!" which presents a target face from the front, side, or an angle, followed by a visual mask, followed by a subsequent set of faces, and challenges the participant to identify the target face in the array.

Impaired processing of faces is one of the consistent findings in individuals with ASD. The goal of Face It is to improve the face perception system's ability to process faces efficiently and to improve the ability to identify faces viewed from various directions. This form of game heavily engages the Fusiform Face Area (FFA) of the brain, which has been shown to be disengaged in ASD. As the participant progresses, Face It! presents the target face for shorter and shorter periods of time and with fewer peripheral cues (such as hair). Subjects subsequently need to select the same person (presented from a different angle) from an array of face choices. In the course of training, the number of distractor faces increases, as well as the numbers of directions from which images are shown.

Each trial of Face It! starts with a central 'start' button 342. Once the participant clicks on the start button 342, Face It displays a target face 344 of a person on a computer screen for a first time interval. The target face 344 is presented from either the front, the side, or three-quarters angle. After the first time interval, Face It! clears the image of the target face 344 and presents a visual mask. After a second time interval, Face It! displays an array 346 of facial images on the computer screen. Face It then prompts 347 the game participant to select the target face 344 from the array 346. After receiving the game participant's response, Face It! provides an indication of whether the game participant's response was correct along with an indication or measure of a length of the first time interval. Face It! repeats the preceding steps over a plurality of trials.

To force the participant to memorize key facial characteristics—such as the look and relative proportions of the eyes, nose, and lips—each facial image is cropped. Each image is cropped at the top along the person's forehead, so that the top of the head is not shown, on the sides along the cheeks so that the ears do not show, and at the bottom below the mouth so that the chin does not show. The cropping trains the participant's attention on the eyes, eyebrows, nose, and mouth of the facial image.

As the participant's accuracy improves, Face It! progressively reduces the first time interval. In some advanced trials, the target face in the array is a rotated or mirrored version of the target image. Adaptivity and threshold calculation is done using 1up-2down procedure, with a step size of 50 ms, converging to 71% correct.

4. Speeded Emotional Cue Identification

It is believed that training targeting social-emotional control systems, including explicit facial affect recognition training, will broadly improve emotional self-monitoring abilities in stable, chronic schizophrenics. It is believed that training will effectively re-balance distorted responses to emotionally negative or disturbing stimuli. Training targeting implicit affect attribution (e.g., falsely interpreting neutral facial expression as sad) should reduce "attention capture" effects (i.e., effectively reducing dwell time to sad stimuli). In this form of training, explicit task instructions are orthogonal to the implicit dimension (i.e., explicit speeded gender discrimination challenge is accompanied by adapted presentation of emotional expressions).

Figure 74:
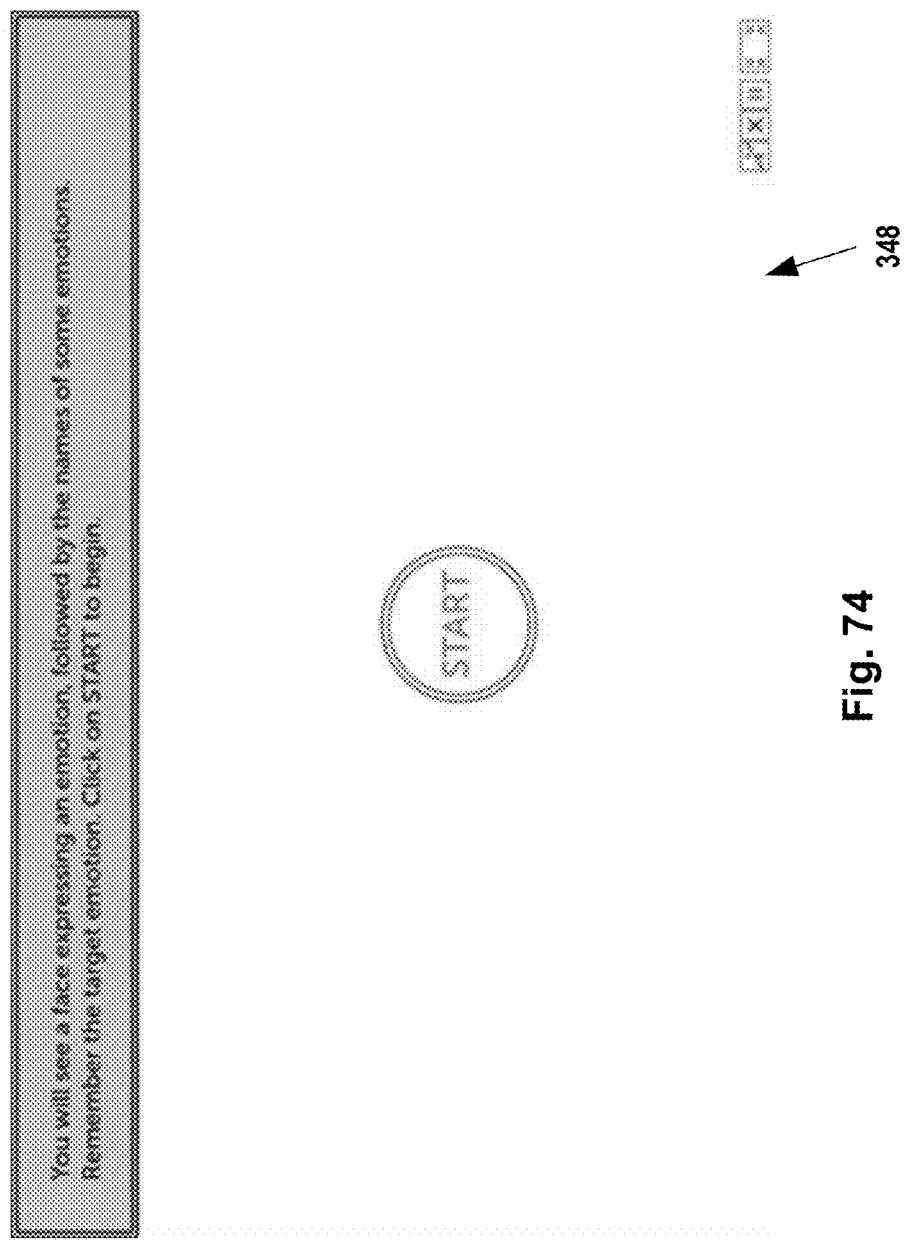
FIG. 74 illustrates a screenshot of one embodiment of an emotional cue processing speed game called "Name That Feeling," which presents a target face expressing an emotion, followed by a visual mask, and challenges the participant to indicate the emotion that best expresses the emotion exhibited by the target face.
Figure 75:
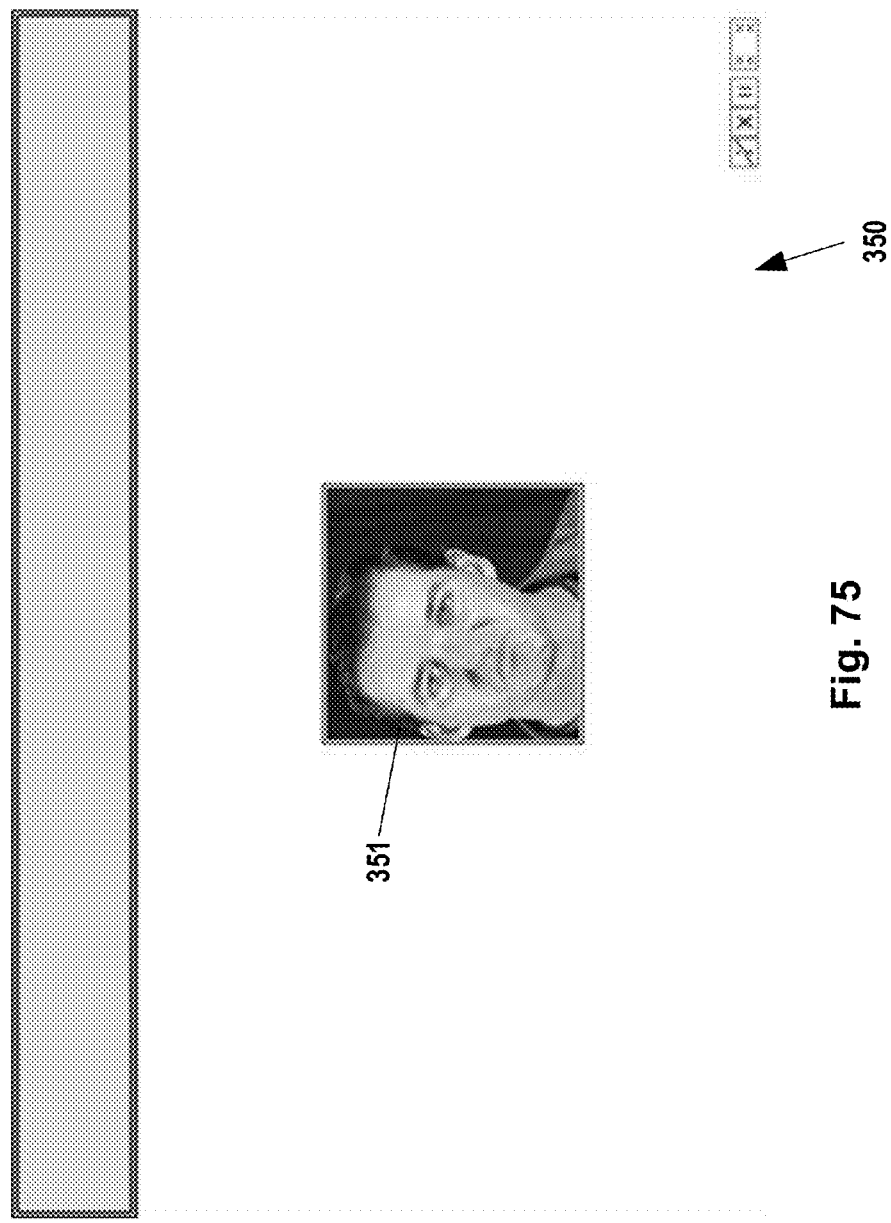
FIG. 75 illustrates another screenshot of the game illustrated in the previous figure.
Figure 76:
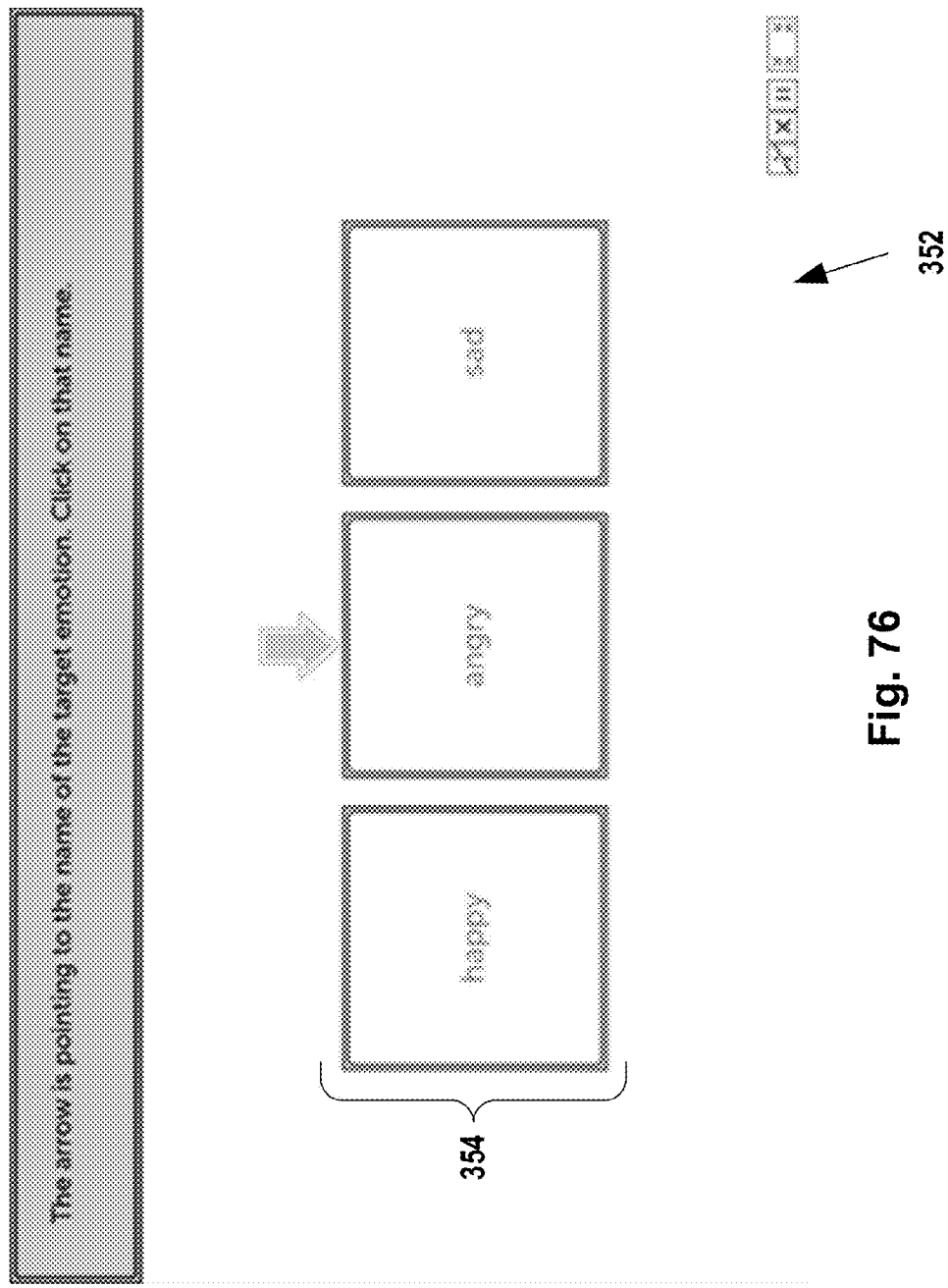
FIG. 76 illustrates another screenshot of the game illustrated in the previous figure.

FIGS. 74-76 illustrate screenshots 348, 350 and 352 of one embodiment of an emotional cue processing speed game called "Name That Feeling." Name That Feeling presents a target face 351 expressing an implicit emotion, followed by a visual mask, and challenges the participant to indicate the emotion that best expresses the emotion exhibited by the target face.

Name That Feeling's structure is similar to that of Speeded Gaze Cast game described above, except here the target face 351 features an emotion, and the response array 354 is comprised of 2-10 verbal labels of basic emotions (e.g. 'happy', 'sad', 'angry'). Name That Feeling challenges the game participant to select the emotion that correctly describes the emotion presented by the target face. Feedback, adaptivity and threshold calculation are performed similarly to that of the Speeded Gaze Match game.

Figure 77:
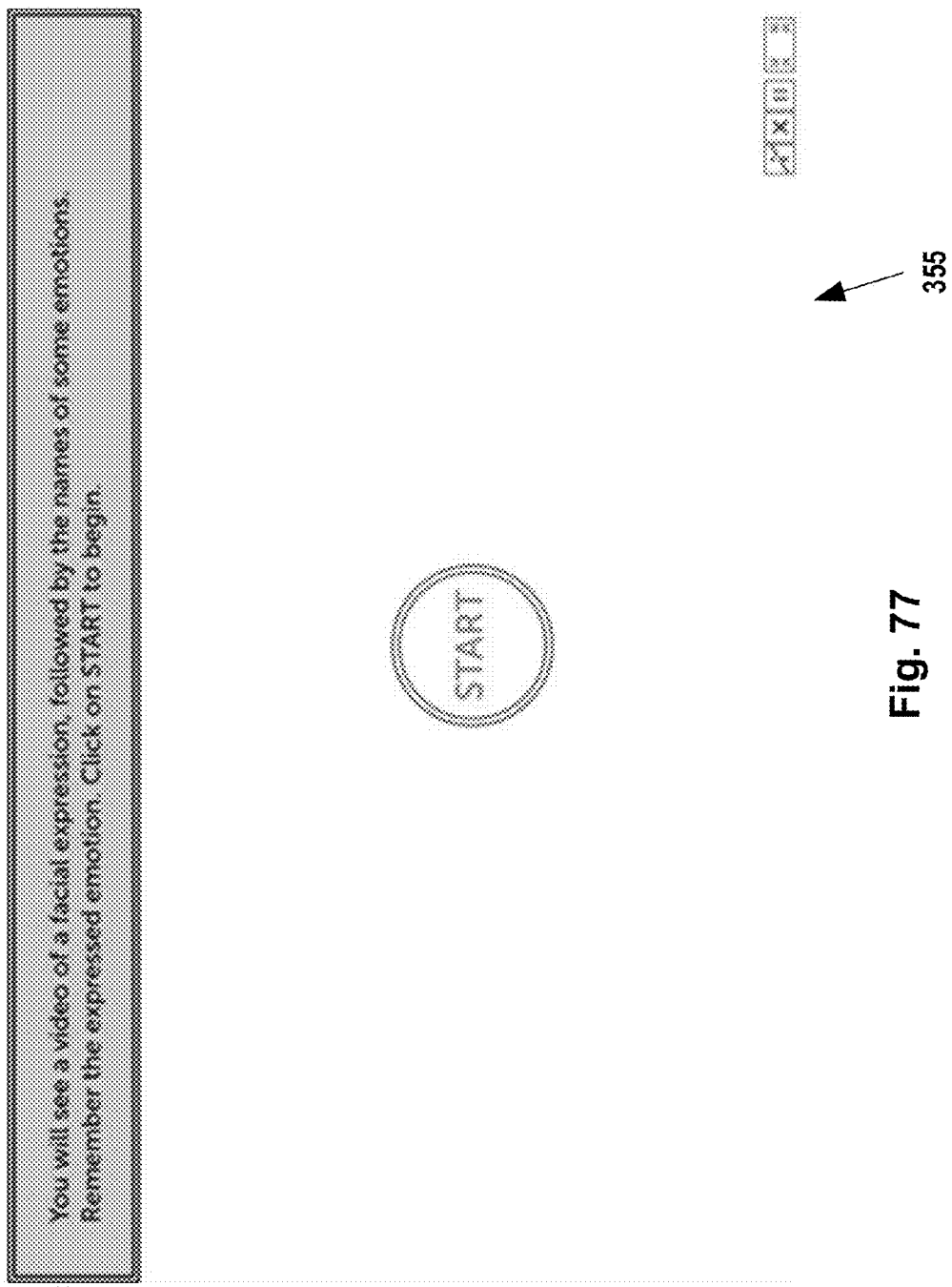
FIG. 77 illustrates a screenshot of one embodiment of an emotional cue processing speed game called "Emotion Motion," which presents a video clip of a face expressing an emotion, followed by a visual mask, and challenges the participant to indicate the emotion that best expresses the emotion exhibited by the target face.
Figure 78:
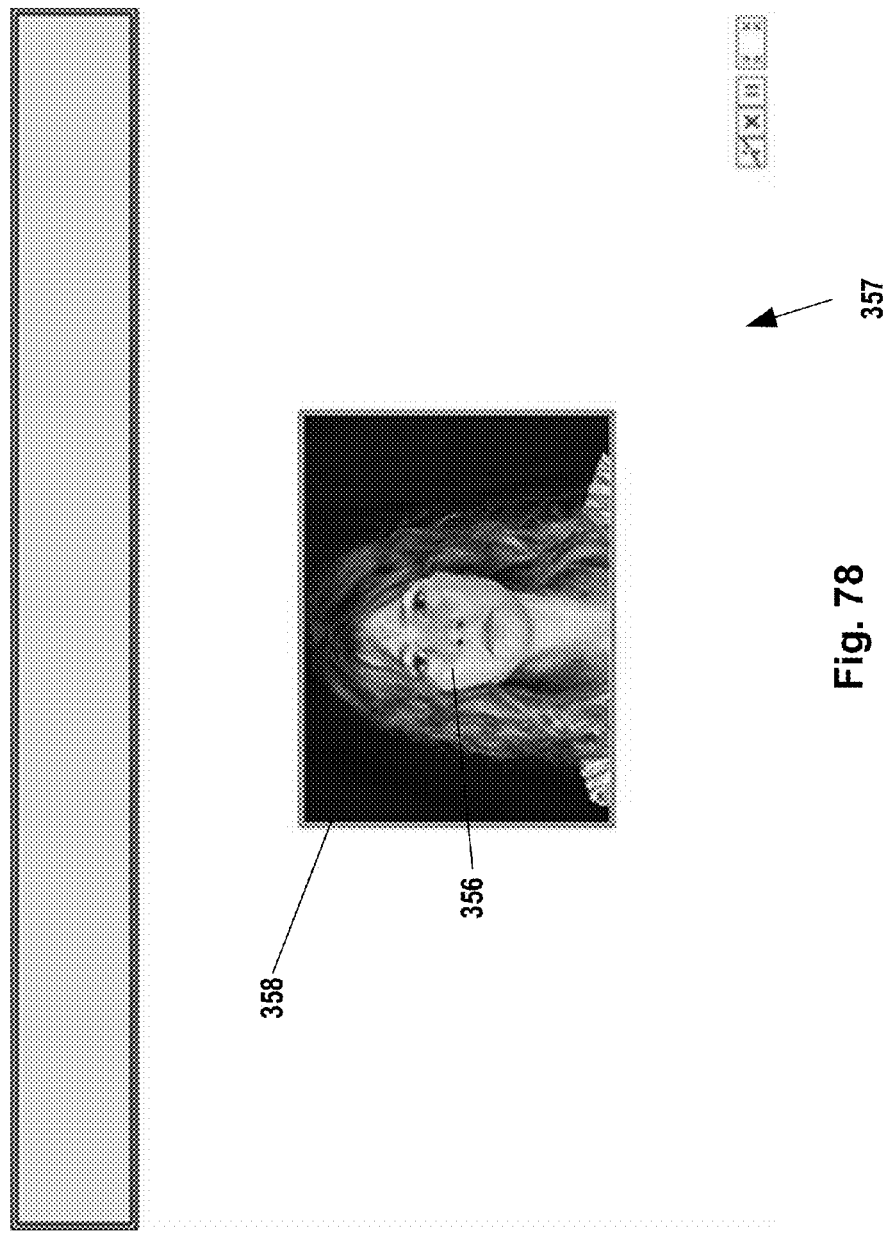
FIG. 78 illustrates another screenshot of the game illustrated in the previous figure.
Figure 79:
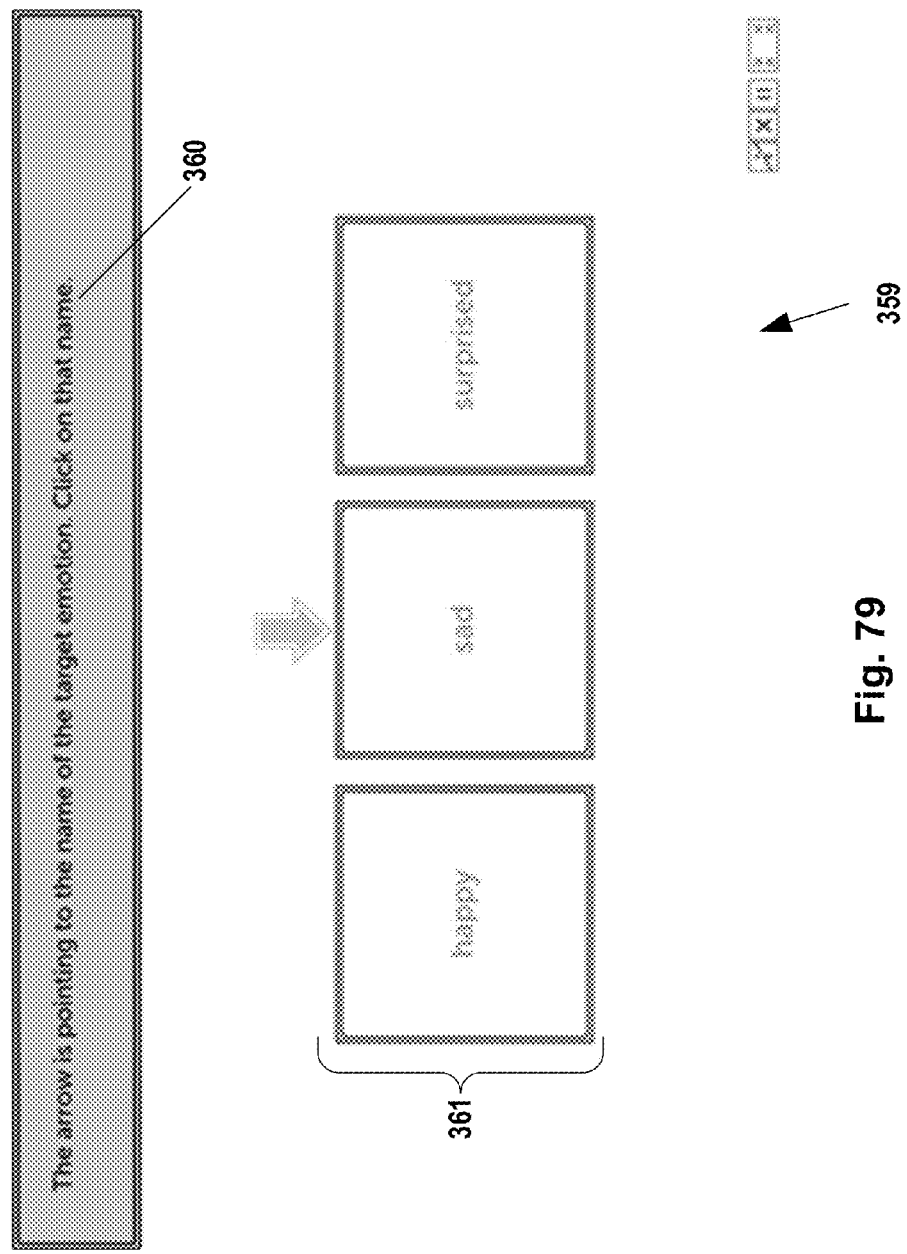
FIG. 79 illustrates another screenshot of the game illustrated in the previous figure.

FIGS. 77-79 illustrate screenshots 355, 357 and 359 of another embodiment of a processing speed game called "Emotion Motion," which presents a video clip 358 of a face 356 expressing an implicit emotion followed by a visual mask. Afterwards, Emotion Motion challenges the participant to indicate the emotion that best expresses the emotion exhibited by the target face. Emotion Motion displays a set of words 361 representing a variety of emotions and prompts 360 the game participant to select the word that best expresses the emotion of the target face 356. After receiving the game participant's response and recording the speed of that response, Emotion Motion provides an indication of whether the game participant's response was correct along with an indication of a speed of the response.

Emotion Motion is similar in structure to the Name That Feeling game described above, but instead of using still images of facial emotions, Emotion Motion uses video clips portraying facial emotions. Feedback, adaptivity and threshold calculation are done similarly to the Speeded Gaze Direction Identification game described above.

The goals of this game are similar to the ones of the Poke that Feeling game described below, with the exceptions that: (1) here the affect processing is explicit (rather than implicit); (2) the game further strengthens the link between different systems of affect processing by associating an emotion with a written emotion tag; and (3) the game uses video clips of emotions, which have more ecological validity than stills. Subjects need to decide which emotion is presented in a video clip.

5. Speeded Face Emotion Match

Figure 80:
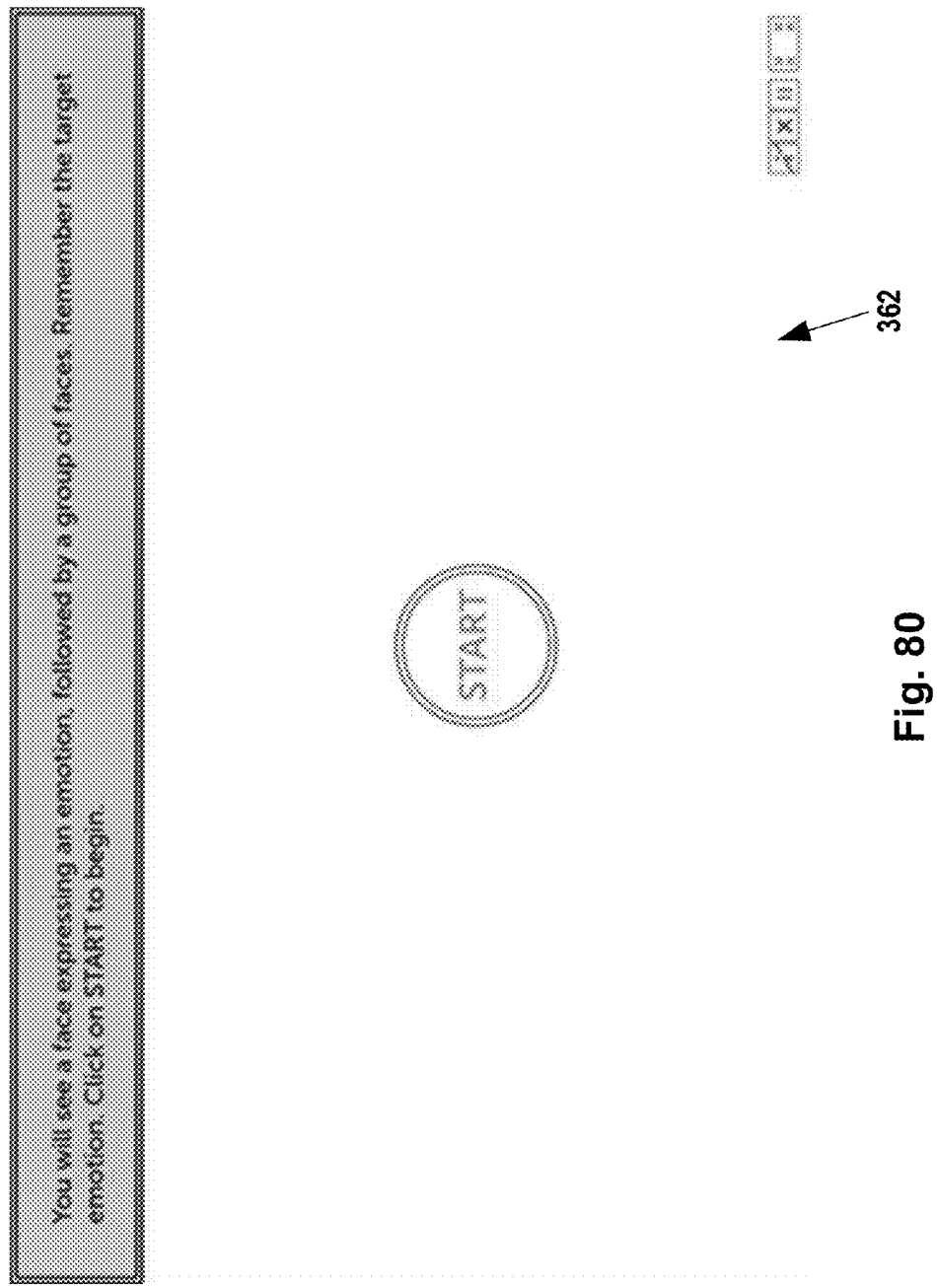
FIG. 80 illustrates a screenshot of yet another embodiment of an emotional cue processing speed game called "Poke That Feeling," which presents a target image of a face expressing an emotion, followed by a visual mask, followed by a set of facial images each expressing a different emotion, and challenges the participant to select a facial image whose expressed emotion best matches the emotion expressed by the target image.
Figure 81:
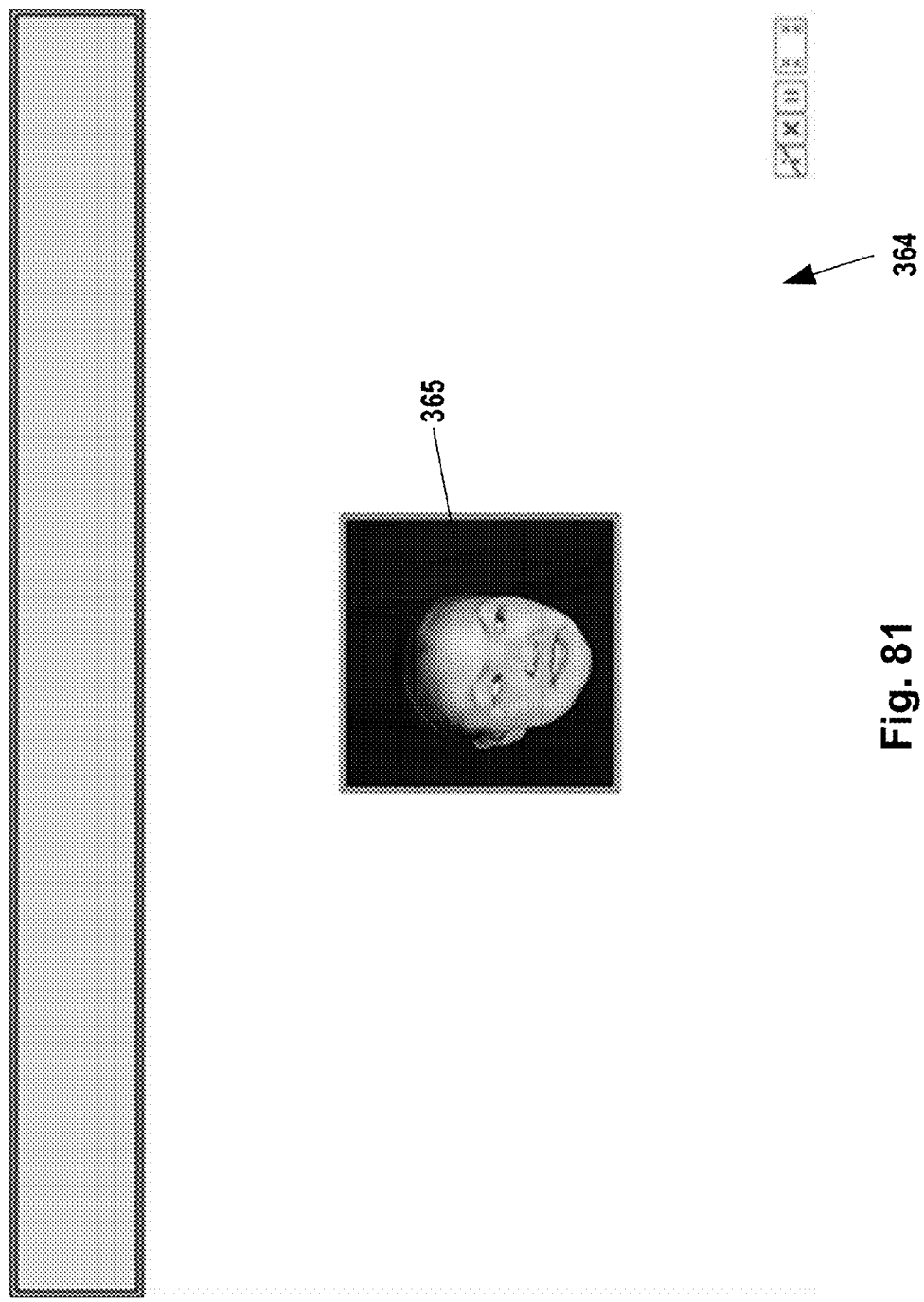
FIG. 81 illustrates another screenshot of the game illustrated in the previous figure.
Figure 82:
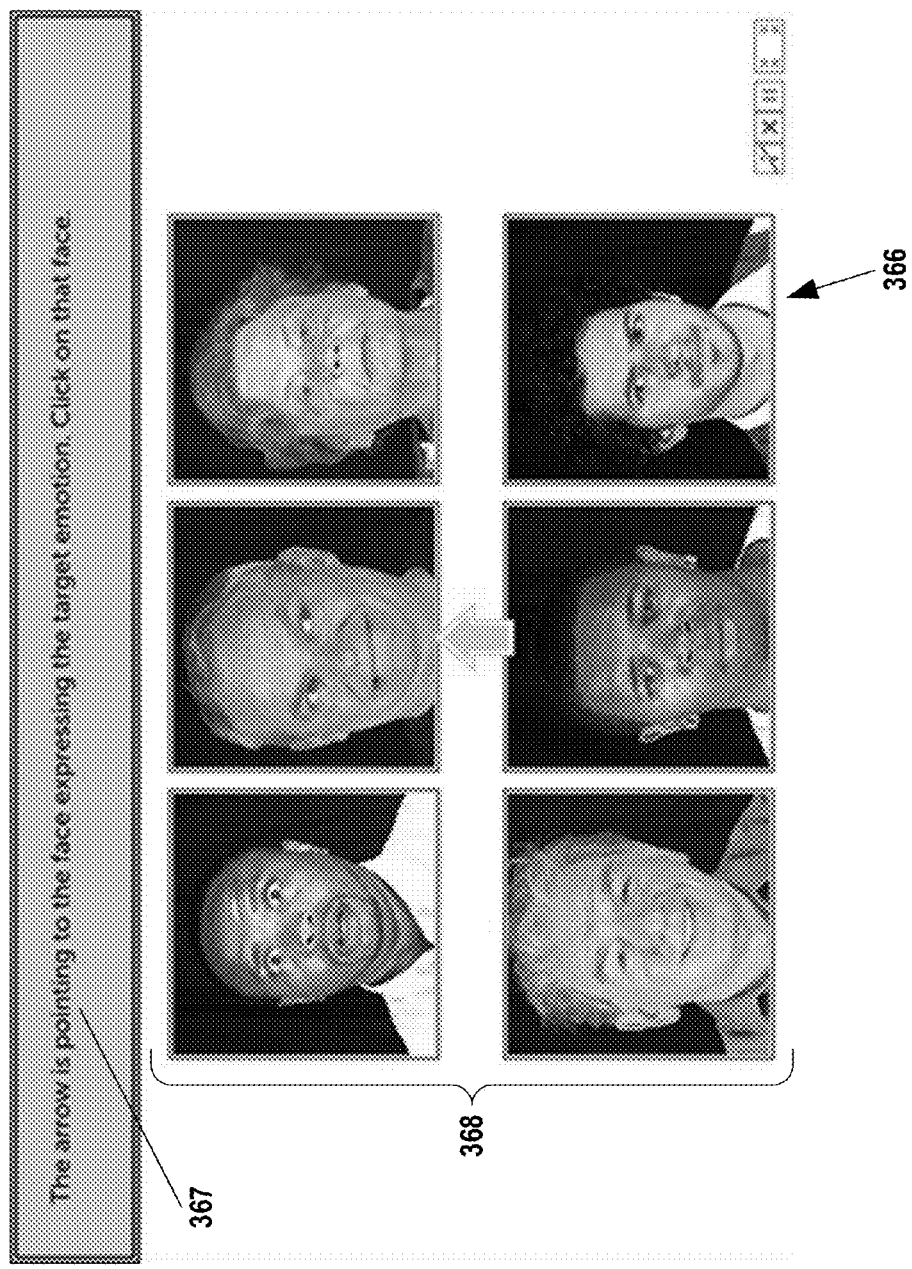
FIG. 82 illustrates another screenshot of the game illustrated in the previous figure.
Figure 83:
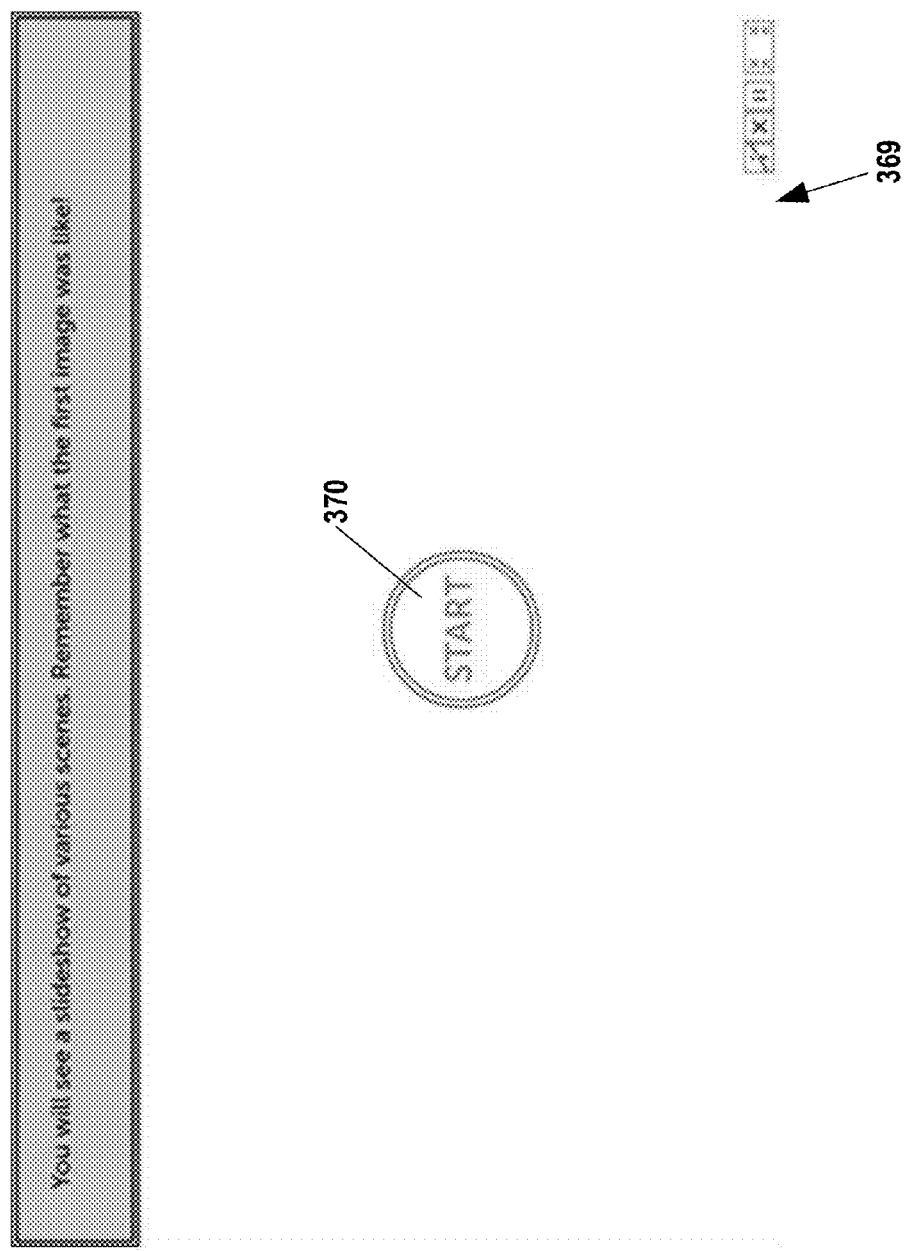
FIG. 83 illustrates a screenshot of one embodiment of a processing speed game called "Mass Affect," which presents a target image that has a characteristic valence and challenges the participant to match it with another image having a similar valence.
Figure 84:
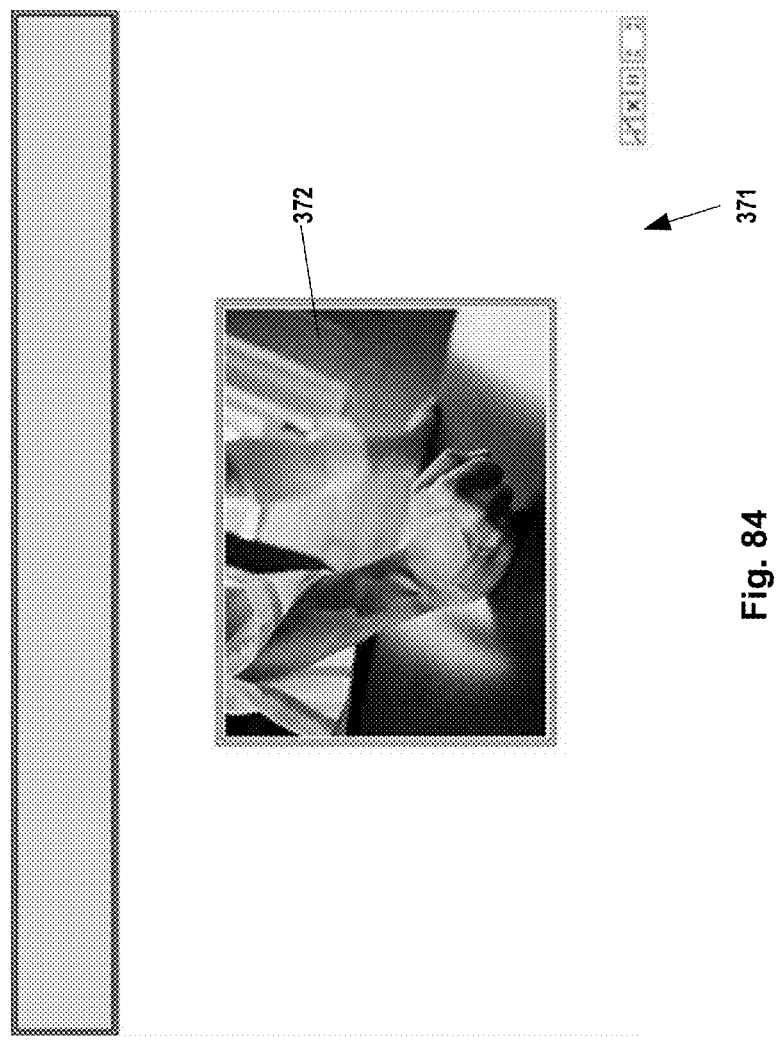
FIG. 84 illustrates another screenshot of the game illustrated in the previous figure.
Figure 85:
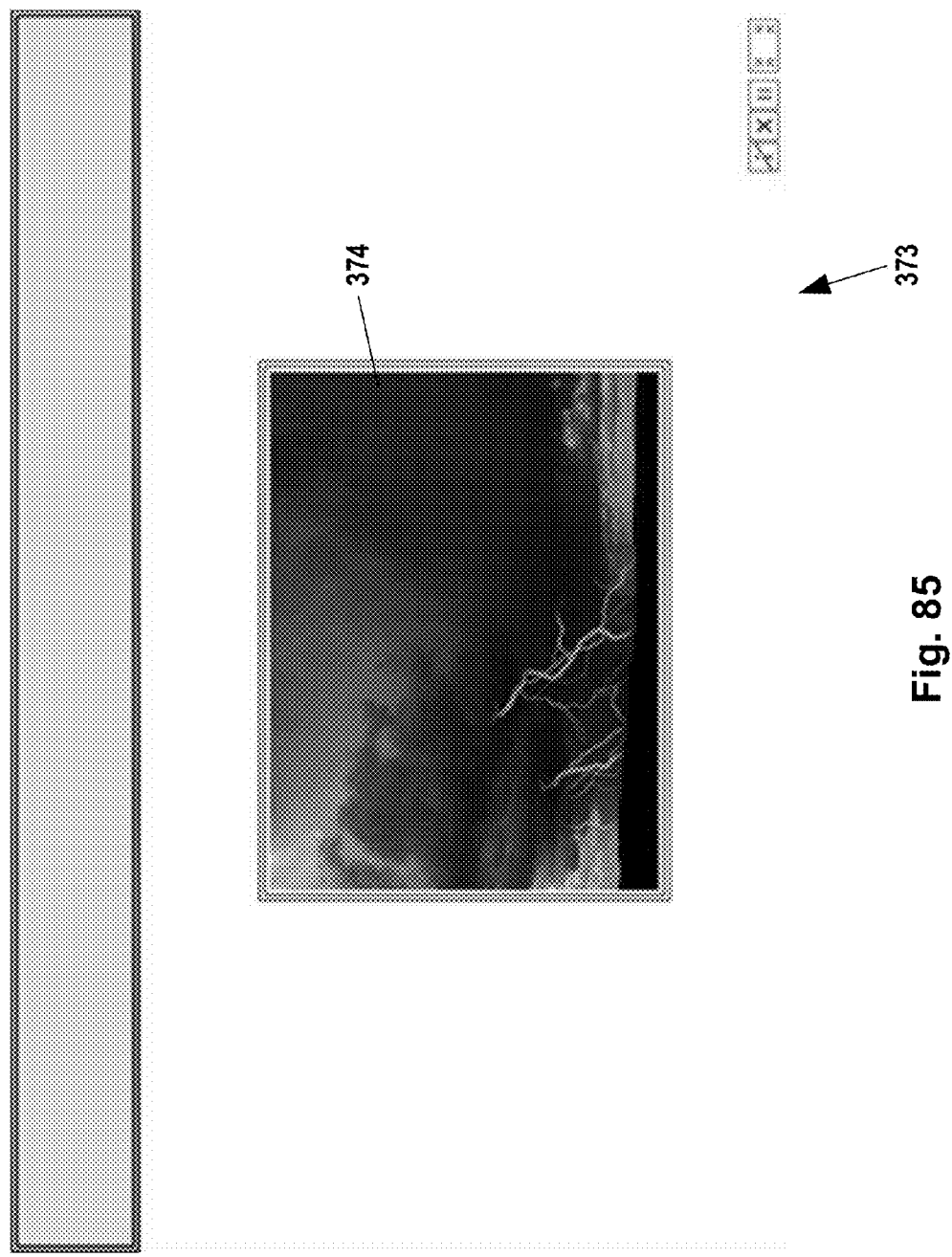
FIG. 85 illustrates another screenshot of the game illustrated in the previous figure.
Figure 86:
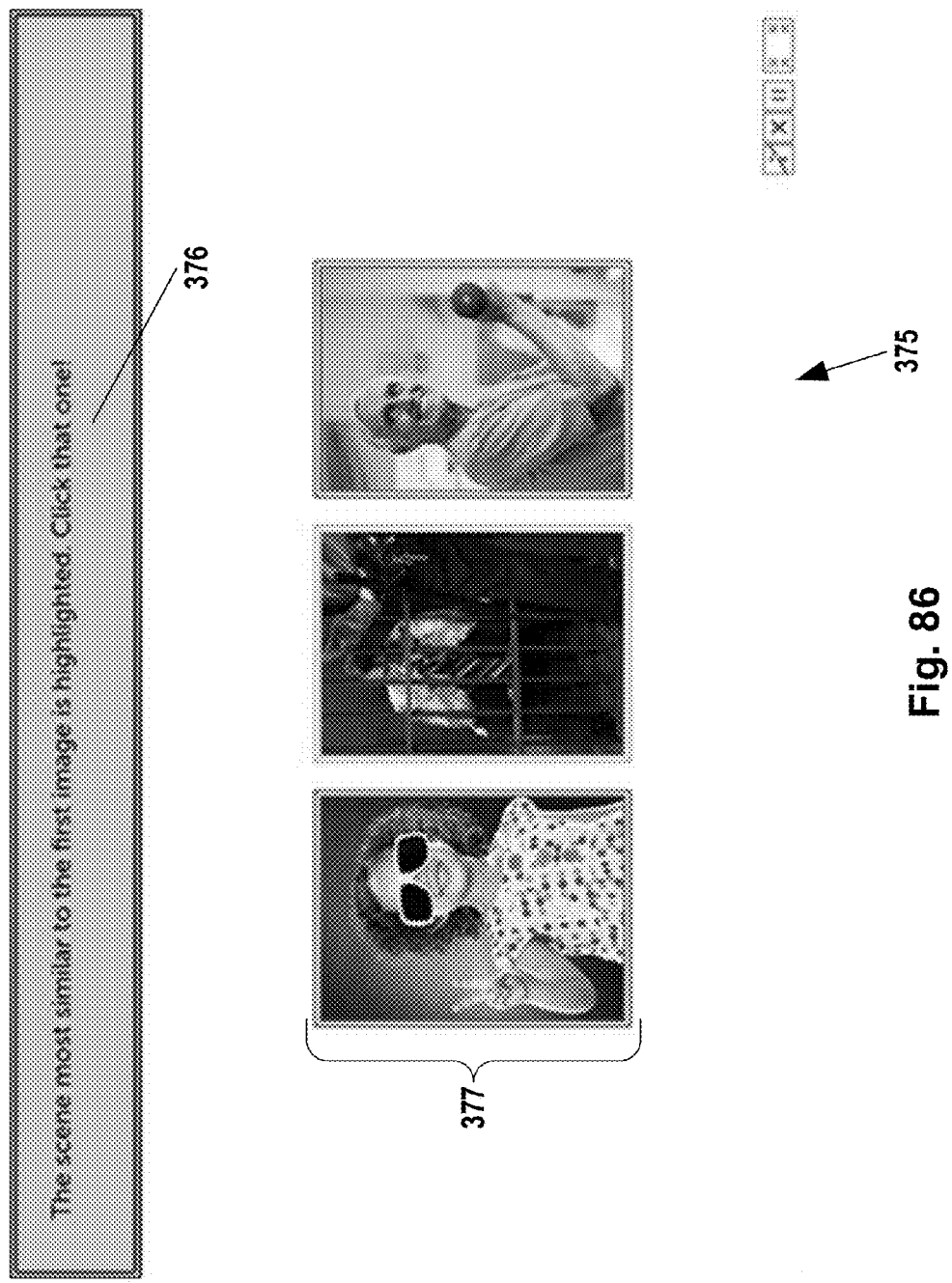
FIG. 86 illustrates another screenshot of the game illustrated in the previous figure.

FIGS. 80-82 illustrate screenshots 362, 364, 366 of one embodiment of a processing speed game called "Poke That Feeling." Poke That Feeling presents a target image 365 of a face expressing an implicit emotion, followed by a visual mask, followed by a set of facial images 368 each expressing a different implicit emotion. Poke That Feeling prompts 367 the participant to select a facial image 368 who's expressed emotion best matches the emotion expressed by the target image 365. After receiving the game participant's response and recording the speed of that response, Poke That Feeling provides an indication of whether the game participant's response was correct along with an indication or measure of a length of the first time interval.

The goals of this game are to implicitly strengthen the distributed emotion perception system in the brain, including areas as the amygdala, prefrontal cortex, and superior temporal sulcus that are hypothesized to be at the core of the social deficits for ASD). The game heavily exercises this perceptual system by presenting many images of people portraying affect.

Poke That Feeling is similar in structure to the Speeded Gaze Match game, but here the target face features an emotion and the response array features two to eight faces (depending on difficulty), each showing a different emotion. As the game participant's performance improves, Poke That Feeling reduces the first time interval, requiring the game participant to identify the implicit emotion more rapidly, and "forcing" the affect perception system to process the relevant affective features more and more efficiently. Throughout training, the intensity of the emotion gradually decreases and the number of foils in the array increases, forcing the system to uniquely process the attributes relevant for a given emotion but not others. Feedback, adaptivity, and threshold calculation are done similarly to the Speeded Gaze Match game.

6. Speeded Valence Match

FIGS. 83-86 illustrate screenshots 369, 371, 373 and 375 of one embodiment of a processing speed game called "Mass Affect," which presents a target image that has a characteristic valence and challenges the participant to match it with another image having a similar valence.

Each trial starts with a central 'start' button 370. Once the participant clicks on the start button 370, Mass Affect briefly presents an image 372 with a certain valence (which may be rated through a survey), followed by a plurality of distracting images, such as the image 374 illustrated in FIG. 85. At the end of the sequence, Mass Affect presents a set of images 377, a single one of which has a characteristic valence that matches the first image 372. Mass Affect prompts 376 the participant to select the image that has a valence matching that of the target image 372. Mass Affect provides auditory feedback for both correct and incorrect responses. The duration of target image presentation adaptively changes based on the participant's responses, using an up-down procedure.

7. Facial Emotion CPT

Figure 87:
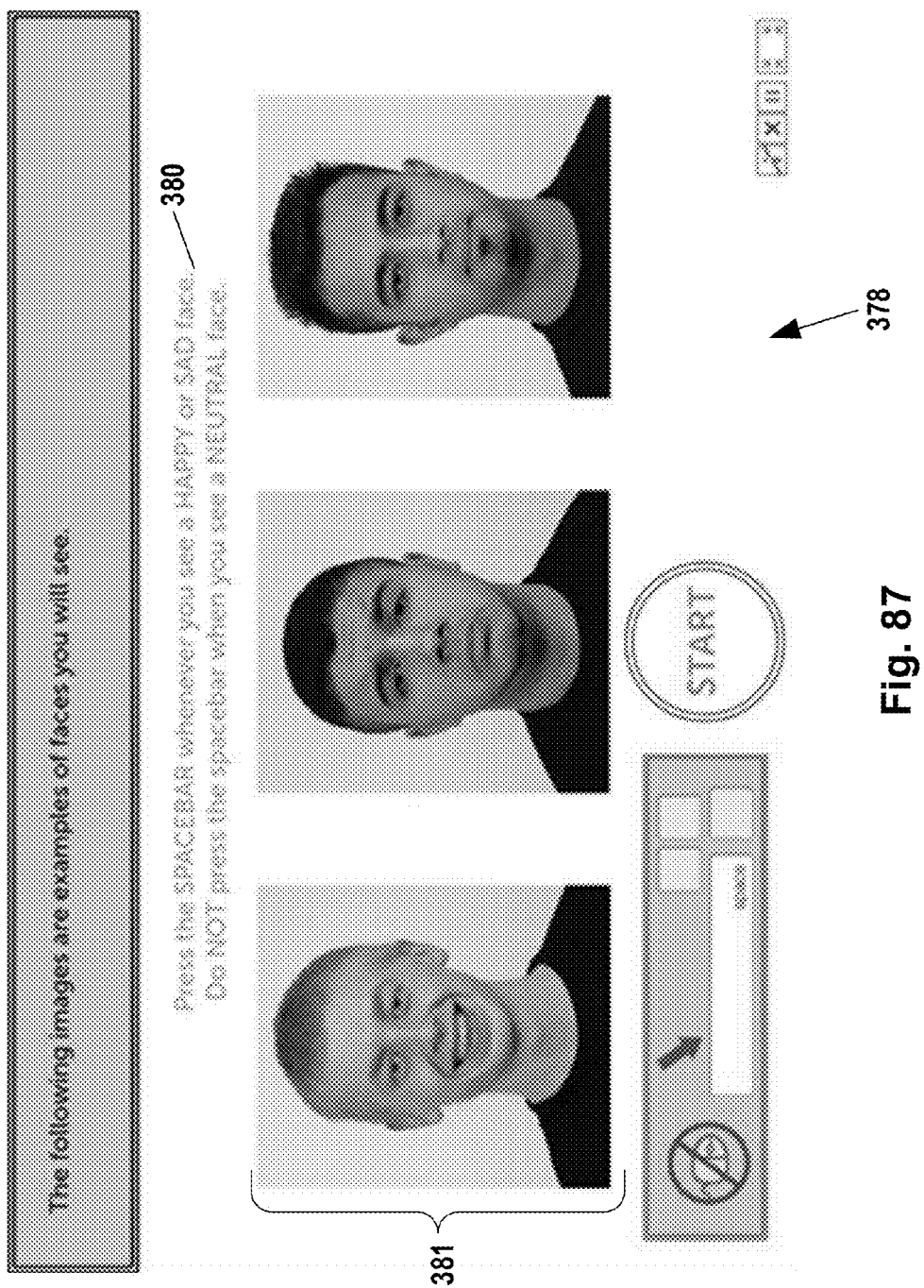
FIG. 87 illustrates a screenshot of one embodiment of a processing speed game called "TAPAT MDD," which presents a series of smiling, frowning, and neutral facial images and challenges the participant to press the spacebar when seeing a smiling or frowning image but to withhold pressing the spacebar when seeing a neutral image.
Figure 88:
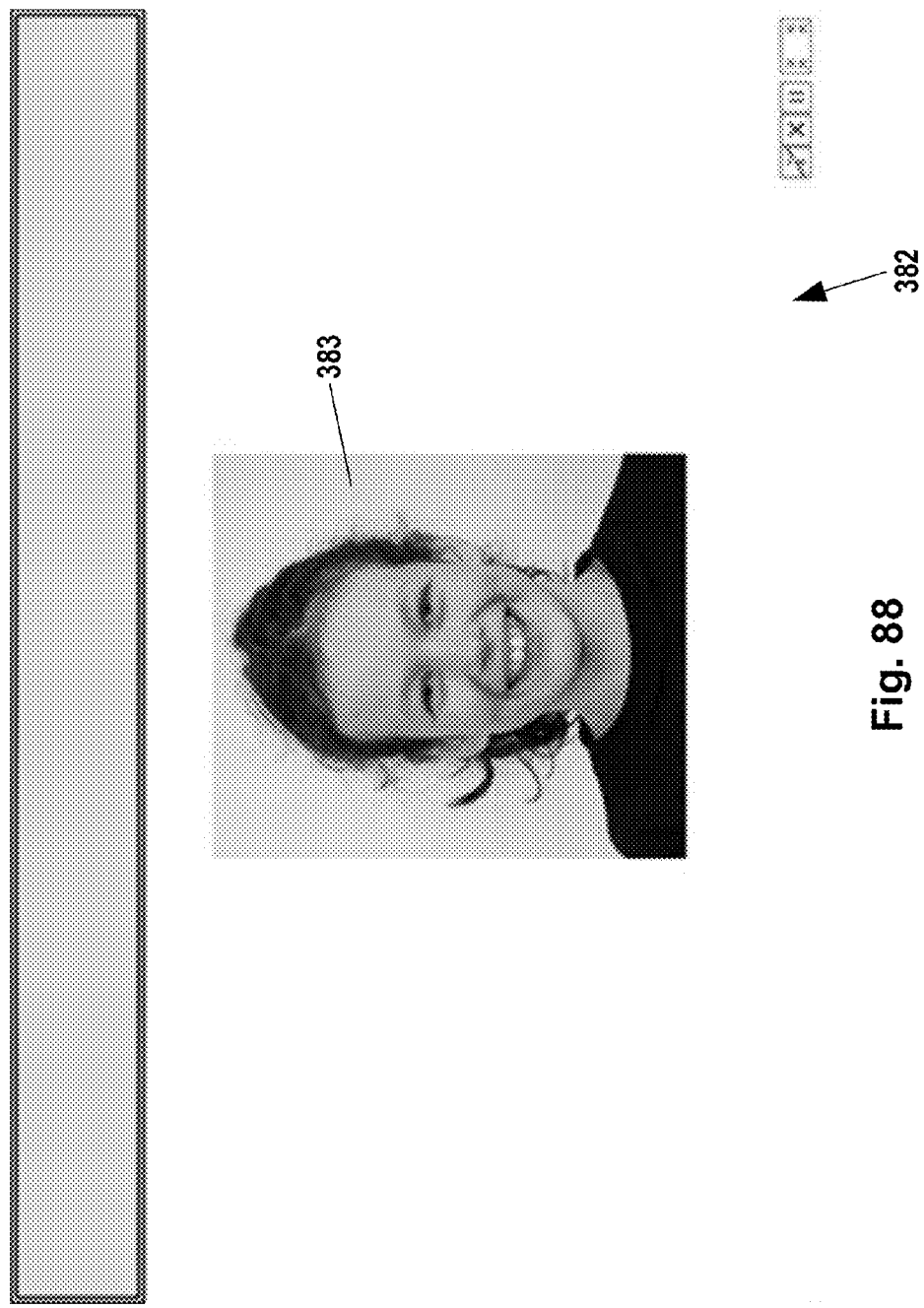
FIG. 88 illustrates another screenshot of the game illustrated in the previous figure.
Figure 89:
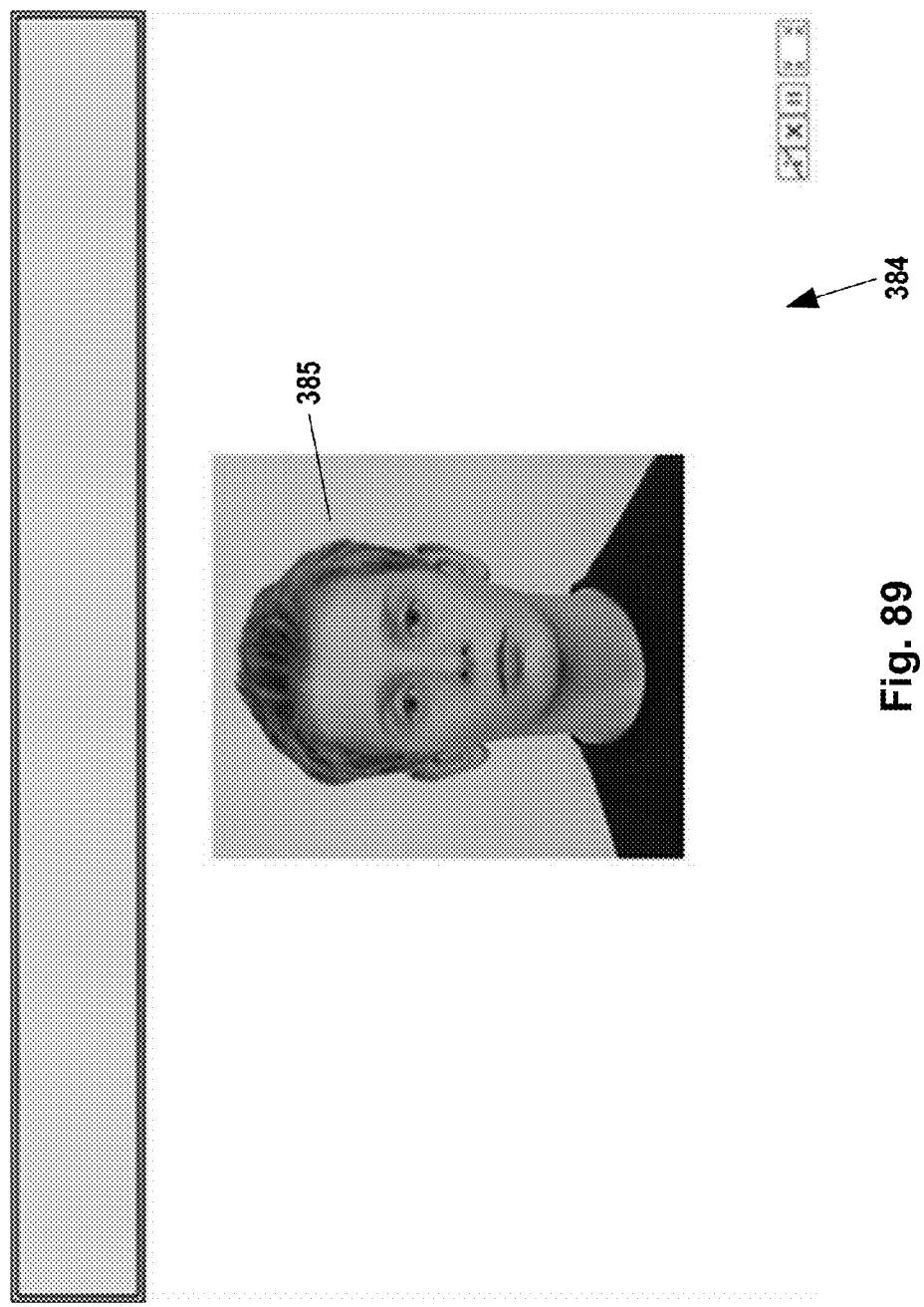
FIG. 89 illustrates another screenshot of the game illustrated in the previous figure.

FIGS. 87-89 illustrate screenshots 378, 382 and 384 of one embodiment of a processing speed game called "TAPAT MDD," which presents a series of smiling, frowning, and neutral facial images. The game challenges the participant to press the spacebar when seeing a smiling or frowning image but to withhold pressing the spacebar when seeing a neutral image. In so doing, the game trains the participant to quickly recognize emotionally expressive faces and distinguish them from emotionally neutral faces.

The game is structured as a tonic and phasic alertness training (TAPAT) task that trains both moment-to-moment and extended aspects of alertness. Tonic alertness refers to intrinsic arousal that fluctuates on the order of minutes to hours. Tonic alertness is intimately involved in sustaining attention and provides the cognitive tone for performing complicated functions such as working memory and executive control. Phasic alertness, by contrast, is the rapid change in attention due to a brief event and is the basis for operations such as orienting and selective attention.

The game prompts 380 the participant to press the spacebar on his or her keyboard when shown an image 381 of a smiling (80% occurrence) or frowning (10% occurrence) face—such as face 383 in FIG. 88—but to withhold such action in response to a neutral face (10% occurrence)—such as face 385 in FIG. 89. The images in this task are of male and female individuals from children to adults. Inter-stimulus-interval is randomly selected to be either 600, 1800 or, 3000 ms, with equal probability. The participant is instructed to respond as quickly as possible to an emotional image.

8. Emotion Maintenance

FIGS. 90-93 illustrate screenshots 386, 388, 392 and 395 of one embodiment of an emotional reversal game called "Bright Whites." Bright Whites repeatedly challenges the participant to adjust to changing emotional outputs by two characters and identify which character was most recently smiling.

The goals of this game are to improve: (1) social cue perception, and (2) the ability to flexibly adapt to a new social rule. The game utilizes 'reversal learning' logic. At the beginning of each trial, Bright Whites presents two neutral faces. The subject is prompted to select one of them to be their "friend." Following that selection, one person smiles or exhibits an implicitly "nice" expression, while the other becomes angry or remains neutral. The subject should continue to select the "nice" person, or switch to selecting the "nice" person, as applicable, until a rule change (after a few trials), and the person that was previously smiling (for example) now becomes angry.

Figure 90:
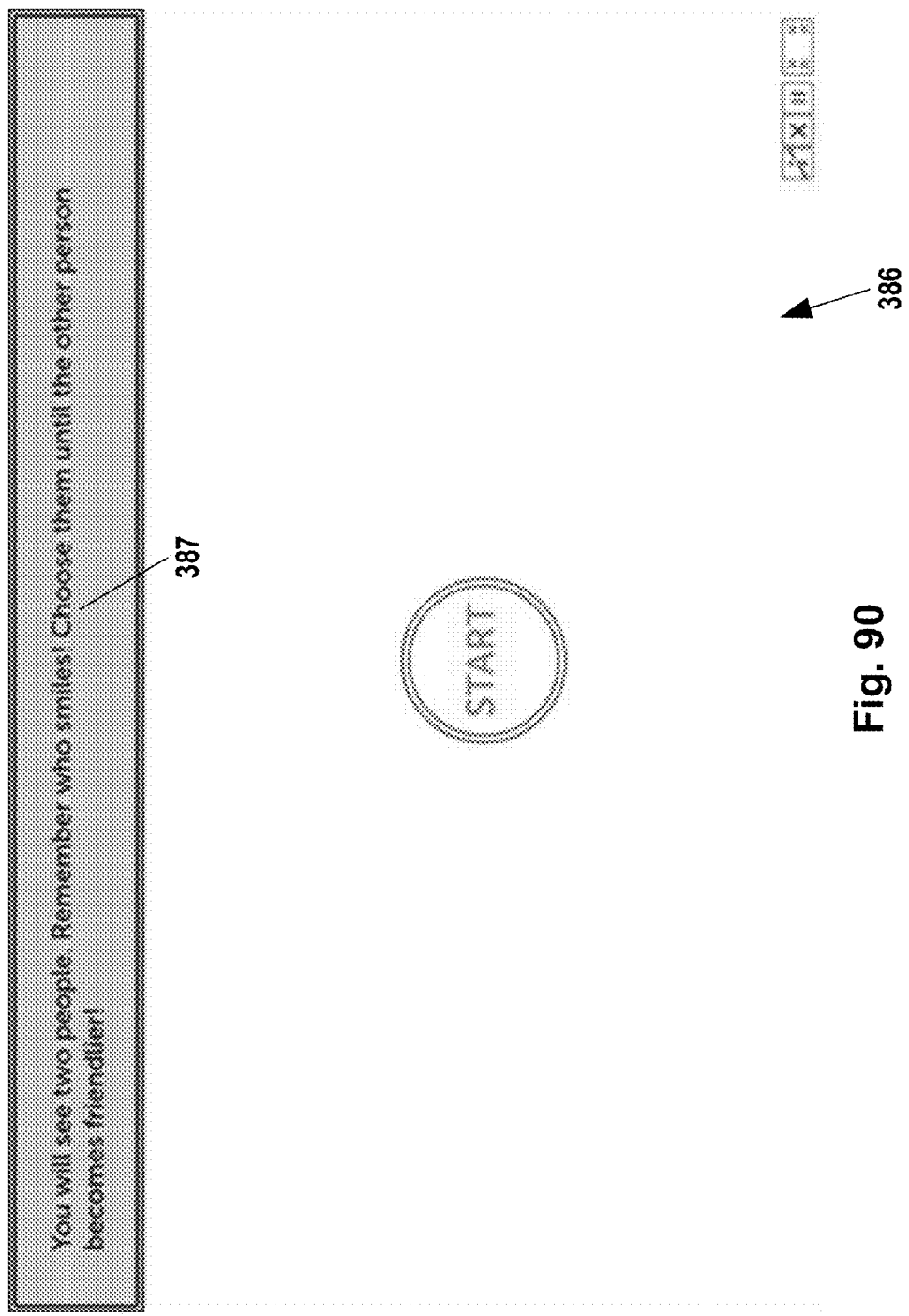
FIG. 90 illustrates a screenshot of one embodiment of a game called "Bright Whites," which repeatedly challenges the participant to adjust to changing emotional outputs by two characters and identify which character was most recently smiling.
Figure 91:
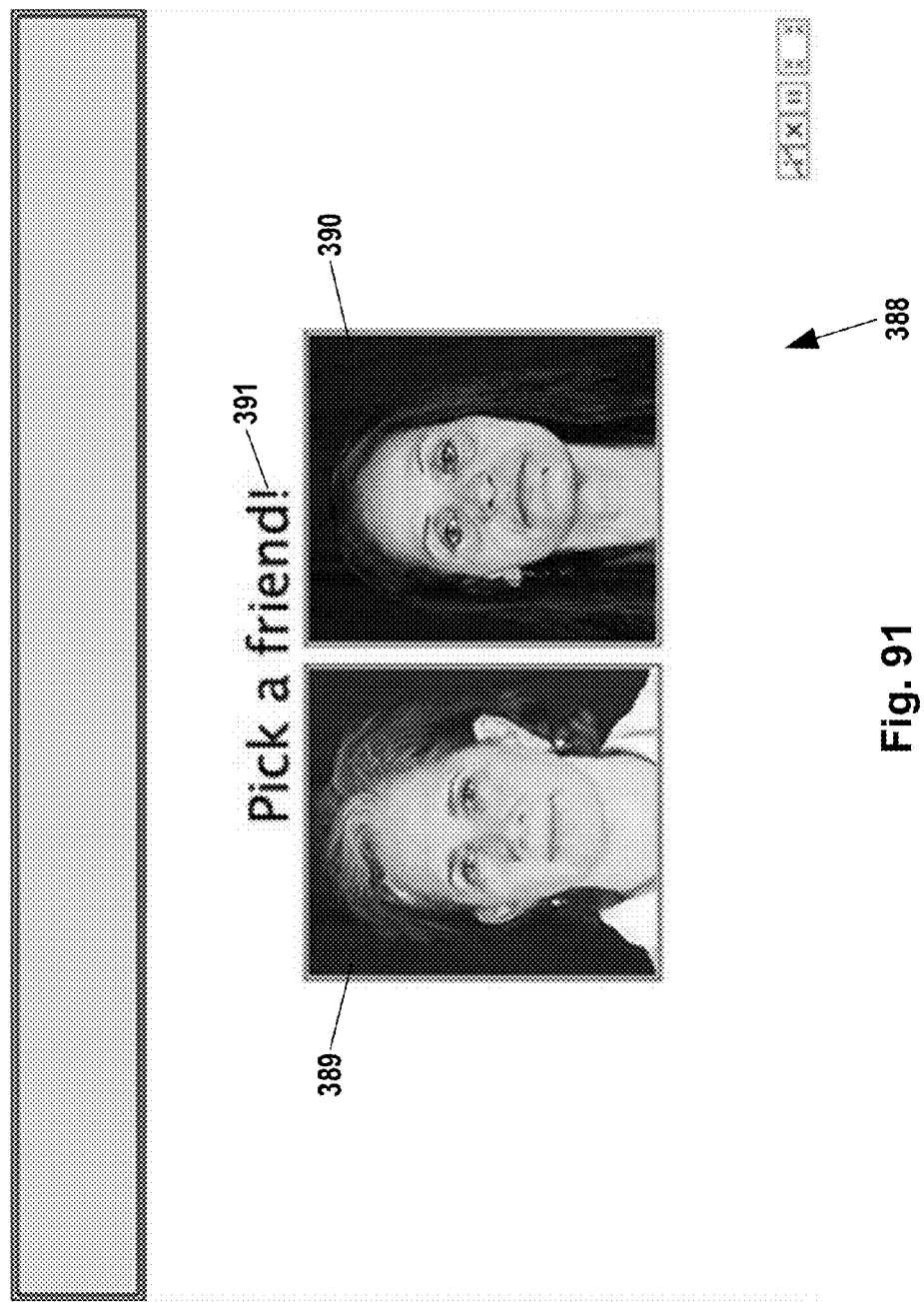
FIG. 91 illustrates another screenshot of the game illustrated in the previous figure.
Figure 92:
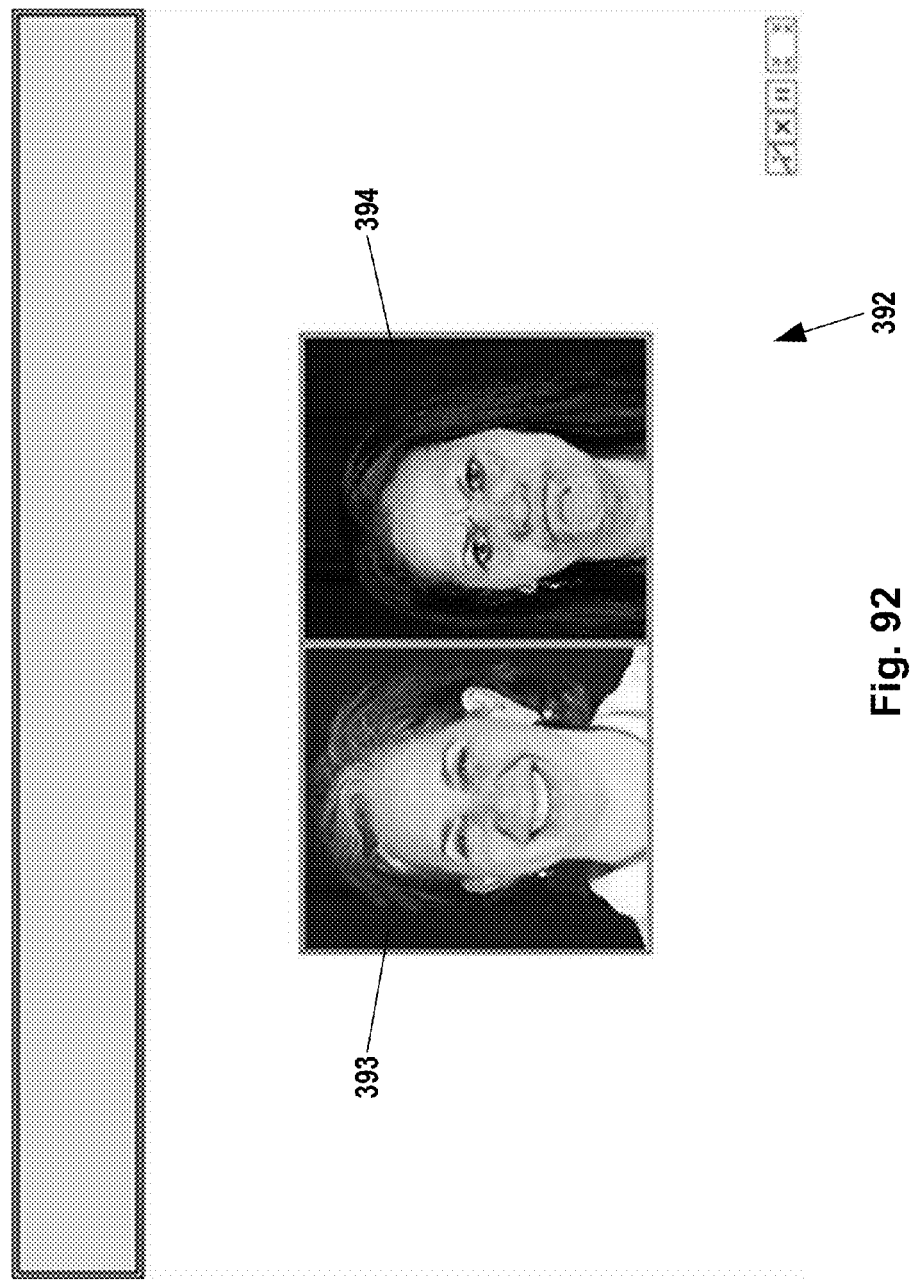
FIG. 92 illustrates another screenshot of the game illustrated in the previous figure.
Figure 93:
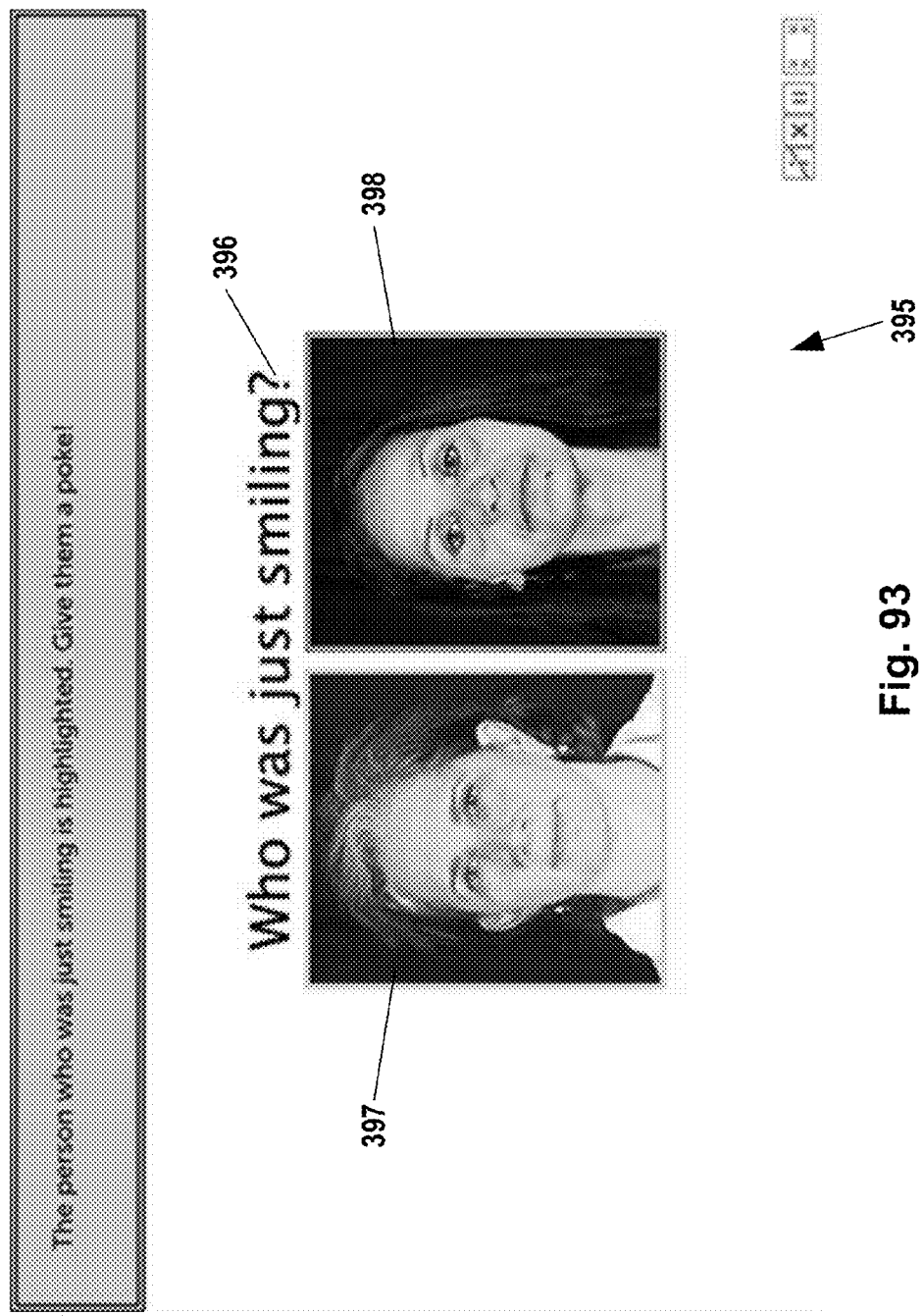
FIG. 93 illustrates another screenshot of the game illustrated in the previous figure.
Figure 94:
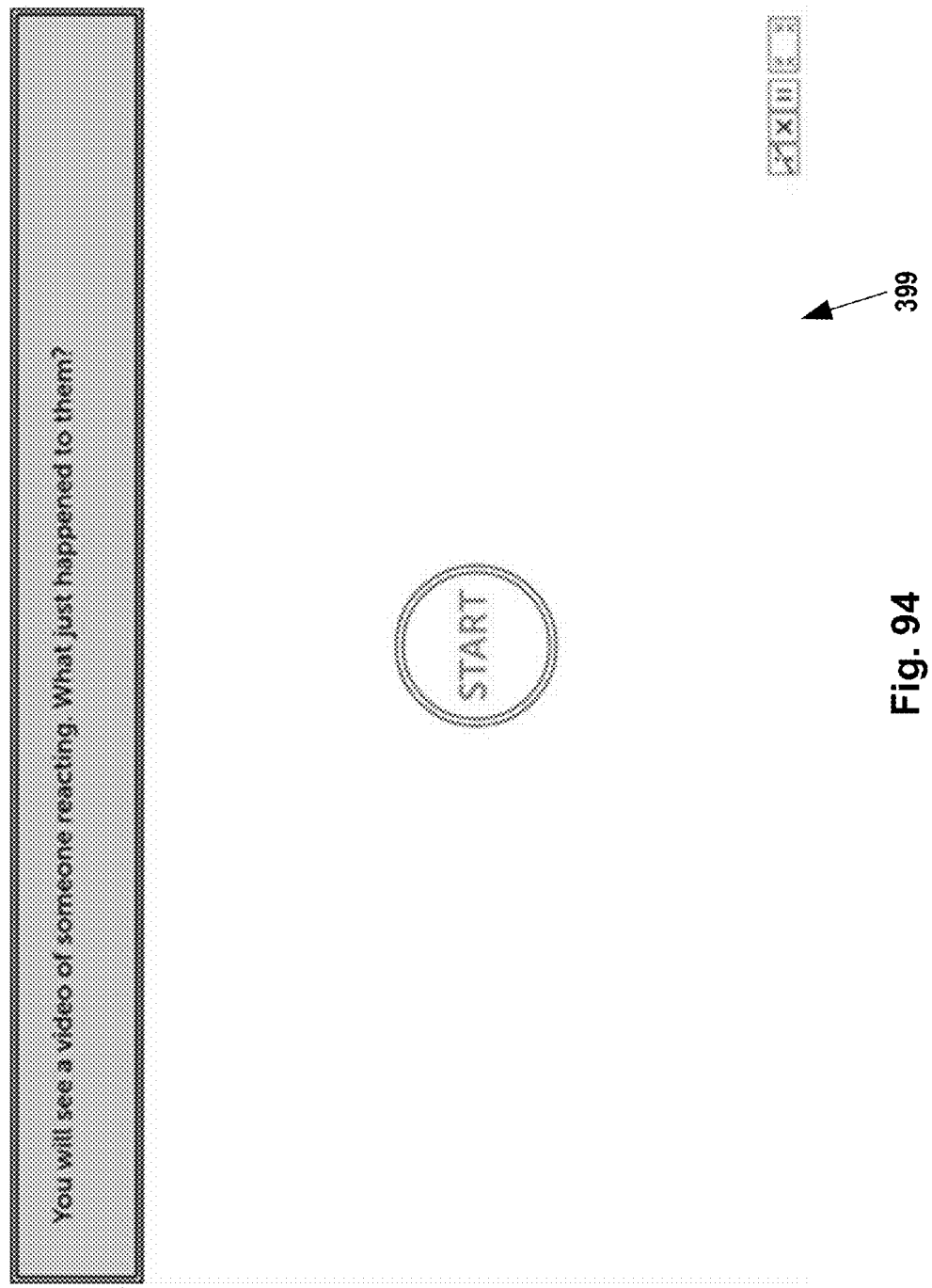
FIG. 94 illustrates a screenshot of one embodiment of a game called "What Just Happened?," which plays short video clips of actors expressing emotion or a neutral face followed by challenging the participant to identify which of multiple options would best describe an experience that elicited the actors' expressed emotions.
Figure 95:
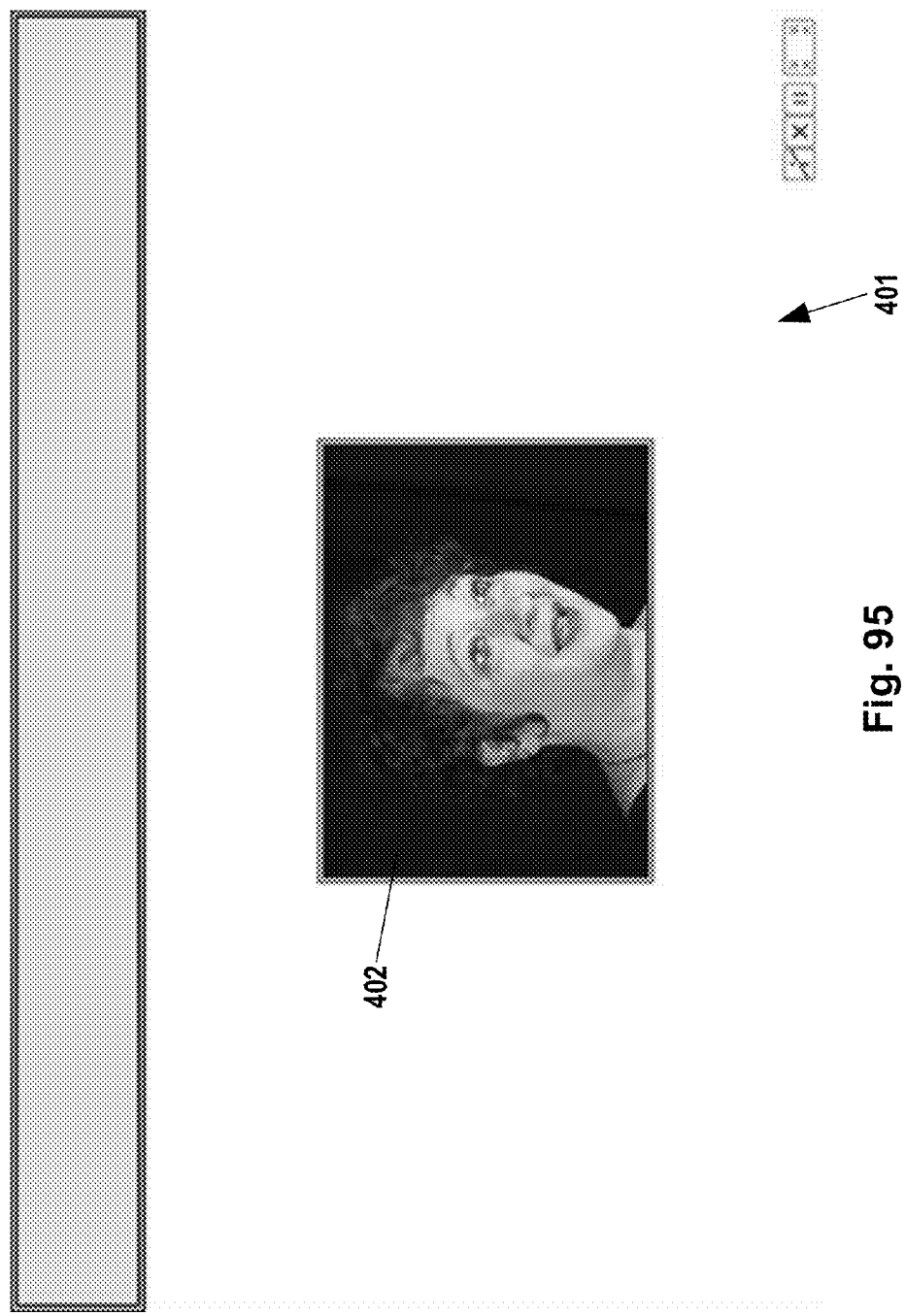
FIG. 95 illustrates another screenshot of the game illustrated in the previous figure.
Figure 96:
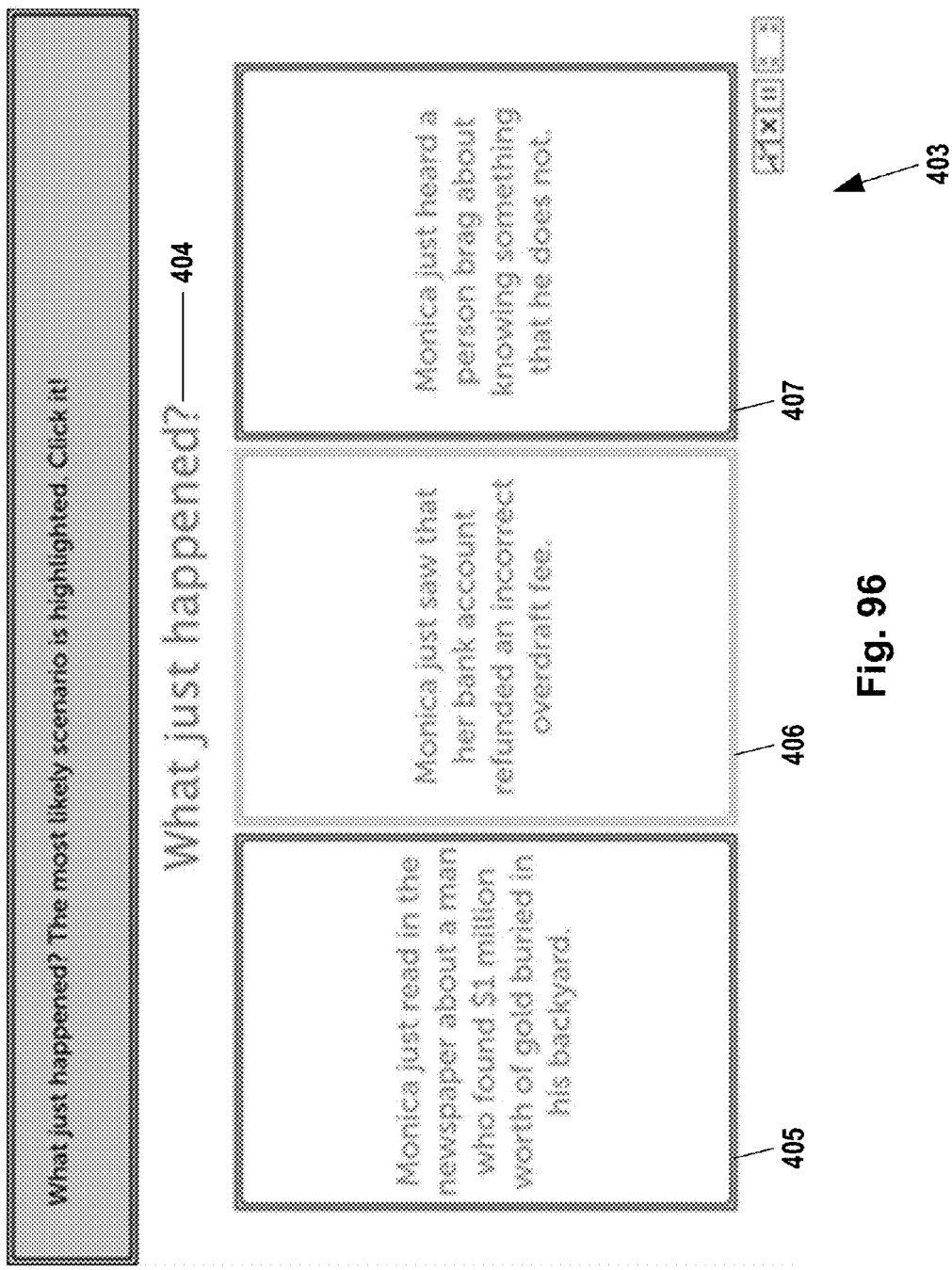
FIG. 96 illustrates another screenshot of the game illustrated in the previous figure.
Figure 97:
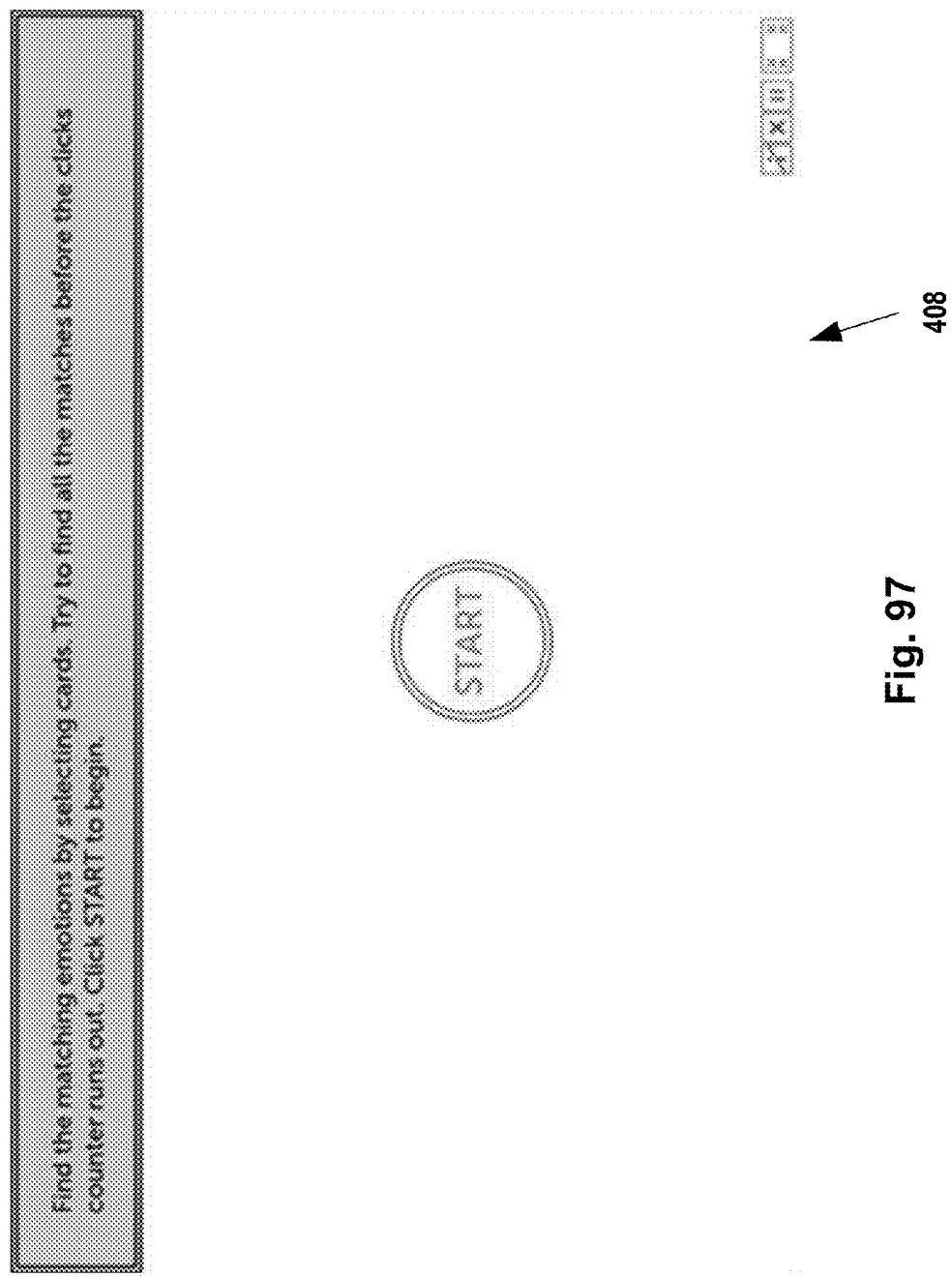
FIG. 97 illustrates a screenshot of one embodiment of a working memory emotional cue game called "Second That Emotion," which presents an array of down-facing cards and challenges a participant to select card pairs that show matching facial emotions.

Turning to FIG. 90, Bright Whites prompts 387 the game participant that images of two or more people will be displayed, and to remember who smiles or who is implicitly being nice. Next, Bright Whites displays a set of neutral target facial images 389, 390 and prompts 391 the participant to "pick a friend." After the participant makes a selection, Bright Whites displays a visual mask followed by a set of target facial images 393, 394 that it presents simultaneously for a brief time interval. No two of the facial images in any given set is of the same person. One of the images of each set is of a smiling face or of a person who is implicitly being nice. Each set is followed by a visual mask such as static, followed by a display of images 397, 398 of the same faces as shown during the time interval but all having neutral expressions. Bright White prompts 396 the participant to choose who was smiling.

After receiving the game participant's response, Bright Whites provides an indication of whether the game participant's response was correct along with an indication of a length of the time interval. Bright White repeats the preceding steps for multiple trials while progressively decreasing the time interval in response to correct identifications.

After five to eight trials, the frowning actor becomes the smiling stimulus and the smiling actor becomes the frowning stimulus. The game participant continues to be prompted to select the smiling face. The speed of presentation—that is, the length of the time interval—adaptively changes based on the participant's responses using a 2down-1up adaptive procedure.

9. Facial Affect Theory of Mind

FIGS. 94-97 illustrate screenshots 399, 401 and 403 of one embodiment of a facial affect theory of mind game called "What Just Happened?" which trains a game participant to apprehend an emotional state of mind. What Just Happened? plays short video clips 402 of actors expressing emotion or a neutral face and then prompts 404 the participant to identify which of multiple options 405, 406 or 407 would best describe an experience that elicited the actors' expressed emotions. The speed of presentation adaptively changes based on the participant's responses.

10. Working Memory Emotion Cue

FIGS. 97-100 illustrate screenshots 408, 410, 413 and 416 of one embodiment of a working memory emotional cue game called "Second That Emotion." Second That Emotion presents an array 411 of down-facing cards and challenges a participant to select card pairs that show matching facial emotions.

In addition to improving the function of the emotion perception system, this game also targets visual spatial working memory for emotions. Participants need to find cards of matching facial expressions in larger and larger card arrays.

Figure 98:
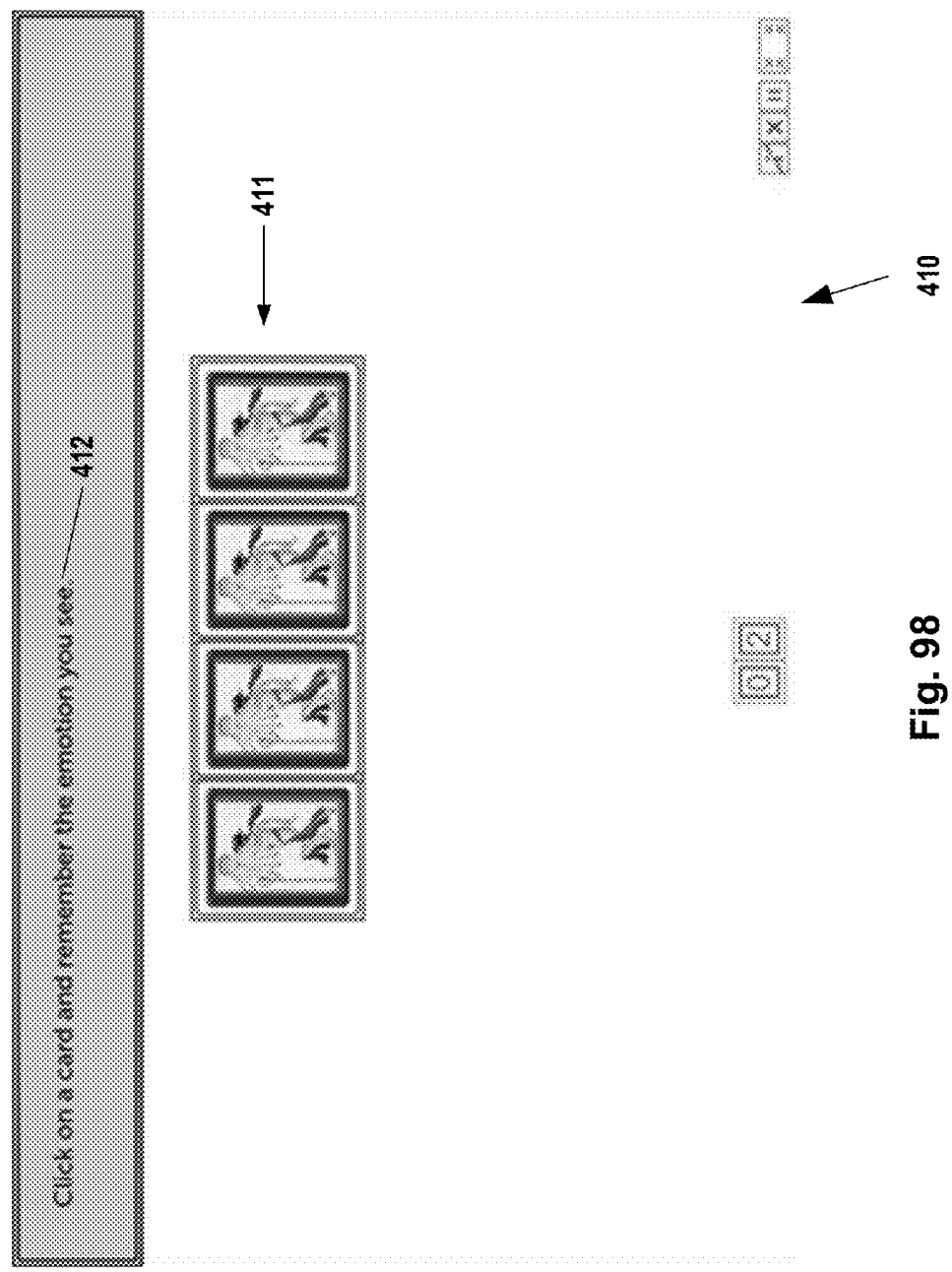
FIG. 98 illustrates another screenshot of the game illustrated in the previous figure.
Figure 99:
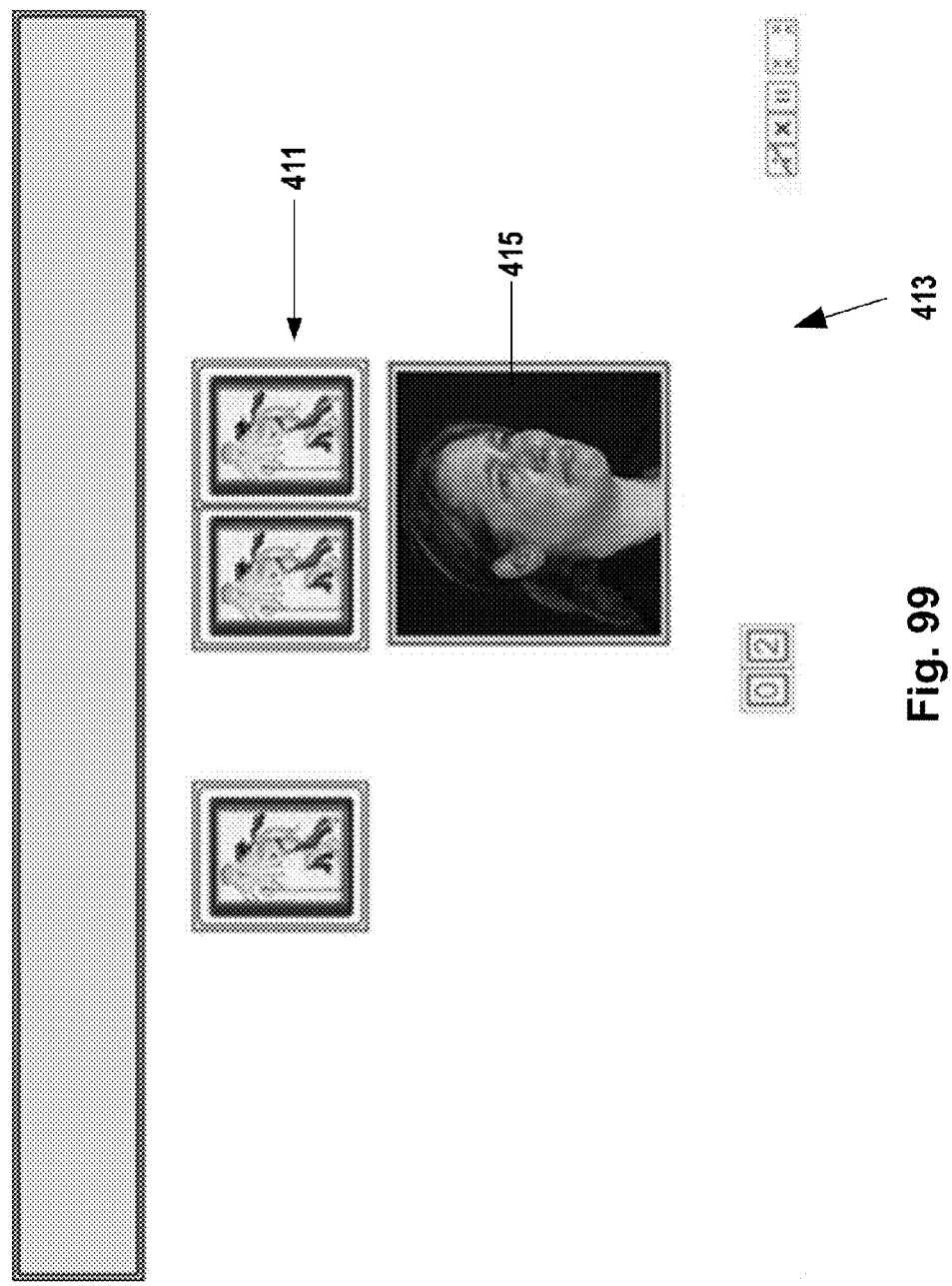
FIG. 99 illustrates another screenshot of the game illustrated in the previous figure.
Figure 100:
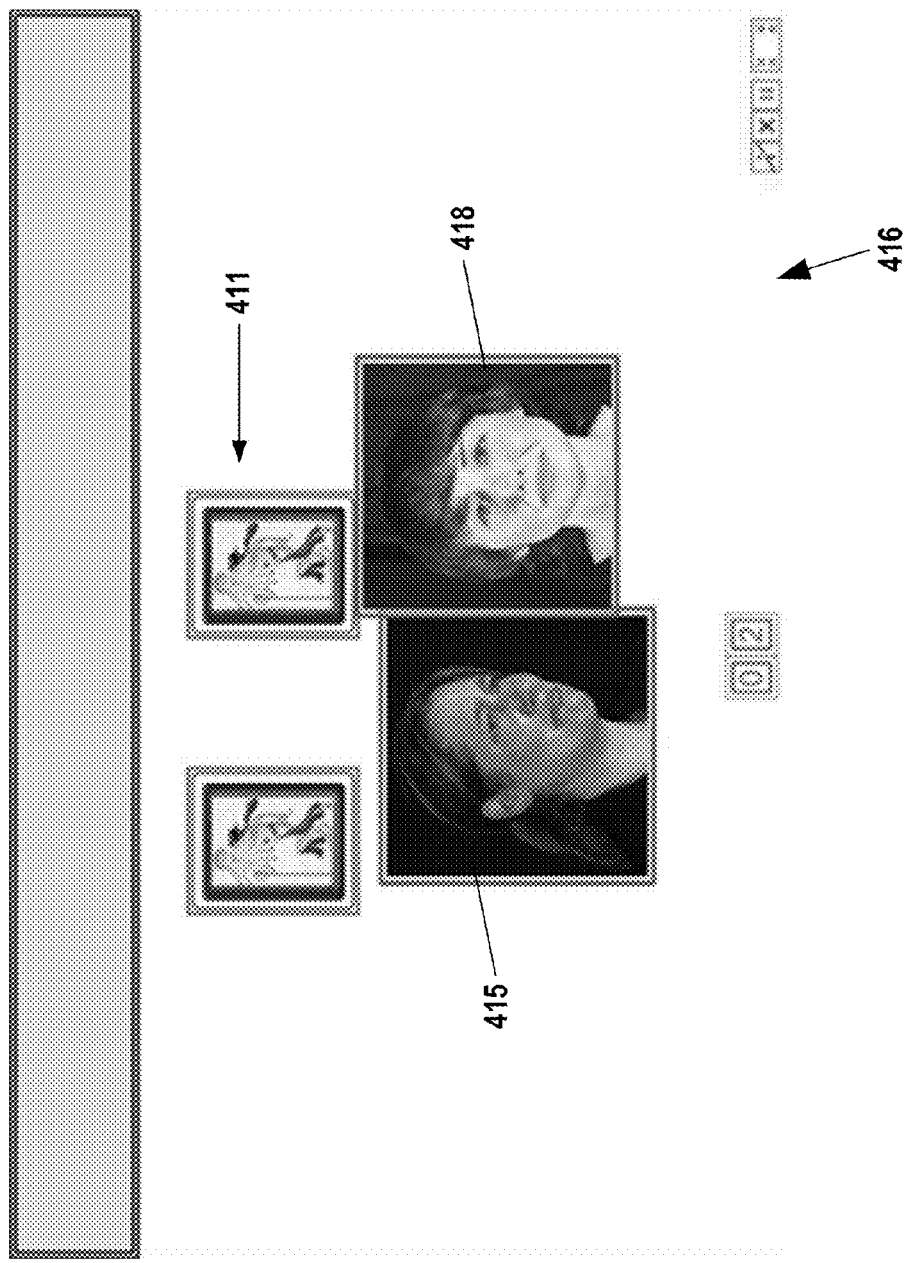
FIG. 100 illustrates another screenshot of the game illustrated in the previous figure.

During each trial, Second That Emotion presents the participant with an array 411 of down-facing "cards" and prompts 412 the participant to click on card pairs that show matching facial emotions. As an example, FIG. 98 illustrates the first card 415, face up, of a selected pair of cards, and FIG. 99 illustrates the first and second cards 415, 418, face up, of a selected pair of cards. Both cards implicitly reveal sadness. When the cards in a selected pair display the same facial emotion—as they do in FIG. 99—Second that Emotion plays a positive feedback and causes the two cards to disappear.

Second That Emotion challenges the participant to find all matching pairs in the array within a certain number of clicks (set to be equal to the number of card pairs) by maintaining representations of facial emotion and of their spatial location in order to guide behavior. If the participant matches up all of the correct pairs of facial emotion before running out of clicks, the participant's performance on the trial is considered correct. Otherwise, the participant's performance is graded as incorrect.

The number of card pairs in the array 411 is adaptively varied based on the participant responses. The number of card pairs is increased following two consecutive correct trials, and decreased following a single incorrect trial. The emotions included in this game are: neutral, happy, sad, angry, surprised, afraid, disgusted, proud, contemptuous, pleasantly surprised and embarrassed. In one embodiment, a total of twenty trials are used, and the threshold (number of card pairs) is determined as the arithmetic mean of the last five reversals. Here, a reversal refers to the act of flipping over a card to reveal an emotion. Therefore, the last five reversals refers to the last five cards the participant flipped over.

11. Working Memory Vocal Emotions

Figure 101:
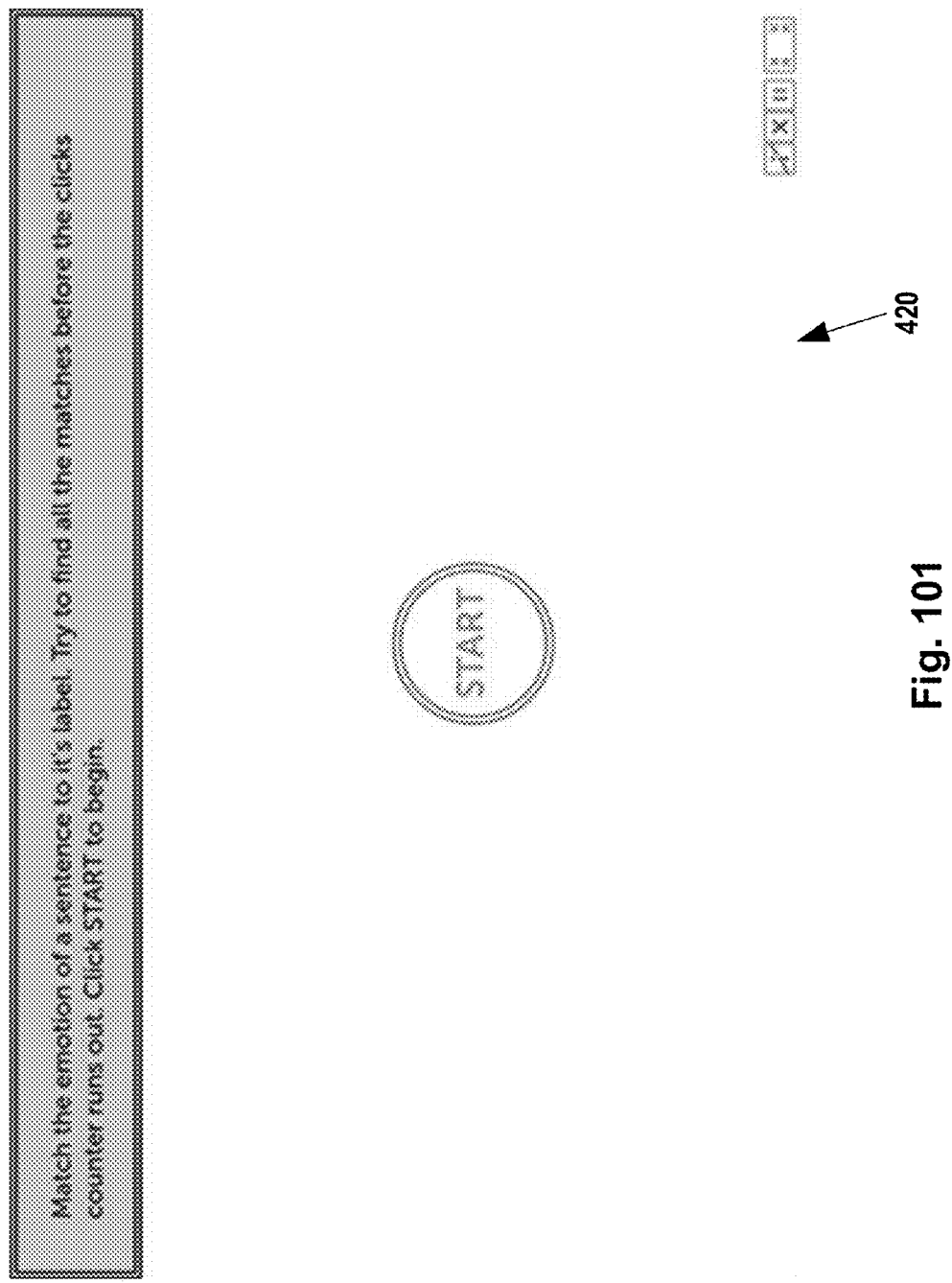
FIG. 101 illustrates a screenshot of another embodiment of a working memory prosody game called "Second That Intonation," which presents an array of down-facing cards associated with spoken sentences and challenges a participant to select card pairs that match a spoken sentence's prosody with a label.
Figure 102:
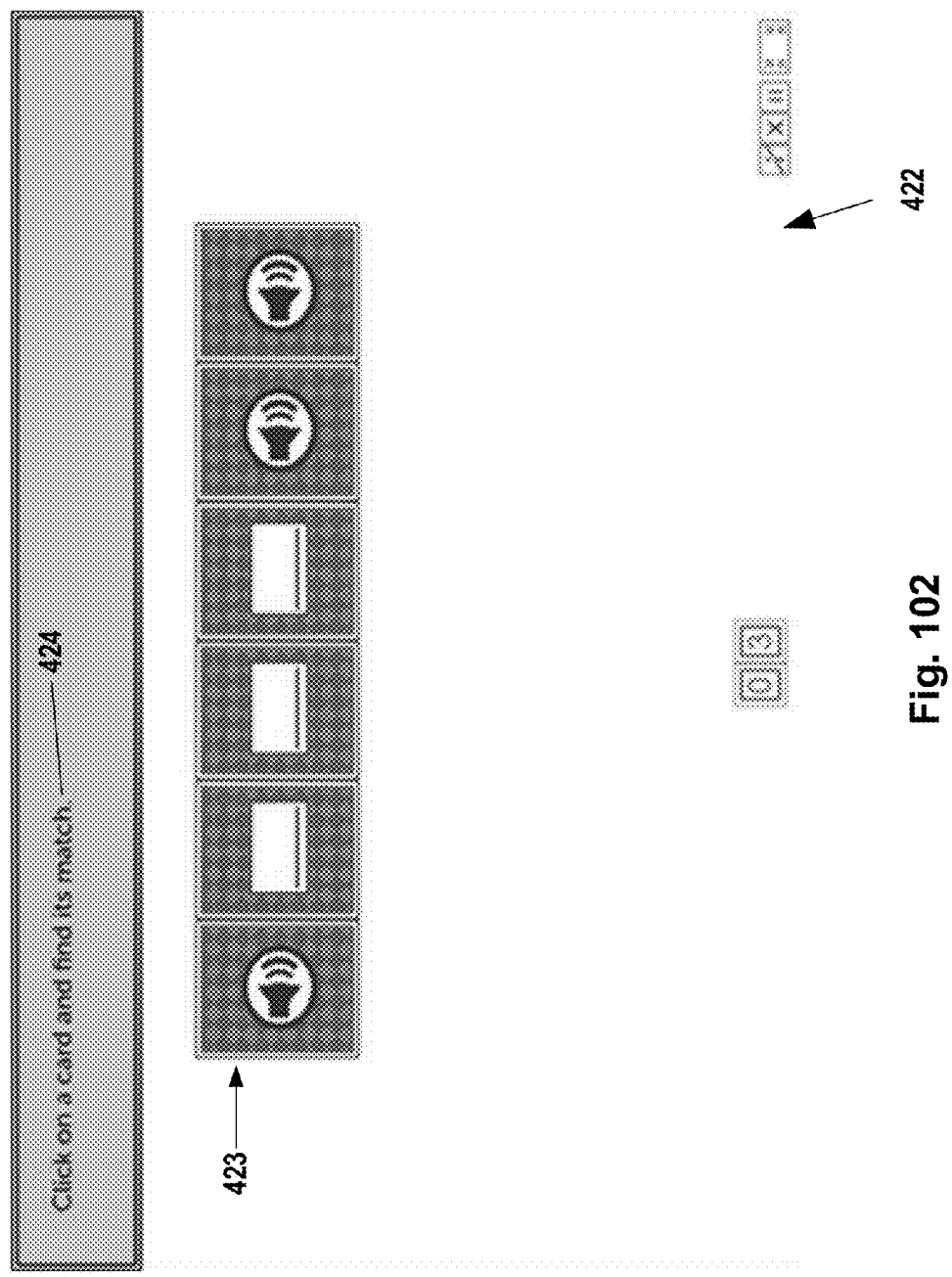
FIG. 102 illustrates another screenshot of the game illustrated in the previous figure.
Figure 103:
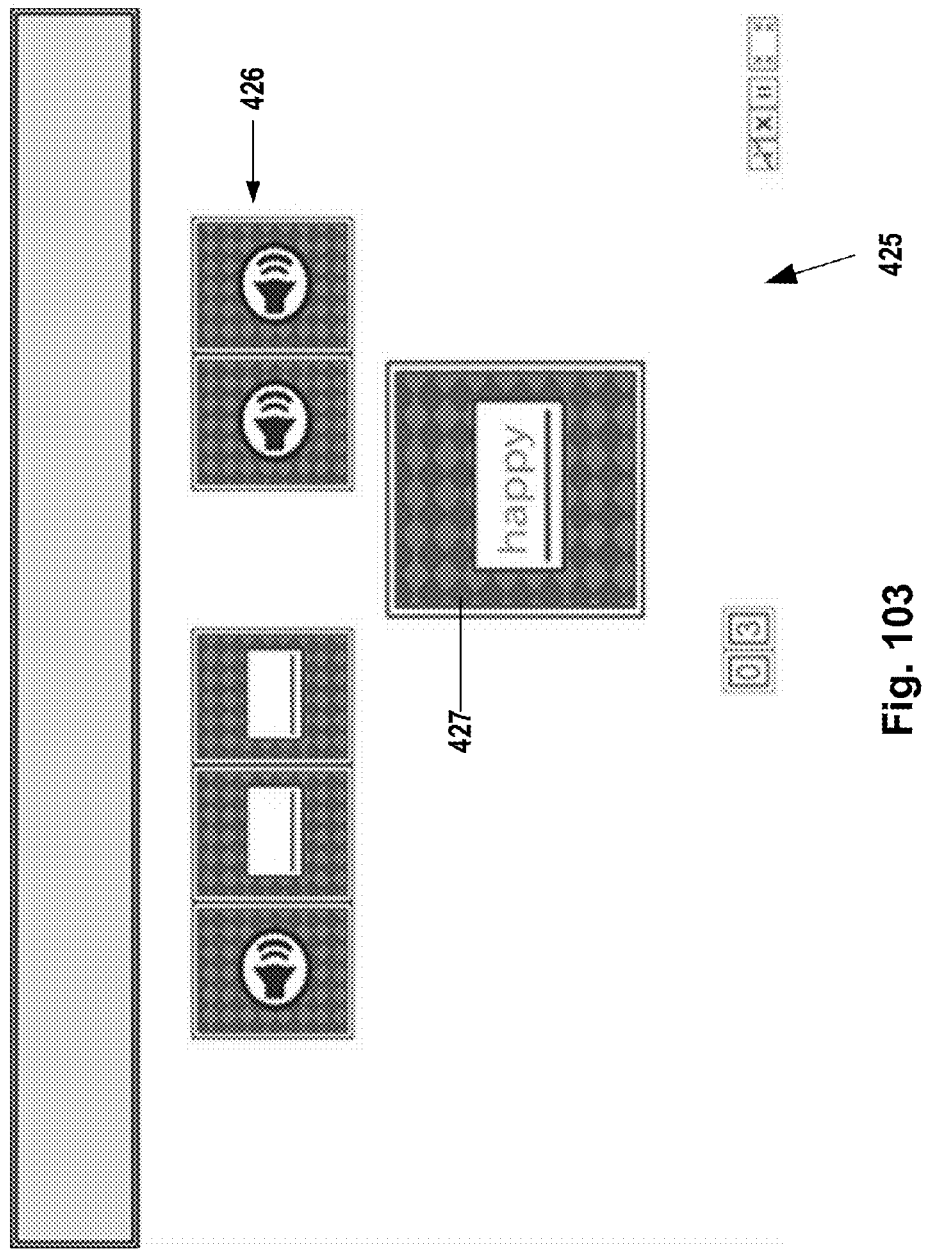
FIG. 103 illustrates another screenshot of the game illustrated in the previous figure.
Figure 104:
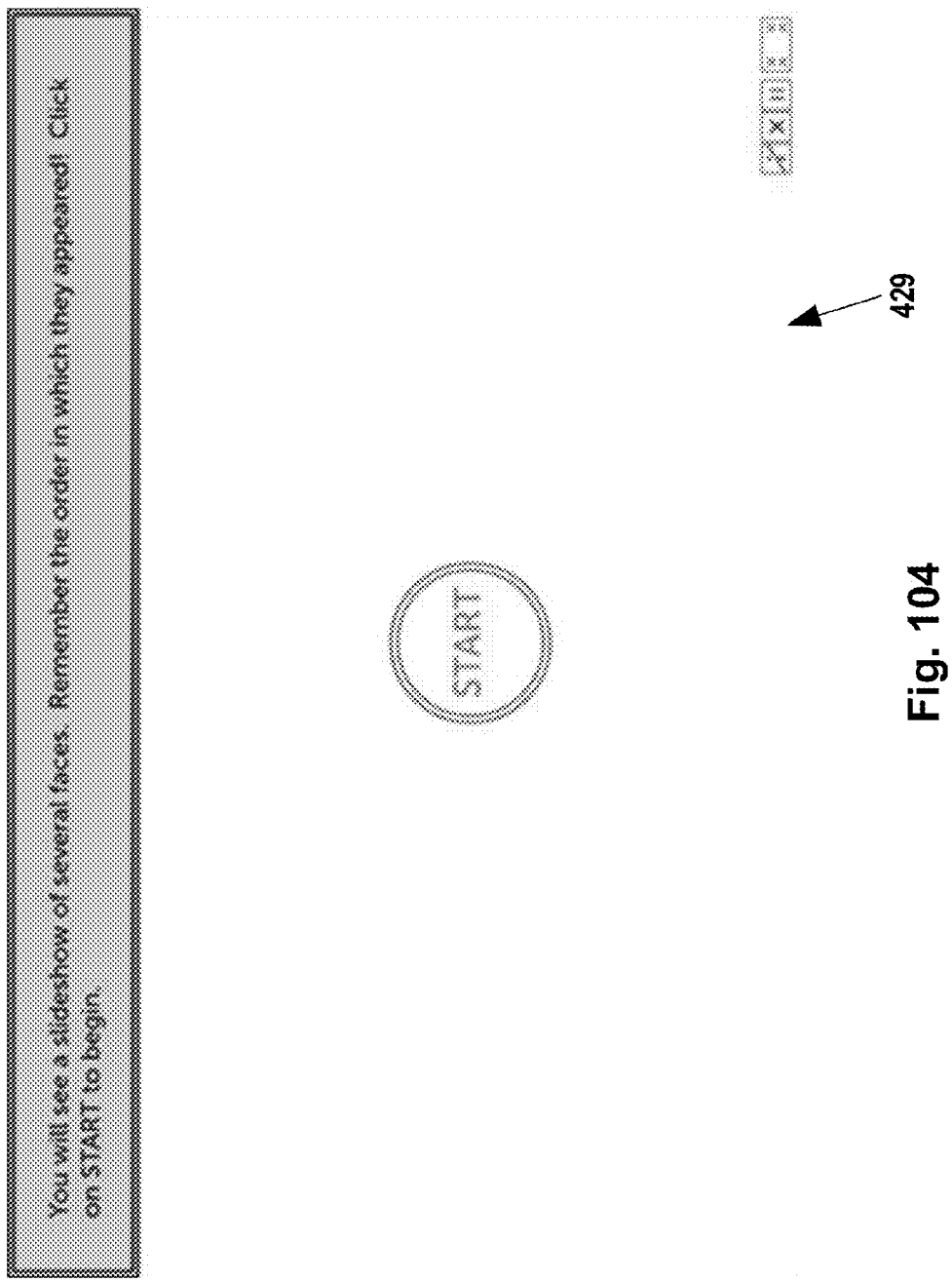
FIG. 104 illustrates a screenshot of one embodiment of a memory spa game called "Face It: Flashback," which presents a sequence of faces followed by challenging the participant to select the faces in the order they were presented.

FIGS. 101-103 illustrate screenshots 420, 422 and 425 of an embodiment of a working memory prosody game called "Second That Intonation." Second That Intonation presents an array 423 of down-facing cards associated with spoken sentences, and challenges a participant to select card pairs that match a spoken sentence's prosody with a label.

The goals of this game are similar to the ones in the Second That Emotion game, but Second That Intonation uses video clips of emotions (rather than stills), which have more ecological validity and resemble more everyday stimuli. Subjects are required to find matching pairs of emotion clips and emotion tags.

This game is similar to Second That Emotion (see above), but requires matching pairs of emotion clips and emotion labels rather than still images. The face-down sides of half of the cards in the array 426 are labeled with audio symbol such as a speaker. The other half of the cards are labeled with a symbol indicating that the card contains a label, such as "happy" or "angry."

As an example, FIG. 103 illustrates the first card 427, face up, of a selected pair of cards, labeled "happy." If the second card in the selected pair represents an audio clip of a sentence with a happy prosody, then Second That Intonation plays a positive feedback and causes the two cards to disappear. Emotions, logic, adaptivity, threshold calculation, and feedback are similar to the Second That Emotion game described above.

The emotions included in the Second That Intonation game are: neutral, happy, sad, afraid and angry. In one embodiment, Second That Intonation samples a set of 100 sentences, all recorded by the same voice-over artist using five different implicit emotions. The maximal size of the array 423 is ten (five emotion pairs).

Another embodiment of working memory prosody game, called "Voice Match" is similar to "Second That Intonation," but challenges participants to match pairs of spoken sentences, sentence fragments, or words that exhibit the same prosody. Participants press buttons that are associated with different prosodies. Using their auditory working memory to encode the spatial positions of different prosodies, participants try to press consecutive buttons that play identical prosodies. The goals of both Second That Intonation and Voice Match are to improve the processing of prosodic information, and to improve auditory working memory for prosodic inputs.

12. Faces Span

FIGS. 104-110 illustrate screenshots 429, 431, 433, 435, 437, 440 and 443 of an embodiment of a working memory facial recognition game called "Face It: Flashback." Face It: Flashback presents a sequence of faces with neutral expressions and then challenges the participant to select the faces in the order they were presented.

The goals of this game are multifold. In addition to improving the face perception system's ability to process faces, the goals of this game are to improve the visual face perception system's: (1) temporal modulation transfer functions and processing speed, and; (2) ability to respond to successively presented face stimuli (memory span abilities for facial stimuli). Participants are required to reconstruct the identity and order of faces stimuli presented in a sequence, which gets longer and longer as the subject gets better. The requirement to match faces in the sequence from different angles (frontal, side, profile, ¾ etc.) is also added at later phases of the game, to further boost and automatize these key face perception system operations.

Figure 105:
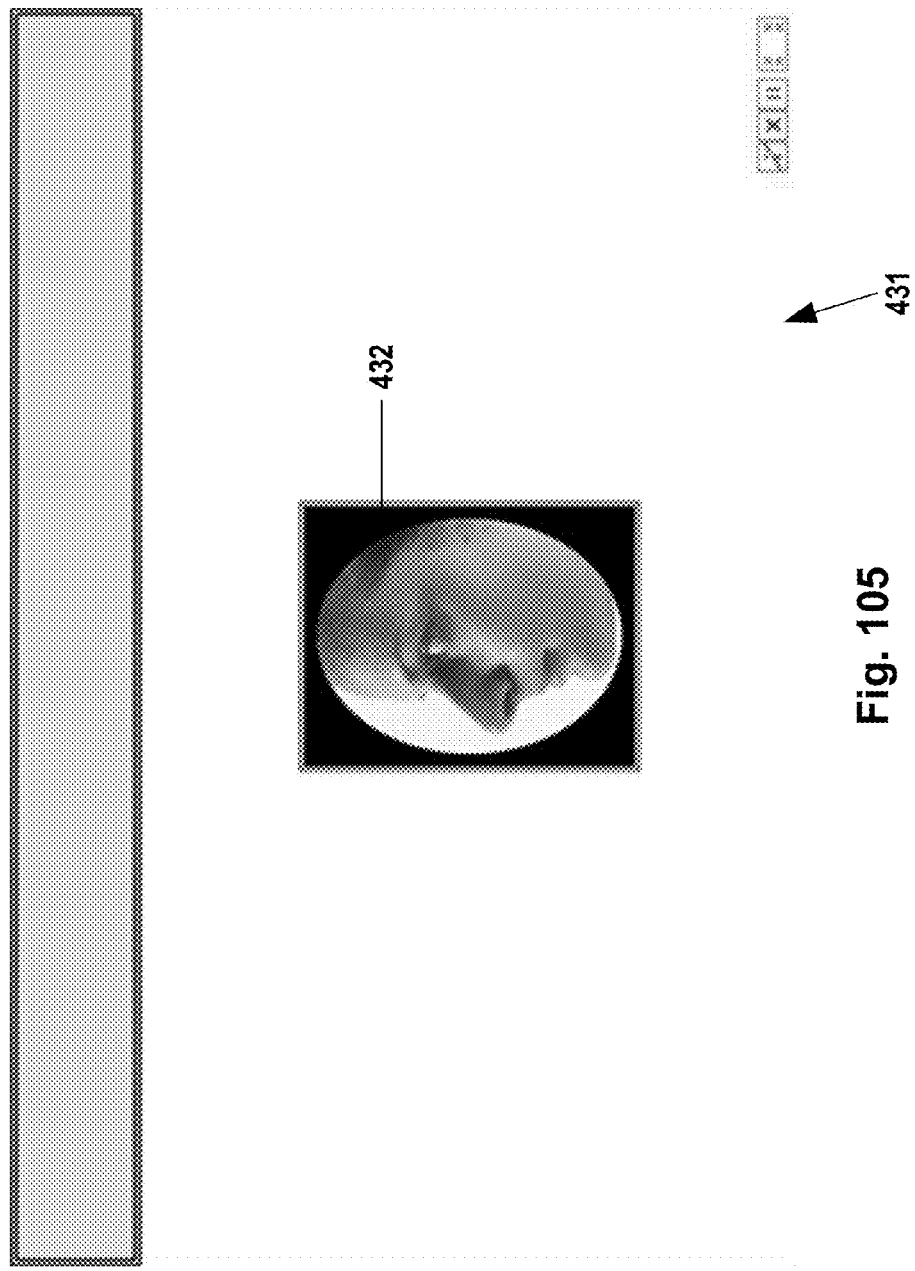
FIG. 105 illustrates another screenshot of the game illustrated in the previous figure.
Figure 106:
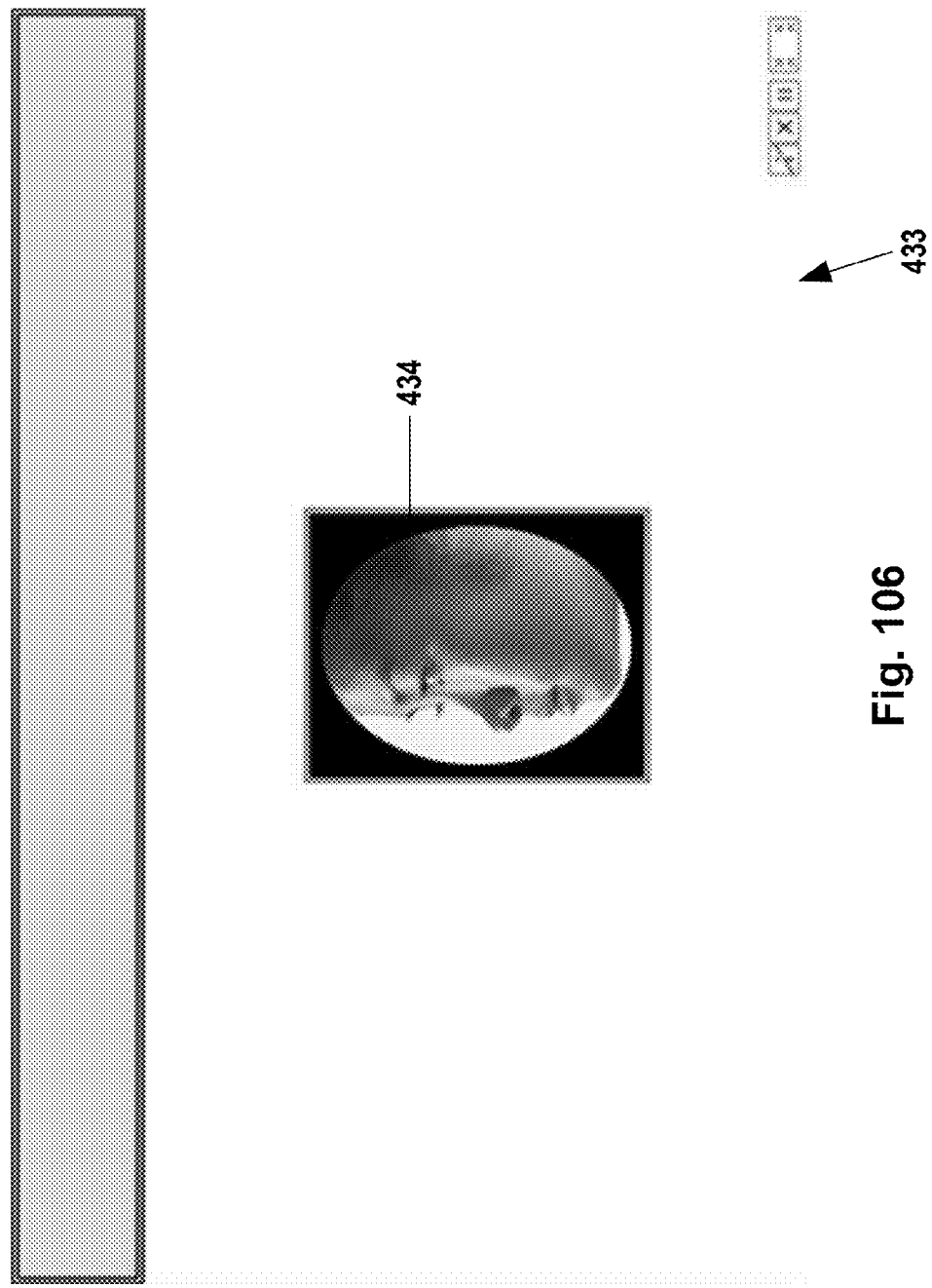
FIG. 106 illustrates another screenshot of the game illustrated in the previous figure.
Figure 107:
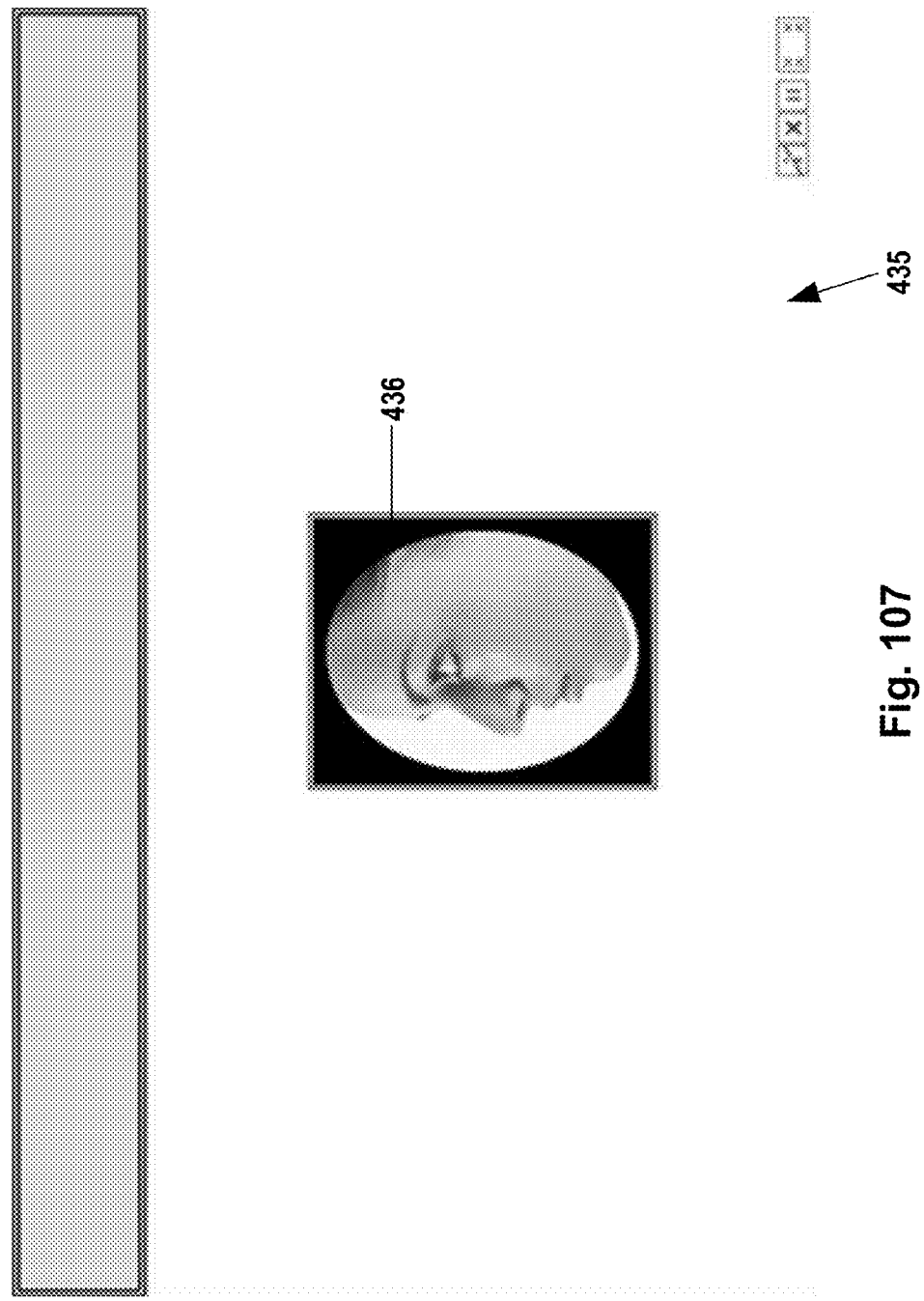
FIG. 107 illustrates another screenshot of the game illustrated in the previous figure.
Figure 108:
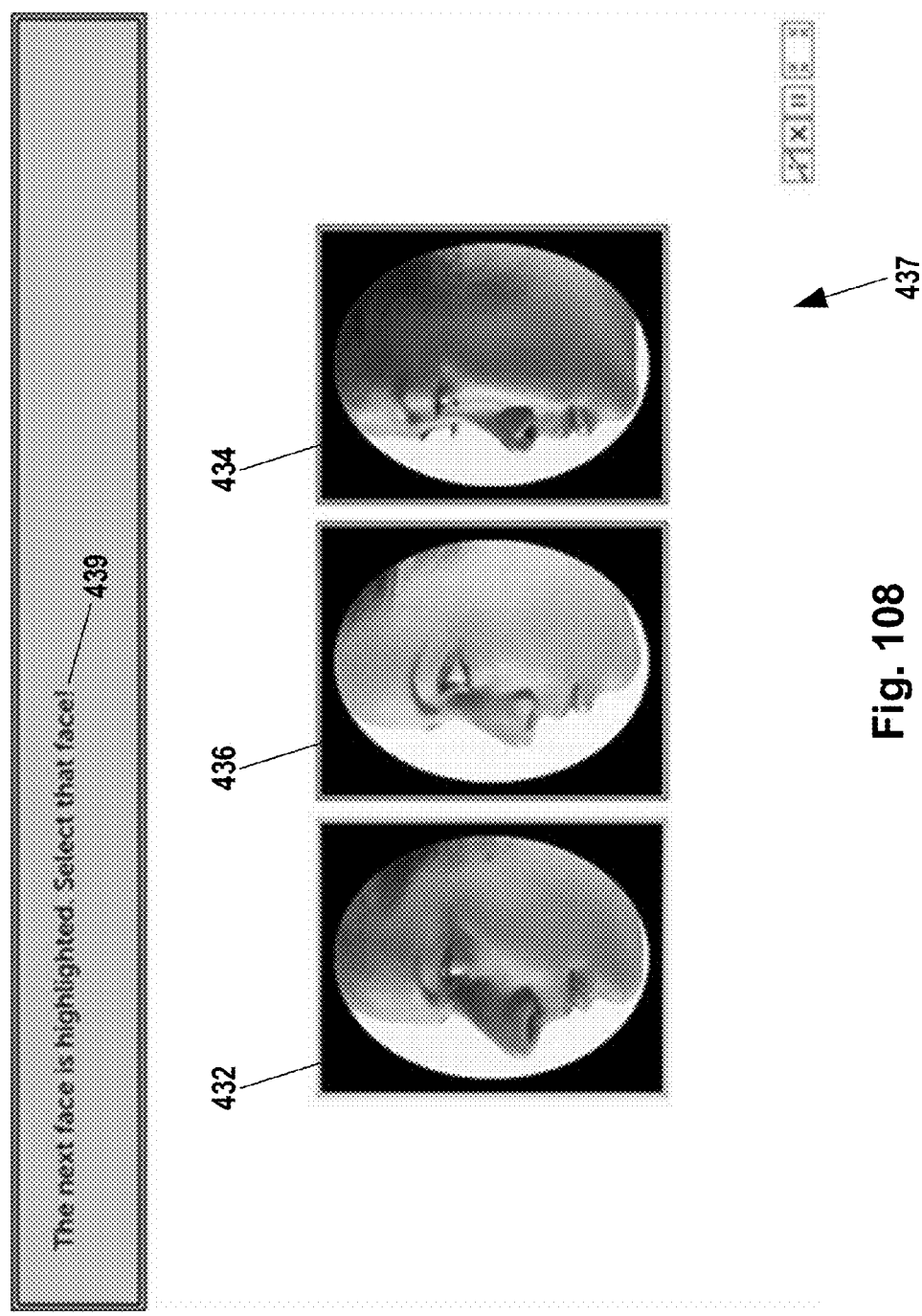
FIG. 108 illustrates another screenshot of the game illustrated in the previous figure.
Figure 109:
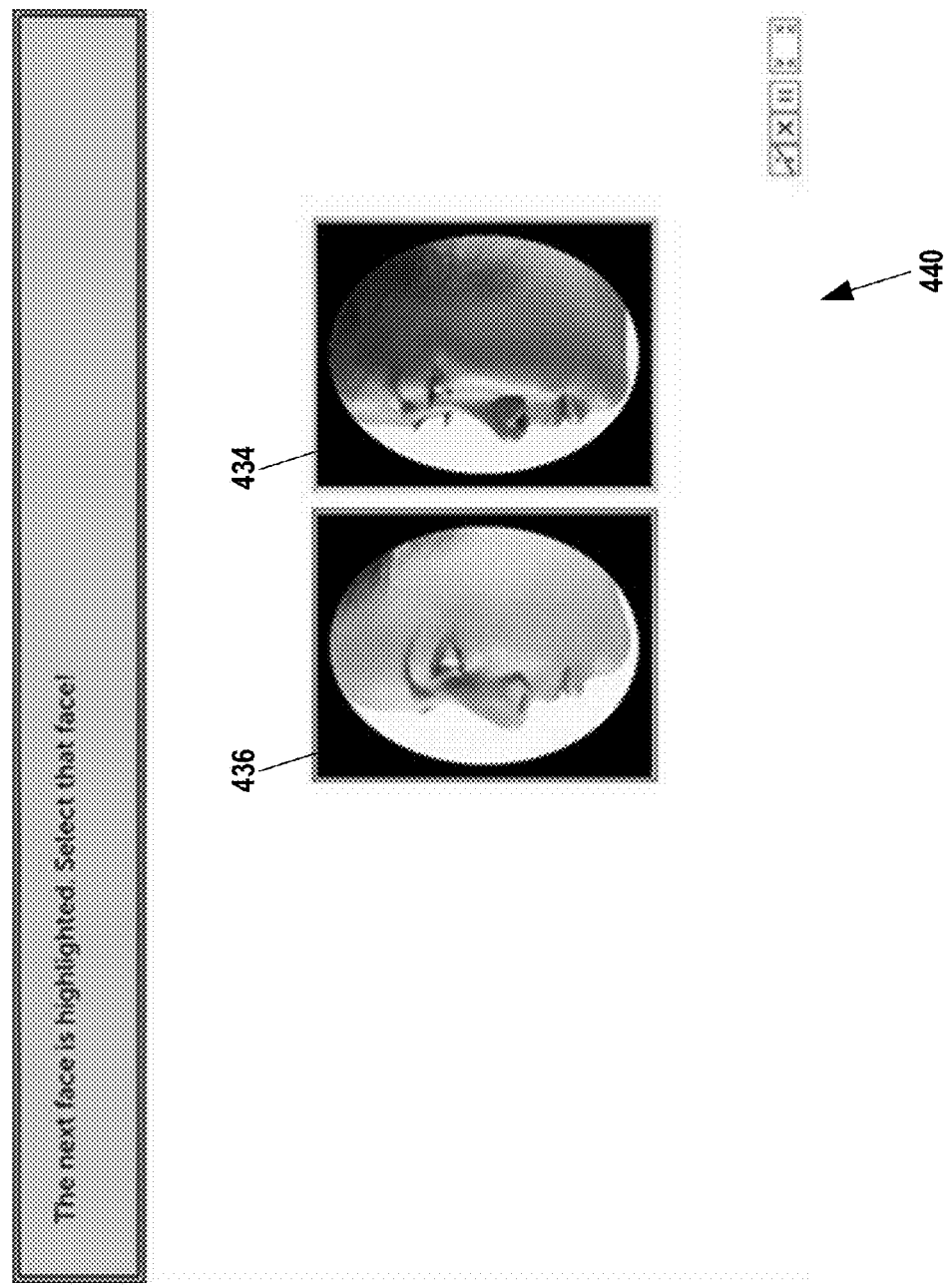
FIG. 109 illustrates another screenshot of the game illustrated in the previous figure.
Figure 110:
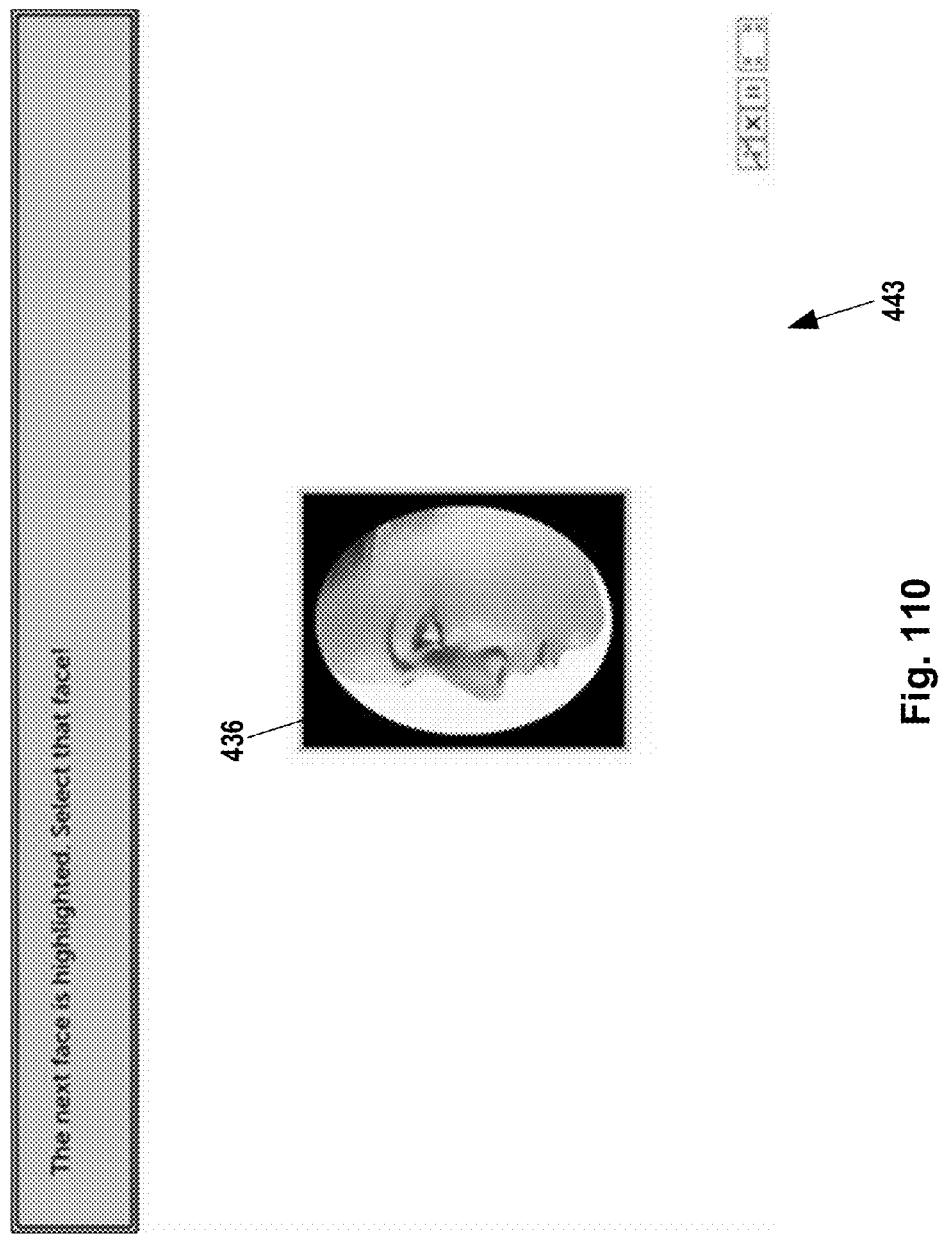
FIG. 110 illustrates another screenshot of the game illustrated in the previous figure.
Figure 111:
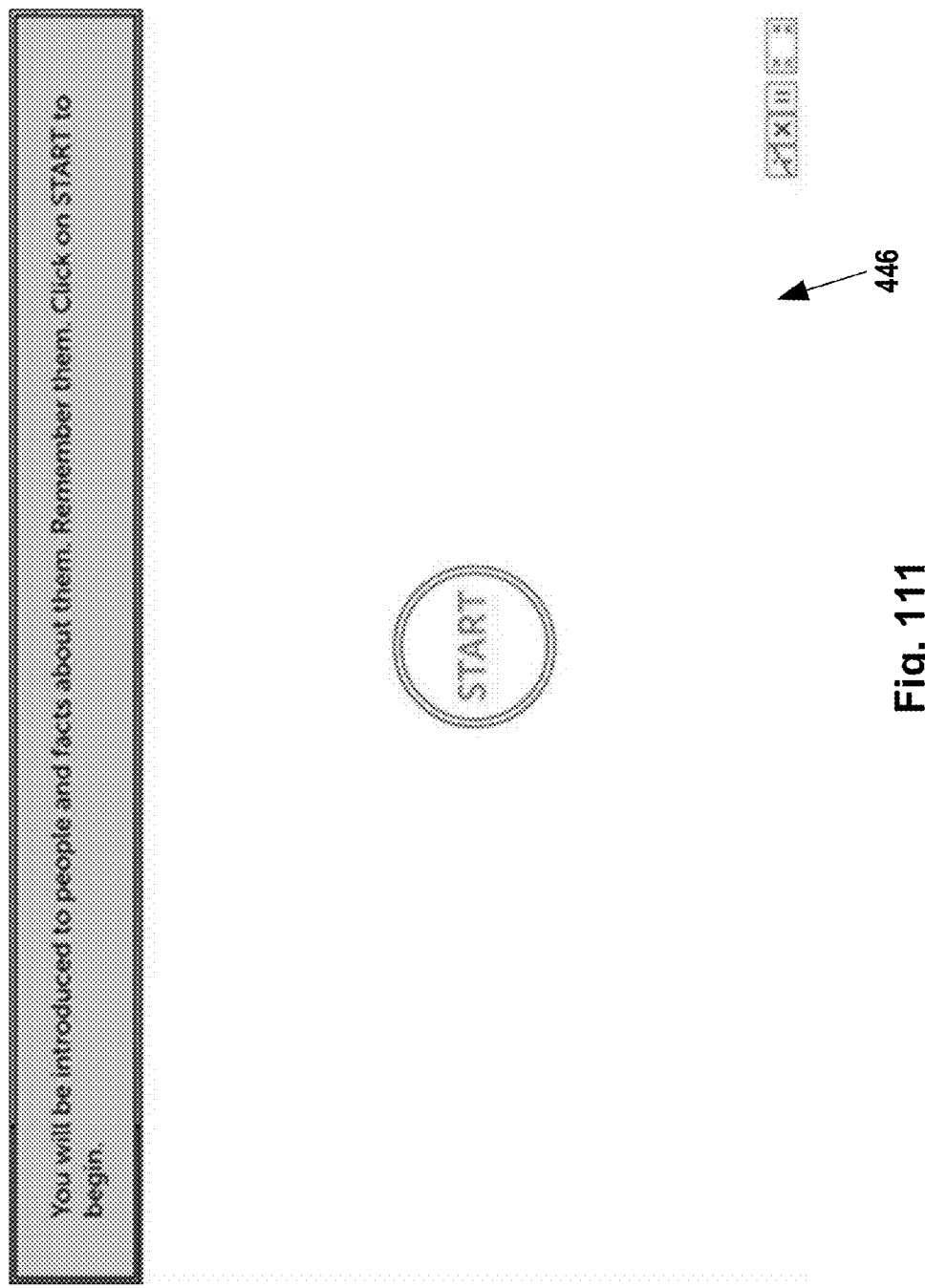
FIG. 111 illustrates a screenshot of one embodiment of a social memory span game called "Face Facts," which presents pictures of individuals together with facts about each individual and challenges the participant to select facts that are true about the individuals.

FIGS. 105-107 illustrate the game presenting a sequence of side views of three faces 432, 434 and 436, all having neutral expressions. After briefly presenting a visual mask, in FIG. 108, Face It: Flashback presents all three faces 432, 434 and 436 simultaneously and prompts 439 the participant to select the faces in the order they were presented. After the participant selects the first face 432, FIG. 109 shows Face It: Flashback presenting the two remaining faces 434 and 436. After the participant selects the second face 434, FIG. 110 shows Face It: Flashback presenting the last face 296.

The length of the faces sequence (i.e., the number of faces shown) is adaptively set using a 2up-1down adaptive rule. Each face is presented for 1500 ms, with an inter-face interval of 500 ms. One second after the sequence is presented, the same faces appear on the screen, and the participant is required to click on them in the order they appeared in the sequence. The faces used in Face It: Flashback are selected from the same corpus as that of the "Face It" game.

Similar to FIGS. 104-110, an embodiment of a working memory emotional cue game is called "Emotion Motion: Flashback." Emotion Motion: Flashback presents a sequence of videos of faces expressing implicit emotions and then challenges the participant to select the emotions in the order they were presented.

13. Face Stories Span

FIGS. 111-115 illustrate screenshots 446, 448, 454, 460 and 466 of one embodiment of a social memory span game called "Face Facts." Face Facts presents pictures of individuals together with facts about each individual and challenges the participant to select facts that are true about the individuals.

The goal of this game is to improve working memory for social details, which is problematic in individuals with ASD. On every trial, subjects are presented with one or more characters and with social details associated with them. Subjects are challenged to memorize those details, as they are later prompted with statements about the face(s) and are challenged to select the correct ones from the list.

Figure 112:
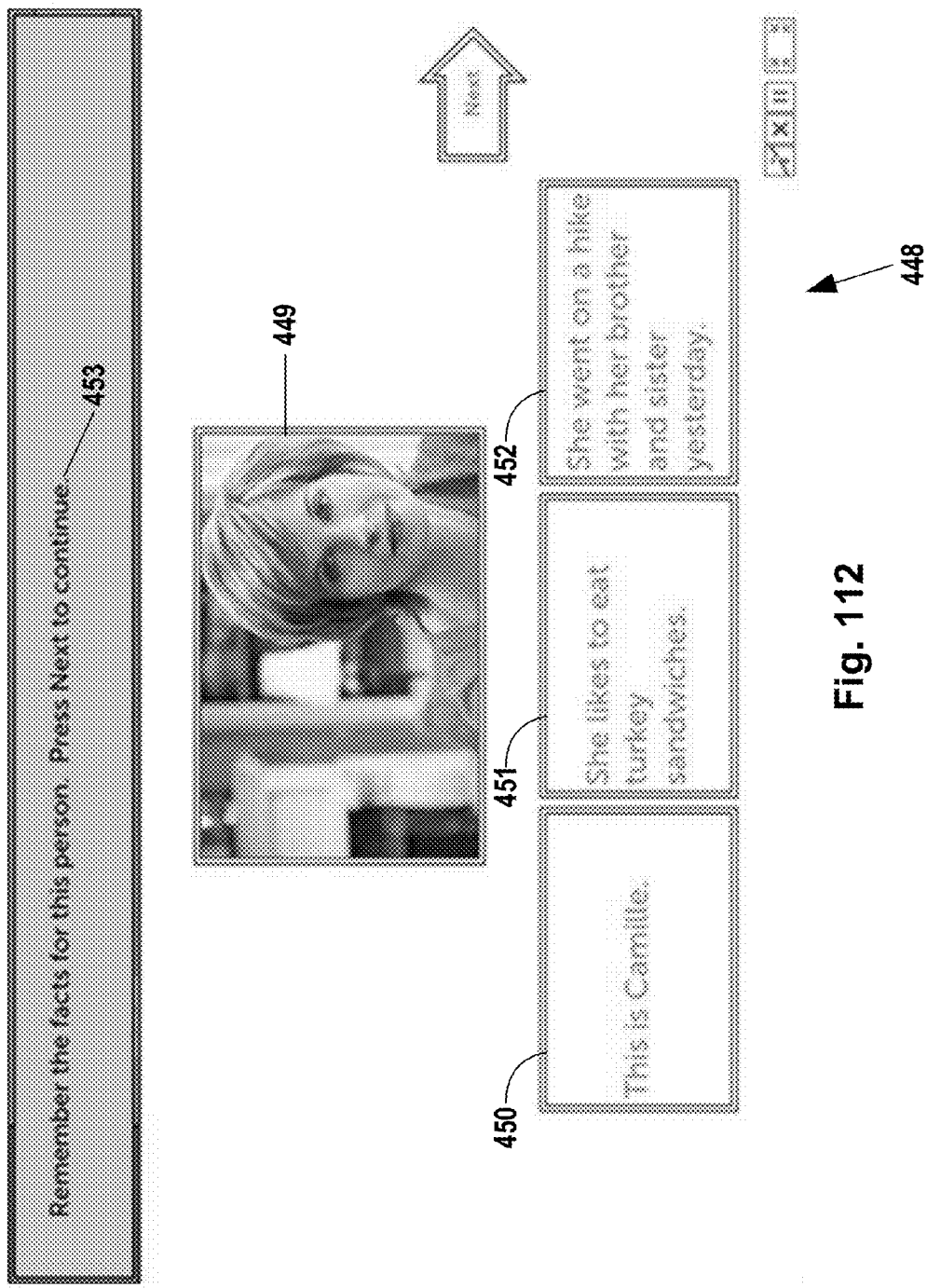
FIG. 112 illustrates another screenshot of the game illustrated in the previous figure.
Figure 113:
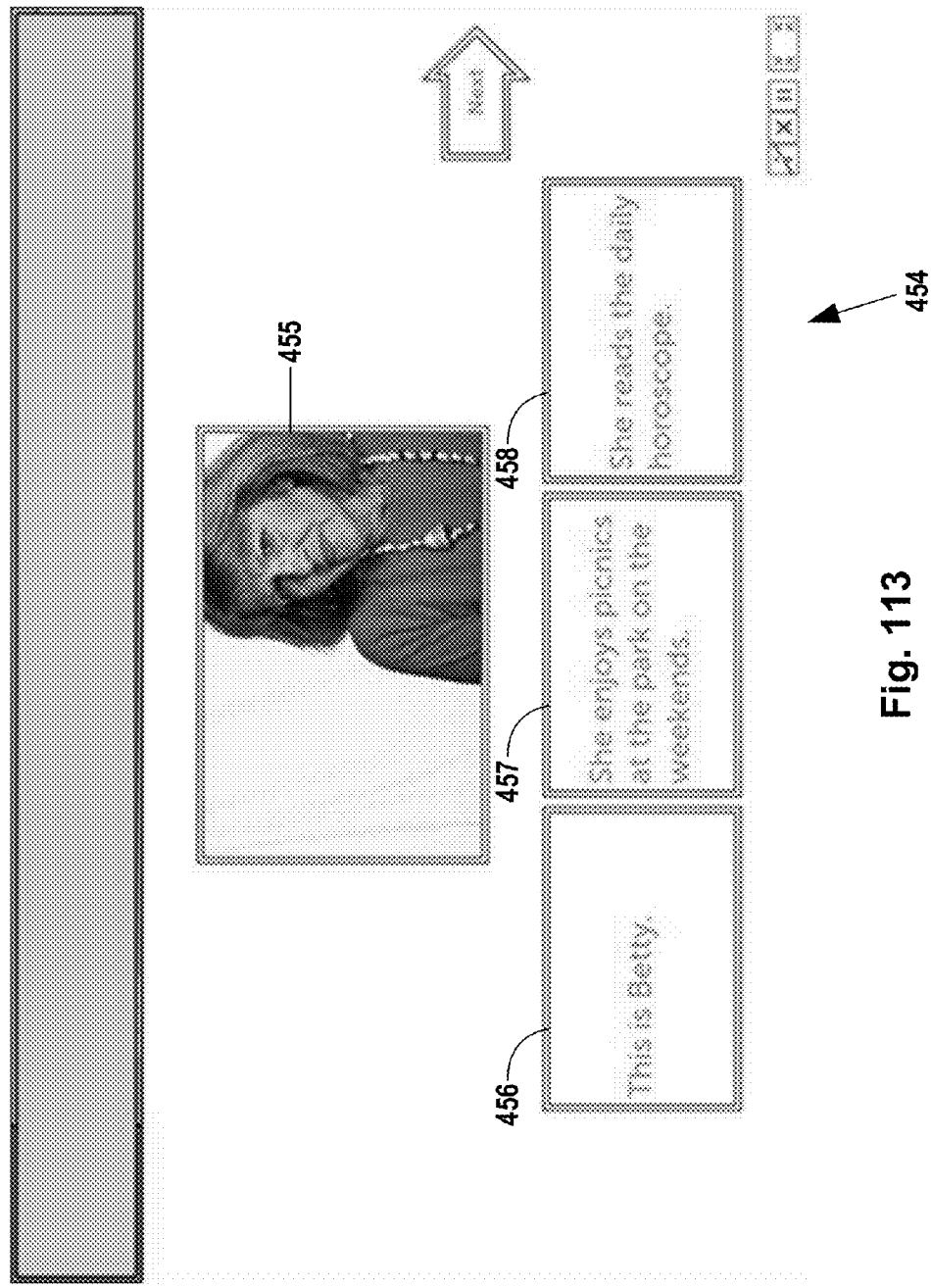
FIG. 113 illustrates another screenshot of the game illustrated in the previous figure.

For each trial, Face Facts presents pictures of persons along with three facts about each person. For example, FIG. 112 illustrates a picture 449 of a first person looking into the camera and simulating eye contact with the game participant. Below the picture 449, Face Facts presents three facts 450, 451 and 452 about the first person. Similarly, FIG. 113 illustrates a picture 455 of a second person looking into the camera, also simulating eye contact with the game participant. Below the picture 455, Face Facts presents three facts 456, 457 and 458 about the second person.

Face Facts then presents the faces in random order together with a set of declarative statements, only one of which is consistent with the previously presented facts, about that person. Face Facts prompts the game participant to select the correct statements for each person.

Figure 114:
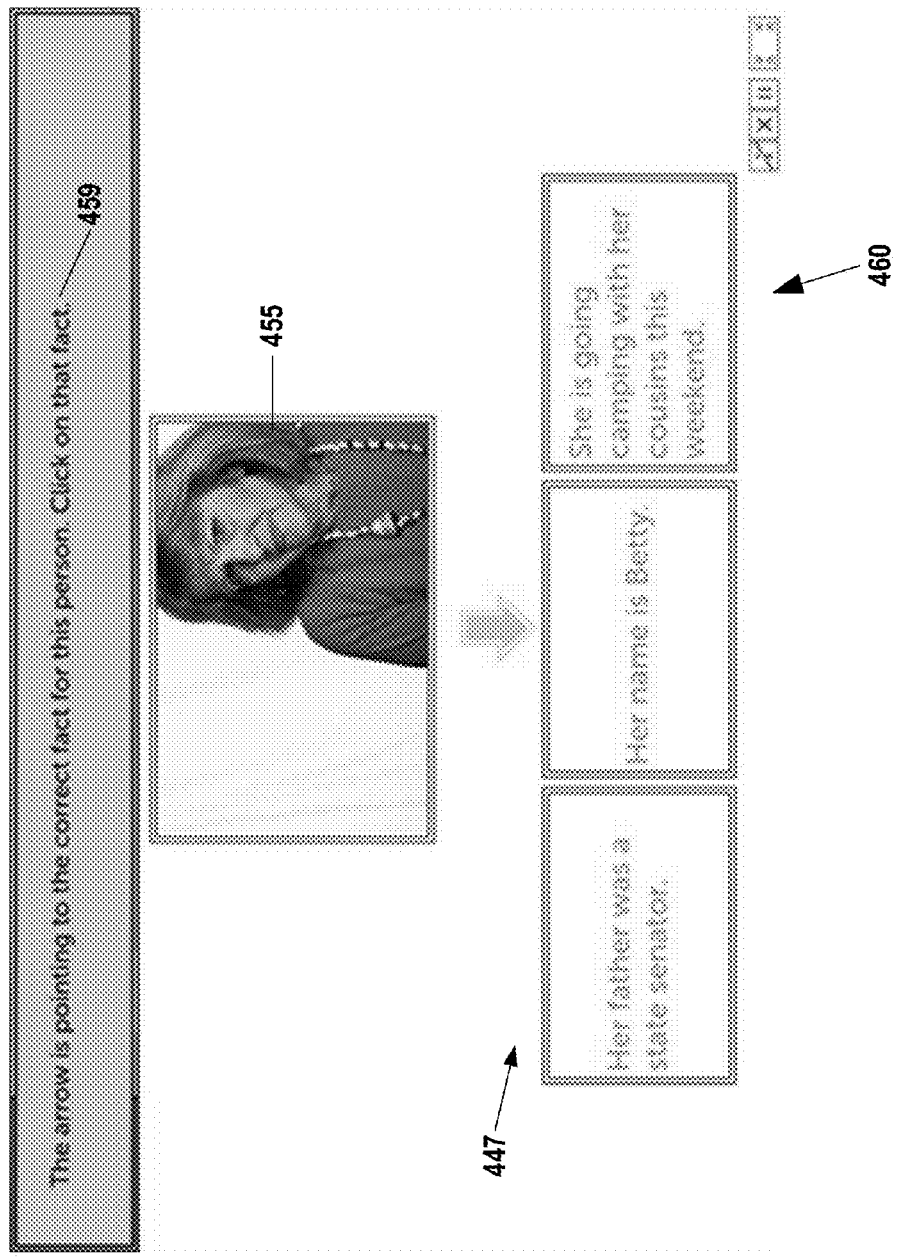
FIG. 114 illustrates another screenshot of the game illustrated in the previous figure.
Figure 115:
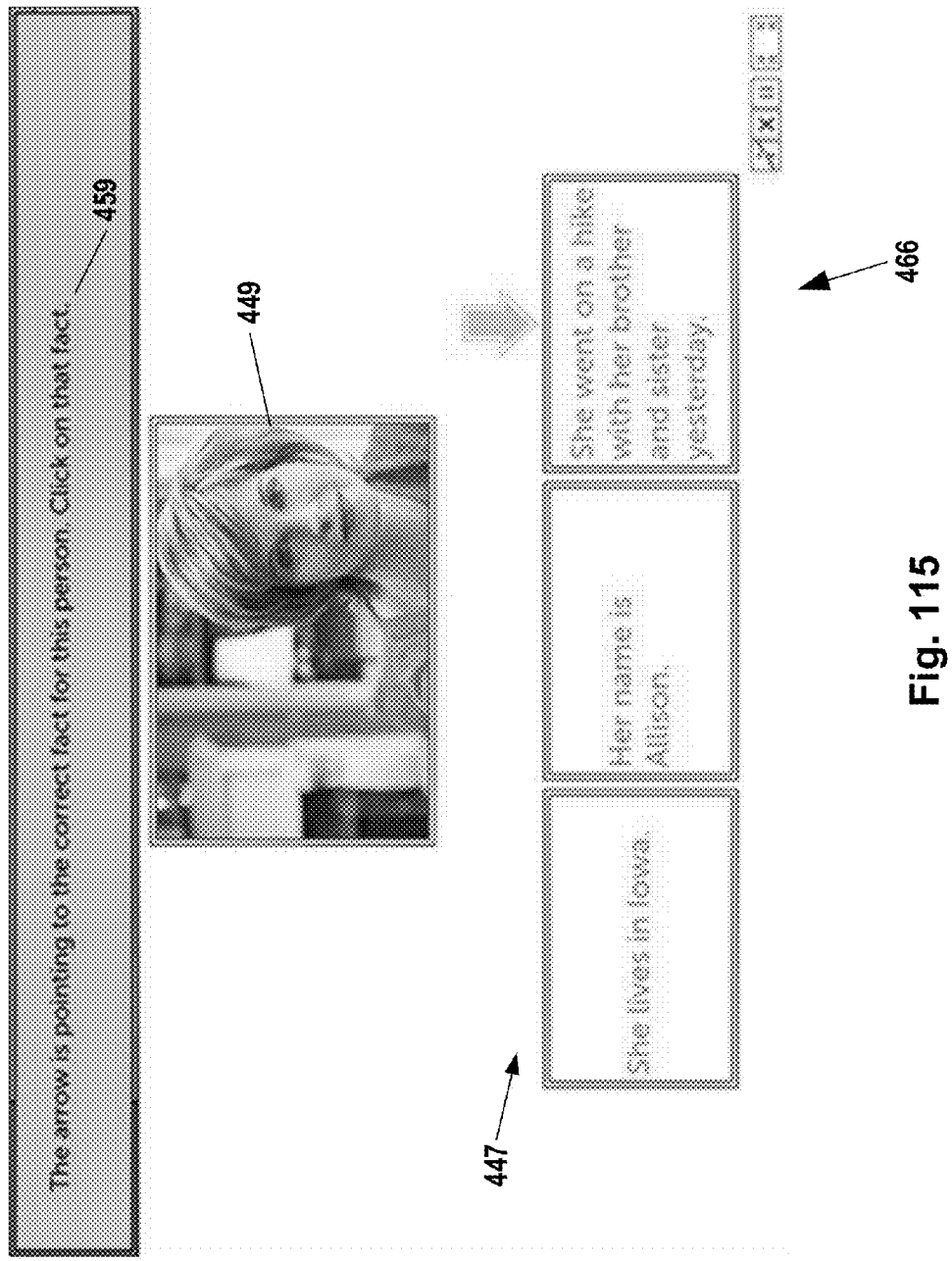
FIG. 115 illustrates another screenshot of the game illustrated in the previous figure.
Figure 116:
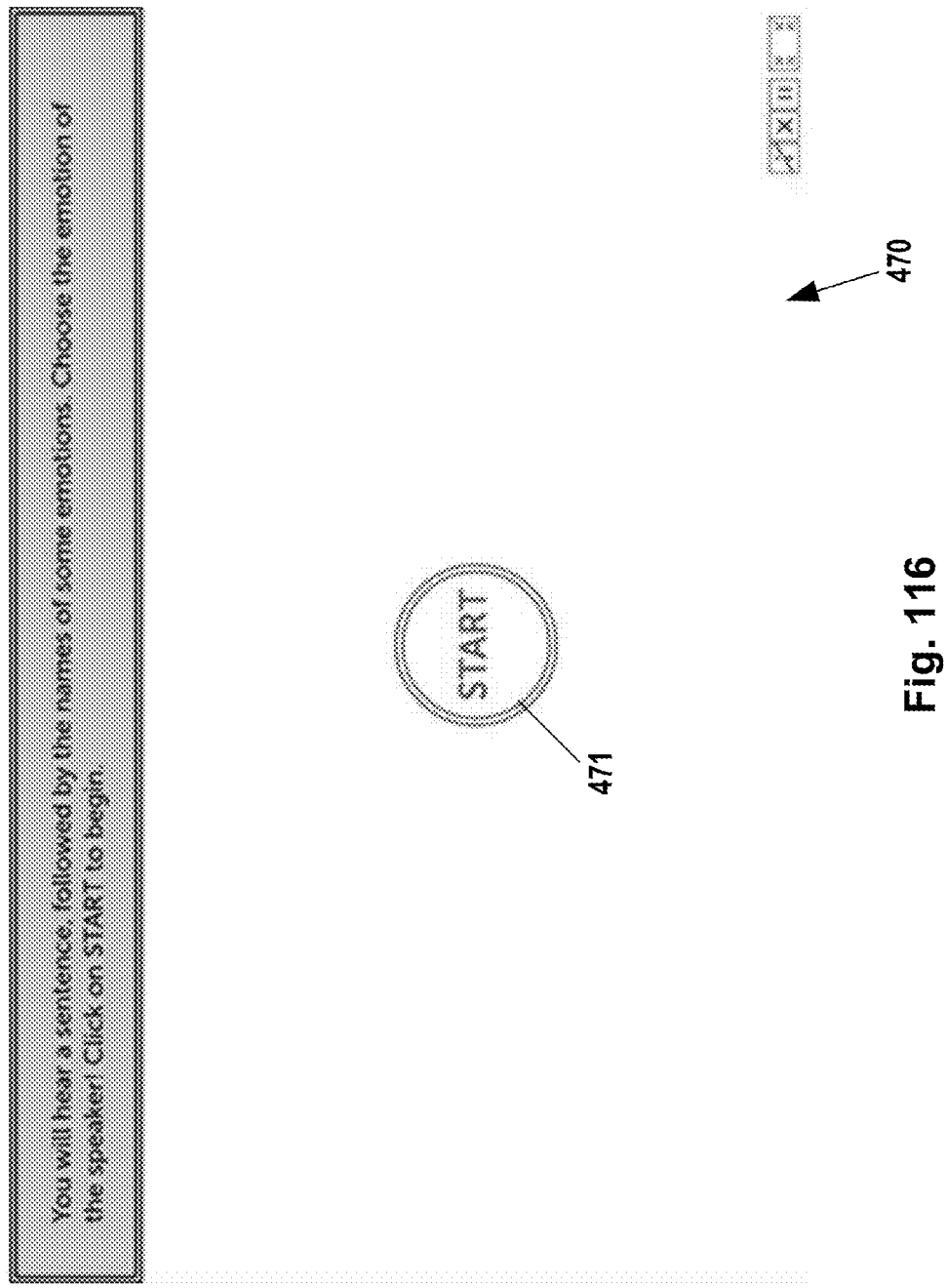
FIG. 116 illustrates a screenshot of one embodiment of a prosody apprehension game called "Voice Choice," which challenges the game participant to identify the emotion of a neutral sentence spoken with an emotional prosody.
Figure 117:
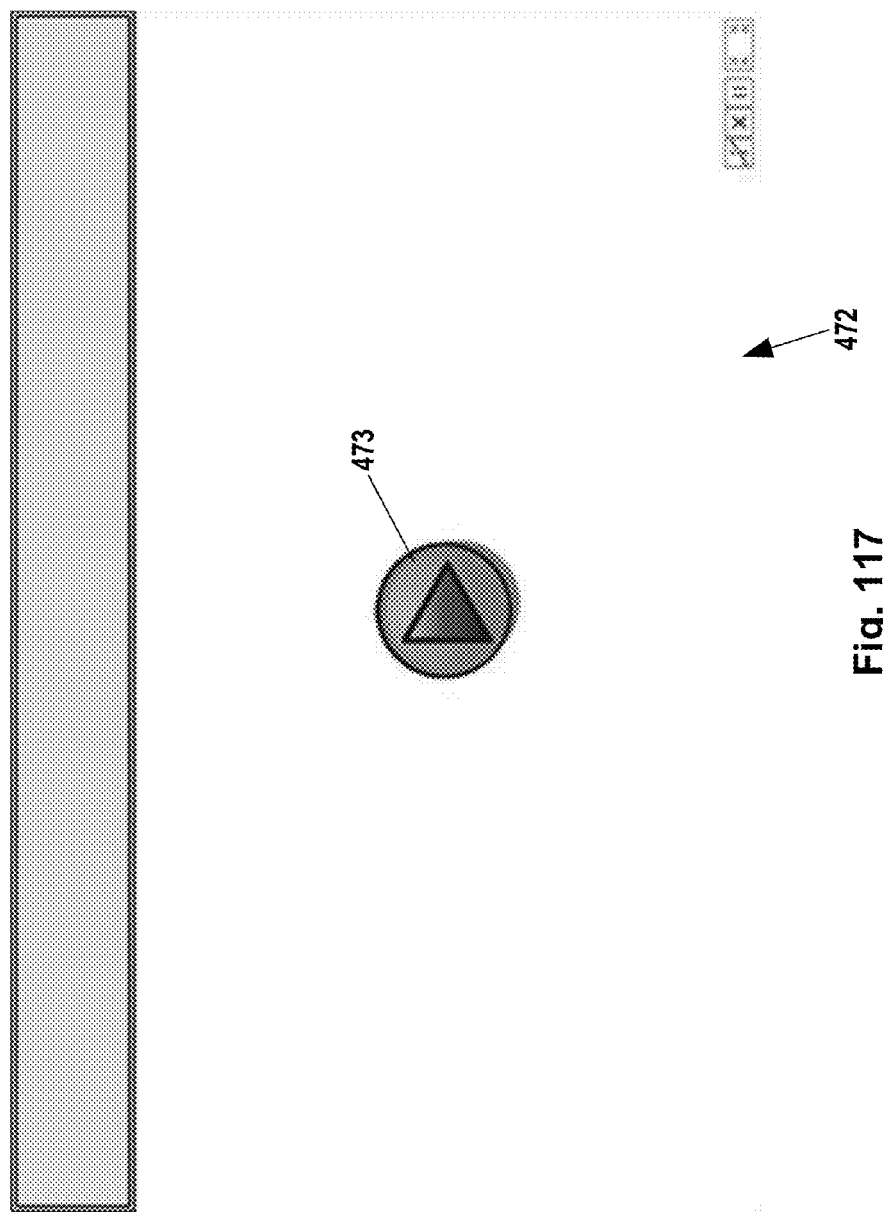
FIG. 117 illustrates another screenshot of the game illustrated in the previous figure.
Figure 118:
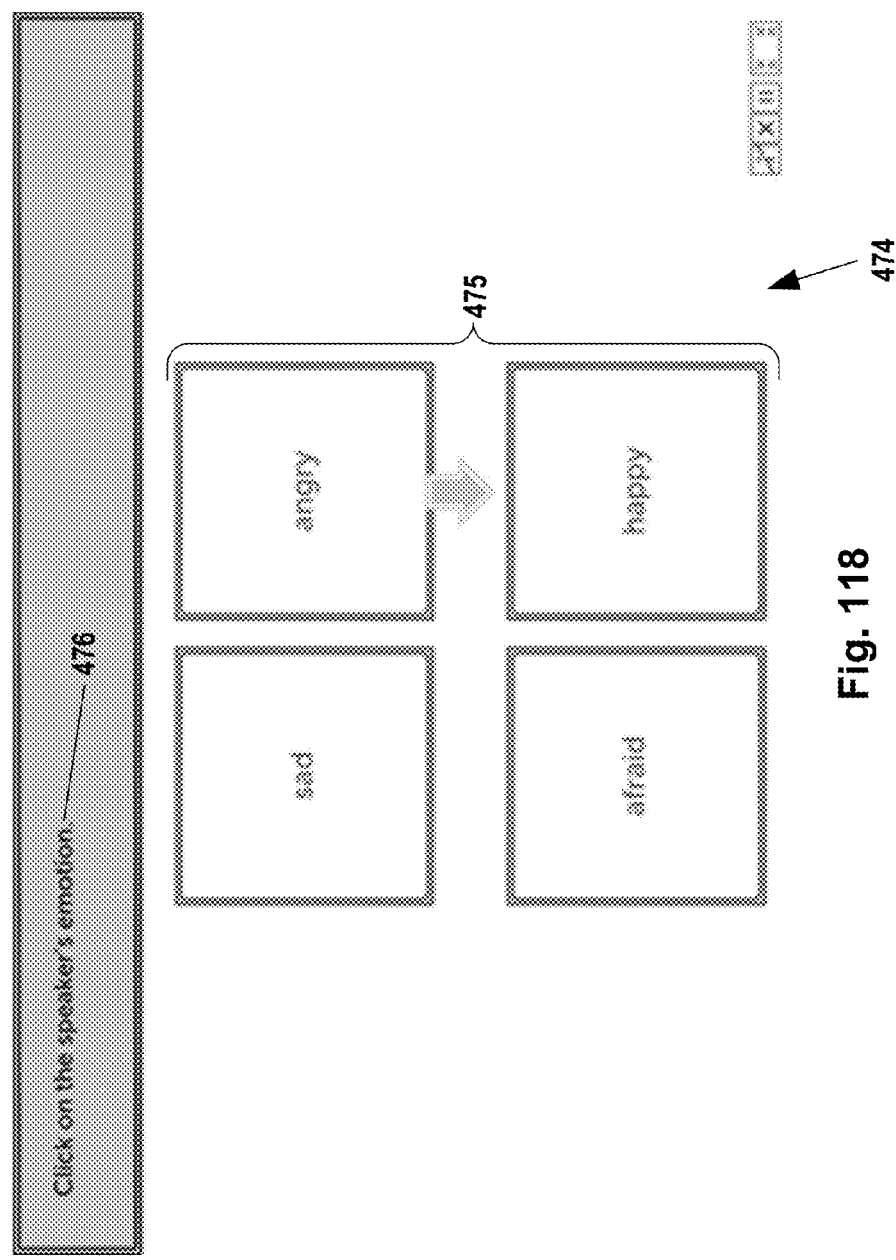
Figure 119:
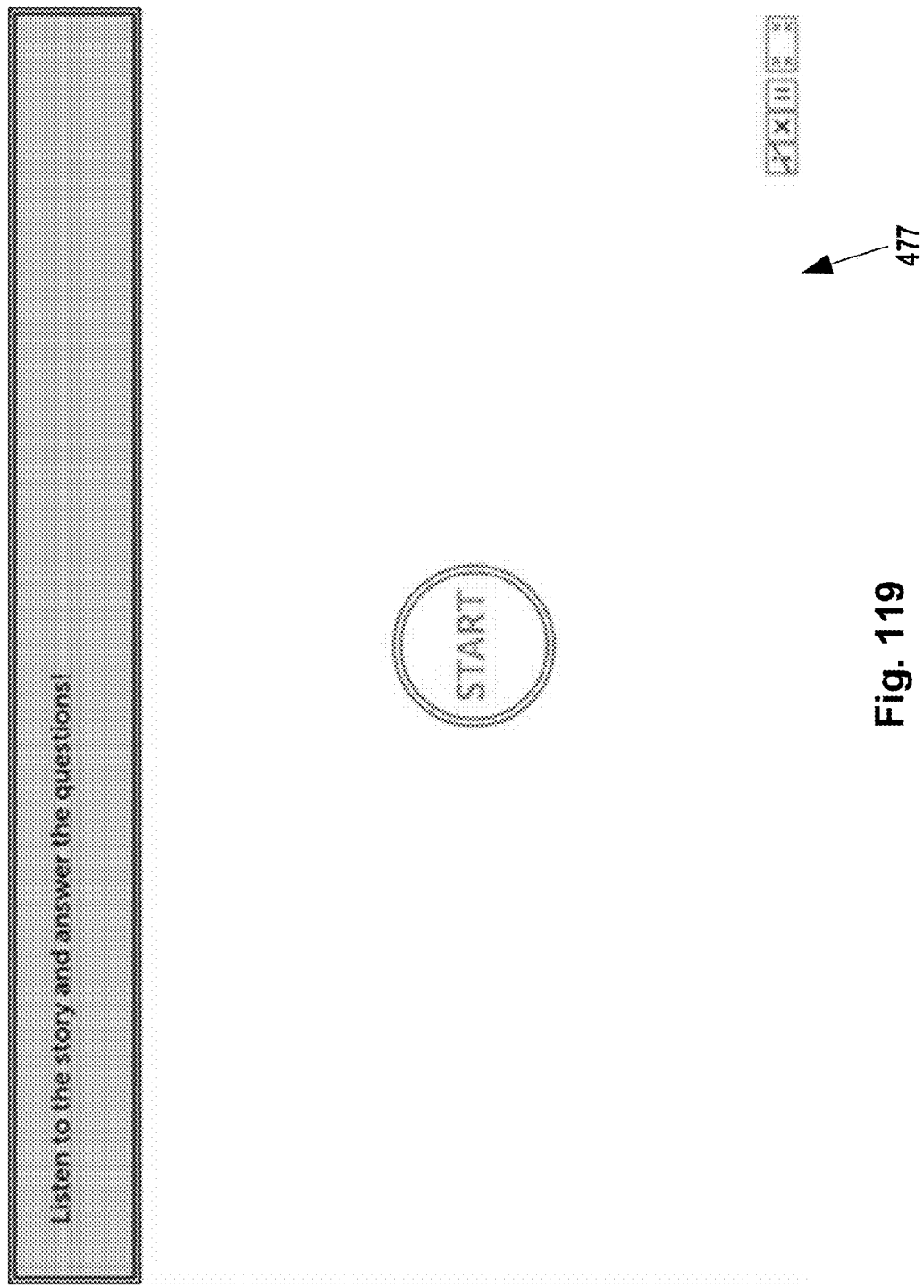

For example, in FIG. 114, Face Facts re-presents the picture 455 of the second person along with three declarative statements 447 about her. Face Facts then prompts 459 the game participant to select the statement that is consistent with the previously presented facts 456, 457 and 458 about the second person. Similarly, in FIG. 115, Face Facts re-presents the picture 449 of the first person along with three declarative statements 447 about her. Face Facts then prompts 459 the game participant to select the statement that is consistent with the previously presented facts 450, 451 and 452 about the first person.

As the participant progresses through the game, more and more details are presented about each character, and the number of characters in the narrative increases. The length of the sequence (i.e., the number of individuals and facts presented) is adaptively set using a 2up-1down adaptive rule.

14. Vocal Emotion ID

FIGS. 116-119 illustrate screenshots 470, 472 and 474 of one embodiment of a prosody apprehension game called "Voice Choice," which challenges the game participant to identify the emotion of a neutral sentence spoken with an emotional prosody.

The goals of this game are: (1) to improve the ability of the auditory system to discriminate pitch and contour differences in speech related to emotions, and (2) to improve the ability of the vocal affective system to process prosodic information across time. Subjects are required to detect the emotion expressed in the sentence regardless of its content, while sentences become shorter and shorter.

Every trial of Voice Choice starts with a presentation of a 'start' button 471. After clicking it, there is a 1000 ms delay. This is followed by a sentence played with neutral content (e.g. 'Today is Tuesday') but spoken with emotional prosody, such as a happy voice. The prosody or emotion is unrelated to the content of the sentence. While the sentence is being played, Voice Choice displays a play button 473 on a visually undistracting, uncluttered screen, which helps the participant to focus on listening to the story segment.

Next, Voice Choice displays a set of two to five words 475 on the computer screen, wherein each word is the name of a different emotion. Voice Choice prompts 476 the game participant to select the word 475 that best expresses the emotion of the voice recording. Voice Choice receives the participant's response and provides an indication of whether the participant's response was correct.

The target emotion is randomly selected with equal probability from the following five basic emotions: neutral, happy, sad, angry and afraid. The length of the target sentence is adaptively changed between short (1-2 words), medium (3-4 words) and long (5-7 words) based on a 2down-1up adaptive rule, where the sentence gets longer if the participant makes a mistake and gets shorter if the participant is correct two consecutive times. Threshold is calculated as the arithmetic mean of last five reversals.

15. Social Stories

FIGS. 119-122 illustrate screenshots 477, 479, 481 and 485 of one embodiment of a social cue apprehension game called "Life Stories," which challenges game participants to listen to a story and apprehend social details in the story.

The goals of this game are: 1) to improve the ability of working memory systems to maintain and use auditory information in a narrative context; 2) to improve the perception of social cues and social nuances; and (3) to improve Theory of Mind (ToM) abilities. In this task, participants are required to answer questions about key plot elements (both details and social elements) of a verbally presented story. The questions heavily involve ToM aspects by requiring subjects to make social inferences based on the story.

Life Stories plays segmented stories, each containing multiple social details, to the game participant. Life Stories challenges the game participant to answer questions regarding the story. If the participant answers more than 80% of the questions correctly, more segments are played before the questions appear. Each story has twenty segments and 100 questions.

Figure 120:
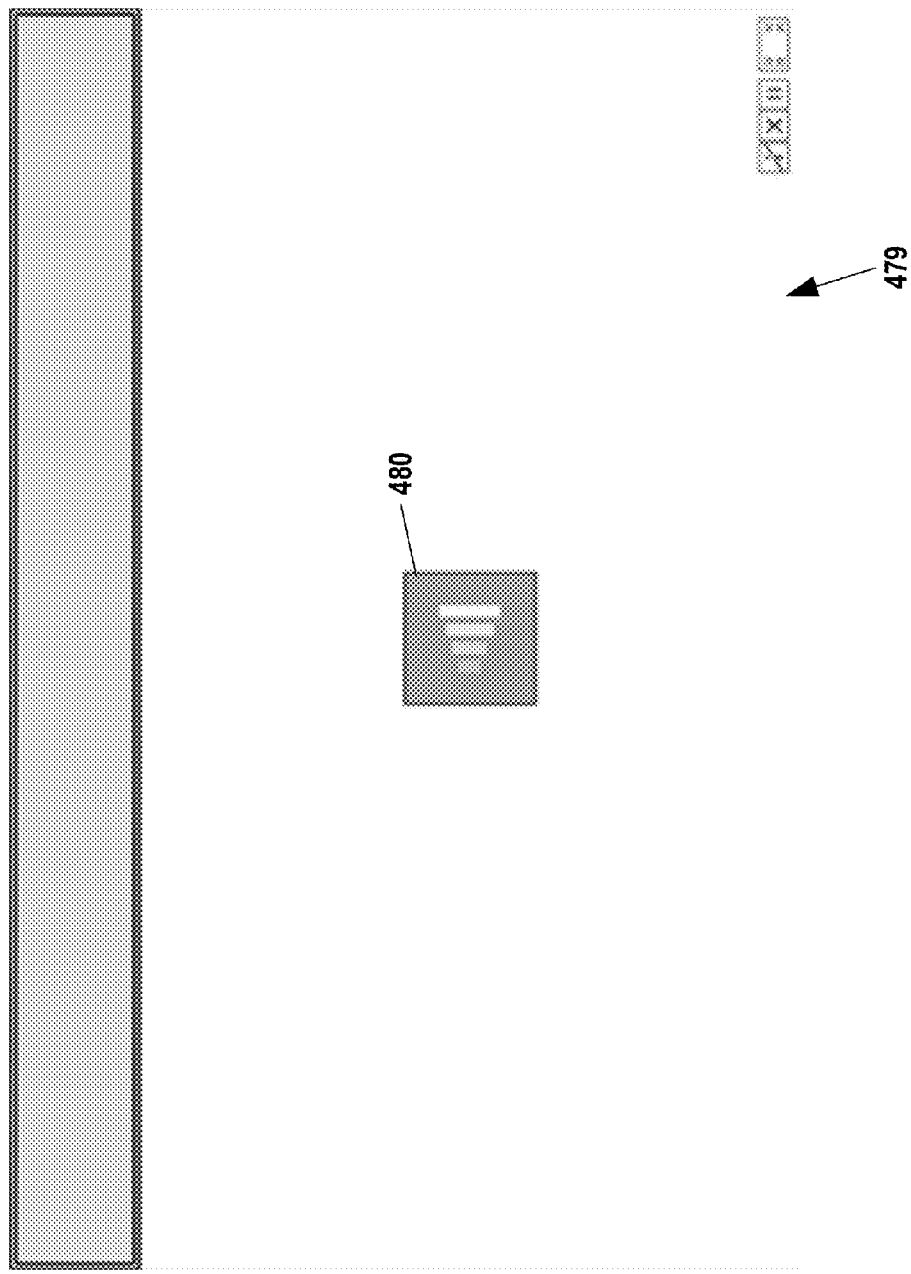
Figure 121:
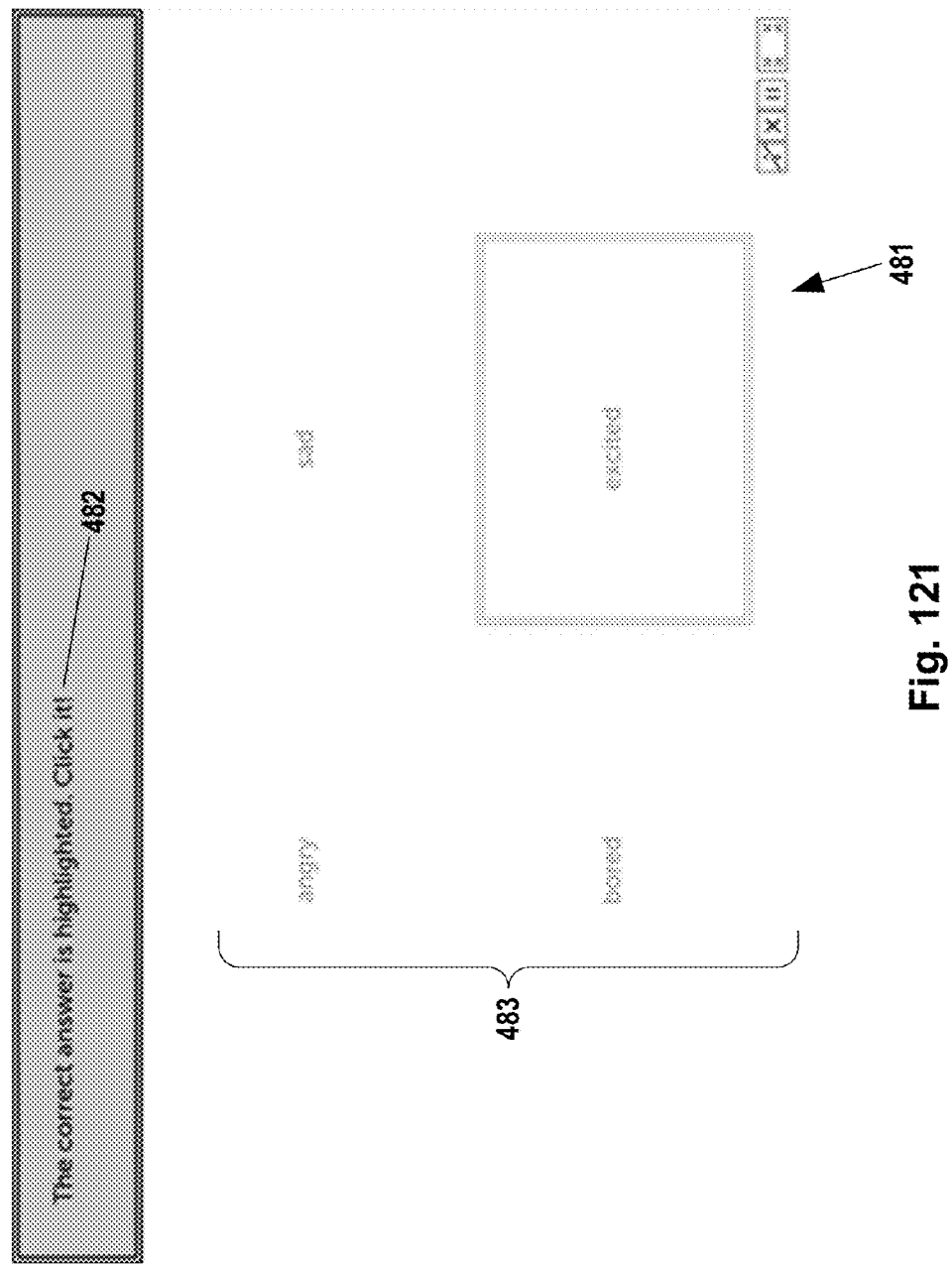
Figure 122:
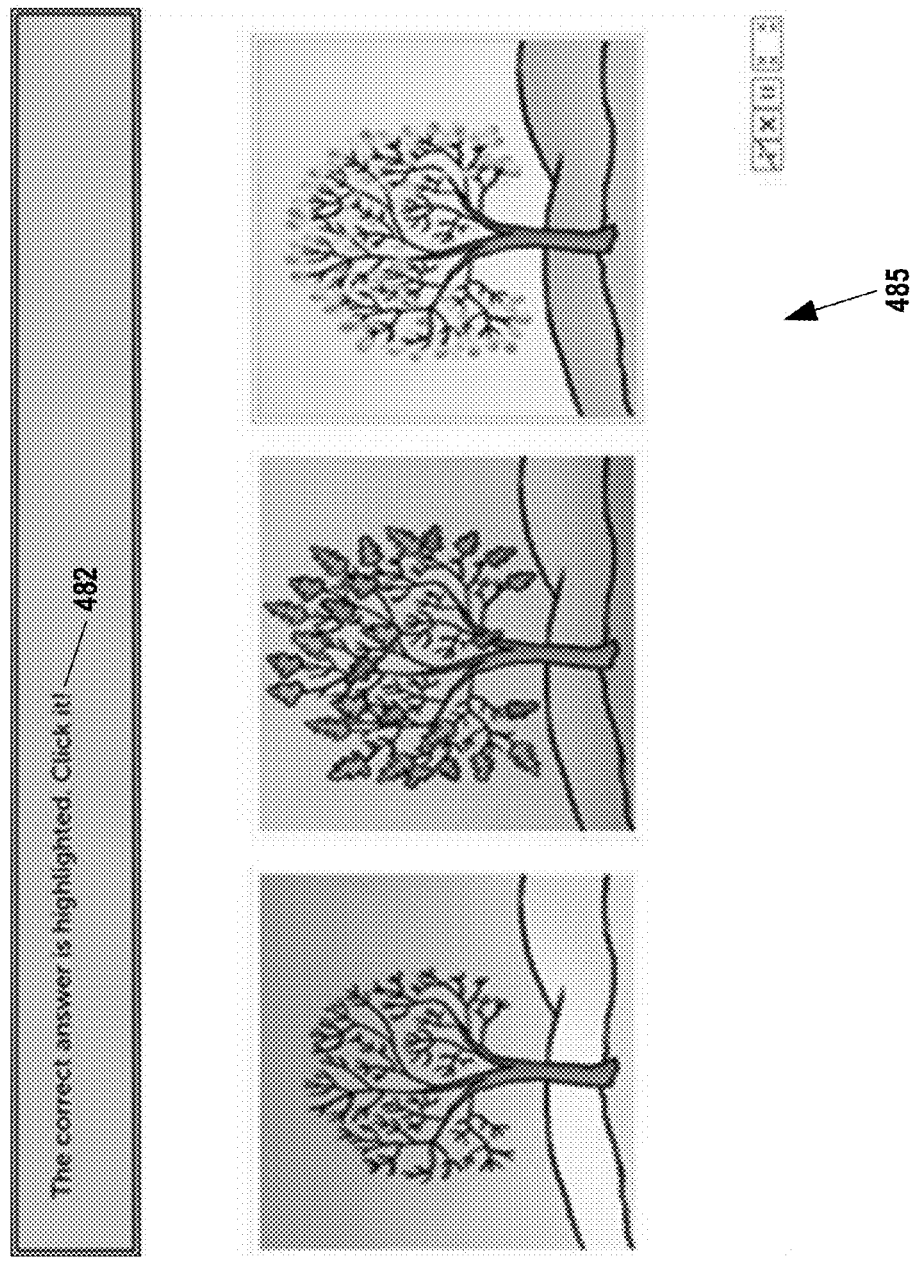

To illustrate, FIG. 120 shows a play button 480 on a visually undistracting screen, which helps the participant to focus on listening to the story segment. After playing the story segment, Life Stories plays a series of questions such as "As Molly spoke into the phone, what tone of voice did she use?" (FIG. 121) and "What season was it?" (FIG. 122). For each question, Life Stories displays a set of answer choices 483 or 485, prompting 482 the participant to select the best answer choice 483 or 485. Life Stories receives the game participant's response and provides an indication of whether the game participant's response was correct.

16. Vocal Affect Theory of Mind

Figure 123:
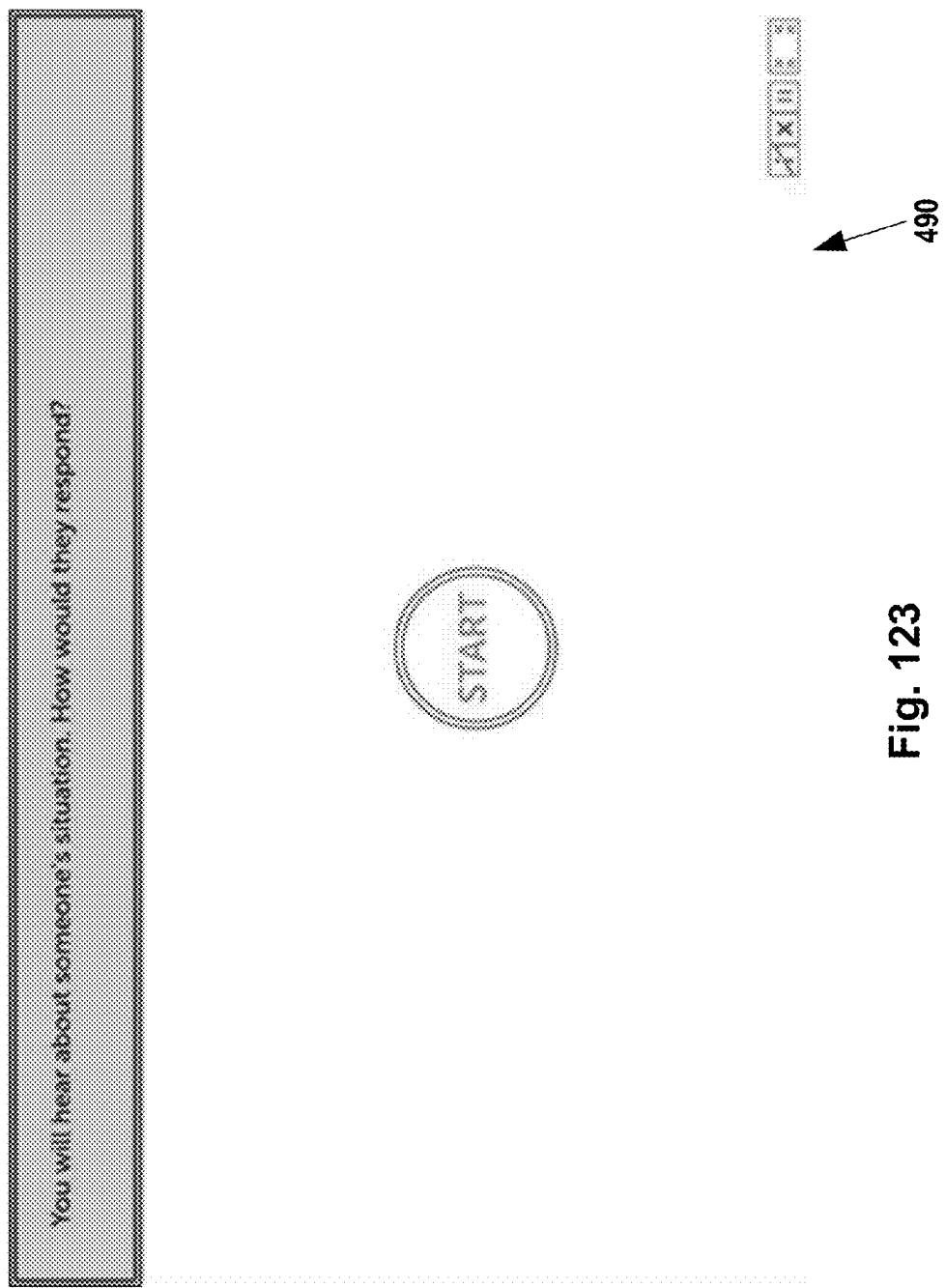
Figure 124:
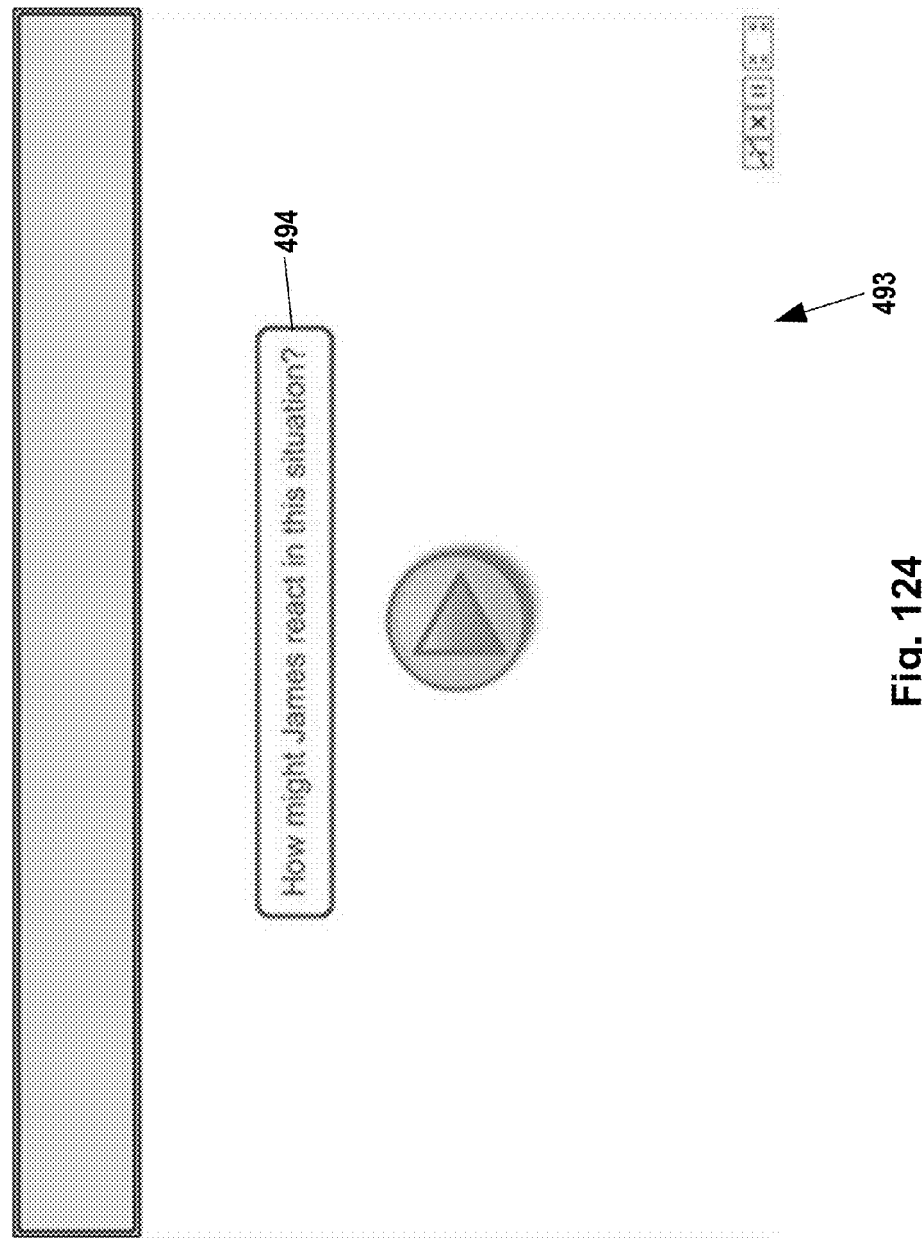
Figure 125:
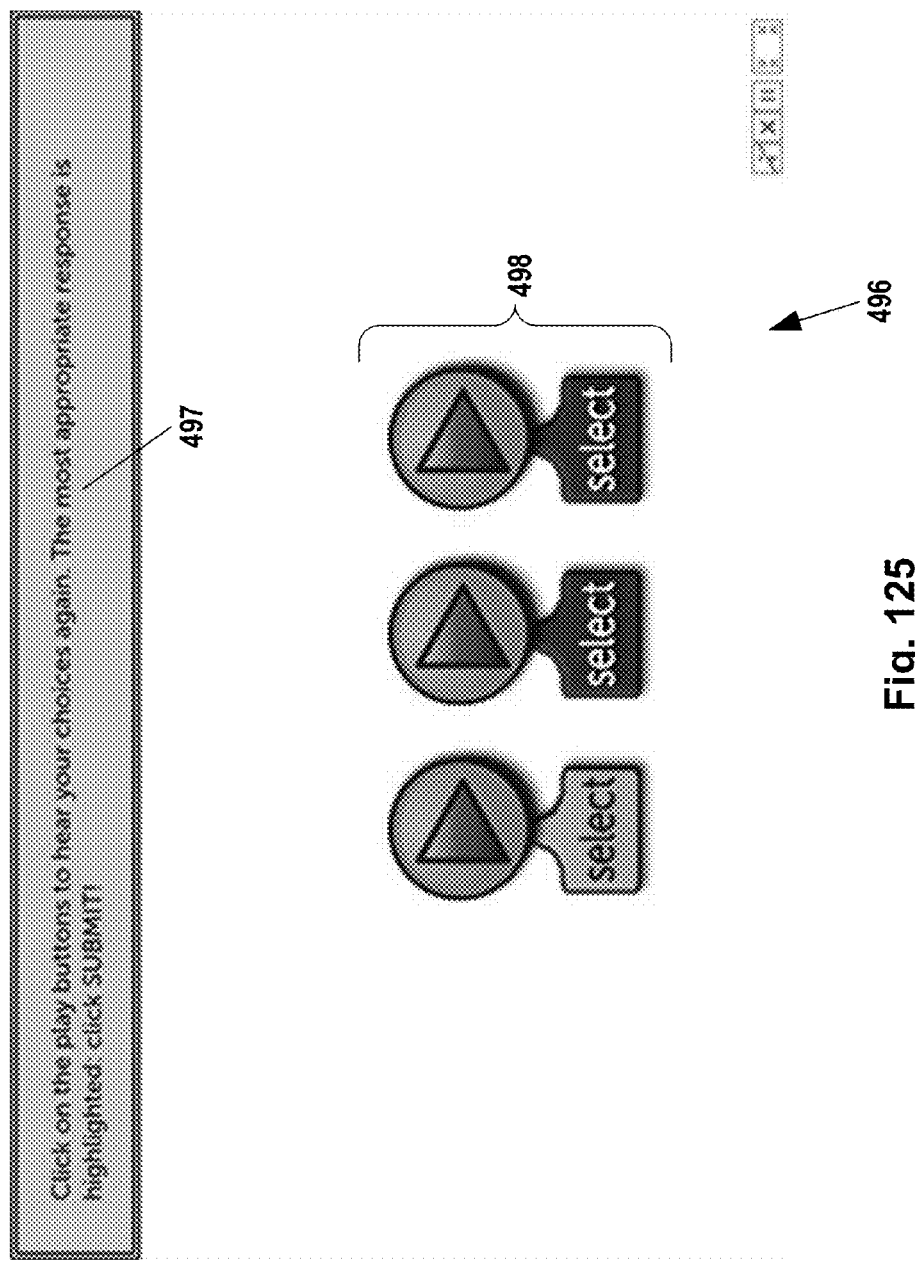
Figure 126:
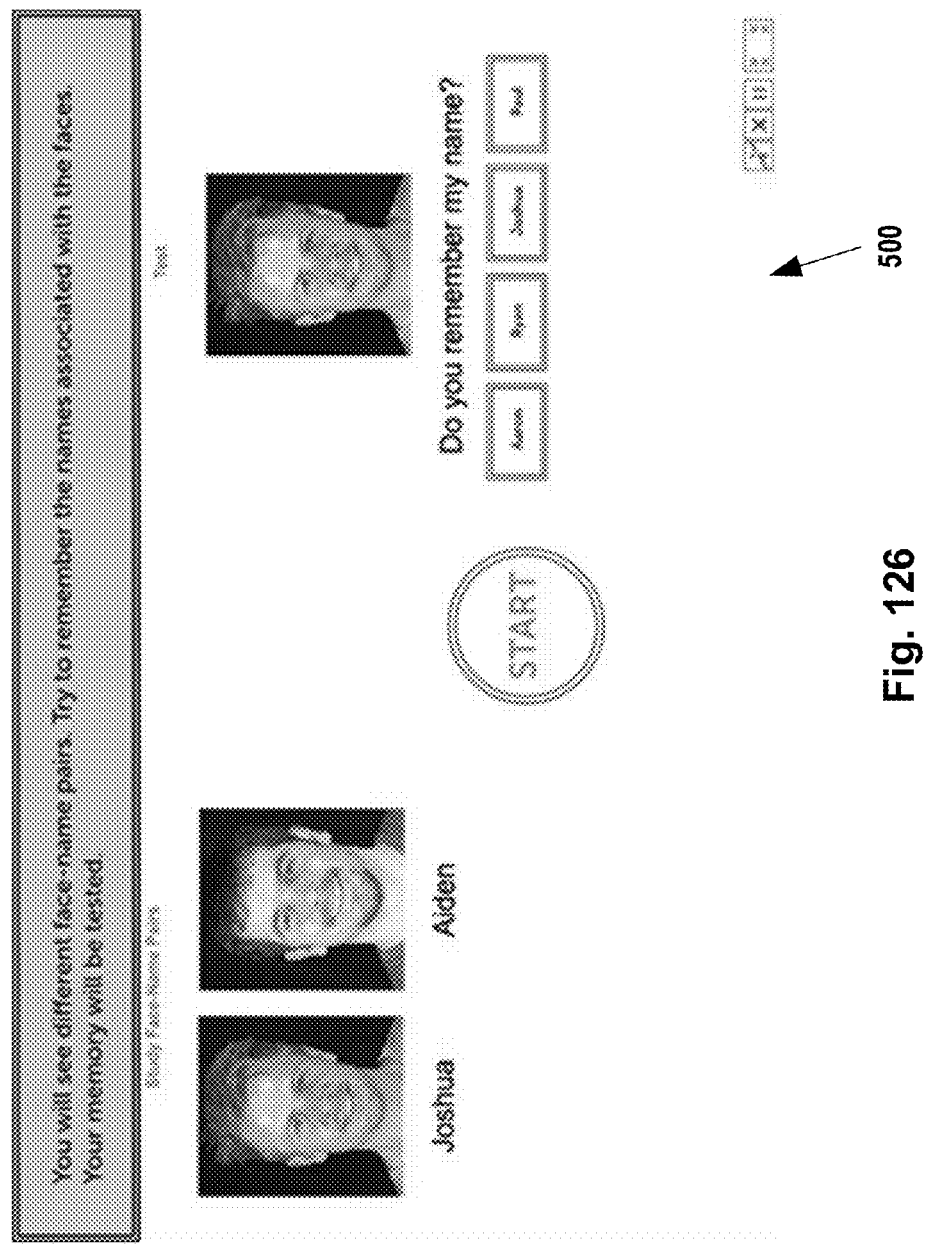
Figure 127:
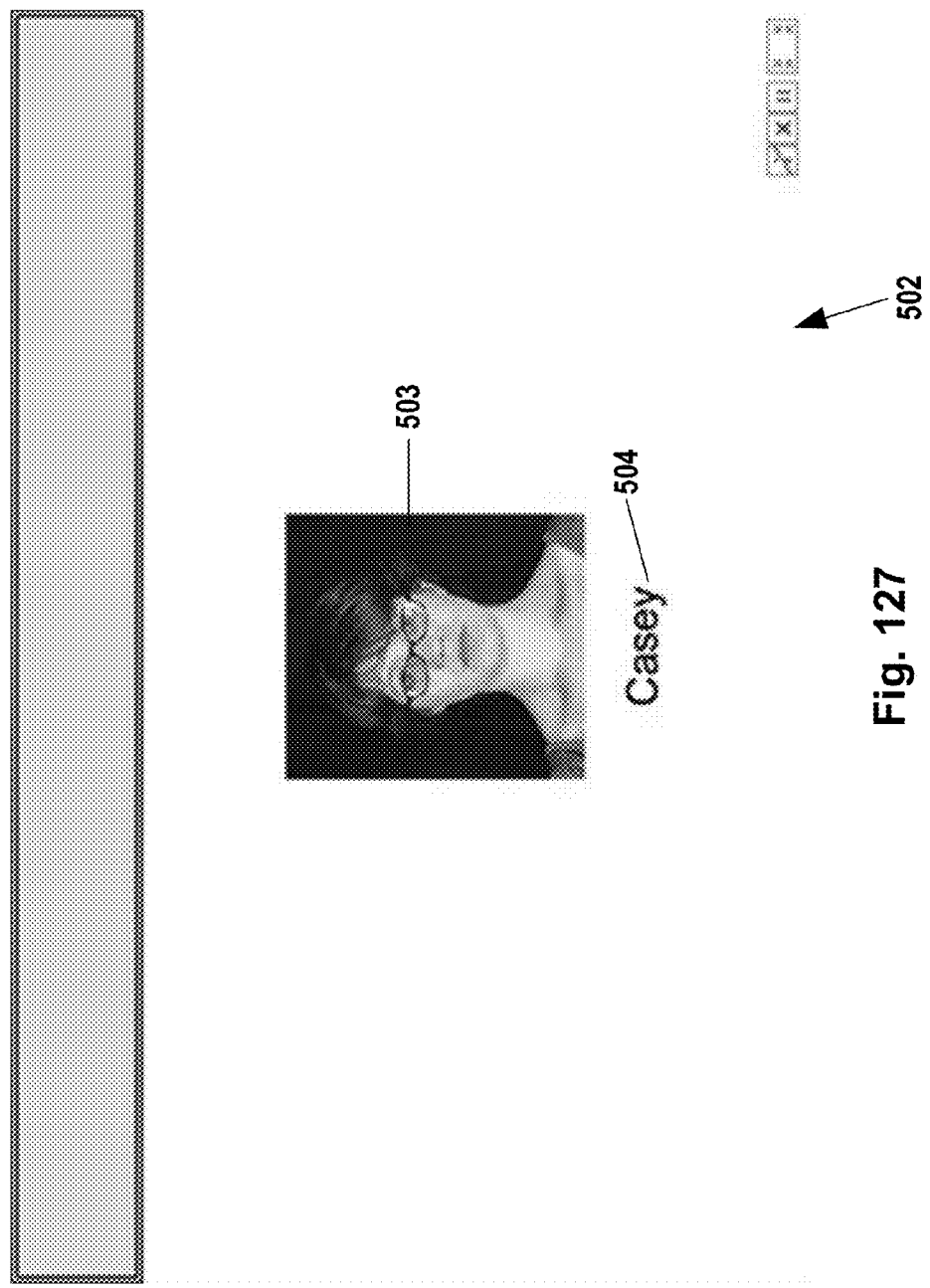
Figure 128:
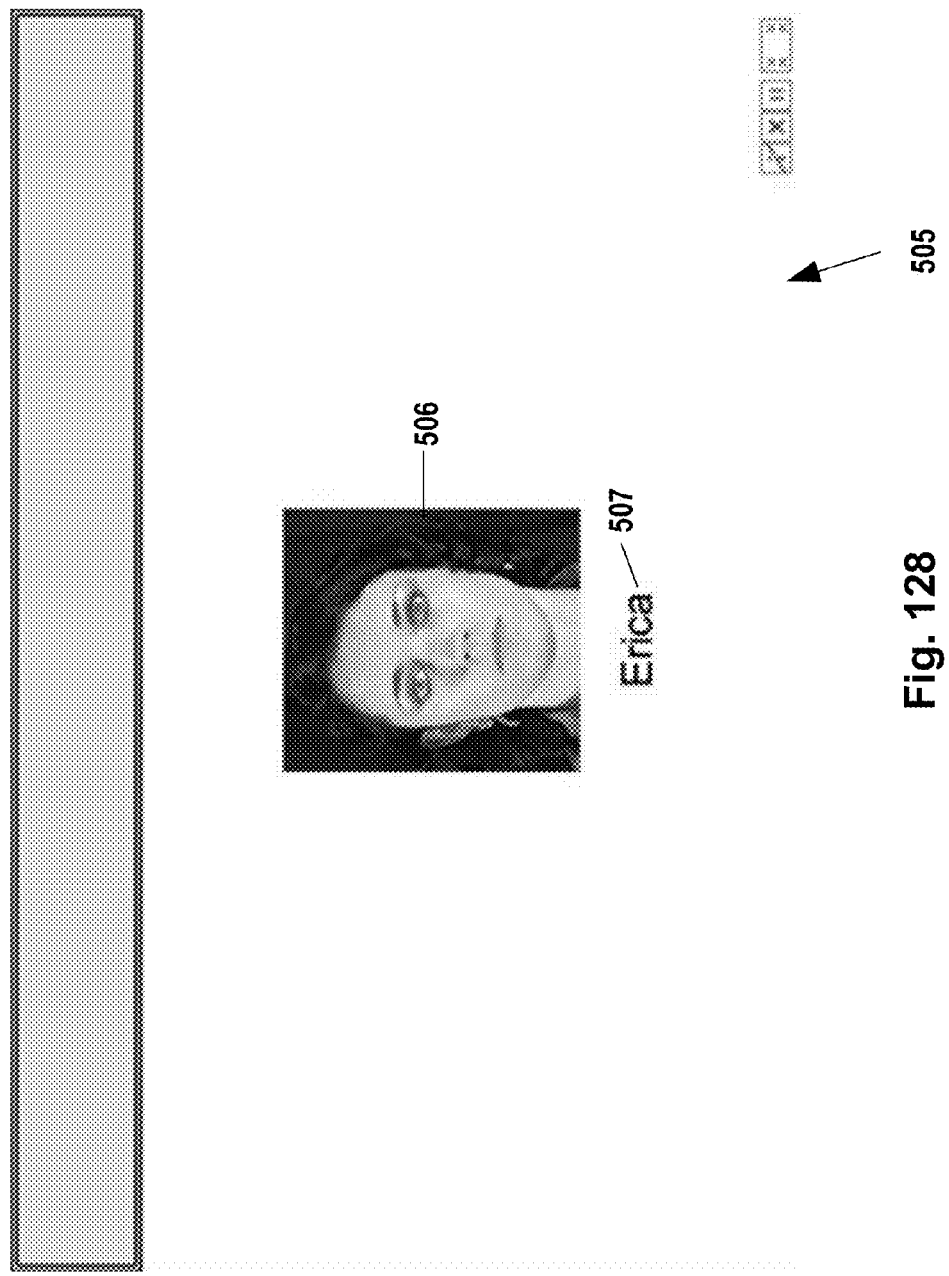
Figure 129:
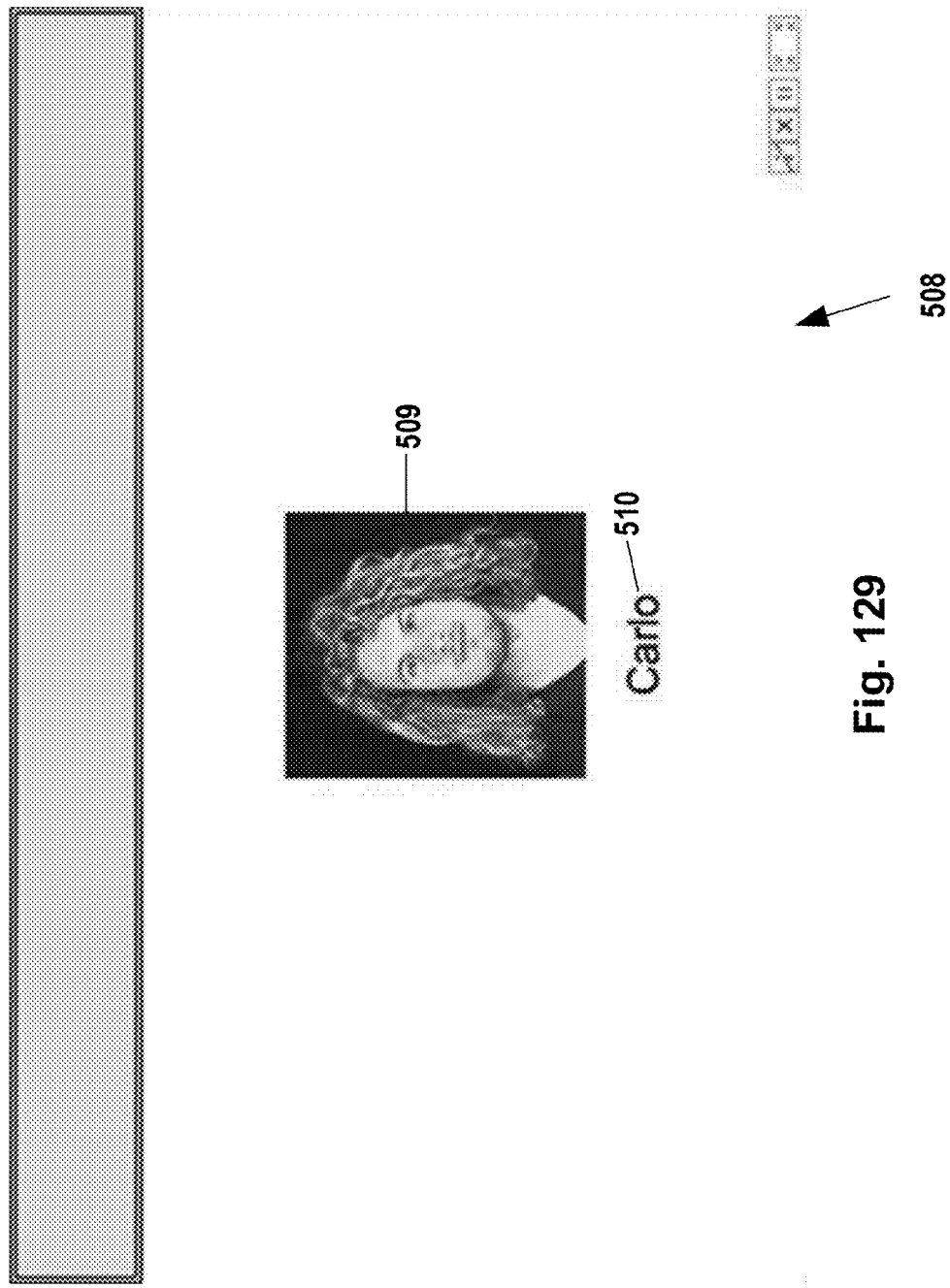

FIGS. 123-125 illustrate screenshots 490, 493 and 496 of one embodiment of a vocal affect theory of mind game called "Say What?" which challenges game participants to apprehend a social situation and the meanings conveyed by voice inflection.

This game heavily engages the ToM prosodic system, by requiring subjects to make judgments about how a person should sound in a given social situation, based on the knowledge that they are given about that situation. Subjects are presented with social scenarios, and are asked to decide how the characters should sound given the information a) that they have about that scenario, and b) given the knowledge that the characters have about the scenario.

With each trial, Say What? plays a short script describing a person's circumstances in a social situation. Say What? then prompts 494 the participant with a theory-of-mind question. For example, in FIG. 124, Say What? asks "How might James react in this situation?" Next, Say What? presents three aurally-presented response choices 498. Each option is in the form of the same sentence spoken by the same character, but with a different prosody and voice inflection (e.g. to reflect angry, excited, or happy mood). Say What? prompts 497 the participant to select the sentence with the prosody that best fits the person's circumstances related in the script. The length of the response sentences is varied based on the participant responses, with longer sentences being played if the participant makes mistakes.

17. Working Memory Name Span

FIGS. 126-130 illustrate screenshots 500, 502, 505, 508 and 511 of one embodiment of a name memorization game called "Face and Name," which challenges game participants to associate a plurality of names with a plurality of faces.

In each trial, Face and Name presents pictures of faces 503, 506, 509 with names 504, 507, 510. Next, Face and Name randomly selects and presents previously presented facial images 512, one at a time, with a set of name choices 514, prompting 513 the game participant to select the correct name. A trial is deemed successful if the participant correctly selects all the names presented. The length of the sequence is adaptively set using a 2up-1down adaptive rule.

18. Auditory Chatter

FIGS. 131-135 illustrate screenshots 516, 518, 520, 522 and 525 of one embodiment of a vocal emotional cue and theory of mind game called "Auditory Chatter," which challenges game participants to answer questions about persons discussed in a social conversation.

As an example, Auditory Chatter presents, as a visual background to the story, a pencil-sketch-like storyboard rendering 517 of three persons engaged in conversation around a table. Auditory Chatter plays a conversation constituting recordings by voice actors. Auditory Chatter presents the three persons taking their turns talking about other people—other than the people identified in the rendering 517—that they know. The name of each person being talked about is mentioned at least once, but preferably only once, in the conversation. As each person speaks, Auditory Chatter highlights the person 519, 521 to indicate that that person is speaking.

After presenting the conversation, Auditory Chatter prompts 523 the game participant with questions 523, 526 about persons discussed in the conversation. The participant is challenged to select from a set of answer choices 524, 527.

19. Social Theory of Mind

FIGS. 136-140 illustrate screenshots 529, 531, 533, 539 and 541 of one embodiment of a theory-of-mind game called "Social Scenes," which presents a short written narrative about a person and challenges the participant to infer what that person would have thought or felt based on the narrated circumstances.

Social Scene taps into neural ToM mechanisms, by helping subjects practice more and more complex scenarios that require ToM inferences, ranging from first- to second- to third-level ToM. Social Scene presents participants with more and more complex social scenes featuring at least two people, and challenges participants to figure out the knowledge that each of the characters has, then infer, based on this knowledge, what that character will do next.

Social Scenes displays a short written narrative describing a social situation. After the game participant hits "Enter" or selects the "OK" button, Social Scenes presents a social question 534 about the narrative, such as "how is John feeling right now?" Social Scenes also presents a set of response choices 535, 536 and 537, and prompts 538 the participant to select the response choices in the order from most to least likely. Each time the participant makes a correct selection, the corresponding choice disappears from the display, as illustrated in the progression from FIGS. 138 to 140.

20. What's Joe Thinking

FIGS. 141-143 illustrate screenshots of one embodiment of a theory of mind game called "What's Joe Thinking?" which challenges game participants to follow the direction of different people's eye gazes and interpret those gazes as denoting their thoughts.

What's Joe Thinking? displays, for a first time interval, a plurality of facial images 544-545 or 560-568 and plurality of objects 546-547 or 552-559 on a display area. A first target facial image 544, 568 is of a first person (for, example, "Joe") whose eyes are directed toward a targeted one 546, 556 of the plurality of objects. A second target facial image 545, 563 is approximately located along the direction of the first person's eyes. The second target facial image 545, 563 is of a second person whose eyes are either directed toward or away from the target object 546. Next, What's Joe Thinking? clears the display area, briefly displays a visual mask, and then displays a set of object choices 572 on the display area.

In a first challenge, What's Joe Thinking? prompts 571 the game participant to select the object choice 572 that matches the target object 546, 556. After receiving the participant's response to the first challenge, What's Joe Thinking? prompts the game participant to indicate whether the second person's eyes were directed toward or away from the target object 546, 556.

What's Joe Thinking? provides an indication of whether the game participant's responses were correct along with an indication or measure of a length of the first time interval. What's Joe Thinking? also progressively reduces the first time interval as the game participant's accuracy improves. In a typical trial, What's Joe Thinking? presents the target facial image 568 in the middle of a matrix of facial images 560-568 and objects 552-559, challenging the game participant to identify one of eight possible directions in which the target image's gaze is directed.

X. Conclusion

Those skilled in the art should appreciate that they can readily use the disclosed conception and specific embodiments as a basis for designing or modifying other structures for carrying out the same purposes of the present invention without departing from the spirit and scope of the invention as defined by the appended claims. The detailed description describes several distinct training programs, schemas, games, and categories of cognition, stimuli, and disorders. It will be understood that not all of that, while exemplary, not all of that detail is essential to the claimed invention. Training programs that employ different schemas, provide different games, or that cover more or fewer categories of stimuli and cognition may also be effective in treating any given disorder. Moreover, it will be understood that the invention disclosed herein may well have applications to other cognitive deficits and disorders.

The invention claimed is:

1. A training program configured to systematically drive neurological changes to overcome social cognitive deficits, the training program including at least one computerized social cue perception game that challenges a game participant to observe gaze directions in facial images and is configured to:

present a plurality of target and/or distractor stimuli;
prompt the game participant to respond to the target and/or distractor stimuli;
receive the game participant's input through a game piece;
provide an indication to the game participant of whether the game participant's input was accurate or apt;
provide a signal indicative of the game participant's performance or game difficulty; and
repeat the presenting through providing a signal steps over multiple repetitions while adapting one or more difficulty parameters to target maintenance of a success rate within a predetermined range.

2. The training program of claim 1, wherein the at least one computerized social cue perception game challenges the game participant to find a face with the same gaze direction as a target face.

3. The training program of claim 1, wherein the at least one computerized social cue perception game challenges the game participant to select a peripheral object at which the target face is gazing.

4. The training program of claim 1, wherein the at least one computerized social cue perception game challenges the game participant to match a face gazing in one direction with the same face gazing in a different direction.

5. The training program of claim 1, wherein the at least one computerized social cue perception game shows a face making a speeded glance shift in one of many possible directions and challenges the game participant to select an object in the direction of the speeded glance.

6. The training program of claim 1, wherein the at least one computerized social cue perception game challenges the game participant to follow a direction of different faces' eye gazes in relation to a plurality of objects, including a target object, and to identify the target object.

7. A training program configured to systematically drive neurological changes to overcome social cognitive deficits, the training program including at least one computerized emotional perception game that challenges a game participant to observe and make judgments about emotional expressions and is configured to:
present a plurality of target and/or distractor stimuli;
prompt the game participant to respond to the target and/or distractor stimuli;
receive the game participant's input through a game piece;
provide an indication to the game participant of whether the game participant's input was accurate or apt;
provide a signal indicative of the game participant's performance or game difficulty; and
repeat the presenting through providing a signal steps over multiple repetitions while adapting one or more difficulty parameters to target maintenance of a success rate within a predetermined range.

8. The training program of claim 7, wherein the at least one computerized emotional perception game challenges the game participant to find a face with the same facially expressed emotion as a target face.

9. The training program of claim 7, wherein the at least one computerized emotional perception game challenges the game participant to name a facial expression shown in a video clip showing a person facially expressing an emotion.

10. The training program of claim 7, wherein the at least one computerized emotional perception game challenges the game participant to match pairs of similar facial expressions.

11. The training program of claim 7, wherein the at least one computerized emotional perception game challenges the game participant to match video clips of emotional expressions with labels describing the emotion.

12. The training program of claim 7, wherein the at least one computerized emotional perception game challenges the game participant to reconstruct a sequence of emotion clips.

13. The training program of claim 7, wherein the at least one computerized emotional perception game presents a series of progressively shorter sentences, each associated with an emotional prosody, and challenging the game participant to identify the emotional prosody of each sentence.

14. The training program of claim 7, wherein the at least one computerized emotional perception game challenges the game participant to match pairs of emotionally-suggestive sentences with tags describing the emotion.

15. A training program configured to systematically drive neurological changes to overcome social cognitive deficits, the training program including at least one computerized theory of mind game that challenges a game participant to infer the mental states of others, wherein the game is configured to:
present a plurality of target and/or distractor stimuli;
prompt the game participant to respond to the target and/or distractor stimuli;
receive the game participant's input through a game piece;
provide an indication to the game participant of whether the game participant's input was accurate or apt;
provide a signal indicative of the game participant's performance or game difficulty; and
repeat the presenting through providing a signal steps over multiple repetitions while adapting one or more difficulty parameters to target maintenance of a success rate within a predetermined range.

16. The training program of claim 15, wherein the at least one computerized theory of mind game challenges game participants to apprehend a social situation and the meanings conveyed by voice inflection.

17. The training program of claim 15, wherein the at least one computerized theory of mind game challenges the game participant to answer questions about persons discussed in a social conversation.

18. The training program of claim 15, wherein the at least one computerized theory of mind game presents a short written narrative about a person and challenges the game participant to infer what the person would have thought or felt based on the narrated circumstances.

19. The training program of claim 15, wherein the at least one computerized theory of mind game challenges the game participant to follow the direction of different people's eye gazes and interpret those gazes as denoting their thoughts.

20. A training program configured to systematically drive neurological changes to overcome social cognitive deficits, the training program comprising:
computerized games from each of the following categories:
social cue perception games that challenge a game participant to observe gaze directions in facial images;
emotional perception games that challenge the game participant to observe and make judgments about emotional expressions; and
theory of mind games that challenge the game participant to infer the mental states of others;
wherein each game is configured to:
present a plurality of target and/or distractor stimuli;
prompt the game participant to respond to the target and/or distractor stimuli;

receive the game participant's input through a game piece;
provide an indication to the game participant of whether the game participant's input was accurate or apt;
provide a signal indicative of the game participant's performance or game difficulty; and
repeat the presenting through providing a signal steps over multiple repetitions while adapting one or more difficulty parameters to target maintenance of a success rate within a predetermined range.

\* \* \* \* \*